United States Patent
Regev et al.

(10) Patent No.: US 10,870,885 B2
(45) Date of Patent: Dec. 22, 2020

(54) DENDRITIC CELL RESPONSE GENE EXPRESSION, COMPOSITIONS OF MATTERS AND METHODS OF USE THEREOF

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Aviv Regev, Cambridge, MA (US); Alexander K. Shalek, Cambridge, MA (US); Rahul Satija, New York, NY (US); Hongkun Park, Lexington, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 268 days.

(21) Appl. No.: 14/846,219

(22) Filed: Sep. 4, 2015

(65) Prior Publication Data
US 2015/0368719 A1 Dec. 24, 2015

Related U.S. Application Data

(63) Continuation-in-part of application No. PCT/US2014/030429, filed on Mar. 17, 2014.

(60) Provisional application No. 61/787,378, filed on Mar. 15, 2013.

(51) Int. Cl.
| | | |
|---|---|---|
| C12Q 1/68 | (2018.01) | |
| G01N 33/53 | (2006.01) | |
| C12Q 1/6883 | (2018.01) | |
| G01N 33/50 | (2006.01) | |
| G01N 33/68 | (2006.01) | |

(52) U.S. Cl.
CPC ....... *C12Q 1/6883* (2013.01); *G01N 33/5047* (2013.01); *G01N 33/6893* (2013.01); *C12Q 2600/158* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 7,442,547 B2 | 10/2008 | Granucci et al. | |
| 2003/0134283 A1 | 7/2003 | Peterson et al. | |
| 2003/0228617 A1* | 12/2003 | Aune | C12Q 1/6883 435/6.16 |
| 2005/0036993 A1* | 2/2005 | Kohn | A61K 31/4164 424/93.21 |
| 2012/0294831 A1 | 11/2012 | Rossignol | |

FOREIGN PATENT DOCUMENTS

| | | |
|---|---|---|
| CN | 101590105 A | 12/2009 |
| JP | 2005500842 A | 1/2005 |
| JP | 2006505280 A | 2/2006 |
| JP | 2012521199 A | 9/2012 |
| JP | 2014513725 A | 6/2014 |
| RU | 2011111509 A | 10/2012 |
| RU | 2011111598 A | 10/2012 |
| WO | 03012078 A2 | 2/2003 |
| WO | 2008088849 A9 | 7/2008 |
| WO | WO 2008/088849 | 7/2008 |
| WO | 2009143719 | 12/2009 |
| WO | 2014145631 A1 | 9/2014 |

OTHER PUBLICATIONS

International Preliminary Report on Patentability and Written Opinion dated Sep. 24, 2015, which issued during prosecution of International Application No. PCT/US2014/030429.
Supplementary Partial European Search Report dated Aug. 12, 2016, which issued during prosecution of European Application No. 14762551.1.
Hashimoto, et al. "Serial Analysis of Gene Expression in Human Monocyte-Derived Dendritic Cells" Blood, 1999, 94(3):845-852.
The Broad Institute, Inc., Extended European Search Report received for European Patent Application No. 14762551.1, dated Nov. 15, 2016, 11 pages.
The Broad Institute, Inc., Office Action received for European Patent Application No. 14762551.1, dated Dec. 21, 2017, 4 pages.
The Broad Institute, Inc., Office Action for Japanese Application No. 2016503400, dated Mar. 5, 2018, 7 pages of English Translation and 6 pages of Japanese Office Action.
The Broad Institute, Inc., Office Action received for Russian Application No. 2015144160, dated Mar. 8, 2018, 5 pages of English Translation and 10 pages of Office Action.
The Broad Institute, Inc., International Search Report and Written Opinion for PCT Application No. PCT/US2014/030429, dated Aug. 27, 2014, 11 pages.
The Broad Institute, Inc., International Preliminary Report on Patentability for PCT Application No. PCT/US2014/030429, dated Sep. 15, 2015, 8 pages.

(Continued)

*Primary Examiner* — James Martinell
(74) *Attorney, Agent, or Firm* — Johnson, Marcou, Isaacs & Nix, LLC; F. Brent Nix, Esq.; Michael Scher, Esq.

(57) ABSTRACT

This invention relates generally to compositions and methods for identifying the regulatory network that modulates, controls or otherwise influences dendritic cell (DC) response(s), for example, dendritic cell maturation, dendritic cell antiviral response(s) and/or dendritic cell inflammatory response(s), as well compositions and methods for exploiting the regulatory network that modulates, controls or otherwise influences dendritic cell response(s) in a variety of therapeutic and/or diagnostic indications.

6 Claims, 61 Drawing Sheets

Specification includes a Sequence Listing.

(56) References Cited

OTHER PUBLICATIONS

The Broad Institute, Inc., Office Action received for Israel Patent Application No. 241294, dated Jul. 26, 2018, 3 Pages of English Translation and 3 Pages of Office Action.
The Broad Institute, Inc., "Chinese Office Action issued in Chinese Application No. 201480025302.2", dated Aug. 3, 2018, 18 pages of English Translation and 17 pages of Chinese Office Action.
Amit, et al., "Unbiased Reconstruction of a Mammalian Transcriptional Network Mediating the Differential Response to Pathogens", Science, vol. 326, No. 5950, Oct. 9, 2009, pp. 257-263.
Banchereau, et al., "Type I Interferon in Systemic Lupus Erythematosus and Other Autoimmune Diseases", Immunity, vol. 25, Issue 3, Sep. 2006, pp. 383-392.
Cabili, et al., "Integrative Annotation of Human Large Intergenic Noncoding RNAs Reveals Global Properties and Specific Subclasses", Genes & Development, vol. 25, Sep. 15, 2011, pp. 1915-1927.
Chevrier, et al., "Systematic Discovery of TLR Signaling Components Delineates Viral-Sensing Circuits", Cell, vol. 147, No. 4, Nov. 11, 2011, pp. 853-867.
Darnell, et al., "Jak-STAT Pathways and Transcriptional Activation in Response to IFNs and Other Extracellular Signaling Proteins", Science, vol. 264, No. 5164, Jul. 1994, pp. 1415-1421.
Gough, et al., "Functional Crosstalk between Type I and II Interferon through the Regulated Expression of STAT1", PLoS Biology, vol. 8, Issue 4, Apr. 2010, pp. 1-12.
Jiang, et al., "Disruption of E-Cadherin-Mediated Adhesion Induces a Functionally Distinct Pathway of Dendritic Cell Maturation", Immunity, vol. 27, No. 4, Oct. 2007, pp. 610-624.
Lutz, "Therapeutic Potential of Semi-Mature Dendritic Cells for Tolerance Induction", Frontiers in Immunology, vol. 3, Article 123, May 2012, pp. 1-9.
Ning, et al., "Regulation of the Transcriptional Activity of the IRF7 Promoter by a Pathway Independent of Interferon Signaling", The Journal of Biological Chemistry, vol. 280, No. 13, Apr. 1, 2005, pp. 12262-12270.
Ousman, et al., "Differential Regulation of Interferon Regulatory Factor (IRF)-7 and IRF-9 Gene Expression in the Central Nervous System during Viral Infection", Journal of Virology, vol. 79, No. 12, Jun. 2005, pp. 7514-7527.
Palucka, et al., "Dendritic Cells and Immunity Against Cancer", Journal of Internal Medicine, vol. 269, No. 1, pp. 64-73, Jan. 2011.
Rand, et al., "Multi-Layered Stochasticity and Paracrine Signal Propagation Shape the Type-I Interferon Response", Molecular Systems Biology, vol. 8, No. 584, May 22, 2012, 13 pages.
Shalek, et al., "Single-cell Transcriptomics Reveals Bimodality in Expression and Splicing in Immune Cells", Nature, vol. 498, No. 7453, 2013, pp. 236-240.
St. John, et al., "Dendritic cell activation and maturation induced by mucosal nuid from women with bacterial vaginosis", Clinical Immunology, vol. 125, 2007, pp. 95-102.
Steinman, et al., "Taking Dendritic Cells into Medicine", Nature, vol. 449, Sep. 27, 2007, pp. 419-426.
Todd, et al., "Challenges of Single-Cell Diagnostics: Analysis of Gene Expression", Trends in Molecular Medicine, vol. 8, Issue 6, Jun. 1, 2002, pp. 254-257.
Zhao, et al., "Stochastic Expression of the Interferon-β Gene", PLoS Biology, vol. 10, Issue 1, Jan. 2012, 16 pages.

* cited by examiner

Average densities

FIGURE 9C 81 reads, 23 unique 4-mers

Number of Unique Molecular Barcodes (MB)

| Gene | MB SC1 | MB SC2 | MB SC3 |
|---|---|---|---|
| Sat1 | 52 | 17 | 55 |
| Srsf7 | 6 | 7 | 25 |
| Zfp207 | 5 | 17 | 32 |
| Psmg4 | 6 | 8 | 18 |
| Rer1 | 16 | 14 | 21 |
| Abi1 | 9 | 8 | 27 |

Scales are log(Count+1)

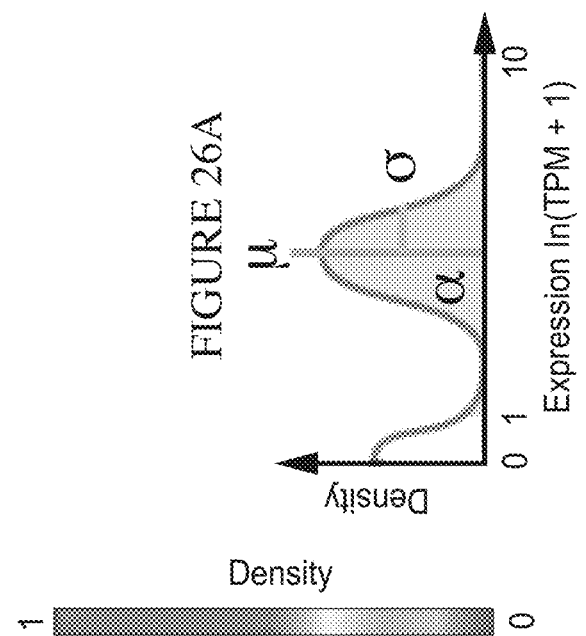
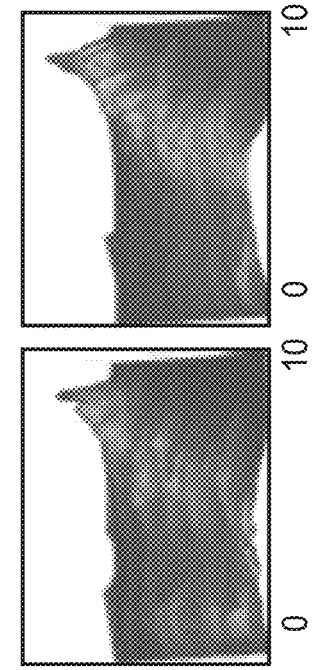

SEQUENCE LISTING

```
<160> NUMBER OF SEQ ID NOS: 369

<210> SEQ ID NO 1
<211> LENGTH: 20
<212> TYPE: DNA
<213> ORGANISM: Mus sp.

<400> SEQUENCE: 1
gcaattattc cccatgaacg                                              20

<210> SEQ ID NO 2
<211> LENGTH: 20
<212> TYPE: DNA
<213> ORGANISM: Mus sp.

<400> SEQUENCE: 2
tcatcagacc ccagaaaagg                                              20

<210> SEQ ID NO 3
<211> LENGTH: 20
<212> TYPE: DNA
<213> ORGANISM: Mus sp.

<400> SEQUENCE: 3
ctaaggccaa ccgtgaaaag                                              20

<210> SEQ ID NO 4
<211> LENGTH: 20
<212> TYPE: DNA
<213> ORGANISM: Mus sp.

<400> SEQUENCE: 4
gaacgtctcc tcgtgtccat                                              20

<210> SEQ ID NO 5
<211> LENGTH: 21
<212> TYPE: DNA
<213> ORGANISM: Mus sp.
```

```
<400> SEQUENCE: 5
actggtctag gacccgagaa g                                              21

<210> SEQ ID NO 6
<211> LENGTH: 19
<212> TYPE: DNA
<213> ORGANISM: Mus sp.

<400> SEQUENCE: 6
gatgcgcatt ttgatggtt                                                 19

<210> SEQ ID NO 7
<211> LENGTH: 19
<212> TYPE: DNA
<213> ORGANISM: Mus sp.

<400> SEQUENCE: 7
tatggtccag ctgccattc                                                 19

<210> SEQ ID NO 8
<211> LENGTH: 21
<212> TYPE: DNA
<213> ORGANISM: Mus sp.

<400> SEQUENCE: 8
gctggagtca gttaccgtca a                                              21

<210> SEQ ID NO 9
<211> LENGTH: 18
<212> TYPE: DNA
<213> ORGANISM: Mus sp.

<400> SEQUENCE: 9
atgatggctt ggccagtg                                                  18

<210> SEQ ID NO 10
<211> LENGTH: 21
<212> TYPE: DNA
<213> ORGANISM: Mus sp.

<400> SEQUENCE: 10
ttctggtgct tgtctcactg a                                              21

<210> SEQ ID NO 11
<211> LENGTH: 23
<212> TYPE: DNA
<213> ORGANISM: Mus sp.

<400> SEQUENCE: 11
ctcctgagac tattcccaca gaa                                            23

<210> SEQ ID NO 12
<211> LENGTH: 19
<212> TYPE: DNA
<213> ORGANISM: Mus sp.

<400> SEQUENCE: 12
ccagggaaac ctcctcaga                                                 19

<210> SEQ ID NO 13
<211> LENGTH: 18
<212> TYPE: DNA
```

```
<213> ORGANISM: Mus sp.

<400> SEQUENCE: 13
catccacgtg ttggctca                                                 18

<210> SEQ ID NO 14
<211> LENGTH: 20
<212> TYPE: DNA
<213> ORGANISM: Mus sp.

<400> SEQUENCE: 14
tgcccttgct gttcttctct                                               20

<210> SEQ ID NO 15
<211> LENGTH: 20
<212> TYPE: DNA
<213> ORGANISM: Mus sp.

<400> SEQUENCE: 15
ttctgtgcct gctgctcata                                               20

<210> SEQ ID NO 16
<211> LENGTH: 21
<212> TYPE: DNA
<213> ORGANISM: Mus sp.

<400> SEQUENCE: 16
ctgtgcattt acaccgacaa c                                             21

<210> SEQ ID NO 17
<211> LENGTH: 21
<212> TYPE: DNA
<213> ORGANISM: Mus sp.

<400> SEQUENCE: 17
ctccttgtca ttttccaggt g                                             21

<210> SEQ ID NO 18
<211> LENGTH: 22
<212> TYPE: DNA
<213> ORGANISM: Mus sp.

<400> SEQUENCE: 18
aaagaaactg aagcctttct cg                                            22

<210> SEQ ID NO 19
<211> LENGTH: 18
<212> TYPE: DNA
<213> ORGANISM: Mus sp.

<400> SEQUENCE: 19
tgatgcaatc cggatcaa                                                 18

<210> SEQ ID NO 20
<211> LENGTH: 18
<212> TYPE: DNA
<213> ORGANISM: Mus sp.

<400> SEQUENCE: 20
atcgcaaaga cggaagga                                                 18

<210> SEQ ID NO 21
<211> LENGTH: 20
```

```
<212> TYPE: DNA
<213> ORGANISM: Mus sp.

<400> SEQUENCE: 21
gcctccatcc tgtttctcag                                              20

<210> SEQ ID NO 22
<211> LENGTH: 23
<212> TYPE: DNA
<213> ORGANISM: Mus sp.

<400> SEQUENCE: 22
ctgggattca cctcaagaac atc                                          23

<210> SEQ ID NO 23
<211> LENGTH: 19
<212> TYPE: DNA
<213> ORGANISM: Mus sp.

<400> SEQUENCE: 23
gccgtcattt tctgcctca                                               19

<210> SEQ ID NO 24
<211> LENGTH: 26
<212> TYPE: DNA
<213> ORGANISM: Mus sp.

<400> SEQUENCE: 24
aaaatcatcc aaaagatact gaacaa                                       26

<210> SEQ ID NO 25
<211> LENGTH: 21
<212> TYPE: DNA
<213> ORGANISM: Mus sp.

<400> SEQUENCE: 25
gaagattctg gaccccacct a                                            21

<210> SEQ ID NO 26
<211> LENGTH: 20
<212> TYPE: DNA
<213> ORGANISM: Mus sp.

<400> SEQUENCE: 26
acacagggcc cgttacttct                                              20

<210> SEQ ID NO 27
<211> LENGTH: 20
<212> TYPE: DNA
<213> ORGANISM: Mus sp.

<400> SEQUENCE: 27
cagttttcgt gggacactca                                              20

<210> SEQ ID NO 28
<211> LENGTH: 26
<212> TYPE: DNA
<213> ORGANISM: Mus sp.

<400> SEQUENCE: 28
ttgggatagc tatacgacaa ataaga                                       26

<210> SEQ ID NO 29
```

```
<211> LENGTH: 21
<212> TYPE: DNA
<213> ORGANISM: Mus sp.

<400> SEQUENCE: 29
gctcccagcg ctataaaaac t                                              21

<210> SEQ ID NO 30
<211> LENGTH: 19
<212> TYPE: DNA
<213> ORGANISM: Mus sp.

<400> SEQUENCE: 30
tcctcctcag accgctttt                                                 19

<210> SEQ ID NO 31
<211> LENGTH: 25
<212> TYPE: DNA
<213> ORGANISM: Mus sp.

<400> SEQUENCE: 31
ctattaaccg tgttcaaaac atgaa                                          25

<210> SEQ ID NO 32
<211> LENGTH: 19
<212> TYPE: DNA
<213> ORGANISM: Mus sp.

<400> SEQUENCE: 32
tctaaacagg gccttgcag                                                 19

<210> SEQ ID NO 33
<211> LENGTH: 20
<212> TYPE: DNA
<213> ORGANISM: Mus sp.

<400> SEQUENCE: 33
gcaagatgca ccaagatgag                                                20

<210> SEQ ID NO 34
<211> LENGTH: 18
<212> TYPE: DNA
<213> ORGANISM: Mus sp.

<400> SEQUENCE: 34
tgaactgctc agcccaca                                                  18

<210> SEQ ID NO 35
<211> LENGTH: 20
<212> TYPE: DNA
<213> ORGANISM: Mus sp.

<400> SEQUENCE: 35
ctggcttcca tcatgaacaa                                                20

<210> SEQ ID NO 36
<211> LENGTH: 21
<212> TYPE: DNA
<213> ORGANISM: Mus sp.

<400> SEQUENCE: 36
gggagagtct ttgcctgatt c                                              21
```

-continued

```
<210> SEQ ID NO 37
<211> LENGTH: 20
<212> TYPE: DNA
<213> ORGANISM: Mus sp.

<400> SEQUENCE: 37
gattcagact ccaggggaca                                              20

<210> SEQ ID NO 38
<211> LENGTH: 21
<212> TYPE: DNA
<213> ORGANISM: Mus sp.

<400> SEQUENCE: 38
cagctcagag aggtcaggaa a                                            21

<210> SEQ ID NO 39
<211> LENGTH: 21
<212> TYPE: DNA
<213> ORGANISM: Mus sp.

<400> SEQUENCE: 39
ccagtgccaa cagtagtgac a                                            21

<210> SEQ ID NO 40
<211> LENGTH: 21
<212> TYPE: DNA
<213> ORGANISM: Mus sp.

<400> SEQUENCE: 40
ttggttaaat gacctgcaac a                                            21

<210> SEQ ID NO 41
<211> LENGTH: 24
<212> TYPE: DNA
<213> ORGANISM: Mus sp.

<400> SEQUENCE: 41
acctgtcctg tgtaatgaaa gacg                                         24

<210> SEQ ID NO 42
<211> LENGTH: 25
<212> TYPE: DNA
<213> ORGANISM: Mus sp.

<400> SEQUENCE: 42
gctaccaaac tggatataat cagga                                        25

<210> SEQ ID NO 43
<211> LENGTH: 20
<212> TYPE: DNA
<213> ORGANISM: Mus sp.

<400> SEQUENCE: 43
atcatcacct ttgccgagtc                                              20

<210> SEQ ID NO 44
<211> LENGTH: 18
<212> TYPE: DNA
<213> ORGANISM: Mus sp.

<400> SEQUENCE: 44
gagctgggcc attcacac                                                18
```

```
<210> SEQ ID NO 45
<211> LENGTH: 21
<212> TYPE: DNA
<213> ORGANISM: Mus sp.

<400> SEQUENCE: 45
acagcacctt atggctctct g                                              21

<210> SEQ ID NO 46
<211> LENGTH: 21
<212> TYPE: DNA
<213> ORGANISM: Mus sp.

<400> SEQUENCE: 46
cttcagcact ttcttccgag a                                              21

<210> SEQ ID NO 47
<211> LENGTH: 20
<212> TYPE: DNA
<213> ORGANISM: Mus sp.

<400> SEQUENCE: 47
gagccagatc ctccctgact                                                20

<210> SEQ ID NO 48
<211> LENGTH: 20
<212> TYPE: DNA
<213> ORGANISM: Mus sp.

<400> SEQUENCE: 48
tgaggccacc attagagagg                                                20

<210> SEQ ID NO 49
<211> LENGTH: 22
<212> TYPE: DNA
<213> ORGANISM: Mus sp.

<400> SEQUENCE: 49
gcttttgtta atggtgttgc tg                                             22

<210> SEQ ID NO 50
<211> LENGTH: 22
<212> TYPE: DNA
<213> ORGANISM: Mus sp.

<400> SEQUENCE: 50
agtcgaccca gtctctgact ct                                             22

<210> SEQ ID NO 51
<211> LENGTH: 18
<212> TYPE: DNA
<213> ORGANISM: Mus sp.

<400> SEQUENCE: 51
aagattgcca aggccaga                                                  18

<210> SEQ ID NO 52
<211> LENGTH: 20
<212> TYPE: DNA
<213> ORGANISM: Mus sp.

<400> SEQUENCE: 52
gcacttgtgc tacctgtcca                                                20
```

```
<210> SEQ ID NO 53
<211> LENGTH: 20
<212> TYPE: DNA
<213> ORGANISM: Mus sp.

<400> SEQUENCE: 53
gcattggttc ccctgagata                                           20

<210> SEQ ID NO 54
<211> LENGTH: 20
<212> TYPE: DNA
<213> ORGANISM: Mus sp.

<400> SEQUENCE: 54
cagcaaaaat tcgccctaaa                                           20

<210> SEQ ID NO 55
<211> LENGTH: 18
<212> TYPE: DNA
<213> ORGANISM: Mus sp.

<400> SEQUENCE: 55
catggacccc aactgctc                                             18

<210> SEQ ID NO 56
<211> LENGTH: 24
<212> TYPE: DNA
<213> ORGANISM: Mus sp.

<400> SEQUENCE: 56
ttcaaggatc actcatactt cagc                                      24

<210> SEQ ID NO 57
<211> LENGTH: 22
<212> TYPE: DNA
<213> ORGANISM: Mus sp.

<400> SEQUENCE: 57
cagttcctct cagtcccaag at                                        22

<210> SEQ ID NO 58
<211> LENGTH: 19
<212> TYPE: DNA
<213> ORGANISM: Mus sp.

<400> SEQUENCE: 58
tggccttgtt agaccgtga                                            19

<210> SEQ ID NO 59
<211> LENGTH: 20
<212> TYPE: DNA
<213> ORGANISM: Mus sp.

<400> SEQUENCE: 59
catgatggac ttggagttgc                                           20

<210> SEQ ID NO 60
<211> LENGTH: 20
<212> TYPE: DNA
<213> ORGANISM: Mus sp.

<400> SEQUENCE: 60
```
cactgctcag gtccactgtc                                                  20

<210> SEQ ID NO 61
<211> LENGTH: 20
<212> TYPE: DNA
<213> ORGANISM: Mus sp.

<400> SEQUENCE: 61
acgagcaaat ggtgaaggag                                                  20

<210> SEQ ID NO 62
<211> LENGTH: 20
<212> TYPE: DNA
<213> ORGANISM: Mus sp.

<400> SEQUENCE: 62
cagctgggga agtcattttt                                                  20

<210> SEQ ID NO 63
<211> LENGTH: 23
<212> TYPE: DNA
<213> ORGANISM: Mus sp.

<400> SEQUENCE: 63
ggtcgtgacc aagtataaga tgg                                              23

<210> SEQ ID NO 64
<211> LENGTH: 23
<212> TYPE: DNA
<213> ORGANISM: Mus sp.

<400> SEQUENCE: 64
ctgatcaaga aaatcatcct tcc                                              23

<210> SEQ ID NO 65
<211> LENGTH: 18
<212> TYPE: DNA
<213> ORGANISM: Mus sp.

<400> SEQUENCE: 65
tacctgctgg ctggatgg                                                    18

<210> SEQ ID NO 66
<211> LENGTH: 20
<212> TYPE: DNA
<213> ORGANISM: Mus sp.

<400> SEQUENCE: 66
agtggatcaa agccatccag                                                  20

<210> SEQ ID NO 67
<211> LENGTH: 22
<212> TYPE: DNA
<213> ORGANISM: Mus sp.

<400> SEQUENCE: 67
ttgtagtttt ggagctctgt cg                                               22

<210> SEQ ID NO 68
<211> LENGTH: 19
<212> TYPE: DNA
<213> ORGANISM: Mus sp.

<400> SEQUENCE: 68
catcaccacc attcccact 19

<210> SEQ ID NO 69
<211> LENGTH: 21
<212> TYPE: DNA
<213> ORGANISM: Mus sp.

<400> SEQUENCE: 69
aggaaccctc cgaagactat g 21

<210> SEQ ID NO 70
<211> LENGTH: 20
<212> TYPE: DNA
<213> ORGANISM: Mus sp.

<400> SEQUENCE: 70
tgtgctgagg agactcgatg 20

<210> SEQ ID NO 71
<211> LENGTH: 18
<212> TYPE: DNA
<213> ORGANISM: Mus sp.

<400> SEQUENCE: 71
acgccactgt cgcttttc 18

<210> SEQ ID NO 72
<211> LENGTH: 19
<212> TYPE: DNA
<213> ORGANISM: Mus sp.

<400> SEQUENCE: 72
gatgctcttc cgagctgtg 19

<210> SEQ ID NO 73
<211> LENGTH: 18
<212> TYPE: DNA
<213> ORGANISM: Mus sp.

<400> SEQUENCE: 73
cgctgtgctg gaggaact 18

<210> SEQ ID NO 74
<211> LENGTH: 24
<212> TYPE: DNA
<213> ORGANISM: Mus sp.

<400> SEQUENCE: 74
ttgcagagat ggatactatg aagc 24

<210> SEQ ID NO 75
<211> LENGTH: 20
<212> TYPE: DNA
<213> ORGANISM: Mus sp.

<400> SEQUENCE: 75
atccctccac cctatgacaa 20

<210> SEQ ID NO 76
<211> LENGTH: 20
<212> TYPE: DNA
<213> ORGANISM: Mus sp.

<400> SEQUENCE: 76
gcttcaacgt ggacgaagac                                               20

<210> SEQ ID NO 77
<211> LENGTH: 19
<212> TYPE: DNA
<213> ORGANISM: Mus sp.

<400> SEQUENCE: 77
tgtggacctc agcaaggtg                                                19

<210> SEQ ID NO 78
<211> LENGTH: 19
<212> TYPE: DNA
<213> ORGANISM: Mus sp.

<400> SEQUENCE: 78
ggagaagctg atggcttgg                                                19

<210> SEQ ID NO 79
<211> LENGTH: 20
<212> TYPE: DNA
<213> ORGANISM: Mus sp.

<400> SEQUENCE: 79
tgggtggaac tgctcgtaat                                               20

<210> SEQ ID NO 80
<211> LENGTH: 22
<212> TYPE: DNA
<213> ORGANISM: Mus sp.

<400> SEQUENCE: 80
cgtgctcagt agagcagctt ag                                            22

<210> SEQ ID NO 81
<211> LENGTH: 20
<212> TYPE: DNA
<213> ORGANISM: Mus sp.

<400> SEQUENCE: 81
aggcaactga gcaaagcaac                                               20

<210> SEQ ID NO 82
<211> LENGTH: 19
<212> TYPE: DNA
<213> ORGANISM: Mus sp.

<400> SEQUENCE: 82
atttcgcttc gggactagc                                                19

<210> SEQ ID NO 83
<211> LENGTH: 20
<212> TYPE: DNA
<213> ORGANISM: Mus sp.

<400> SEQUENCE: 83
gcagcacaac atacggaaaa                                               20

<210> SEQ ID NO 84
<211> LENGTH: 20
<212> TYPE: DNA
<213> ORGANISM: Mus sp.

```
<400> SEQUENCE: 84
ggaacagctg gaacagtggt                                          20

<210> SEQ ID NO 85
<211> LENGTH: 19
<212> TYPE: DNA
<213> ORGANISM: Mus sp.

<400> SEQUENCE: 85
attccccagg aaaggctgt                                           19

<210> SEQ ID NO 86
<211> LENGTH: 21
<212> TYPE: DNA
<213> ORGANISM: Mus sp.

<400> SEQUENCE: 86
cagcactctc ttcagcctct c                                        21

<210> SEQ ID NO 87
<211> LENGTH: 22
<212> TYPE: DNA
<213> ORGANISM: Mus sp.

<400> SEQUENCE: 87
cctcggagga acaaagaagt aa                                       22

<210> SEQ ID NO 88
<211> LENGTH: 18
<212> TYPE: DNA
<213> ORGANISM: Mus sp.

<400> SEQUENCE: 88
gacgggcttg aggaacag                                            18

<210> SEQ ID NO 89
<211> LENGTH: 21
<212> TYPE: DNA
<213> ORGANISM: Mus sp.

<400> SEQUENCE: 89
tcttctcatt cctgcttgtg g                                        21

<210> SEQ ID NO 90
<211> LENGTH: 21
<212> TYPE: DNA
<213> ORGANISM: Mus sp.

<400> SEQUENCE: 90
ggagcctttg aaagacctca a                                        21

<210> SEQ ID NO 91
<211> LENGTH: 18
<212> TYPE: DNA
<213> ORGANISM: Mus sp.

<400> SEQUENCE: 91
gaggcccaag ggtttcag                                            18

<210> SEQ ID NO 92
<211> LENGTH: 20
<212> TYPE: DNA
```

```
<213> ORGANISM: Mus sp.

<400> SEQUENCE: 92
aaaggaccct ccaatccaaa                                               20

<210> SEQ ID NO 93
<211> LENGTH: 19
<212> TYPE: DNA
<213> ORGANISM: Mus sp.

<400> SEQUENCE: 93
cagggcagac caagaattg                                                19

<210> SEQ ID NO 94
<211> LENGTH: 19
<212> TYPE: DNA
<213> ORGANISM: Mus sp.

<400> SEQUENCE: 94
agcaccgtgg tcacaaaac                                                19

<210> SEQ ID NO 95
<211> LENGTH: 21
<212> TYPE: DNA
<213> ORGANISM: Mus sp.

<400> SEQUENCE: 95
aacagctttc gatgaagcca t                                             21

<210> SEQ ID NO 96
<211> LENGTH: 20
<212> TYPE: DNA
<213> ORGANISM: Mus sp.

<400> SEQUENCE: 96
ttcacgacac accagatcct                                               20

<210> SEQ ID NO 97
<211> LENGTH: 18
<212> TYPE: DNA
<213> ORGANISM: Mus sp.

<400> SEQUENCE: 97
cagagcagga gccagagc                                                 18

<210> SEQ ID NO 98
<211> LENGTH: 20
<212> TYPE: DNA
<213> ORGANISM: Mus sp.

<400> SEQUENCE: 98
acattgctgc tgctacttgc                                               20

<210> SEQ ID NO 99
<211> LENGTH: 20
<212> TYPE: DNA
<213> ORGANISM: Mus sp.

<400> SEQUENCE: 99
gaacaacagc ctgaacatgg                                               20

<210> SEQ ID NO 100
<211> LENGTH: 20
```

```
<212> TYPE: DNA
<213> ORGANISM: Mus sp.

<400> SEQUENCE: 100
gtgggaacca gaggagaaca                                          20

<210> SEQ ID NO 101
<211> LENGTH: 20
<212> TYPE: DNA
<213> ORGANISM: Mus sp.

<400> SEQUENCE: 101
actgtaacct gctgcccaag                                          20

<210> SEQ ID NO 102
<211> LENGTH: 20
<212> TYPE: DNA
<213> ORGANISM: Mus sp.

<400> SEQUENCE: 102
cgccaggttt gattcttcag                                          20

<210> SEQ ID NO 103
<211> LENGTH: 20
<212> TYPE: DNA
<213> ORGANISM: Mus sp.

<400> SEQUENCE: 103
aaccccagat gctgacaaag                                          20

<210> SEQ ID NO 104
<211> LENGTH: 21
<212> TYPE: DNA
<213> ORGANISM: Mus sp.

<400> SEQUENCE: 104
gggacagcct ttcctactac c                                        21

<210> SEQ ID NO 105
<211> LENGTH: 20
<212> TYPE: DNA
<213> ORGANISM: Mus sp.

<400> SEQUENCE: 105
aaggcctagg cgagaatgtt                                          20

<210> SEQ ID NO 106
<211> LENGTH: 20
<212> TYPE: DNA
<213> ORGANISM: Mus sp.

<400> SEQUENCE: 106
ggcaaattca acggcacagt                                          20

<210> SEQ ID NO 107
<211> LENGTH: 20
<212> TYPE: DNA
<213> ORGANISM: Mus sp.

<400> SEQUENCE: 107
tcagaatcgc cgagctaaat                                          20

<210> SEQ ID NO 108
```

```
<211> LENGTH: 19
<212> TYPE: DNA
<213> ORGANISM: Mus sp.

<400> SEQUENCE: 108
atgaggaggc tcccctttc                                                  19

<210> SEQ ID NO 109
<211> LENGTH: 20
<212> TYPE: DNA
<213> ORGANISM: Mus sp.

<400> SEQUENCE: 109
tcaagccatc cttgtgctaa                                                 20

<210> SEQ ID NO 110
<211> LENGTH: 24
<212> TYPE: DNA
<213> ORGANISM: Mus sp.

<400> SEQUENCE: 110
ccatcagcag atcattctag acaa                                            24

<210> SEQ ID NO 111
<211> LENGTH: 20
<212> TYPE: DNA
<213> ORGANISM: Mus sp.

<400> SEQUENCE: 111
ttggtgaagc caggctagag                                                 20

<210> SEQ ID NO 112
<211> LENGTH: 21
<212> TYPE: DNA
<213> ORGANISM: Mus sp.

<400> SEQUENCE: 112
ccagaagatg gtgtggtgtt t                                               21

<210> SEQ ID NO 113
<211> LENGTH: 20
<212> TYPE: DNA
<213> ORGANISM: Mus sp.

<400> SEQUENCE: 113
ccacggaggg agagaaaatc                                                 20

<210> SEQ ID NO 114
<211> LENGTH: 20
<212> TYPE: DNA
<213> ORGANISM: Mus sp.

<400> SEQUENCE: 114
ccaacaggca ggaatcactc                                                 20

<210> SEQ ID NO 115
<211> LENGTH: 18
<212> TYPE: DNA
<213> ORGANISM: Mus sp.

<400> SEQUENCE: 115
ccatcccaat ggcgtatc                                                   18
```

```
<210> SEQ ID NO 116
<211> LENGTH: 21
<212> TYPE: DNA
<213> ORGANISM: Mus sp.

<400> SEQUENCE: 116
acgttaccag caactgaaac c                                        21

<210> SEQ ID NO 117
<211> LENGTH: 18
<212> TYPE: DNA
<213> ORGANISM: Mus sp.

<400> SEQUENCE: 117
tggaacagcc caaacagc                                            18

<210> SEQ ID NO 118
<211> LENGTH: 24
<212> TYPE: DNA
<213> ORGANISM: Mus sp.

<400> SEQUENCE: 118
tggagatcct agtgacaaaa atcc                                     24

<210> SEQ ID NO 119
<211> LENGTH: 18
<212> TYPE: DNA
<213> ORGANISM: Mus sp.

<400> SEQUENCE: 119
cttgccctgg accacaaa                                            18

<210> SEQ ID NO 120
<211> LENGTH: 18
<212> TYPE: DNA
<213> ORGANISM: Mus sp.

<400> SEQUENCE: 120
catccggagc agagacca                                            18

<210> SEQ ID NO 121
<211> LENGTH: 18
<212> TYPE: DNA
<213> ORGANISM: Mus sp.

<400> SEQUENCE: 121
ggctggcagc tcgattag                                            18

<210> SEQ ID NO 122
<211> LENGTH: 20
<212> TYPE: DNA
<213> ORGANISM: Mus sp.

<400> SEQUENCE: 122
gaaaaccaaa aaggctgtgg                                          20

<210> SEQ ID NO 123
<211> LENGTH: 20
<212> TYPE: DNA
<213> ORGANISM: Mus sp.

<400> SEQUENCE: 123
gcggcaacta cagcctagag                                          20
```

```
<210> SEQ ID NO 124
<211> LENGTH: 19
<212> TYPE: DNA
<213> ORGANISM: Mus sp.

<400> SEQUENCE: 124
cccagaccgc agtatccat                                              19

<210> SEQ ID NO 125
<211> LENGTH: 22
<212> TYPE: DNA
<213> ORGANISM: Mus sp.

<400> SEQUENCE: 125
gtgacctctc ttccctgtca ct                                          22

<210> SEQ ID NO 126
<211> LENGTH: 20
<212> TYPE: DNA
<213> ORGANISM: Mus sp.

<400> SEQUENCE: 126
ctccgtgcta cccactcact                                             20

<210> SEQ ID NO 127
<211> LENGTH: 18
<212> TYPE: DNA
<213> ORGANISM: Mus sp.

<400> SEQUENCE: 127
cggtgcagtg tcagcttc                                               18

<210> SEQ ID NO 128
<211> LENGTH: 20
<212> TYPE: DNA
<213> ORGANISM: Mus sp.

<400> SEQUENCE: 128
ggtggtggag agtgaggact                                             20

<210> SEQ ID NO 129
<211> LENGTH: 20
<212> TYPE: DNA
<213> ORGANISM: Mus sp.

<400> SEQUENCE: 129
ggtccgagaa cagagtggtt                                             20

<210> SEQ ID NO 130
<211> LENGTH: 20
<212> TYPE: DNA
<213> ORGANISM: Mus sp.

<400> SEQUENCE: 130
tcgtcgtcct cgagatgatt                                             20

<210> SEQ ID NO 131
<211> LENGTH: 18
<212> TYPE: DNA
<213> ORGANISM: Mus sp.

<400> SEQUENCE: 131
gccagggctt ggaagatt                                               18
```

<210> SEQ ID NO 132
<211> LENGTH: 19
<212> TYPE: DNA
<213> ORGANISM: Mus sp.

<400> SEQUENCE: 132
cggcatctgc tagctcagt                                                19

<210> SEQ ID NO 133
<211> LENGTH: 20
<212> TYPE: DNA
<213> ORGANISM: Mus sp.

<400> SEQUENCE: 133
gagtcctcag cgagaccttg                                               20

<210> SEQ ID NO 134
<211> LENGTH: 19
<212> TYPE: DNA
<213> ORGANISM: Mus sp.

<400> SEQUENCE: 134
ccaagagcgt tttcccaat                                                19

<210> SEQ ID NO 135
<211> LENGTH: 21
<212> TYPE: DNA
<213> ORGANISM: Mus sp.

<400> SEQUENCE: 135
gcgaggccac acagatatta c                                             21

<210> SEQ ID NO 136
<211> LENGTH: 20
<212> TYPE: DNA
<213> ORGANISM: Mus sp.

<400> SEQUENCE: 136
agcgtaatgc gagaaacctc                                               20

<210> SEQ ID NO 137
<211> LENGTH: 20
<212> TYPE: DNA
<213> ORGANISM: Mus sp.

<400> SEQUENCE: 137
gggacttaat caacgcaagc                                               20

<210> SEQ ID NO 138
<211> LENGTH: 20
<212> TYPE: DNA
<213> ORGANISM: Mus sp.

<400> SEQUENCE: 138
gattcggcag gtgagttgtt                                               20

<210> SEQ ID NO 139
<211> LENGTH: 20
<212> TYPE: DNA
<213> ORGANISM: Mus sp.

<400> SEQUENCE: 139
accagaggca tacagggaca                                          20

<210> SEQ ID NO 140
<211> LENGTH: 18
<212> TYPE: DNA
<213> ORGANISM: Mus sp.

<400> SEQUENCE: 140
ggccatctgg tggttcac                                            18

<210> SEQ ID NO 141
<211> LENGTH: 20
<212> TYPE: DNA
<213> ORGANISM: Mus sp.

<400> SEQUENCE: 141
tcccaccttg tctccagtct                                          20

<210> SEQ ID NO 142
<211> LENGTH: 27
<212> TYPE: DNA
<213> ORGANISM: Mus sp.

<400> SEQUENCE: 142
ttcagtttat acagaattgt cgtcttg                                  27

<210> SEQ ID NO 143
<211> LENGTH: 22
<212> TYPE: DNA
<213> ORGANISM: Mus sp.

<400> SEQUENCE: 143
ccaaagtctt ttaggtggca tc                                       22

<210> SEQ ID NO 144
<211> LENGTH: 19
<212> TYPE: DNA
<213> ORGANISM: Mus sp.

<400> SEQUENCE: 144
cgcctccttt tcctctcat                                           19

<210> SEQ ID NO 145
<211> LENGTH: 22
<212> TYPE: DNA
<213> ORGANISM: Mus sp.

<400> SEQUENCE: 145
ccattttctc caacatccaa tc                                       22

<210> SEQ ID NO 146
<211> LENGTH: 22
<212> TYPE: DNA
<213> ORGANISM: Mus sp.

<400> SEQUENCE: 146
cagtatgttc ggcttcccat tc                                       22

<210> SEQ ID NO 147
<211> LENGTH: 25
<212> TYPE: DNA
<213> ORGANISM: Mus sp.

<400> SEQUENCE: 147

```
caagatgttg ctgtatcatc atagg                                         25

<210> SEQ ID NO 148
<211> LENGTH: 20
<212> TYPE: DNA
<213> ORGANISM: Mus sp.

<400> SEQUENCE: 148
ccggatggga acagtgtaga                                               20

<210> SEQ ID NO 149
<211> LENGTH: 23
<212> TYPE: DNA
<213> ORGANISM: Mus sp.

<400> SEQUENCE: 149
gatcatcttg ctggtgaatg agt                                           23

<210> SEQ ID NO 150
<211> LENGTH: 20
<212> TYPE: DNA
<213> ORGANISM: Mus sp.

<400> SEQUENCE: 150
gtggaatctt ccggctgtag                                               20

<210> SEQ ID NO 151
<211> LENGTH: 21
<212> TYPE: DNA
<213> ORGANISM: Mus sp.

<400> SEQUENCE: 151
ttgacatagc agcatgtgga t                                             21

<210> SEQ ID NO 152
<211> LENGTH: 21
<212> TYPE: DNA
<213> ORGANISM: Mus sp.

<400> SEQUENCE: 152
cactaccagt tcccactcca g                                             21

<210> SEQ ID NO 153
<211> LENGTH: 21
<212> TYPE: DNA
<213> ORGANISM: Mus sp.

<400> SEQUENCE: 153
tggtattctc gccgatgtag t                                             21

<210> SEQ ID NO 154
<211> LENGTH: 19
<212> TYPE: DNA
<213> ORGANISM: Mus sp.

<400> SEQUENCE: 154
agcaacaagc caagcacac                                                19

<210> SEQ ID NO 155
<211> LENGTH: 19
<212> TYPE: DNA
<213> ORGANISM: Mus sp.
```

<400> SEQUENCE: 155
cacgtgtgtt gcgtcagtc                                                19

<210> SEQ ID NO 156
<211> LENGTH: 18
<212> TYPE: DNA
<213> ORGANISM: Mus sp.

<400> SEQUENCE: 156
tgctgctggt gatgatgc                                                 18

<210> SEQ ID NO 157
<211> LENGTH: 21
<212> TYPE: DNA
<213> ORGANISM: Mus sp.

<400> SEQUENCE: 157
tgagagctgc gatatgttac g                                             21

<210> SEQ ID NO 158
<211> LENGTH: 19
<212> TYPE: DNA
<213> ORGANISM: Mus sp.

<400> SEQUENCE: 158
cagggtcaag gcaagcctc                                                19

<210> SEQ ID NO 159
<211> LENGTH: 19
<212> TYPE: DNA
<213> ORGANISM: Mus sp.

<400> SEQUENCE: 159
cgtccttgcg agagggatc                                                19

<210> SEQ ID NO 160
<211> LENGTH: 20
<212> TYPE: DNA
<213> ORGANISM: Mus sp.

<400> SEQUENCE: 160
ctttggttct tccgttgagg                                               20

<210> SEQ ID NO 161
<211> LENGTH: 21
<212> TYPE: DNA
<213> ORGANISM: Mus sp.

<400> SEQUENCE: 161
tgaatgtact gcacctcctc a                                             21

<210> SEQ ID NO 162
<211> LENGTH: 19
<212> TYPE: DNA
<213> ORGANISM: Mus sp.

<400> SEQUENCE: 162
tcacagtgga tgccaaagg                                                19

<210> SEQ ID NO 163
<211> LENGTH: 20
<212> TYPE: DNA
<213> ORGANISM: Mus sp.

```
<400> SEQUENCE: 163
aagggagcac agcaaacaga                                              20

<210> SEQ ID NO 164
<211> LENGTH: 18
<212> TYPE: DNA
<213> ORGANISM: Mus sp.

<400> SEQUENCE: 164
ggcgtaggca caggtcat                                                18

<210> SEQ ID NO 165
<211> LENGTH: 18
<212> TYPE: DNA
<213> ORGANISM: Mus sp.

<400> SEQUENCE: 165
tgagcacggg gatacagc                                                18

<210> SEQ ID NO 166
<211> LENGTH: 21
<212> TYPE: DNA
<213> ORGANISM: Mus sp.

<400> SEQUENCE: 166
cctggttcat catcgctaat c                                            21

<210> SEQ ID NO 167
<211> LENGTH: 22
<212> TYPE: DNA
<213> ORGANISM: Mus sp.

<400> SEQUENCE: 167
cacctgcaat tccaaaatct ta                                           22

<210> SEQ ID NO 168
<211> LENGTH: 22
<212> TYPE: DNA
<213> ORGANISM: Mus sp.

<400> SEQUENCE: 168
gcagagccct ttttgataat gt                                           22

<210> SEQ ID NO 169
<211> LENGTH: 23
<212> TYPE: DNA
<213> ORGANISM: Mus sp.

<400> SEQUENCE: 169
cttctaatga agtgctccag acc                                          23

<210> SEQ ID NO 170
<211> LENGTH: 18
<212> TYPE: DNA
<213> ORGANISM: Mus sp.

<400> SEQUENCE: 170
tcccggttga cctcactc                                                18

<210> SEQ ID NO 171
<211> LENGTH: 19
<212> TYPE: DNA
```

```
<213> ORGANISM: Mus sp.

<400> SEQUENCE: 171
agagggctgt ggtggagaa                                            19

<210> SEQ ID NO 172
<211> LENGTH: 20
<212> TYPE: DNA
<213> ORGANISM: Mus sp.

<400> SEQUENCE: 172
atctcctggg cttggctatc                                           20

<210> SEQ ID NO 173
<211> LENGTH: 23
<212> TYPE: DNA
<213> ORGANISM: Mus sp.

<400> SEQUENCE: 173
tggttagctt ctgaggacac atc                                       23

<210> SEQ ID NO 174
<211> LENGTH: 20
<212> TYPE: DNA
<213> ORGANISM: Mus sp.

<400> SEQUENCE: 174
catgaagagg cagtgctttg                                           20

<210> SEQ ID NO 175
<211> LENGTH: 20
<212> TYPE: DNA
<213> ORGANISM: Mus sp.

<400> SEQUENCE: 175
ttgggagaga aagcttctgg                                           20

<210> SEQ ID NO 176
<211> LENGTH: 19
<212> TYPE: DNA
<213> ORGANISM: Mus sp.

<400> SEQUENCE: 176
gagcgctcac gaacagttg                                            19

<210> SEQ ID NO 177
<211> LENGTH: 20
<212> TYPE: DNA
<213> ORGANISM: Mus sp.

<400> SEQUENCE: 177
tgggtattgc ttgggatcca                                           20

<210> SEQ ID NO 178
<211> LENGTH: 24
<212> TYPE: DNA
<213> ORGANISM: Mus sp.

<400> SEQUENCE: 178
ccaggtagct atggtactcc agaa                                      24

<210> SEQ ID NO 179
<211> LENGTH: 20
```

<212> TYPE: DNA
<213> ORGANISM: Mus sp.

<400> SEQUENCE: 179
tcactgcctt ccttggaaat                                                  20

<210> SEQ ID NO 180
<211> LENGTH: 19
<212> TYPE: DNA
<213> ORGANISM: Mus sp.

<400> SEQUENCE: 180
tccatgtctt gggatctgg                                                   19

<210> SEQ ID NO 181
<211> LENGTH: 20
<212> TYPE: DNA
<213> ORGANISM: Mus sp.

<400> SEQUENCE: 181
atggggtggc atcatgtagt                                                  20

<210> SEQ ID NO 182
<211> LENGTH: 20
<212> TYPE: DNA
<213> ORGANISM: Mus sp.

<400> SEQUENCE: 182
tgtagtgtgg tgacccttgc                                                  20

<210> SEQ ID NO 183
<211> LENGTH: 19
<212> TYPE: DNA
<213> ORGANISM: Mus sp.

<400> SEQUENCE: 183
ggcatatccg gtcaccagt                                                   19

<210> SEQ ID NO 184
<211> LENGTH: 20
<212> TYPE: DNA
<213> ORGANISM: Mus sp.

<400> SEQUENCE: 184
agcagcagcg agtagtctga                                                  20

<210> SEQ ID NO 185
<211> LENGTH: 20
<212> TYPE: DNA
<213> ORGANISM: Mus sp.

<400> SEQUENCE: 185
ggcttccgat agagctgtga                                                  20

<210> SEQ ID NO 186
<211> LENGTH: 20
<212> TYPE: DNA
<213> ORGANISM: Mus sp.

<400> SEQUENCE: 186
ccccagcatc ttcaccttta                                                  20

<210> SEQ ID NO 187

```
<211> LENGTH: 21
<212> TYPE: DNA
<213> ORGANISM: Mus sp.

<400> SEQUENCE: 187
tgttgttcca gcactctgtc a                                              21

<210> SEQ ID NO 188
<211> LENGTH: 19
<212> TYPE: DNA
<213> ORGANISM: Mus sp.

<400> SEQUENCE: 188
tccaggcaga acacgacat                                                 19

<210> SEQ ID NO 189
<211> LENGTH: 20
<212> TYPE: DNA
<213> ORGANISM: Mus sp.

<400> SEQUENCE: 189
tccagtaaag gggatgatcg                                                20

<210> SEQ ID NO 190
<211> LENGTH: 20
<212> TYPE: DNA
<213> ORGANISM: Mus sp.

<400> SEQUENCE: 190
agtgcagctc cacctctctg                                                20

<210> SEQ ID NO 191
<211> LENGTH: 18
<212> TYPE: DNA
<213> ORGANISM: Mus sp.

<400> SEQUENCE: 191
agcaggagca gcagcttt                                                  18

<210> SEQ ID NO 192
<211> LENGTH: 19
<212> TYPE: DNA
<213> ORGANISM: Mus sp.

<400> SEQUENCE: 192
gggaggtgag ctcctcagt                                                 19

<210> SEQ ID NO 193
<211> LENGTH: 18
<212> TYPE: DNA
<213> ORGANISM: Mus sp.

<400> SEQUENCE: 193
tgcggttgtg agcctctt                                                  18

<210> SEQ ID NO 194
<211> LENGTH: 23
<212> TYPE: DNA
<213> ORGANISM: Mus sp.

<400> SEQUENCE: 194
aagtatttct ggcagtcctc ctc                                            23
```

```
<210> SEQ ID NO 195
<211> LENGTH: 21
<212> TYPE: DNA
<213> ORGANISM: Mus sp.

<400> SEQUENCE: 195
cctccaaagg atgtcaatca a                                           21

<210> SEQ ID NO 196
<211> LENGTH: 21
<212> TYPE: DNA
<213> ORGANISM: Mus sp.

<400> SEQUENCE: 196
ctgtcactat cccggagttc a                                           21

<210> SEQ ID NO 197
<211> LENGTH: 19
<212> TYPE: DNA
<213> ORGANISM: Mus sp.

<400> SEQUENCE: 197
atgattgcca agtgcagga                                              19

<210> SEQ ID NO 198
<211> LENGTH: 21
<212> TYPE: DNA
<213> ORGANISM: Mus sp.

<400> SEQUENCE: 198
ggcaacagca atatggagaa a                                           21

<210> SEQ ID NO 199
<211> LENGTH: 20
<212> TYPE: DNA
<213> ORGANISM: Mus sp.

<400> SEQUENCE: 199
cagacacacc tgagctggaa                                             20

<210> SEQ ID NO 200
<211> LENGTH: 20
<212> TYPE: DNA
<213> ORGANISM: Mus sp.

<400> SEQUENCE: 200
accgtttggg agagatccat                                             20

<210> SEQ ID NO 201
<211> LENGTH: 20
<212> TYPE: DNA
<213> ORGANISM: Mus sp.

<400> SEQUENCE: 201
cacagcctcg gcatatttct                                             20

<210> SEQ ID NO 202
<211> LENGTH: 21
<212> TYPE: DNA
<213> ORGANISM: Mus sp.

<400> SEQUENCE: 202
tcagtgattc tcggtgtcct c                                           21
```

<210> SEQ ID NO 203
<211> LENGTH: 20
<212> TYPE: DNA
<213> ORGANISM: Mus sp.

<400> SEQUENCE: 203
agtgccttcc tcctcttgtg                                                     20

<210> SEQ ID NO 204
<211> LENGTH: 21
<212> TYPE: DNA
<213> ORGANISM: Mus sp.

<400> SEQUENCE: 204
tcgtaacact ttgcaaatcc a                                                   21

<210> SEQ ID NO 205
<211> LENGTH: 20
<212> TYPE: DNA
<213> ORGANISM: Mus sp.

<400> SEQUENCE: 205
ttcctcctgt atggcttgct                                                     20

<210> SEQ ID NO 206
<211> LENGTH: 20
<212> TYPE: DNA
<213> ORGANISM: Mus sp.

<400> SEQUENCE: 206
tgagccagtc tgctgatttc                                                     20

<210> SEQ ID NO 207
<211> LENGTH: 20
<212> TYPE: DNA
<213> ORGANISM: Mus sp.

<400> SEQUENCE: 207
gcaaacagct cgaaggagac                                                     20

<210> SEQ ID NO 208
<211> LENGTH: 21
<212> TYPE: DNA
<213> ORGANISM: Mus sp.

<400> SEQUENCE: 208
ggattggaac agcaaggatt t                                                   21

<210> SEQ ID NO 209
<211> LENGTH: 22
<212> TYPE: DNA
<213> ORGANISM: Mus sp.

<400> SEQUENCE: 209
gggaagaaaa ttgctgtttc ac                                                  22

<210> SEQ ID NO 210
<211> LENGTH: 22
<212> TYPE: DNA
<213> ORGANISM: Mus sp.

<400> SEQUENCE: 210
caccgaatac ccaaattttg aa                                                  22

<210> SEQ ID NO 211
<211> LENGTH: 19
<212> TYPE: DNA
<213> ORGANISM: Mus sp.

<400> SEQUENCE: 211
gccccaggta agcaaactt                                                19

<210> SEQ ID NO 212
<211> LENGTH: 20
<212> TYPE: DNA
<213> ORGANISM: Mus sp.

<400> SEQUENCE: 212
cctcaattag gaggcactgg                                               20

<210> SEQ ID NO 213
<211> LENGTH: 22
<212> TYPE: DNA
<213> ORGANISM: Mus sp.

<400> SEQUENCE: 213
cctcaacatc agtgctcttc at                                            22

<210> SEQ ID NO 214
<211> LENGTH: 20
<212> TYPE: DNA
<213> ORGANISM: Mus sp.

<400> SEQUENCE: 214
caggcgaatc ttttcttgc                                                20

<210> SEQ ID NO 215
<211> LENGTH: 20
<212> TYPE: DNA
<213> ORGANISM: Mus sp.

<400> SEQUENCE: 215
aggatgtagc gtccaaatgc                                               20

<210> SEQ ID NO 216
<211> LENGTH: 21
<212> TYPE: DNA
<213> ORGANISM: Mus sp.

<400> SEQUENCE: 216
catcggtgat gttcattttc c                                             21

<210> SEQ ID NO 217
<211> LENGTH: 20
<212> TYPE: DNA
<213> ORGANISM: Mus sp.

<400> SEQUENCE: 217
ttgcattttc cagctgaatg                                               20

<210> SEQ ID NO 218
<211> LENGTH: 20
<212> TYPE: DNA
<213> ORGANISM: Mus sp.

<400> SEQUENCE: 218
aacttgctgt gggtgaccat                                                20

<210> SEQ ID NO 219
<211> LENGTH: 21
<212> TYPE: DNA
<213> ORGANISM: Mus sp.

<400> SEQUENCE: 219
tctgtacggg atcttcttgg a                                              21

<210> SEQ ID NO 220
<211> LENGTH: 18
<212> TYPE: DNA
<213> ORGANISM: Mus sp.

<400> SEQUENCE: 220
gtagctgccg aaggtgga                                                  18

<210> SEQ ID NO 221
<211> LENGTH: 22
<212> TYPE: DNA
<213> ORGANISM: Mus sp.

<400> SEQUENCE: 221
ttggttaaga aaaggcttcc aa                                             22

<210> SEQ ID NO 222
<211> LENGTH: 19
<212> TYPE: DNA
<213> ORGANISM: Mus sp.

<400> SEQUENCE: 222
tatgggtgag gacggtcag                                                 19

<210> SEQ ID NO 223
<211> LENGTH: 20
<212> TYPE: DNA
<213> ORGANISM: Mus sp.

<400> SEQUENCE: 223
tccagatatt gcaccagacg                                                20

<210> SEQ ID NO 224
<211> LENGTH: 21
<212> TYPE: DNA
<213> ORGANISM: Mus sp.

<400> SEQUENCE: 224
cctggggtaa ttaaggctgt g                                              21

<210> SEQ ID NO 225
<211> LENGTH: 20
<212> TYPE: DNA
<213> ORGANISM: Mus sp.

<400> SEQUENCE: 225
ggtctgggcc atagaactga                                                20

<210> SEQ ID NO 226
<211> LENGTH: 22
<212> TYPE: DNA
<213> ORGANISM: Mus sp.

<400> SEQUENCE: 226

```
gaacttctta aacagcggct tc                                        22

<210> SEQ ID NO 227
<211> LENGTH: 18
<212> TYPE: DNA
<213> ORGANISM: Mus sp.

<400> SEQUENCE: 227
ggcttccgtg ggaagaat                                             18

<210> SEQ ID NO 228
<211> LENGTH: 20
<212> TYPE: DNA
<213> ORGANISM: Mus sp.

<400> SEQUENCE: 228
agttgcccat cctcacatct                                           20

<210> SEQ ID NO 229
<211> LENGTH: 18
<212> TYPE: DNA
<213> ORGANISM: Mus sp.

<400> SEQUENCE: 229
ggtctgtgag cccatgct                                             18

<210> SEQ ID NO 230
<211> LENGTH: 21
<212> TYPE: DNA
<213> ORGANISM: Mus sp.

<400> SEQUENCE: 230
cagcctttgc agaactacct g                                         21

<210> SEQ ID NO 231
<211> LENGTH: 21
<212> TYPE: DNA
<213> ORGANISM: Mus sp.

<400> SEQUENCE: 231
tgggtatccg atgtccacaa t                                         21

<210> SEQ ID NO 232
<211> LENGTH: 21
<212> TYPE: DNA
<213> ORGANISM: Mus sp.

<400> SEQUENCE: 232
tgagcatctt gttacccttg c                                         21

<210> SEQ ID NO 233
<211> LENGTH: 22
<212> TYPE: DNA
<213> ORGANISM: Mus sp.

<400> SEQUENCE: 233
gccaagttca tcatacacgt tc                                        22

<210> SEQ ID NO 234
<211> LENGTH: 19
<212> TYPE: DNA
<213> ORGANISM: Mus sp.
```

<400> SEQUENCE: 234
gtactggggg ttggtccag                                        19

<210> SEQ ID NO 235
<211> LENGTH: 18
<212> TYPE: DNA
<213> ORGANISM: Mus sp.

<400> SEQUENCE: 235
tctgagcgtt cacgttgg                                         18

<210> SEQ ID NO 236
<211> LENGTH: 18
<212> TYPE: DNA
<213> ORGANISM: Mus sp.

<400> SEQUENCE: 236
tcagctgctc ctgccttt                                         18

<210> SEQ ID NO 237
<211> LENGTH: 24
<212> TYPE: DNA
<213> ORGANISM: Mus sp.

<400> SEQUENCE: 237
aggaatatca aagttgcggt attt                                  24

<210> SEQ ID NO 238
<211> LENGTH: 18
<212> TYPE: DNA
<213> ORGANISM: Mus sp.

<400> SEQUENCE: 238
cctcctggcg agtcactg                                         18

<210> SEQ ID NO 239
<211> LENGTH: 24
<212> TYPE: DNA
<213> ORGANISM: Mus sp.

<400> SEQUENCE: 239
ccacctttat tttaggtttc ttgg                                  24

<210> SEQ ID NO 240
<211> LENGTH: 20
<212> TYPE: DNA
<213> ORGANISM: Mus sp.

<400> SEQUENCE: 240
gatctgcgca aaagtcctgt                                       20

<210> SEQ ID NO 241
<211> LENGTH: 23
<212> TYPE: DNA
<213> ORGANISM: Mus sp.

<400> SEQUENCE: 241
cataggctgt ccagttttct tgt                                   23

<210> SEQ ID NO 242
<211> LENGTH: 19
<212> TYPE: DNA
<213> ORGANISM: Mus sp.

```
<400> SEQUENCE: 242
agatggtgat gggcttccc                                                19

<210> SEQ ID NO 243
<211> LENGTH: 20
<212> TYPE: DNA
<213> ORGANISM: Mus sp.

<400> SEQUENCE: 243
ctgtccaacg catccttttt                                               20

<210> SEQ ID NO 244
<211> LENGTH: 19
<212> TYPE: DNA
<213> ORGANISM: Mus sp.

<400> SEQUENCE: 244
accttctcca gggggaatc                                                19

<210> SEQ ID NO 245
<211> LENGTH: 24
<212> TYPE: DNA
<213> ORGANISM: Mus sp.

<400> SEQUENCE: 245
gtcttttgat gtgaagaggt tcaa                                          24

<210> SEQ ID NO 246
<211> LENGTH: 22
<212> TYPE: DNA
<213> ORGANISM: Mus sp.

<400> SEQUENCE: 246
cgccattatg attcagagac tg                                            22

<210> SEQ ID NO 247
<211> LENGTH: 20
<212> TYPE: DNA
<213> ORGANISM: Mus sp.

<400> SEQUENCE: 247
cttcagggca ttgaagtcgt                                               20

<210> SEQ ID NO 248
<211> LENGTH: 18
<212> TYPE: DNA
<213> ORGANISM: Mus sp.

<400> SEQUENCE: 248
ctgaccctct ccccttgc                                                 18

<210> SEQ ID NO 249
<211> LENGTH: 19
<212> TYPE: DNA
<213> ORGANISM: Mus sp.

<400> SEQUENCE: 249
agttggcagc tgtgcgtaa                                                19

<210> SEQ ID NO 250
<211> LENGTH: 19
<212> TYPE: DNA
```

<213> ORGANISM: Mus sp.

<400> SEQUENCE: 250
cttctgctgg gctcttcgt                    19

<210> SEQ ID NO 251
<211> LENGTH: 21
<212> TYPE: DNA
<213> ORGANISM: Mus sp.

<400> SEQUENCE: 251
ccatggattc tttggagttt g                 21

<210> SEQ ID NO 252
<211> LENGTH: 23
<212> TYPE: DNA
<213> ORGANISM: Mus sp.

<400> SEQUENCE: 252
gaactgtatc aaaagcagca caa               23

<210> SEQ ID NO 253
<211> LENGTH: 18
<212> TYPE: DNA
<213> ORGANISM: Mus sp.

<400> SEQUENCE: 253
cacctggcaa acctccat                     18

<210> SEQ ID NO 254
<211> LENGTH: 22
<212> TYPE: DNA
<213> ORGANISM: Mus sp.

<400> SEQUENCE: 254
ctggaaaggc tcccatagat ac                22

<210> SEQ ID NO 255
<211> LENGTH: 21
<212> TYPE: DNA
<213> ORGANISM: Mus sp.

<400> SEQUENCE: 255
gtcaatcttg aagcagcgaa t                 21

<210> SEQ ID NO 256
<211> LENGTH: 18
<212> TYPE: DNA
<213> ORGANISM: Mus sp.

<400> SEQUENCE: 256
atgcactggt ggggtttc                     18

<210> SEQ ID NO 257
<211> LENGTH: 19
<212> TYPE: DNA
<213> ORGANISM: Mus sp.

<400> SEQUENCE: 257
gttgggagtg ccacagatg                    19

<210> SEQ ID NO 258
<211> LENGTH: 20

```
<212> TYPE: DNA
<213> ORGANISM: Mus sp.

<400> SEQUENCE: 258
tccttcagac gcacactctc                                              20

<210> SEQ ID NO 259
<211> LENGTH: 20
<212> TYPE: DNA
<213> ORGANISM: Mus sp.

<400> SEQUENCE: 259
tgcggcaagc aacatataaa                                              20

<210> SEQ ID NO 260
<211> LENGTH: 19
<212> TYPE: DNA
<213> ORGANISM: Mus sp.

<400> SEQUENCE: 260
gctccaggtc tcgcttctt                                               19

<210> SEQ ID NO 261
<211> LENGTH: 22
<212> TYPE: DNA
<213> ORGANISM: Mus sp.

<400> SEQUENCE: 261
tgtattcgtc gatgatttcc aa                                           22

<210> SEQ ID NO 262
<211> LENGTH: 19
<212> TYPE: DNA
<213> ORGANISM: Mus sp.

<400> SEQUENCE: 262
atgacggtga ccagagtgc                                               19

<210> SEQ ID NO 263
<211> LENGTH: 20
<212> TYPE: DNA
<213> ORGANISM: Mus sp.

<400> SEQUENCE: 263
ctcccgcaaa caacagagtt                                              20

<210> SEQ ID NO 264
<211> LENGTH: 22
<212> TYPE: DNA
<213> ORGANISM: Mus sp.

<400> SEQUENCE: 264
gctcatcaat ttctctgaag ca                                           22

<210> SEQ ID NO 265
<211> LENGTH: 21
<212> TYPE: DNA
<213> ORGANISM: Mus sp.

<400> SEQUENCE: 265
cctttaagtc ctgccagctt c                                            21

<210> SEQ ID NO 266
```

-continued

```
<211> LENGTH: 19
<212> TYPE: DNA
<213> ORGANISM: Mus sp.

<400> SEQUENCE: 266
ctccttcttg gggatctgc                                              19

<210> SEQ ID NO 267
<211> LENGTH: 19
<212> TYPE: DNA
<213> ORGANISM: Mus sp.

<400> SEQUENCE: 267
cagatggctc tgcaggaag                                              19

<210> SEQ ID NO 268
<211> LENGTH: 24
<212> TYPE: DNA
<213> ORGANISM: Mus sp.

<400> SEQUENCE: 268
tgccatagtt tcattgttag aagc                                        24

<210> SEQ ID NO 269
<211> LENGTH: 20
<212> TYPE: DNA
<213> ORGANISM: Mus sp.

<400> SEQUENCE: 269
tgtcttcttc ttgccgatcc                                             20

<210> SEQ ID NO 270
<211> LENGTH: 20
<212> TYPE: DNA
<213> ORGANISM: Mus sp.

<400> SEQUENCE: 270
gttggatttg gtggctcatc                                             20

<210> SEQ ID NO 271
<211> LENGTH: 19
<212> TYPE: DNA
<213> ORGANISM: Mus sp.

<400> SEQUENCE: 271
cgaaggatgt gctggtctg                                              19

<210> SEQ ID NO 272
<211> LENGTH: 20
<212> TYPE: DNA
<213> ORGANISM: Mus sp.

<400> SEQUENCE: 272
ttctttgttt ccatggctca                                             20

<210> SEQ ID NO 273
<211> LENGTH: 57
<212> TYPE: DNA
<213> ORGANISM: Artificial Sequence
<220> FEATURE:
<223> OTHER INFORMATION: SMART primer
<220> FEATURE:
<221> NAME/KEY: misc_feature
<222> LOCATION: (56)..(56)
<223> OTHER INFORMATION: n is a, c or g
```

```
<220> FEATURE:
<221> NAME/KEY: misc_feature
<222> LOCATION: (57)..(57)
<223> OTHER INFORMATION: n is a, c, g, or t

<400> SEQUENCE: 273
aagcagtggt atcaacgcag agtactttt tttttttttt tttttttttt tttttnn         57

<210> SEQ ID NO 274
<211> LENGTH: 30
<212> TYPE: DNA
<213> ORGANISM: Artificial Sequence
<220> FEATURE:
<223> OTHER INFORMATION: SMARTer II A Oligo
<220> FEATURE:
<221> NAME/KEY: misc_feature
<222> LOCATION: (26)..(30)
<223> OTHER INFORMATION: n is a, c, g, or t

<400> SEQUENCE: 274
aagcagtggt atcaacgcag agtacnnnnn                                      30

<210> SEQ ID NO 275
<211> LENGTH: 23
<212> TYPE: DNA
<213> ORGANISM: Artificial Sequence
<220> FEATURE:
<223> OTHER INFORMATION: IS PCR primer

<400> SEQUENCE: 275
aagcagtggt atcaacgcag agt                                             23

<210> SEQ ID NO 276
<211> LENGTH: 30
<212> TYPE: DNA
<213> ORGANISM: Artificial Sequence
<220> FEATURE:
<223> OTHER INFORMATION: Barcoded SMARTer II A Oligo
<220> FEATURE:
<221> NAME/KEY: misc_feature
<222> LOCATION: (24)..(27)
<223> OTHER INFORMATION: n is a, c, g, t or u
<220> FEATURE:
<221> NAME/KEY: misc_feature
<222> LOCATION: (28)..(30)
<223> OTHER INFORMATION: g may be a ribonucleotide

<400> SEQUENCE: 276
aagcagtggt atcaacgcag agtnnnnggg                                      30

<210> SEQ ID NO 277
<211> LENGTH: 45
<212> TYPE: DNA
<213> ORGANISM: Artificial Sequence
<220> FEATURE:
<223> OTHER INFORMATION: universal indexing forward primer

<400> SEQUENCE: 277
aatgatacgg cgaccaccga gatctacact ctttccctac acgac                     45

<210> SEQ ID NO 278
<211> LENGTH: 24
<212> TYPE: DNA
<213> ORGANISM: Artificial Sequence
<220> FEATURE:
<223> OTHER INFORMATION: universal indexing reverse primer

<400> SEQUENCE: 278
```
caagcagaag acggcatacg agat                                      24

<210> SEQ ID NO 279
<211> LENGTH: 17
<212> TYPE: DNA
<213> ORGANISM: Mus sp.

<400> SEQUENCE: 279
gagcatgggt ggcatgg                                              17

<210> SEQ ID NO 280
<211> LENGTH: 20
<212> TYPE: DNA
<213> ORGANISM: Mus sp.

<400> SEQUENCE: 280
cagaatgggc tgcagtagaa                                           20

<210> SEQ ID NO 281
<211> LENGTH: 21
<212> TYPE: DNA
<213> ORGANISM: Mus sp.

<400> SEQUENCE: 281
gacatcactg cagccataca a                                         21

<210> SEQ ID NO 282
<211> LENGTH: 17
<212> TYPE: DNA
<213> ORGANISM: Mus sp.

<400> SEQUENCE: 282
ccatgccacc catgctc                                              17

<210> SEQ ID NO 283
<211> LENGTH: 21
<212> TYPE: DNA
<213> ORGANISM: Mus sp.

<400> SEQUENCE: 283
agttgctatc ttcgggttca g                                         21

<210> SEQ ID NO 284
<211> LENGTH: 20
<212> TYPE: DNA
<213> ORGANISM: Mus sp.

<400> SEQUENCE: 284
accacatcct tggtgacatt                                           20

<210> SEQ ID NO 285
<211> LENGTH: 20
<212> TYPE: DNA
<213> ORGANISM: Mus sp.

<400> SEQUENCE: 285
caaacactcc actggtcctt                                           20

<210> SEQ ID NO 286
<211> LENGTH: 20
<212> TYPE: DNA
<213> ORGANISM: Mus sp.

<400> SEQUENCE: 286

```
aggtttcacc acatccttgg                                              20

<210> SEQ ID NO 287
<211> LENGTH: 20
<212> TYPE: DNA
<213> ORGANISM: Mus sp.

<400> SEQUENCE: 287
ggcaaattca acggcacagt                                              20

<210> SEQ ID NO 288
<211> LENGTH: 19
<212> TYPE: DNA
<213> ORGANISM: Mus sp.

<400> SEQUENCE: 288
agatggtgat gggcttccc                                               19

<210> SEQ ID NO 289
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 289
aagcagtggt atcaacgcag agtgcggggg gaaaaggggc tgtttcaggg tttgggttag   60
tgagcctcat cctggcagtt attttatagt aaagaacatt caagtgctct gcctacctag  120
ggccc                                                             125

<210> SEQ ID NO 290
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 290
aagcagtggt atcaacgcag agtagagggg gagggctgtt tcagggtttg ggttagtgag   60
cctcatcctg gcagttattt tatagtaaag aacattcaag tgctctgcct acctagggcc  120
ctgtg                                                             125

<210> SEQ ID NO 291
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 291
aagcagtggt atcaacgcag agtacgaggg gggctgtttc agggtttggg ttagtgagcc   60
tcatcctggc ggttatttta gtaaagaa cattcaagtg ctctgcctac ctagggccct   120
gtgaa                                                             125

<210> SEQ ID NO 292
<211> LENGTH: 125
<212> TYPE: DNA
<213> ORGANISM: Artificial Sequence
```

```
<220> FEATURE:
<223> OTHER INFORMATION: Exemplary SMARTer amplified PCR partial
      transcript

<400> SEQUENCE: 292
aagcagtggt atcaacgcag agtcggggggg gaaaaggggc tgtttcaggg tttgggttag    60
tgagcctcat cctggcagtt attttatagt aaagaacatt caagtgctct gcctacctag   120
ggccc                                                                125

<210> SEQ ID NO 293
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 293
aagcagtggt atcaacgcag agtagcgggg agggctgttt cagggtttgg gttagtgagc    60
ctcatcctgg cagttatttt atagtaaaga acattcaagt gctctgccta cctagggccc   120
tgtga                                                                125

<210> SEQ ID NO 294
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 294
aagcagtggt atcaacgcag agtccggggg gcaaagggct gtttcagggt ttgggttagt    60
gagcctcatc ctggcagtta ttttatagta aagaacattc aagtgctctg cctacctagg   120
gccct                                                                125

<210> SEQ ID NO 295
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 295
aagcagtggt atcaacgcag agtcgagggg ggctgtttca gggtttgggt tagtgagcct    60
catcctggca gttattttat agtaaagaac attcaagtgc tctgcctacc tagggccctg   120
tgaag                                                                125

<210> SEQ ID NO 296
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 296
aagcagtggt atcaacgcag agtcccgggg gaaaaggggc tgtttcaggg tttgggttag    60
tgagcctcat cctggcagtt attttatagt aaagaacatt caagtgctct gcctacctag   120
ggccc                                                                125
```

<210> SEQ ID NO 297
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 297
aagcagtggt atcaacgcag agtagcgggg agggctgctt cagggtttgg gttagtgagc    60
ctcatcctgg cagttatttt atagtaaaga acattcaagt gctctgccta cctagggccc   120
tgtga                                                                125

<210> SEQ ID NO 298
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 298
aagcagtggt atcaacgcag agtagagggg gagggctgtt tcagggcttg ggttagtgag    60
cctcatcctg gcagttattt tatagtaaag aacattcaag tgctctgcct acctagggcc   120
ctgtg                                                                125

<210> SEQ ID NO 299
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 299
aagcagtggt atcaacgcag agtagcgggg agggctgttt cagggtttgg gttagtgagc    60
ctcatcctgg cagttatttt atagtaaaga acattcaagt gctctgccta cctagggccc   120
tgtga                                                                125

<210> SEQ ID NO 300
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 300
aagcagtggt atcaacgcag agtcccgggg gaaaaggggc tgtttcaggg tttggggttag   60 tgagcctcat cctggcagtt attttatagt aaagaacatt caagtgctct gcctacctag   120
ggccc                                                                125

<210> SEQ ID NO 301
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 301
aagcagtggt atcaacgcag agtgtatggg caacgcagag taatcgggga gggctgtttc    60
agggtttggg ttagtgagcc tcatcctggc agttatttta tagtaaagaa cattcaagtg    120
ctctg                                                                125

<210> SEQ ID NO 302
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 302
aagcagtggt atcaacgcag agtaagggggg gagggctgtt tcagggtttg ggttagtgag    60
cctcatcctg gcagttattt tatagtaaag aacattcaag tgctctgcct acctagggcc    120
ctgtg                                                                125

<210> SEQ ID NO 303
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 303
aagcagtggt atcaacgcag agtaagggggg gagggctgtt tcagggtttg ggttagtgag    60
cctcatcctg gcagttattt tatagtaaag aacattcaag tgctctgcct acctagggcc    120
ctgtg                                                                125

<210> SEQ ID NO 304
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 304
aagcagtggt atcaacgcag agtgtctggg gggagggctg tttcagggtt tgggttagtg    60
agcctcatcc tggcagttat tttatagtaa agaacattca agtgctctgc ctacctaggg    120
ccctg                                                                125

<210> SEQ ID NO 305
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 305
aagcagtggt atcaacgcag agtgtatggg caacgcagag taatcgggga gggctgtttc    60
agggtttggg ttagtgagcc tcatcctggc agttatttta tagtaaagaa cattcaagtg    120
ctctc                                                                125

<210> SEQ ID NO 306
<211> LENGTH: 125
<212> TYPE: DNA

```
<213> ORGANISM: Artificial Sequence
<220> FEATURE:
<223> OTHER INFORMATION: Exemplary SMARTer amplified PCR partial
      transcript

<400> SEQUENCE: 306
aagcagtggt atcaacgcag agtagcgggg gagggctgtt tcagggtttg ggttagtgag      60
cctcatcctg gcagttattt tatagtaaag aacattcaag tgctctgcct acctagggcc     120
ctgtg                                                                 125

<210> SEQ ID NO 307
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 307
aagcagtggt atcaacgcag agtcccgggg gaaaaggggc tgtttcaggg tttggttag      60 tgagcctcat cctggcagtt attttatagt aaagaacatt caagtgctct gcctacctag    120
ggccc                                                                125

<210> SEQ ID NO 308
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 308
aagcagtggt atcaacgcag agtaaggggg gagggctgtt tcagggtttg ggttagtgag      60
cctcatcctg gcagttattt tatagtaaag aacattcaag tgctctgcct acctagggcc     120
ctgtg                                                                 125

<210> SEQ ID NO 309
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 309
aagcagtggt atcaacgcag agtagcgggg agggctgttt ttgggtttgg gttagtgagc      60
ctcatcctgg cagttatttt atagtaaaga acattcaagt gctctgccta cctagggccc    120
tgtga                                                                125

<210> SEQ ID NO 310
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 310
aagcagtggt atcaacgcag agtggtcggg gagggctgtt tcagggtttg ggttagtgag      60
cctcatcctg gcagttattt tatagtaaag aacattcaag tgctctgcct acctagggcc     120
``` ctgtg    125

<210> SEQ ID NO 311
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 311
aagcagtggt atcaacgcag agtcccgggg gaaaaggggc tgtttcaggg tttgggttag    60
tgagcctcat cctggcagtt attttatagt aaagaacatt caagtgctct gcctacctag    120
ggccc    125

<210> SEQ ID NO 312
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 312
aagcagtggt atcaacgcag agtaggggg gagggctgtt tcagggtttg ggttagtgag    60
cctcatcctg gcagttattt tatagtaaag aacattcaag tgctctgcct acctagggcc    120
ctgtg    125

<210> SEQ ID NO 313
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 313
aagcagtggt atcaacgcag agtgtatggg caacgcagag taatcgggga gggctgtttc    60
agggtttggg ttagtgagcc tcatcctggc agttatttta gtaaagaa cattcaagtg    120 ctctg    125

<210> SEQ ID NO 314
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 314
aagcagtggt atcaacgcag agtagcgggg agggctgttt cagggtttgg gttagtgagc    60
ctcatcctgg cagttatttt atagtaaaga acattcaagt gctctgccta cctagggccc    120
tgtga    125

<210> SEQ ID NO 315
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

```
<400> SEQUENCE: 315
aagcagtggt atcaacgcag agttccgggg ggcaaagggc tgtttcaggg tttgggttag    60
tgagcctcat cctggcagtt attttatagt aaagaacatt caagtactct gcctacctag   120
ggccc                                                               125

<210> SEQ ID NO 316
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 316
aagcagtggt atcaacgcag agtaaggggg gagggctgtt tcagggtttg ggttagtgag    60
cctcatcctg gcagttattt tatagtaaag aacattcaag tgctctgcct acctagggcc   120
ctgtg                                                               125

<210> SEQ ID NO 317
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 317
aagcagtggt atcaacgcag agtcagaggg gagggctgtt tcagggtttg ggttagtgag    60
cctcatcctg gcagttattt tatagtaaag aacattcaag tgctctgcct acctagggcc   120
ctgtg                                                               125

<210> SEQ ID NO 318
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 318
aagcagtggt atcaacgcag agtagagggg gagggctgtt tcagggtttg ggttagtgag    60
ccccatcctg gcagttattt tatagtaaag aacattcaag tgctctgcct acctagggcc   120
ctgtg                                                               125

<210> SEQ ID NO 319
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 319
aagcagtggt atcaacgcag agtaagcggg ggagggctgt ttcagggttt gggttagtga    60
gcctcatcct ggcagttatt ttatagtaaa gaacattcaa gtgctctgcc tacctagggc   120
cctgt                                                               125

<210> SEQ ID NO 320
<211> LENGTH: 125
```

```
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 320
aagcagtggt atcaacgcag agtgggggg ctgtttcagg gtttgggtta gtgagcctca      60
tcctggcagt tattttatag taaagaacat tcaagtgctc tgcctaccta gggccctgtg    120
aagca                                                                125

<210> SEQ ID NO 321
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 321
aagcagtggt atcaacgcag agtcgagggg ggctgtttca gggtttgggt tagtgagcct     60
catcctggca gttattttat agtaaagaac attcaagtgc tctgcctacc tagggccctg   120
tgaag                                                                125

<210> SEQ ID NO 322
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 322
aagcagtggt atcaacgcag agtcccgggg gaaaaggggc tgtttcaggg tttggggttag    60 tgagcctcat cctggcagtt attttatagt aaagaacatt caagtgctct gcctacctag   120
ggccc                                                                125

<210> SEQ ID NO 323
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 323
aagcagtggt atcaacgcag agttccgggg ggcaaagggc tgtttcaggg tttgggttag     60
tgagcctcat cctggcagtt attttatagt aaagaacatt caagtgctct gcctacctag   120
ggccc                                                                125

<210> SEQ ID NO 324
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 324
aagcagtggt atcaacgcag agtaaggggg gagggctgtt tcagggcttg ggttagtgag     60
cctcatcctg gcagttattt tatagtaaag aacattcaag tgctctgcct acctagggcc   120
``` ctgtg                                                                      125

<210> SEQ ID NO 325
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 325
aagcagtggt atcaacgcag agtcccgggg gaaaaggggc tgtttcaggg tttgggttag      60
tgagcctcat cctggcagtt attttatagt aaagaacatt caagtgctct gcctacctag     120
ggccc                                                                     125

<210> SEQ ID NO 326
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 326
aagcagtggt atcaacgcag agttccgggg ggcaaagggc tgtctcaggg tttgggttag      60
tgagcctcat cctggcagtt attttatagt aaagaacatt caagtgctct gcctacctag     120
ggccc                                                                     125

<210> SEQ ID NO 327
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 327
aagcagtggt atcaacgcag agtaggggg agggctgttt cagggtttgg gttagtgagc      60
ctcatcctgg cagttatttt atagtaaaga acattcaagt gctctgccta cctagggccc     120
tgtga                                                                     125

<210> SEQ ID NO 328
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 328
aagcagtggt atcaacgcag agttccgggg ggcaaagggc tgtttcaggg tttgggttag      60
tgagcctcat cctggcagtt attttatagt aaagaacatt caagtgctct gcctacctag     120
ggccc                                                                     125

<210> SEQ ID NO 329
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 329
aagcagtggt atcaacgcag agtggtcggg gagggctgtt tcagggtttg ggttagtgag    60
cctcatcctg gcagttattt tatagtaaag aacattgaag tgctctgcct acctagggcc   120
ctgtg                                                              125

<210> SEQ ID NO 330
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 330
aagcagtggt atcaacgcag agtaaggggg gagggctgtt tcagggtttg ggttagtgag    60
cctcatcctg gcagttattt tatagtaaag aacattcaag ggctctgcct ccctagggcc   120
ctgtg                                                              125

<210> SEQ ID NO 331
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 331
aagcagtggt atcaacgcag agtagctggg gagggctgtt tcagggtttg ggttagtgag    60
cctcatcctg gcagttattt tatagtaaag aacattcaag tgctctgcct acctatgggc   120
ctgtg                                                              125

<210> SEQ ID NO 332
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 332
aagcagtggt atcaacgcag agtaaggggg gagggctgtt tcagggtttg ggttagtgag    60
cctcatcctg gcagttattt tatagtaaag aacattcaag tgctctgcct acctagggcc   120
ctgtg                                                              125

<210> SEQ ID NO 333
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 333
aagcagtggt atcaacgcag agtagagggg gagggctgtt tcagggtttg ggttagtgag    60
cctcatcctg gcagttattt tatagtaaag aacattcaag tgctctgcct acctagggcc   120
ctgtg                                                              125

<210> SEQ ID NO 334

```
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 334
aagcagtggt atcaacgcag agtagagggg gagggctgat tcagggtttg ggttagtgag        60
cctcatcctg gcagttattt tatagtaaag aacattcaag tgctctgact acctagggcc       120
ctgtg                                                                    125

<210> SEQ ID NO 335
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 335
aagcagtggt atcaacgcag agttccgggg ggcaaagggc tgtttcaggg tttgggttag        60
tgagcctcat cctggcagtt attttatagt aaagaacatt caagtgctct gcctacctag       120
ggccc                                                                    125

<210> SEQ ID NO 336
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 336
aagcagtggt atcaacgcag agtggtcggg gagggctgtt tcagggtttg ggttagtgag        60
cctcatcctg gcagttattt tatagtaaag aacattcaag tgctctgcct acctagggcc       120
ctgtg                                                                    125

<210> SEQ ID NO 337
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 337
aagcagtggt atcaacgcag agtagcgggg agggctgttt cagggtttgg gttagtgagc        60
ctcatcctgg cagttatttt atagtaaaga acattcaagt gctctgccta cctagggccc       120
tgtga                                                                    125

<210> SEQ ID NO 338
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 338
aagcagtggt atcaacgcag agttccaggg gggcaaaggg ctgtttcagg gtttgggtta       60
```

```
gtgagcctca tcctggcagt tattttatag taaagaacat tcaagtgctc tgcctaccta    120
gggcc                                                                125

<210> SEQ ID NO 339
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 339
aagcagtggt atcaacgcag agtggtcggg gagggctgtt tcagggtttg ggttagtgag    60
cctcatcctg gcagttattt tatagtaaag aacattcaag tgctctgcct acctagggcc    120
ctgtg                                                                125

<210> SEQ ID NO 340
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 340
aagcagtggt atcaacgcag agtgtatggg caacgcagag taatcgggga gggctgtttc    60
agggtttggg ttagtgagcc tcatcctggc agttattttc tagtaaagaa cattcaagtg    120
ctctg                                                                125

<210> SEQ ID NO 341
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 341
aagcagtggt atcaacgcag agtaaagggg gagggctgtt tcagggtttg ggttagtgag    60
cctcatcctg gcagttattt tatagtaaag aacattcaag tgctctgcct acctagggcc    120
ctgtg                                                                125

<210> SEQ ID NO 342
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 342
aagcagtggt atcaacgcag agtcccgggg gaaaagggc tgtttcaggg tttgggttag    60
tgagcctcat cctggcagtt attttatagt aaagaacatt caagtgctct gcctacctag    120
ggccc                                                                125

<210> SEQ ID NO 343
<211> LENGTH: 125
<212> TYPE: DNA
<213> ORGANISM: Artificial Sequence
<220> FEATURE:
<223> OTHER INFORMATION: Exemplary SMARTer amplified PCR partial
``` transcript

<400> SEQUENCE: 343
aagcagtggt atcaacgcag agtaaggggg gagggctgtt tcagggtttg ggttagtgag        60
cctcatcctg gcagttattt tatagtaaag aacattcaag tgctctgcct acctagggcc       120
ctgtg                                                                  125

<210> SEQ ID NO 344
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 344
aagcagtggt atcaacgcag agtgtatggg caacgcagag taatcgggga gggctgtttc        60
agggtttggg ttagtgagcc tcatcctggc agttatttta tagtaaagaa cattcaagtg       120
ctctg                                                                  125

<210> SEQ ID NO 345
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 345
aagcagtggt atcaacgcag agttccgggg ggcaaagggc tgtttcaggg tttgggttag        60
tgagcctcat cctggcagtt attttatagt aaagaacatt caagtactct gcctacctag       120
ggccc                                                                  125

<210> SEQ ID NO 346
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 346
aagcagtggt atcaacgcag agtagcgggg agggctgttt cagggtttgg gttagtgagc        60
ctcatcctgg cagttatttt atagtaaaga acattcaagt gctctgccta cctagggccc       120
tgtga                                                                  125

<210> SEQ ID NO 347
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 347
aagcagtggt atcaacgcag agttccgggg ggcaaagggc tgtttcaggg tttgggttag        60
tgagcctcat cctggcagtt attttatagt aaagaacatt caagtgctct gcctacctag       120
ggccc                                                                  125

-continued

```
<210> SEQ ID NO 348
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 348
aagcagtggt atcaacgcag agtagagggg gagggctgtt tcagggtttg ggttagtgag      60
cctcatcctg gcagttattt tatagtaaag aacattcaag tgctctgcct acctagggcc     120
ctgtg                                                                 125

<210> SEQ ID NO 349
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 349
aagcagtggt atcaacgcag agtagcgggg agggctgttt cagggtttgg gttagtgagc      60
ctcatcctgg cagttattt atagtaaaga acattcaagt gctctgccta cctagggccc     120
tgtga                                                                 125

<210> SEQ ID NO 350
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 350
aagcagtggt atcaacgcag agtcgtgggg aaagggctgt ttcagggttt gggttagtga      60
gcctcatcct ggcagttatt ttatagtaaa gaacattcaa gtgctctgcc tacctagggc     120
cctgt                                                                 125

<210> SEQ ID NO 351
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 351
aagcagtggt atcaacgcag agtcccgggg gaaaaggggc tgtttcaggg tttgggttag      60
tgagcctcat cctggcagtt attttatagt aaagaacatt caagtgctct gcctacctag     120
ggccc                                                                 125

<210> SEQ ID NO 352
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 352
aagcagtggt atcaacgcag agtaagggggg gagggctgtt tcagggtttg ggttagtgag      60
```
cctcatcctg gcagttattt tatagtaaag aacattcaag tgctctgcct acctagggcc    120
ctgtg    125

<210> SEQ ID NO 353
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 353
aagcagtggt atcaacgcag agtcgagggg ggctgtttca gggtttgggt tagtgagcct    60
catcctggca gttatttat agtaaagaac attcaagtgc tctgcctacc tagggccctg    120
tgaag    125

<210> SEQ ID NO 354
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 354
aagcagtggt atcaacgcag agtggtcggg gagggctgtt tcagggtttg ggttagtgag    60
cctcatcctg gcagttattt tatagtaaag aacattcaag tgctctgcct acctagggcc    120
ctgtg    125

<210> SEQ ID NO 355
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 355
aagcagtggt atcaacgcag agtcgagggg ggctgtttca gggtttgggt tagtgagcct    60
catcctggca gttatttat agtaaagaac attcaagtgc tctgcctacc tagggccctg    120
tgaag    125

<210> SEQ ID NO 356
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 356
aagcagtggt atcaacgcag agtcccgggg gaaaagggc tgtttcaggg tttgggttag    60
tgagcctcat cctggcagtt attttatagt aaagaacatt caagtgctct gcctacctag    120
ggccc    125

<210> SEQ ID NO 357
<211> LENGTH: 125
<212> TYPE: DNA
<213> ORGANISM: Artificial Sequence
<220> FEATURE:

<223> OTHER INFORMATION: Exemplary SMARTer amplified PCR partial
      transcript

<400> SEQUENCE: 357
aagcagtggt atcaacgcag agttccgggg ggcaaagggc tgtttcaggg tttgggttag    60
tgagcctcat cctggcagtt attttatagt aaagaacatt caagtgctct gcctacctag   120
ggccc                                                               125

<210> SEQ ID NO 358
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 358
aagcagtggt atcaacgcag agtggtcggg gagggctgtt tcagggtttg ggttagtgag    60
cctcatcctg gcagttattt tatagtaaag aacattcaag tgctctgcct acctagggcc   120
ctgtg                                                               125

<210> SEQ ID NO 359
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 359
aagcagtggt atcaacgcag agtagagggg gagggctgtt tcagggtttg ggttagcgag    60
cctcatcctg gcagttattt tatagtaaag aacattcaag tgctctgcct acctagggcc   120
ctgtg                                                               125

<210> SEQ ID NO 360
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 360
aagcagtggt atcaacgcag agtcgagggg ggctgtttca gggtttgggt tagtgagcct    60
catcctggca gttattttat agtaaagaac attcaagtgc tctgcctacc tagggccctg   120
tgaag                                                               125

<210> SEQ ID NO 361
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 361
aagcagtggt atcaacgcag agttccgggg ggcaaagggc tgtttcaggg tttgggttag    60
tgagcctcat cctggcagtt attttatagt aaagaacatt caagtaatct gcctacctag   120
ggccc                                                               125

<210> SEQ ID NO 362
<211> LENGTH: 125
<212> TYPE: DNA
<213> ORGANISM: Artificial Sequence
<220> FEATURE:
<223> OTHER INFORMATION: Exemplary SMARTer amplified PCR partial transcript

<400> SEQUENCE: 362
aagcagtggt atcaacgcag agtcccgggg gaaaaggggc tgtttcaggg tttgggttag    60
tgagcctcat cctggcagtt attttatagt aaagaacatt caagtgctct gcctacctag   120
ggccc                                                               125

<210> SEQ ID NO 363
<211> LENGTH: 125
<212> TYPE: DNA
<213> ORGANISM: Artificial Sequence
<220> FEATURE:
<223> OTHER INFORMATION: Exemplary SMARTer amplified PCR partial transcript

<400> SEQUENCE: 363
aagcagtggt atcaacgcag agtgtatggg caacgcagag taatcgggga gggctgtttc    60
agggtttggg ttagtgtgcc tcatcctggc agttatttta tagtaaagaa cattcaagtg   120
ctctg                                                               125

<210> SEQ ID NO 364
<211> LENGTH: 125
<212> TYPE: DNA
<213> ORGANISM: Artificial Sequence
<220> FEATURE:
<223> OTHER INFORMATION: Exemplary SMARTer amplified PCR partial transcript

<400> SEQUENCE: 364
aagcagtggt atcaacgcag agtcgacggg gggcaaaggg ctgtttgagg gtttgggtta    60
gtgagcctca tcctggcagt tattttatag taaagaacat tcaagtgctc tgcctaccta   120
gggcc                                                               125

<210> SEQ ID NO 365
<211> LENGTH: 125
<212> TYPE: DNA
<213> ORGANISM: Artificial Sequence
<220> FEATURE:
<223> OTHER INFORMATION: Exemplary SMARTer amplified PCR partial transcript

<400> SEQUENCE: 365
aagcagtggt atcaacgcag agtacggggg gaaaaggggc tgtttcaggg tttgggttag    60
tgagcctcat cctggcagtt attttatagt aaagaacatt caagtgctct gcctacctag   120
ggccc                                                               125

<210> SEQ ID NO 366
<211> LENGTH: 125
<212> TYPE: DNA
<213> ORGANISM: Artificial Sequence
<220> FEATURE:
<223> OTHER INFORMATION: Exemplary SMARTer amplified PCR partial transcript

<400> SEQUENCE: 366

```
aagcagtggt atcaacgcag agttccgggg ggcaaagggc tgtttcaggg tttgggttag      60
tgagcctcat cctggcagtt attttatagt aaagaacatt caagtgctct gcctacctag     120
ggccc                                                                 125

<210> SEQ ID NO 367
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 367
aagcagtggt atcaacgcag agtagagggg gggggctgtt tcagggtttg ggttagtgag      60
cctcatcctg gcagttattt tatagtaaag aacattcaag tgctctgcct acctagggcc     120
cttg                                                                  125

<210> SEQ ID NO 368
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 368
aagcagtggt atcaacgcag agtagagggg gagggctgtt tcagggtttg ggttagtgag      60
cctcatcctg gcagttattt tatagtaaag aacattcaag tgctctgcct acctagggcc     120
ctgtg                                                                 125

<210> SEQ ID NO 369
<211> LENGTH: 125
<212> TYPE: DNA
<213> ORGANISM: Artificial Sequence
<220> FEATURE:
<223> OTHER INFORMATION: Exemplary SMARTer amplified PCR partial
      transcript

<400> SEQUENCE: 369
aagcagtggt atcaacgcag agtgtctggg gggagggctg tttcagggtt tgggttagtg      60
agcctcatcc tggcagttat tttatagtaa agaacattca agtgctctgc ctacctaggg     120
ccctg                                                                 125
```

DENDRITIC CELL RESPONSE GENE EXPRESSION, COMPOSITIONS OF MATTERS AND METHODS OF USE THEREOF

RELATED APPLICATIONS AND INCORPORATION BY REFERENCE

This application is a continuation-in-part application of international patent application Serial No. PCT/US2014/030429 filed Mar. 17, 2014, which published as PCT Publication No. WO 2014/145631 on Sep. 18, 2014, which claims benefit of and priority to U.S. Provisional Application No. 61/787,378, filed Mar. 15, 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under Grant Nos. OD003958, OD003893, HG006193, HD075541, and HG005062 awarded by the National Institutes of Health. The government has certain rights in the invention.

FIELD OF THE INVENTION

This invention relates generally to compositions and methods for identifying the regulatory network that modulates, controls or otherwise influences dendritic cell (DC) response(s), for example, dendritic cell maturation, dendritic cell antiviral response(s) and/or dendritic cell inflammatory response(s), as well compositions and methods for exploiting the regulatory network that modulates, controls or otherwise influences dendritic cell response(s) in a variety of therapeutic and/or diagnostic indications.

BACKGROUND OF THE INVENTION

Despite their importance, the molecular circuits that control dendritic cell responses, including antiviral responses, inflammatory responses, maturation, recruitment of T cells and B cells, remain largely unknown or unrefined. Recent studies that reconstructed regulatory networks in dendritic cells have focused on measurements across cell populations that can fail to detect signals across the entire population and/or can fail to distinguish between signal(s) that are expressed only in certain subsets of cells. Accordingly, there exists a need for a better understanding of the network that modulates, controls, or otherwise influences dendritic cell response and means for exploiting this network in a variety of therapeutic and diagnostic methods.

Citation or identification of any document in this application is not an admission that such document is available as prior art to the present invention.

SUMMARY OF THE INVENTION

The invention provides compositions and methods for modulating one or more dendritic cell responses. As used herein, the term "modulating" includes up-regulation of, or otherwise increasing, the expression of one or more genes; down-regulation of, or otherwise decreasing, the expression of one or more genes; inhibiting or otherwise decreasing the expression, activity and/or function of one or more gene products; neutralizing or otherwise inactivating the expression, activity and/or function of one or more gene products; and/or enhancing or otherwise increasing the expression, activity and/or function of one or more gene products.

As used herein, the term "modulating a response of dendritic cells" includes the modulation of any of a variety of dendritic cell functions and/or activities, including by way of non-limiting example, controlling or otherwise influencing the networks that regulate dendritic cell maturation; controlling or otherwise influencing the networks that regulate an immune response of a dendritic cell; controlling or otherwise influencing the networks that regulate an antiviral immune response of a dendritic cell, for example, an antiviral immune response of a dendritic cell including a core antiviral response and/or a secondary antiviral response; controlling or otherwise influencing the networks that regulate an inflammatory immune response of a dendritic cell, for example, an induced inflammatory response and/or a sharped peak inflammatory response; controlling or otherwise influencing the networks that regulate a Toll-like receptor (TLR) response of dendritic cells; controlling or otherwise influencing the networks that regulate T cell and B cell recruitment; controlling or otherwise influencing the networks that regulate DC promotion of $T_H1$-cell response(s); controlling or otherwise influencing the networks that regulate DC induction of $T_H2$-cell response(s); controlling or otherwise influencing the networks that regulate DC induction, impact or other effect on any cell that is downstream of the D; controlling or otherwise influencing the networks that regulate DC induction of T cells including regulatory T cells (Tregs), Th17 cells, memory T cells and other T cells; controlling or otherwise influencing the networks that regulate a shift in a DC phenotype, for example, between a mature and immature phenotype and/or between subsets of DCs; manipulating or otherwise influencing at least one function or biological activity of a dendritic cell; manipulating or otherwise influencing dendritic cell control of pathogen-drive T cell polarization; and/or manipulating or otherwise influence the production of cytokines, chemokines and other molecules secreted by the DC.

The invention provides modulating agents that modulate one or more dendritic cell response(s). Suitable modulating agents include an antibody, a soluble polypeptide, a polypeptide agent, a peptide agent, a nucleic acid agent, a nucleic acid ligand, or a small molecule agent.

The invention provides a series of gene signatures, including a "Core Antiviral" gene signature, a "Secondary Antiviral" gene signature, a "Maturation" gene signature, an "Induced Inflammatory" gene signature, and a "Sharp Peaked Inflammatory" gene signature. These signatures were identified by clustering gene expression values across single cells, for example, coherent groups of single cells. In some embodiments, these signatures significantly refine and improve upon previously identified signatures. In some embodiments, these signatures produce signals that are absent or cannot be reliably detected in cell population measurements.

The "Core Antiviral" gene signature is induced in the earliest of the responding dendritic cells. The "Maturation" gene signature looks similar to the "Induced Inflammatory" gene signature at a population level, but using single cell analysis, it was established that the "Maturation" gene signature is expressed in only a subset of cells. The "Maturation" gene signature is responsible for allowing dendritic cells to recruit T cells and B cells, thereby bridging the gap between the innate and adaptive immunity system.

These genes are targets for use in a number of indications, for example, for treating and/or diagnosis of an immune response, for monitoring an immune response, e.g., inflammation, in transplant and other therapeutic indications and/or for vaccine development.

In some embodiments, the one or more signature genes are selected from those listed in Tables 1, 1A, 2, 2A, 3, 3A, 4, 4A, 5 and/or 5A (i.e., Tables 1, 1A, 2, 2A, 3, 3A, 4, 4A, 5 and/or 5A).

A desired target gene or combination of target genes is selected, and after determining whether the selected target gene(s) is overexpressed or under-expressed during a dendritic cell response, a suitable antagonist or agonist is used depending on the desired maturation and/or function outcome. Suitable antagonists and/or agonists include an antibody, a soluble polypeptide, a polypeptide agent, a peptide agent, a nucleic acid agent, a nucleic acid ligand, or a small molecule agent.

The modulating agents are used to modulate the expression of one or more target genes or one or more products of one or more target genes that have been identified as genes responsive to dendritic cell-related perturbations. These target genes are identified, for example, by contacting a dendritic cell with a modulating agent and monitoring the effect, if any, on the expression of one or more signature genes or one or more products of one or more signature genes. In some embodiments, the one or more signature genes are selected from those listed in Tables 1-5A. The modulating agent can act directly on the expression of one or more target genes or one or more products of one or more target genes and/or the modulating agent can act indirectly on the expression of one or more target genes or one or more products of one or more target genes by modulating the expression, activity and/or function of a gene or a product of a gene that is known to be associated with the target gene(s).

In some embodiments, the target gene is tumor necrosis factor receptor (TNFR). In some embodiments, the modulating agent alters the expression, activity and/or function of TNFR. In some embodiments, the modulating agent alters the expression, activity and/or function of a gene that is associated with TNFR, such as, by way of non-limiting example, a gene from those shown in Table 6.

In some embodiments, the target gene is a Toll/interleukin-1 receptor (TIR) domain-containing adapter protein (TIRAP). In some embodiments, the modulating agent alters the expression, activity and/or function of TIRAP. In some embodiments, the modulating agent alters the expression, activity and/or function of a gene that is associated with TIRAP, such as, by way of non-limiting example, a gene from those shown in Table 7.

In some embodiments, the target gene is Stat1. In some embodiments, the modulating agent alters the expression, activity and/or function of Stat1. In some embodiments, the modulating agent alters the expression, activity and/or function of a gene that is associated with Stat1, such as, by way of non-limiting example, a gene from those shown in Table 8.

In some embodiments, the target gene is interferon production regulator (IFNR). In some embodiments, the modulating agent alters the expression, activity and/or function of IFNR. In some embodiments, the modulating agent alters the expression, activity and/or function of a gene that is associated with IFNR, such as, by way of non-limiting example, a gene from those shown in Table 9.

In some embodiments, the target gene is one or more genes from those listed below in Table 10, Table 11 or Table 12. In some embodiments, the modulating agent alters the expression, activity and/or function of the target gene(s).

In some embodiments, the invention provides a method of identifying genes or genetic elements associated with a dendritic cell response comprising: a) contacting a dendritic cell with an inhibitor of a dendritic cell response or an agent that enhances a dendritic cell response; and b) identifying a gene or genetic element whose expression is modulated by step (a). In some embodiments, the method also comprises c) perturbing expression of the gene or genetic element identified in step b) in a dendritic cell that has been in contact with an inhibitor of the dendritic cell response or an agent that the dendritic cell response; and d) identifying a gene whose expression is modulated by step c). In some embodiments, the antagonist and/or agonist is an antibody, a soluble polypeptide, a polypeptide antagonist, a peptide antagonist, a nucleic acid antagonist, a nucleic acid ligand, or a small molecule antagonist.

In some embodiments, the invention provides a method of modulating one or more dendritic cell response(s) comprising contacting a dendritic cell with an agent that modulates expression, activity and/or function of one or more genes or one or more products of one or more genes selected from those listed in Table 1 or Table 1A. In some embodiments, the invention provides a method of modulating one or more dendritic cell response(s) comprising contacting a dendritic cell with an agent that modulates expression, activity and/or function of one or more genes or one or more products of one or more genes selected from those listed in Table 2 or Table 2A. In some embodiments, the invention provides a method of modulating one or more dendritic cell response(s) comprising contacting a dendritic cell with an agent that modulates expression, activity and/or function of one or more genes or one or more products of one or more genes selected from those listed in Table 3 or Table 3A. In some embodiments, the invention provides a method of modulating one or more dendritic cell response(s) comprising contacting a dendritic cell with an agent that modulates expression, activity and/or function of one or more genes or one or more products of one or more genes selected from those listed in Table 4 or Table 4A. In some embodiments, the invention provides a method of modulating one or more dendritic cell response(s) comprising contacting a dendritic cell with an agent that modulates expression, activity and/or function of one or more genes or one or more products of one or more genes selected from those listed in Table 5 or Table 5A.

In some embodiments, the invention provides a method of diagnosing an immune response in a subject, comprising detecting a level of expression, activity and/or function of one or more signature genes or one or more products of one or more signature genes selected from those listed in Tables 1, 1A, 2, 2A, 3, 3A, 4, 4A, 5 and/or 5A and comparing the detected level to a control of level of signature gene or gene product expression, activity and/or function, wherein a difference between the detected level and the control level indicates that the presence of an immune response in the subject. In some embodiments, the immune response is an autoimmune response. In some embodiments, the immune response is an inflammatory response, including inflammatory response(s) associated with an autoimmune response and/or inflammatory response(s) associated with an infectious disease or other pathogen-based disorder.

In some embodiments, the invention provides a method of monitoring an immune response in a subject, comprising detecting a level of expression, activity and/or function of one or more signature genes or one or more products of one or more signature genes, e.g., one or more signature genes selected from those listed in Tables 1, 1A, 2, 2A, 3, 3A, 4, 4A, 5 and/or 5A at a first time point, detecting a level of expression, activity and/or function of one or more signature genes or one or more products of one or more signature genes, e.g., one or more signature genes selected from those listed in Tables 1, 1A, 2, 2A, 3, 3A, 4, 4A, 5 and/or 5A at a second time point, and comparing the first detected level of expression, activity and/or function with the second detected level of expression, activity and/or function, wherein a change between the first and second detected levels indicates a change in the immune response in the subject. In some embodiments, the immune response is an autoimmune response. In some embodiments, the immune response is an inflammatory response.

In some embodiments, the invention provides a method of diagnosing an aberrant dendritic cell response in a subject, comprising detecting a level of expression, activity and/or function of one or more signature genes or one or more products of one or more signature genes selected from those listed in Tables 1, 1A, 2, 2A, 3, 3A, 4, 4A, 5 and/or 5A and comparing the detected level to a control of level of signature gene or gene product expression, activity and/or function, wherein a difference between the detected level and the control level indicates that the presence of an aberrant dendritic cell response in the subject. In some embodiments, the aberrant dendritic cell response is an autoimmune response. In some embodiments, the aberrant dendritic cell response is an inflammatory response, including inflammatory response(s) associated with an autoimmune response and/or inflammatory response(s) associated with an infectious disease or other pathogen-based disorder. In some embodiments, the aberrant dendritic cell response is an altered ability of the dendritic cell to recruit T cells and B cells. In some embodiments, the aberrant dendritic cell response is the absence of a response. In some embodiments, the aberrant dendritic cell response is a reduction in a dendritic cell response. In some embodiments, the aberrant dendritic cell response is an enhancement in a dendritic cell response.

In some embodiments, the invention provides a method of monitoring an aberrant dendritic cell response in a subject, comprising detecting a level of expression, activity and/or function of one or more signature genes or one or more products of one or more signature genes, e.g., one or more signature genes selected from those listed in Tables 1, 1A, 2, 2A, 3, 3A, 4, 4A, 5 and/or 5A at a first time point, detecting a level of expression, activity and/or function of one or more signature genes or one or more products of one or more signature genes, e.g., one or more signature genes selected from those listed in Tables 1, 1A, 2, 2A, 3, 3A, 4, 4A, 5 and/or 5A at a second time point, and comparing the first detected level of expression, activity and/or function with the second detected level of expression, activity and/or function, wherein a change between the first and second detected levels indicates a change in the dendritic cell response in the subject. In some embodiments, the dendritic cell response is an autoimmune response. In some embodiments, the dendritic cell response is an inflammatory response. In some embodiments, the dendritic cell response is the ability of the dendritic cell to recruit T cells and B cells.

Suitable modulating agent(s) for use in any of the compositions and methods provided herein include an antibody, a soluble polypeptide, a polypeptide agent, a peptide agent, a nucleic acid agent, a nucleic acid ligand, or a small molecule agent.

In some embodiments, the modulating agent is used to modulate the expression of one or more genes from the "Core Antiviral" gene signature, e.g., one or more genes from those listed in Tables 1 and 1A. These modulating agents are referred to herein as "core antiviral modulating agent(s)."

For example, in some embodiments the core antiviral modulating agent is a kinase, such as, by way of non-limiting example, a kinase selected from the group consisting of: MAPK1, EIF2AK2, TBK1, PLK4, IKBKE, PLK2, MAP3K7, CHUK, JAK1, CRKL, MKNK2, TYK2, RPS6KB2, IKBKB, MKNK1, NEK7, PIK3R2, IKBKG, RIPK2, MAP2K6, MET, RPS6KB1, MARK2, DGKA, and BUB1B.

For example, in some embodiments, the core antiviral modulating agent is a transmembrane receptor, a mammalian endogenous chemical drug, a chemical drug, e.g., a chemical kinase inhibitor drug or other chemical drug such as a chemical reagent, toxicant or other chemical drug, a biologic drug or any combination thereof. Suitable core antiviral modulating agents include any of those described herein.

In some embodiments, the modulating agent is used to modulate the expression of one or more genes from the "Secondary Antiviral" gene signature, e.g., one or more genes from those listed in Tables 2 and 2A. These modulating agents are referred to herein as "second antiviral modulating agents."

For example, in some embodiments the secondary antiviral modulating agent is a kinase, a transmembrane receptor, a non-mammalian endogenous chemical drug, a chemical drug, e.g., a chemical kinase inhibitor drug or another chemical drug such as a chemical reagent, toxicant or other chemical drug, or any combination thereof. Suitable secondary antiviral modulating agents include any of those described herein.

In some embodiments, the modulating agent is used to modulate the expression of one or more genes from the "Maturation" gene signature, e.g., one or more genes from those listed in Tables 3 and 3A. These modulating agents are referred to herein as "maturation modulating agents."

For example, in some embodiments the maturation modulating agent is a kinase, a transmembrane receptor, a mammalian endogenous chemical drug, a non-mammalian endogenous chemical drug, a chemical drug, e.g., a chemical kinase inhibitor drug or another chemical drug such as a chemical reagent, chemical toxicant or other chemical drug, a biologic drug, or any combination thereof. Suitable maturation modulating agents include any of those described herein.

In some embodiments, the modulating agent is used to modulate the expression of one or more genes from the "Peaked Inflammatory" gene signature, e.g., one or more genes from those listed in Tables 4 and 4A. These modulating agents are referred to herein as "peaked inflammatory modulating agents."

For example, in some embodiments the peaked inflammatory modulating agent is a kinase, such as, by way of non-limiting example, a kinase, a transmembrane receptor, a mammalian endogenous chemical drug, a non-mammalian endogenous chemical drug, a chemical drug, e.g., a chemical kinase inhibitor or another chemical drug such as a chemical reagent, toxicant or other chemical drug, a biologic drug, or other modulating agent, or any combination thereof. Suitable peaked inflammatory modulating agents include any of those described herein.

In some embodiments, the modulating agent is used to modulate the expression of one or more genes from the "Induced Inflammatory" gene signature, e.g., one or more genes from those listed in Tables 5 and 5A. These modulating agents are referred to herein as "induced inflammatory modulating agents."

For example, in some embodiments the induced inflammatory modulating agent is a kinase, a transmembrane receptor, a mammalian endogenous chemical drug, is a non-mammalian endogenous chemical drug, a chemical drug, such as a chemical kinase inhibitor or another chemical drug, such as, by way of non-limiting example, a chemical reagent, chemical toxicant or other chemical drug, a biologic drug, or any combination thereof. Suitable peaked inflammatory modulating agents include those described herein.

One skilled in the art will appreciate that the modulating agents have a variety of uses. For example, the modulating agents are used as therapeutic agents as described herein. The modulating agents can be used as reagents in screening assays, diagnostic kits or as diagnostic tools, or these modulating agents can be used in competition assays to generate therapeutic reagents.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 1a-1c depict correlations of transcript expression levels (x & y-axes: log-scale TPM+1) between two 10,000 cell population replicates (FIG. 1a), two single cells (FIG. 1b), and the 'average' single cell and a population measurement (FIG. 1c). The Pearson correlation coefficient (r) is marked in the upper left corner. FIGS. 1d, 1e, depict example transcripts. Shown are the RNA-Seq read densities in each single cell ("1" on the y axis) and the three population replicates ("10,000" on the y-axis) for three non-variable genes (FIG. 1d) and four variable ones (FIG. 1e). FIGS. 1f-1h depict RNA-FISH of representative transcripts. Shown are micrographs (log filtered, (FIG. 1f, FIG. 1g)) and distributions of expression levels (FIG. 1h) from RNA-FISH staining for the lower variation gene I16 (top panel, n=3193 cells) and the higher variation gene Cxc11 (bottom panel, n=3193 cells). Cell boundaries are represented by light grey outlines.

FIG. 2a depicts inter-cell variation at a broad range of expression levels. Shown is the relationship between the single cell expression average ($\mu$, X axis) and single cell variability (standard deviation, $\sigma$, Y axis). Blue dashed (i.e., upper) line indicates the theoretical maximum standard deviation for an average expression level (Example 1); Grey dashed (i.e., lower) line denotes the constant Fano factor ($\sigma/\mu=0.25$). Immune response and housekeeping genes are marked in magenta and green, respectively; light blue shaded region represents single cell average TPM<250. Notably, even at high average expression levels, BMDC response elements show substantial variability (left), while hESCs (Ramskold, D. et al. Full-length mRNA-Seq from single-cell levels of RNA and individual circulating tumor cells. *Nature Biotechnology* 30, 777-782, doi:papers2://publication/doi/10.1038/nbt.2282 (2012)) (right) do not. FIG. 2b depicts inter-cell variation of the 522 most highly expressed genes. For each gene (rows, sorted by Fano factor from low (top) to high (bottom)) and each expression level bin (columns), shown is the number of cells (strong yellow: 18 cells; black: 0 cells) in which the gene is expressed at the bin defined level. The genes are chosen based on their average single cell expression level (TPM>250, white area in (FIG. 2a)). Grey dashed line denotes the constant Fano factor (0.25) highlighted in (FIG. 2a). FIG. 2c depicts average expression probability density distributions for the 281 low-variability genes (top) and the 241 highly variable genes (bottom).

40 (2013). FIG. 3a depicts examples of genes with significant splicing differences between individual cells. Shown are the RNA-Seq read densities for each of the 18 single cells (1, blue) and 3 population replicates (10K, grey) for two illustrative loci, each with two different isoforms (bottom). FIG. 3b shows the distributions of exon inclusion (Percent Spliced In (PSI) scores, X axis) for alternatively spliced exons of highly expressed genes (single cell TPM>250) in individual cells (blue histogram, top) and in the populations (grey histogram, bottom). Single cells exhibit a strong bias towards expression of one particular isoform. FIG. 3c depicts RNA-FISH validation of splicing variation in Irf7. Left: RNA-Seq read densities (only cells where the transcript is expressed are shown). Color boxes mark exons analyzed by RNA-FISH. Right: RNA-FISH images from simultaneous hybridization with probes for two constitutive ('Constitutive' or 'Con') regions of the transcript (constitutive region A: cyan (C); constitutive region B: magenta (M)) and one alternatively spliced exon ('Specific': orange (O)). White arrows highlight two cells with similarly high expression levels for Irf7, but opposite preferences for the alternatively spliced exon. Histograms: The two constitutive regions (right top and right bottom panels) are detected at similar levels (bottom histogram, deviation from 0.5 is as expected due to probe design), whereas the alternative exon (middle right panel) shows a bias towards inclusion or exclusion in individual cells (top histogram). FIG. 3d demonstrates that similar results were obtained for alternative regulation of mutually exclusive last exons for the gene Acpp.

FIG. 4a depicts PCA of 632 LPS-induced genes. Shown are the contributions of each cell (points) to the first two principle components. PC1 (X axis) discriminates 3 'semi-mature' cells (square) from 15 'maturing' cells (triangles). Light grey triangles denote the most mature cells. FIG. 4b depicts clustered correlation matrix of induced genes. Left: Shown is the Pearson correlation coefficients (r, purple: negative correlation; yellow: positive correlation) between single-cell expression profiles of every pair of 632 LPS-induced genes (rows, columns). The three highlighted clusters are noted on the left along with a few representative loci. Right: The projection score (green: high; blue: low) for each gene (row) onto PC1 (left) and PC2 (right). PC1 differentiates semi-mature from maturing BMDCs; PC2 maps to a cluster of antiviral genes. FIG. 4c depicts confirmation of correlations by RNA-FISH. Shown are the relationships between two pairs of genes (Irf7-Stat2, Irf7-Ifit1) based on RNA-FISH when simultaneously staining for the members of each pair. The square of the Pearson correlation coefficient ($r^2$) and number of measured cells are denoted in the upper left corner. FIGS. 4d-4f depicting how Irf7 propagates variability in an interferon feedback circuit. Shown are expression levels for each of eight genes from the antiviral cluster ('antiviral' rows), along with eight non-variable immune response genes ('non-variable response' rows), in each single immature BMDC (columns), measured using single-cell qRT-PCR in wild type (WT) (n=36) (FIG. 4d), Irf7–/– (n=47) (FIG. 4e), and Ifnr–/– (n=18) (FIG. 4f) BMDCs stimulated with LPS for 4 h.

FIG. 5 is a graph depicting global correlations in mRNA expression between single LPS stimulated BMDCs. Shown are the Pearson correlation coefficients between global expression profiles of each of 18 individual cells, the single cell average, and three populations of 10.000 cells each (rows, columns). All correlations were computed on log-scale expression profiles. Single cells (S) 12, 13, and 16 are Semi-Mature, while 9 and 16 are the most mature, correspond to light grey triangles in FIG. 4a.

FIGS. 9A-9D are a series of graphs and illustrations depicting quantification of unique mRNA molecules in three single cells. FIG. 9a depicts a modified protocol. The SMARTer II A oligo was modified, introducing a random four nucleotide barcode onto each mRNA molecule during reverse transcription. Shown is the structure of modified oligo (barcode is represented by NNNN). This barcode is retained through PCR amplification and library preparation. FIG. 9b depicts an IGV screenshot showing read densities at one locus for the three barcoded single-cell cDNA libraries (blue) as well as the three 10,000 cell replicate experiments (grey). Two single cells express exclusively one of two isoforms. FIG. 9c depicts detailed examination of reads mapping to 5' end of transcript. The 81 reads represent 23 unique barcodes (SEQ ID NOs: 289-369), affirming that the observed splicing result is not simply due to stochastic amplification of one or a few molecules. FIG. 9d depicts the relationship between single-cell TPM (X axis, log scale) and uniquely identified barcodes (Y axis, log scale) for the three barcoded single-cell libraries. Only genes represented by at least one unique barcode are plotted. Light blue shaded area represents single cell TPM<250, the threshold used throughout the study. The two alternate quantifications of single-cell gene expression are well correlated overall (0.82<R<0.86) and exhibit a tightly linear relationship for highly expressed genes (TPM>250).

FIG. 10a depicts IGV screenshots showing read densities for 6 alternatively spliced genes. For each gene, the alternatively spliced exon is boxed in orange. FIG. 10b is a table showing the number of unique molecular barcodes counted for each transcript shown in FIG. 10a. FIG. 10c depicts the distributions of exon inclusion (PSI scores, X axis) for alternatively spliced exons in genes represented by at least 15 barcodes in single cells (blue histogram, top) and in the populations (grey histogram, bottom). Results are highly similar to the splicing analysis of highly expressed genes across the 18 cells (single-cell TPM>250; FIG. 3). Single cells exhibit a strong skew towards one isoform or the other.

FIG. 13a depicts that expression levels for Ccr7 (expressed more in maturing cells) and I11b (expressed more in semi-mature cells) did not correlate strongly (Pearson $r^2=0.12$, n=812). FIG. 13b depicts that expression levels for Stat4 (expressed more in semi-mature cells) and Serpinb9 (expressed more in semi-mature cells) correlated more strongly (Pearson $r^2=0.28$, n=573). FIG. 13c depicts that expression levels for Cxcl10 and Tnf (both expressed more in maturing cells) correlated mildly (Pearson $r^2=0.18$, n=511). FIG. 13d depicts that Cc122 and Irf8 (both expressed in semi-mature cells) showed moderate correlation (Pearson r=0.26, n=1110). FIG. 13e depicts that Stat1 (antiviral, specific to neither) and Cxc11 (inflammatory, specific to neither) correlated very weakly (Pearson $r^2=0.07$, n=631).

FIG. 16a depicts the expression levels of each gene (row) in each cell (column) in unstimulated BMDCs and at 2 h, 4 h, and 6 h post-LPS stimulation. The gene signature consists of nine antiviral cluster genes, two uniformly induced genes, and two housekeeping controls. FIG. 16b depicts the percentage of cells that express each gene (rows) at each time point (column). A cell was scored as positive for a gene if the gene's expression was higher than a Ct of 23 on the Fluidigm BioMark. While some immune response genes, Cxc110 and Clec4e, were uniformly induced in all cells and persisted across time points, the percentage of cells expressing the antiviral cluster genes increased in a time-dependent manner.

FIG. 17a depicts an example of a co-staining image for Stat1 protein (green), Stat1 mRNA (magenta), and Ifit1 mRNA (white). FIG. 17b depicts the distributions of the levels of Ifit1 mRNA (black) and Stat1 (red), pStat1 (grey), and Stat2 (green) proteins (total fluorescence level, left histogram; average fluorescence level, middle; and percent nuclear localization, right) after exposure to LPS for 0 (top), 2 (middle) or 4 (bottom) hours. While overall protein levels increased in all cases throughout the time course, substantial variation in the induction of Stat1, pStat1, and Stat2 was found. Stat1 levels rose gradually while pStat1's shifts were most pronounced early. Stat2, meanwhile, showed strong nuclear localization by 2 h, followed by strong induction from 2 to 4 h. By 4 hr, protein levels were more homogeneous and nuclear translocation was less pronounced.

FIG. 18a depicts representative scatter plots showing the correlation between Stat proteins (Y axis) and Ifit mRNA levels (X axis) after a 4 h LPS stimulation. Top row: Stat1 middle row: pStat1; bottom row: Stat 2. Left column: total protein fluorescence; middle column: average protein fluorescence; right column: percent of nuclear protein. FIG. 18b depicts heatmaps showing the correlation ($r^2$; blue=0; red=1) between different measured parameters after exposure to LPS for 0 (top), 2 (middle), or 4 hours (bottom).

FIG. 24a depicts a scanning electron micrograph of a BMDC (scale bar: 25 µm). FIG. 24b depicts a simplified schematic of Toll-Like Receptor (TLR) network for sensing of PAM3CSK (PAM, from gram-positive bacteria) by TLR2. Lipopolysaccharide (LPS, from gram-negative bacteria) by TLR4, and polyinosinic:polycytidylic acid (PIC, poly(I:C), a synthetic mimic of viral RNA) by TLR3. FIG. 24c depicts microfluidic capture of a single BMDC (top, cell circled in purple) on the C1 chip (CAD drawing, bottom). FIG. 24d depicts principal component (PC) analysis, computed over samples from all three stimuli and time points together, for the LPS-stimulated cells (left) and the distributions of LPS-stimulated cellular scores for the first three PCs (right). FIG. 24e depicts time course expression profiles for induced genes (rows) in BMDCs at 0, 1, 2, 4, and 6 h post stimulation with PAM (green), LPS (black), and PIC (magenta) within BMDC populations (left columns) and individual BMDCs (right columns). At the far right are gene projection scores onto the first 3 principle components (PCs) (PC1, PC2, and PC3, columns); on the bottom are contributions of each cell (columns) to the first three PCs (PC1, PC2, and PC3, rows).

FIGS. 25A-25D is a series of graphs depicting time dependent behaviors of single cells. FIG. 25a depicts example single-cell expression distributions seen for three genes (one from each of the three clusters in FIG. 24e), at each time point (marked on top) after stimulation with PAM (top, green), LPS (middle, black), and PIC (bottom, magenta). Distributions are scaled to have the same maximum height. Individual cells are plotted as bars underneath each distribution. FIGS. 25b-d depict, for each of the three modules (labeled, top), wave plots of all of its constituent genes at 2 h (left) and 6 h (right) in BMDCs stimulated with LPS (top), PIC (for the "core" antiviral cluster Id, (FIG. 25b) or PAM (for the "peaked" inflammatory cluster (FIG. 25c) and "sustained" inflammatory (FIG. 25d) clusters. X axis: expression level, ln(TPM+1); Y axis: genes; Z axis: single-cell expression density. Genes are ordered from lowest to highest average expression value at the 2 h ("peaked" inflammatory) or 6 h ("core" antiviral, "sustained" inflammatory) LPS time point.

FIGS. 26A-26H are a series of graphs depicting dynamic changes in variation during stimulation. FIG. 26a presents a schematic rendering of the three parameters used to describe single-cell expression distributions, from left to right: µ, the mean RNA abundance levels for cells with detectable level of expression; σ, the dispersion in expression for cells with detectable expression; and α, the fraction of all cells with detectable expression (at ln(TPM+1)>1). FIG. 26b depicts examples of fit (grey) for measured TNF expression distributions (black) at different time points post LPS stimulation. FIG. 26c depicts changes in the values of µ, σ$^2$, and α (Y axes, left to right) estimated for TNF at each time point (X axis). Units for µ and σ$^2$ are ln(TPM+1). FIG. 26d is a maximum likelihood estimate α. Shown are the expression distributions (black, left) of TNF at different time points following LPS stimulation, and the matching likelihood function (dotted blue line) used to determine $α_{MLE}$ (green, right), when considering a null model where expression is distributed in a log-normal fashion and any deviations are due to technical detection limits. FIGS. 26e and 26f depict that the relationship between expression and H3K27ac binding depends on α, but not on µ. Plot shows average promoter read density (intensity; black high; white low; scale bar, bottom) for H3K27ac (LPS 2 h, top), H3K27ac (Unstim, middle), and H3K4me3 (2 h LPS, bottom) genes corresponding to each of 10 quantile bins of population expression (Y axis) and each of 10 quantile bins of α (FIG. 26e, X axis) or µ (FIG. 26f, X axis). The overall population correlation between expression and the H3K27ac (FIG. 26c, top, middle) largely disappears after controlling for the percentage of single cells with detectable expression levels (α: FIG. 26e, middle), but this dependency remains for H3K4Me3 levels (FIG. 26e, bottom). In contrast, controlling for µ (FIG. 26f) does not eliminate the dependency between expression level and K27ac, since within a single range of µ (vertical stripe), the correlation between population expression level and K27ac is maintained, suggesting that µ per se is not the underlying determinant of this relationship. FIG. 26g depicts bar plots showing p-values of correlation between average expression levels and K27ac only for immune response genes either as is (red) or when controlling for µ (blue) or α (green). FIG. 26h depicts dynamic changes in α and µ in each module. Bar plots showing for each module (top: core antiviral; middle: peaked inflammatory; bottom: sustained inflammatory) the fraction of genes (Y axis) with a significant change only in α (by a likelihood ratio test, P<0.01, blue), only in µ (Wilcoxon test, P<0.01, green), or in both (each test independently, light blue), at each transition (X axis), in different conditions (marked on top). In each module and condition, the proportion is calculated out of the total number of genes in the module that are significantly bimodal (by a likelihood ratio test) in at least one timepoint during the response timecourse, and are expressed in at least 10 cells in both conditions. This number is marked on top of each bar.

FIG. 27a depicts single cell expression distributions for Rsad (top) and Stat2 (bottom) after stimulating with LPS (left, black) or IFN-β (right, red) for 2 h. FIG. 27b depicts wave plots showing the distribution of expression of each of the genes in the "core" antiviral cluster (Y axis; ordered as in FIG. 25b) at 2 h stimulation with LPS (left) or IFN-β (right). Whereas the expression of most genes was bimodal at 2 h with LPS, most were unimodally expressed at 2 h with IFN-β (akin to the 4 h LPS time point in FIG. 25b). FIG. 27c depicts the "core" antiviral score (Y axis) for each LPS-stimulated cell (0, 1, 2, 4, and 6 h) and cells simulated for 2 h with IFN-β (rightmost). Two "precocious" cells (yellow stars) have unusually high antiviral scores at 1 h LPS. FIG. 27d Normal quantile plots of the expression of genes from the "core" (cluster Id, left) and secondary (cluster Ic, right) antiviral clusters at 1 h LPS. The two "precocious" cells (yellow stars) express unusually high levels of "core" antiviral genes (left) but not of secondary genes (right). FIG. 27e depicts that RNA-fluorescence in situ hybridization (RNA-FISH) confirmed the presence of rare early responders (arrow; yellow star), positive for both Ifnb1 (magenta) and Ifit1 (cyan). Grey: cell outlines. Scale bar 25 μm. FIG. 27*f* presents a Venn diagram showing the coincidence for detection (>5 copies) of both Ifnb1 (magenta) and Ifit1 (cyan) by RNA-FISH after a 1 h LPS stimulation (P<10-25, test of equal proportions).

FIG. 28A depicts experimental blocking of cell-to-cell communication. Left: C1 chip; Right: On-chip stimulation, followed by actuation of microfluidic valves (red bars), seals the cells at individual chambers, preventing inter-cellular signaling. FIG. 28*b* depicts expression of the genes (rows) in the "core" antiviral (Id, top rows) and "peaked" inflammatory (IIIc, bottom rows) modules in single cells (columns) from the on-chip (left; no cell-to-cell signaling) and in-tube (right) stimulations. Colors represent scaled expression values (z-scores). FIG. 28*c* depicts gene expression distributions for individual representative genes from the "core" antiviral (top) and "peaked" inflammatory (bottom) clusters in the on-chip (left, blue; no paracrine signaling) or in-tube (right; black) 4 h LPS stimulation. FIG. 28*d* depicts violin plots of "core" antiviral (top panel, Y axis), "peaked" inflammatory (middle panel, Y axis), and "sustained" inflammatory (bottom panel. Y axis) scores for individual cells from (left to right): LPS 0 h, LPS 1 h, LPS 2 h, LPS 4 h, LPS 6 h, "On-Chip" Unstimulated, "On-Chip" LPS 4 h, LPS 4 h with GolgiPlug (Brefeldin A) added at 0 h, LPS 4 h with GolgiPlug added at 1 h, LPS 4 h with GolgiPlug added at 2 h, LPS 4 h with Ifnar−/− BMDCs, and LPS 4 h with Stat1−/− BMDCs. The two "precocious" cells (FIG. 28*d*) with unusually high antiviral scores at 1 h LPS are denoted with yellow stars.

FIG. 29*a* is a gene network model showing how positive IFN-β signaling induced the antiviral response and reduced its heterogeneity, while simultaneously activating a negative paracrine feedback loop, possibly including IL-10, which dampened the "peaked" inflammatory cluster and increases its heterogeneity. FIG. 29*b* is a cell population model showing how positive and negative paracrine feedback altered antiviral (magenta) and inflammatory (green) gene expression variability across cells. Grey denotes no expression.

DETAILED DESCRIPTION

Figure 1A:
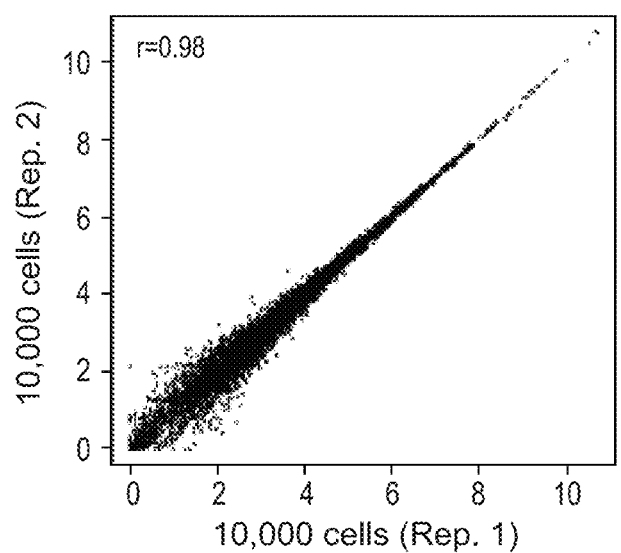
FIGS. 1A-1H are a series of graphs and illustrations depicting that single cell RNA-Seq of LPS-stimulated BMDCs revealed extensive transcriptome heterogeneity. A color version of these figures can be found in Shalek et al., "Single-cell transcriptomics reveals bimodality in expression and splicing in immune cells." Nature 498(7453):236-40 (2013); doi: 10.1038/nature12172.

This invention relates generally to compositions and methods for identifying the regulatory networks that control dendritic cell response, including core antiviral response, secondary antiviral response, maturation, induced inflammatory response and sharp peaked inflammatory response, as well compositions and methods for exploiting the regulatory networks that control dendritic cell response(s) in a variety of therapeutic and/or diagnostic indications.

The studies provided herein used single cell nucleic acid analysis, specifically. Single-Cell RNA-Seq, to profile the mRNA in individual dendritic cells (DCs) responding to various pathogenic components. Using the Single-Cell RNA-Seq profiling methods provides a number of advantages, such as, by way of non-limiting examples, cleaner signatures, a separation of antiviral circuits from maturation ones, and refining signatures identified in cell populations.

Single-cell RNA-Seq offers an unbiased approach for understanding the extent, basis, and function of gene expression variation between seemingly identical cells. However, fulfilling this promise requires a high-throughput workflow for profiling and analyzing many cells across different experimental conditions. The disclosure provides a microfluidics-based approach to prepare single-cell RNA-Seq libraries from over 1,700 primary mouse dendritic cells (DCs) stimulated with three pathogenic components. Substantial variation between individual cells exposed to the same stimulus was found, in both the fraction of cells expressing a given mRNA transcript at a detectable level and the transcript's levels within these expressing cells. Distinct gene modules are characterized by different temporal heterogeneity profiles. In particular, a "core" module of antiviral genes is expressed very early by a few "precocious" cells and then becomes active in all cells at later time points. By stimulating cells individually in sealed microfluidic chambers, analyzing DCs from knockout mice, and modulating secretion and extracellular signaling, this response is propagated and coordinated via interferon-mediated paracrine signaling. Surprisingly, preventing cell-to-cell communication also substantially reduces variability in the expression of a peaked, early-induced inflammatory module, suggesting that paracrine signaling additionally represses a portion of the inflammatory program. The compositions and methods provided herein highlight the importance of cell-to-cell communication in controlling cellular heterogeneity and reveals general strategies that multicellular populations use to establish complex dynamic responses.

Using this analysis for the first time ever, a series of refined gene signatures for different response elements, referred to herein as the "Core Antiviral" gene signature, the "Secondary Antiviral" gene signature, the "Maturation" gene signature, the "Inflammatory Induced" gene signature, and the "Inflammatory Sharp Peaked" gene signature, have been uncovered. These signatures are genes that are expressed in coherent groups of single cells. Each of these gene signatures is provided in Tables 1-5 below.

The "Core Antiviral" gene signature is induced in the earliest of the responding dendritic cells. The "Maturation" gene signature looks similar to the "Induced Inflammatory" gene signature at a population level, but using single cell analysis, it was established that the "Maturation" gene signature is expressed in only a subset of cells. The "Maturation" gene signature is responsible for allowing dendritic cells to recruit T cells and B cells, thereby bridging the gap between the innate and adaptive immunity system.

TABLE 1

| Core Antiviral Signature Genes | | |
| --- | --- | --- |
| ADAR | IFI44 | PML |
| AI607873 | IFIH1 | PRIC285 |
| AK172683 | IFIT1B | PTTG1 |
| AW112010 | IFIT2 | PYHIN1 |
| BST2 | IFIT3 | RNASET2A |
| CA13 | IFITM3 | RSAD2 |
| CASP11 | IGTP | RTP4 |
| CD274 | IIGP1 | SAMD9L |
| CD69 | IL15 | SERPINA3 |
| CMPK2 | IL15RA | SLCO3A1 |
| CXCL10 | IRF7 | SLFN13 |
| DAXX | IRGC | SLFN5 |
| DDX58 | IRGM | SLFN9 |
| DDX60 | ISG15 | SP100 |

TABLE 1-continued

Core Antiviral Signature Genes

| | | |
|---|---|---|
| DHX58 | ISG20 | SP140L |
| DTX3L | MITD1 | STAT1 |
| E030037K03RIK | MNDA | STAT2 |
| EIF2AK2 | MOV10 | TAP1 |
| ETNK1 | MS4A4A | TOR3A |
| FAM26F | MX1 | TREX1 |
| GBP2 | NLRC5 | TRIM5 |
| GBP4 | NT5C3 | UBA7 |
| GBP6 | OAS1 | USP18 |
| GM4951 | OAS2 | USP25 |
| GVINP1 | OAS3 | XAF1 |
| H2-T10 | OASL | ZBP1 |
| HERC6 | OASL2 | ZNFX1 |
| IFI16 | PARP12 | ZUFSP |
| IFI204 | PARP9 | |
| IFI35 | PHF11 | |

TABLE 1A

Subset of Core Antiviral Signature Genes

| | | |
|---|---|---|
| ADAR | GVIN1 | OASL2 |
| AI607873 | H2-T10 | PARP12 |
| AK172683 | HERC6 | PARP9 |
| AW112010 | I830012O16RIK | PHF11 |
| BST2 | IFI203 | PTTG1 |
| CAR13 | IFI204 | PYHIN1 |
| CASP11 | IFI205 | RNASET2A |
| CD274 | IFI35 | RTP4 |
| CD69 | IFI44 | SAMD9L |
| CMPK2 | IFI47 | SERPINA3G |
| D14ERTD668E | IFIH1 | SLCO3A1 |
| DAXX | IFITM3 | SLFN5 |
| DDX58 | IGTP | SLFN8 |
| DDX60 | IRGM1 | SLFN9 |
| DHX58 | IRGM2 | SP100 |
| DTX3L | MITD1 | SP140 |
| E030037K03RIK | MNDAL | TAP1 |
| EIF2AK2 | MOV10 | TOR3A |
| ETNK1 | MPA2L | TREX1 |
| FAM26F | MS4A4C | TRIM30A |
| GBP2 | MX1 | TRIM30D |
| GBP3 | NLRC5 | UBA7 |
| GM12250 | NT5C3 | USP18 |
| GM14446 | OAS1A | XAF1 |
| GM4902 | OAS1G | ZBP1 |
| GM4951 | OAS2 | ZNFX1 |
| GM5431 | OAS3 | ZUFSP |
| GM8979 | SLFN13 | TRIM5 |
| CA13 | GBP6 | GVINP1 |
| IFI16 | IFIT1B | MNDA |
| MS4A4A | OAS1 | PRIC285 |
| SERPINA3 | | |

TABLE 2

Secondary Antiviral Signature Genes

| | | |
|---|---|---|
| 2810474O19RIK | HEATR5B | RNF135 |
| ADAP2 | IFI27L2A | SAMHD1 |
| AFTPH | IL18BP | SETDB2 |
| AIDA | IRF9 | SGCB |
| AIM1 | KIAA0040 | SLAMF7 |
| AIM2 | KIAA0317 | SLC25A22 |
| AK142678 | KIAA1715 | SLFN12 |
| AK163331 | KYNU | SPRED1 |
| AKT3 | LAP3 | STARD3 |
| ALDH1B1 | LGALS9 | STXBP3 |
| AP3M2 | MIER3 | TCF4 |
| APOBEC3 | MINPP1 | TDRD7 |
| AZI2 | MKIAA1823 | TFG |
| BBX | MLKL | TLR3 |
| BC147527 | MTHFR | |

TABLE 2-continued

Secondary Antiviral Signature Genes

| | | |
|---|---|---|
| BFAR | NAA25 | TMCC3 |
| C19orf12 | NMI | TMEM140 |
| CASP7 | NOD1 | TMEM67 |
| CCDC25 | P2RY14 | TNFSF8 |
| CCND2 | PARP11 | TOR1AIP1 |
| CCNJ | PARP8 | TOR1AIP2 |
| CH25H | PCGF5 | TRIM25 |
| DCK | PELI1 | TRIM34 |
| FBXW12 | PFKP | TRIM5 |
| FGL2 | PLA2G16 | UBE2L6 |
| FNDC3A | PPA1 | VCAN |
| FRMD4A | PPHLN1 | VCPIP1 |
| G530011O06RIK | PPM1K | WARS |
| GBP6 | PRPF38A | WHSC1L1 |
| GNB4 | PSMB9 | XKR8 |
| GYPC | RASA4 | XRN1 |
| H2-T23 | RIN2 | ZC3HAV1 |
| H2-T24 | RNF114 | ZNF800 |

TABLE 2A

Subset of Secondary Antiviral Signature Genes

| | | |
|---|---|---|
| 1110018G07RIK | GNB4 | RNF114 |
| 1600014C10RIK | GYPC | RNF135 |
| 2810474O19RIK | H2-T23 | SAMHD1 |
| 3110001I22RIK | H2-T24 | SETDB2 |
| 4930523C07RIK | HEATR5B | SGCB |
| 9230105E10RIK | IFI27L2A | SLAMF7 |
| ADAP2 | IL18BP | SLC25A22 |
| AFTPH | IRF9 | SLFN1 |
| AIDA | KYNU | SPRED1 |
| AIM1 | LAP3 | STARD3 |
| AIM2 | LGALS9 | STXBP3A |
| AK142678 | LNP | TBC1D13 |
| AK163331 | MIER3 | TDRD7 |
| AKT3 | MINPP1 | TFG |
| ALDH1B1 | MKIAA1823 | TMCC3 |
| AP3M2 | MLKL | TMEM140 |
| APOBEC3 | MTHFR | TMEM67 |
| AZI2 | NAA25 | TOR1AIP1 |
| BC147527 | NOD1 | TOR1AIP2 |
| BFAR | P2RY14 | TRIM25 |
| CASP7 | PARP11 | TRIM34 |
| CCDC25 | PARP8 | TRIM5 |
| CCNJ | PCGF5 | UBE2L6 |
| CH25H | PFKP | VCAN |
| DCK | PLA2G16 | VCPIP1 |
| FBXW17 | PPA1 | WARS |
| FNDC3A | PPM1K | WHSC1L1 |
| FRMD4A | PRPF38A | XKR8 |
| G530011O06RIK | PSMB9 | XRN1 |
| GBP4 | RASA4 | ZC3HAV1 |
| GBP6 | RIN2 | ZFP800 |
| GBP9 | FBXW12 | KIAA0040 |
| C19orf12 | KIAA1715 | PPHLN1 |
| KIAA0317 | SLFN12 | |

TABLE 3

Maturation Signature Genes

| | | |
|---|---|---|
| AKNA | ETS2 | PGAP2 |
| APOL7C | ETV3 | PLAT |
| APPL1 | EXOC3L4 | PPP1CB |
| ARL5C | FAM129A | PVR |
| BATF | FAM177A1 | PVRL2 |
| BC035044 | GPR85 | RAB8B |
| BCL2L1 | H2-Q7 | REL |
| BIRC3 | HSD17B11 | RHOB |
| BLNK | IL12B | RND3 |
| CCL22 | IL23A | SAMSN1 |
| CCR7 | IL4I1 | SEMA6D |

TABLE 3-continued

Maturation Signature Genes

| | | |
|---|---|---|
| CD72 | IRF8 | SERPINB9 |
| CD80 | ITGA4 | SRGN |
| CD83 | KTELC1 | ST3GAL1 |
| CD86 | LACC1 | STAT3 |
| CDKN1A | MKIAA0769 | STAT5A |
| CHAC2 | MMP25 | SWAP70 |
| CRLF3 | NFKBIB | TBC1D1 |
| CSF1 | NUDT17 | TIMP1 |
| DENND5A | OSGIN2 | TMEM39A |
| EBI3 | PALM2 | TNIP3 |
| EIF2C3 | PDZK1IP1 | VCAM1 |

TABLE 3A

Subset of Maturation Signature Genes

| | | |
|---|---|---|
| 1200009I06RIK | EIF2C3 | PPP1CB |
| 9030625A04RIK | ETS2 | PVR |
| AKNA | ETV3 | PVRL2 |
| APOL7C | FAM129A | RAB8B |
| APPL1 | FAM177A | REL |
| BC035044 | GPR85 | RHOB |
| BCL2L1 | H2-Q7 | RND3 |
| BIRC3 | HSD17B11 | SAMSN1 |
| BLNK | IRF8 | SEMA6D |
| CCL22 | ITGA4 | SERPINB9 |
| CCR7 | KTELC1 | SERPINB9B |
| CD72 | MKIAA0769 | SRGN |
| CD80 | MMP25 | ST3GAL1 |
| CD83 | NFKBIB | STAT3 |
| CD86 | NUDT17 | SWAP70 |
| CDKN1A | NUP62-IL4I1 | TBC1D1 |
| CHAC2 | OSGIN2 | TIMP1 |
| CRLF3 | PALM2 | TMEM39A |
| CSF1 | PDZK1IP1 | TNIP3 |
| DENND5A | PGAP2 | VCAM1 |
| EBI3 | EXOC3L4 | FAM177A1 |
| IL4I1 | LACC1 | |

TABLE 4

Inflammatory Induced Signature Genes

| | | |
|---|---|---|
| 6330409N04RIK | H2-M2 | PROCR |
| A130040M12RIK | HCK | PTGS2 |
| ACPP | IL1B | PTPRJ |
| ACSL1 | IL1RN | RAB10 |
| AOAH | IL27 | RAB32 |
| B3GNT2 | IL6 | RHBDF2 |
| BCL2A1 | INHBA | RNF19B |
| C15orf48 | IRG1 | RPS6KA2 |
| CALCRL | ITGA5 | SAA3 |
| CAV1 | ITGAV | SBDS |
| CCL3 | JAK2 | SDC4 |
| CCL4 | KPNA3 | SH3BP5 |
| CCL5 | LCN2 | SLC15A3 |
| CD14 | LMO4 | SLC2A6 |
| CD200 | MAPKAPK2 | SLC7A11 |
| CD38 | MARCKSL1 | SLC7A2 |
| CD40 | MARCO | SLFN2 |
| CERS6 | MET | SOD2 |
| CFLAR | MFLJ00294 | SQSTM1 |
| CLEC4E | MKIAA1673 | ST3GAL5 |
| CLIC4 | MMP14 | TAGAP |
| CXCL16 | MTPN | TANK |
| CXCL3 | NAMPT | TARM1 |
| DCBLD2 | NFKB1 | TLR1 |
| EHD1 | NFKB2 | TNFRSF1B |
| ELL2 | NOS2 | TNFSF15 |
| FAM102B | OLR1 | TRAF1 |
| FPR2 | PARP14 | TXNRD1 |
| GADD45B | PIK3R5 | |
| GBP5 | PLEK | |

TABLE 4-continued

Inflammatory Induced Signature Genes

| | |
|---|---|
| GM14005 | PPAP2B |
| GPR84 | PPP4R2 |

TABLE 4A

Subset of Inflammatory Induced Signature Genes

| | | |
|---|---|---|
| 6330409N04RIK | GM14005 | PPAP2B |
| A130040M12RIK | GPR84 | PPP4R2 |
| AA467197 | H2-M2 | PROCR |
| ACSL1 | HCK | PTPRJ |
| AOAH | IL1B | RAB10 |
| B3GNT2 | IL1RN | RAB32 |
| BCL2A1A | IL27 | RHBDF2 |
| BCL2A1B | IL6 | RNF19B |
| BCL2A1C | IRG1 | RPS6KA2 |
| BCL2A1D | ITGA5 | SAA3 |
| CALCRL | ITGAV | SBDS |
| CAV1 | JAK2 | SDC4 |
| CCL5 | KPNA3 | SLC15A3 |
| CD14 | LASS6 | SLC2A6 |
| CD200 | LCN2 | SLC7A11 |
| CD38 | MAPKAPK2 | SLC7A2 |
| CFLAR | MARCKSL1 | SLFN2 |
| CLEC4E | MFLJ00294 | SOD2 |
| CLIC4 | MKIAA1673 | SQSTM1 |
| CXCL16 | MMP14 | ST3GAL5 |
| CXCL3 | MTPN | TAGAP |
| DCBLD2 | NAMPT | TANK |
| EHD1 | NFKB1 | TARM1 |
| ELL2 | NOS2 | TLR1 |
| FAM102B | OLR1 | TNFRSF1B |
| FPR2 | PARP14 | TNFSF15 |
| GADD45B | PIK3R5 | TRAF1 |
| GBP5 | PLEK | TXNRD1 |
| C15orf48 | CERS6 | |

TABLE 5

Inflammatory Sharp Peaked Signature Genes

| | | |
|---|---|---|
| ADORA2B | IRAK-2 | PTX3 |
| AK150559 | IRAK3 | RALGDS |
| AK163103 | KLF7 | RASA2 |
| ARG2 | LCP2 | RASGEF1B |
| ARHGEF3 | LDLR | RBM7 |
| BCL2L11 | LZTFL1 | RCAN1 |
| C1orf55 | MALT1 | RELA |
| C5AR1 | MCOLN2 | RFFL |
| CCRL2 | MPP5 | SERTAD2 |
| CD44 | NCK1 | SGMS2 |
| CDC42EP4 | NFKBIA | SLC16A10 |
| CLCN7 | NFKBID | SLC25A25 |
| CLEC4D | NFKBIE | SLC25A37 |
| CPD | NFKBIZ | SLC39A14 |
| CXCL2 | NLRP3 | SOCS3 |
| CXCL3 | NRP2 | SPATA13 |
| DDHD1 | NUP54 | TGM2 |
| DUSP16 | NUPR1 | TLR2 |
| F10 | ORAI2 | TNF |
| FAM108C1 | OSBPL3 | TNFAIP2 |
| FAM20C | PDE4B | TNFAIP3 |
| FLRT3 | PILRA | TNIP1 |
| FPR1 | PIP5K1A | TOP1 |
| GRAMD1B | PLAGL2 | TREM1 |
| H1F0 | PLEKHO2 | TRIM13 |
| HCAR2 | PLK2 | TSHZ1 |
| ICOSL | PLSCR1 | ZC3H12C |
| IL1A | PSTPIP2 | ZEB2 |
| IL36G | PTAFR | ZSWIM4 |
| INSIG1 | PTPRE | |

TABLE 5A

Subset of Inflammatory Sharp Peaked Signature Genes

| | | |
|---|---|---|
| ADORA2B | IRAK3 | PTX3 |
| AK150559 | KLF7 | RALGDS |
| AK163103 | LCP2 | RASA2 |
| ARG2 | LDLR | RASGEF1B |
| ARHGEF3 | MALT1 | RBM7 |
| BC031781 | MCOLN2 | RCAN1 |
| BCL2L11 | MPP5 | RELA |
| C5AR1 | NCK1 | RFFL |
| CCRL2 | NFKBIA | SERTAD2 |
| CD44 | NFKBID | SGMS2 |
| CDC42EP4 | NFKBIE | SLC16A10 |
| CLCN7 | NIACR1 | SLC25A25 |
| CLEC4D | NLRP3 | SLC25A37 |
| CPD | NRP2 | SLC39A14 |
| DDHD1 | NUP54 | SPATA13 |
| DUSP16 | NUPR1 | TGM2 |
| F10 | ORAI2 | TLR2 |
| FAM108C | OSBPL3 | TNFAIP2 |
| FAM20C | PDE4B | TNFAIP3 |
| FLRT3 | PILRA | TNIP1 |
| FPR1 | PIP5K1A | TOP1 |
| GRAMD1B | PLAGL2 | TREM1 |
| H1F0 | PLEKHO2 | TRIM13 |
| ICOSL | PLSCR1 | TSHZ1 |
| IL1F9 | PSTPIP2 | ZEB2 |
| INSIG1 | PTAFR | ZSWIM4 |
| IRAK-2 | PTPRE | |

A desired target gene or combination of target genes is selected, and after determining whether the selected target gene(s) is overexpressed or under-expressed during a dendritic cell response, a suitable antagonist or agonist is used depending on the desired maturation and/or function outcome. Suitable antagonists and/or agonists include an antibody, a soluble polypeptide, a polypeptide agent, a peptide agent, a nucleic acid agent, a nucleic acid ligand, or a small molecule agent.

The modulating agents are used to modulate the expression of one or more target genes or one or more products of one or more target genes that have been identified as genes responsive to dendritic cell-related perturbations. These target genes are identified, for example, by contacting a dendritic cell with a modulating agent and monitoring the effect, if any, on the expression of one or more signature genes or one or more products of one or more signature genes. In some embodiments, the one or more signature genes are selected from those listed in Tables 1-5A. The modulating agent can act directly on the expression of one or more target genes or one or more products of one or more target genes and/or the modulating agent can act indirectly on the expression of one or more target genes or one or more products of one or more target genes by modulating the expression, activity and/or function of a gene or a product of a gene that is known to be associated with the target gene(s).

In some embodiments, the target gene is tumor necrosis factor receptor (TNFR). In some embodiments, the modulating agent alters the expression, activity and/or function of TNFR. In some embodiments, the modulating agent alters the expression, activity and/or function of a gene that is associated with TNFR, such as, by way of non-limiting example, a gene from those shown in Table 6 below. The underlined genes in Table 6 are genes that are upregulated when TNFR is absent, e.g., knocked out, and the non-underlined genes are genes that are down-regulated when TNFR is absent, e.g., knocked out.

TABLE 6

| | | | | |
|---|---|---|---|---|
| CCL5 | PNRC1 | AKNA | CAV1 | MTHFR |
| ETV3 | CHD1 | TRIM34 | MLKL | FAM53C |
| BLNK | GBP9 | CXCL10 | AK178429 | SLC7A11 |
| SRGN | BTG2 | ARL5C | EGR2 | TMEM140 |
| MCMBP | TMEM39A | OSGIN2 | AZI2 | 9030425E11RIK |
| IRF8 | ARID5B | DENND5A | A130040M12RIK | VCL |
| MARCKSL1 | EIF2C3 | RSAD2 | PLEKHF2 | TLR3 |
| PVRL2 | CST7 | SEPW1 | TRAF1 | MKIAA1994 |
| IFIT2 | RPS6KA2 | IFIT1 | G530011O06RIK | MAF |
| KTELC1 | DLGAP4 | FBXW17 | DUSP1 | SAMSN1 |
| CCND2 | BCL2A1A | SMIF | RELA | TLR6 |
| 9030625A04RIK | PIK3AP1 | RBS2 | SLFN9 | AK138792 |
| CDKN1A | IFIT3 | GRAMDIB | LDLR | NAA25 |
| ISG15 | CSF1 | EPSTI1 | FSTL1 | AK172683 |
| GLIPR2 | FAM129A | BCL2A1C | NFKB2 | ZCCHC2 |
| CD86 | 1110038F14RIK | HERC6 | SERPINB9 | CD14 |
| SDC4 | RNF19B | TRMT61B | A430084P05RIK | F830016B08RIK |
| TNFSF8 | BC006779 | NCOA7 | MKIAA0696 | FILIPIL |
| IFIH1 | KLF7 | CCL4 | SAMD9L | RALGDS |
| CD80 | BCL2A1B | TRA2A | NFKB1 | TNFAIP2 |
| IFI27L2A | ISG20 | CLU | LY6A | A230046K03RIK |
| IIGP1 | TMEM219 | CCRN4L | MAP3K8 | TSHZ1 |
| D14ERTD668E | HMGN3 | TARM1 | RBM7 | TLR7 |
| GBP4 | MTPN | 5031414D18RIK | 2310004I24RIK | SPATA13 |
| STAT5A | APPL1 | MFSD7 | H2-T10 | AK050909 |
| AK163331 | MITD1 | 1110018G07RIK | LRRK2 | INSIG1 |
| RGS1 | ICOSL | OPTN | PDZK1IP1 | PTGS2 |
| LAP3 | TMC03 | BATF2 | EIF2AK2 | H3F3B |
| CCL22 | DYNC1I2 | RANBP2 | PLK2 | SLC7A2 |
| SWAP70 | CDYL2 | IFNB1 | MGAT4A | FOSL2 |
| EBI3 | IL13RA1 | SNX10 | IRG1 | DAB2 |
| AA467197 | CLN3 | TRIM13 | RTP4 | CALCRL |
| SLC2A6 | ALDH1A2 | STAT3 | 1810029B16RIK | SPIC |
| RNASET2A | KATNA1 | ST8SIA4 | PLEKHO2 | ACSL1 |
| FAM26F | WDR37 | RBM43 | SAA3 | SOD2 |
| SLFN5 | AY096003 | CASP7 | GCNT2 | IL1RN |
| P4HA1 | ARHGEF3 | IL6 | EHD1 | CAR4 |
| IL27 | IL23A | CISH | IL20RB | IL1F9 |
| NUP62-IL4I1 | AK200837 | GM6548 | SLFN3 | PTGES |

TABLE 6-continued

| | | | | |
|---|---|---|---|---|
| E030037K03RIK | PMAIP1 | UBE2Q2 | RNF214 | 6330409N04RIK |
| OAS3 | NUPR1 | TRIM5 | FABP3 | DRAM1 |
| SLCO3A1 | IFI205 | TNIP3 | STAT1 | PLEK |
| 4930523C07RIK | REL | FAM177A | PIK3R5 | LY75 |
| PGAP2 | HK3 | WARS | EGR1 | SLC39A2 |
| KLRK1 | DUSP16 | IRF1 | DENND3 | FLRT3 |
| F10 | AK052414 | ZFP80 | CFLAR | SOCS3 |
| PTX3 | TMEM67 | TRIM25 | GYK | CLEC4E |
| MMP25 | PALM3 | LNP | RCAN1 | SQSTM1 |
| CIAPIN1 | MERTK | ZUFSP | PIP5K1A | PDE4B |
| IFT172 | RHOB | CD180 | GPD2 | CXCL3 |
| PNP | LRCH3 | RAP1B | SERPINA3G | MT2 |
| BIRDC3 | BCL2A1D | IER3 | ITGA5 | MET |
| CXCL16 | CD47 | MTMR14 | IL12RB2 | HSPA5 |
| CD72 | LCN2 | CD38 | PPP1R15A | AOAH |
| ATF3 | 9230105E10RIK | DENND4A | ASCC3 | TGM2 |
| HIST3H2A | MXD1 | CMPK2 | NCK1 | NPY |
| DHX58 | GM6644 | CCL2 | C5AR1 | MFLJ00294 |
| ITGA4 | AP3M2 | MINA | ST3GAL1 | 2310016C08RIK |
| IRF7 | UBR4 | LY6C2 | IRF9 | TNFRSF1B |
| RASA4 | D1ERTD622E | EXPI | PTTG1 | MAPKAPK2 |
| LNPEP | MMP13 | 1190002H23RIK | PTPRJ | SLC16A10 |
| ASB13 | PROCR | FCGR1 | PARP14 | AK217941 |
| IL12B | MNDAL | DDX60 | TIFA | TNF |
| NOS2 | 5730508B09RIK | STAT2 | VWA5A | PDPN |
| PPP1CB | JAK2 | TNFSF9 | HK2 | CD44 |
| PRDX1 | GBP5 | STXBP3A | MPP1 | CXCL2 |
| SP100 | RILPL2 | P2RY13 | AFF1 | CCRL2 |
| TDRD7 | NFKBIZ | CCL7 | LMO4 | PTPRE |
| PAPD4 | H2-T23 | IFI203 | HIF1A | MARCO |
| RASGEF1B | DTX3L | PFKFB3 | SLPI | IL1B |
| 1600014C10RIK | GNG12 | FAM46C | GM8979 | SGK1 |
| H1F0 | NOTCH2 | ALDH1B1 | LY6I | |
| CCR7 | CAML | TLE3 | 2010106G01RIK | |
| MINPP1 | SEMA6D | RAB10 | FBXL3 | |

In some embodiments, the target gene is a Toll/interleukin-1 receptor (TIR) domain-containing adapter protein (TIRAP). In some embodiments, the modulating agent alters the expression, activity and/or function of TIRAP. In some embodiments, the modulating agent alters the expression, activity and/or function of a gene that is associated with TIRAP, such as, by way of non-limiting example, a gene from those shown in Table 7 below. The underlined genes in Table 7 are genes that are upregulated when TIRAP is absent, e.g., knocked out, and the non-underlined genes are genes that are down-regulated when TIRAP is absent, e.g., knocked out.

TABLE 7

| | | | | |
|---|---|---|---|---|
| LYZ1 | TLR3 | GBP9 | DDHD1 | ARHGEF3 |
| SGK1 | DENND1B | ST8SIA4 | AW112010 | BTG1 |
| PRDX1 | PMP22 | UBC | CD72 | APPL1 |
| ACSL1 | FAM20C | FOSL2 | ANKRD17 | MTPN |
| MET | FAM102B | MPP1 | NOS2 | MFLJ00294 |
| PDPN | BATF2 | PRDM1 | CD47 | NFKB2 |
| CLEC4D | PTAFR | GTPBP2 | LDLR | IL1A |
| PTPRE | TIFA | FAM53C | DLGAP4 | CD40 |
| 9030425E11RIK | PYHIN1 | LRRK2 | RELA | FBXL3 |
| MMP13 | EPSTI1 | JHDM1D | MINA | ITGA5 |
| LY6C2 | CD274 | PLK2 | EXT1 | 4930523C07RIK |
| MCOLN2 | A430084P05RIK | CRBN | ANKRD57 | SWAP70 |
| DENND3 | F10 | ISG20 | SDC4 | G530011O06RIK |
| SLPI | 1810029B16RIK | MALT1 | WARS | CXCL1 |
| RSAD2 | SLC16A10 | PLEKHN1 | PPP4R2 | SH3BP5 |
| CD38 | DDX60 | LRCH1 | CHAC2 | NFKBIE |
| 1190002H23RIK | OAS2 | MCA32 | CAR13 | 2310004I24RIK |
| SLC7A8 | THBS1 | PTGES | SLC25A22 | PIK3R5 |
| ZCCHC2 | NAA25 | PSMB10 | LZTFL1 | NFKBIA |
| FCGR1 | PHC2 | WHSC1L1 | AK139528 | DNAJB6 |
| LY6A | VCL | MPA2L | FBXO11 | BIRC3 |
| MT2 | BST2 | H3F3B | AK138792 | BCL2L11 |
| IRG1 | CLEC4E | SLFN1 | HSPA5 | ICOSL |
| PPAP2B | MXD1 | TGM2 | JAK2 | A230046K03RIK |
| IFIT3 | HCK | AK178429 | SLFN2 | INSIG1 |
| RALGDS | CCL2 | SLC20A1 | GYPC | DUSP16 |
| EGR2 | MX2 | XRN1 | CXCL3 | PDZK1IP1 |
| PTX3 | IER3 | TMEM67 | TMCO3 | IRF8 |
| LY6I | VWA5A | MS4A4C | PTTG1 | LMO4 |
| SLFN5 | MFSD7 | DNAJB4 | SBDS | MTDH |
| GPR141 | PARP10 | SGMS2 | WDR37 | SOCS3 |

TABLE 7-continued

| | | | | |
|---|---|---|---|---|
| HIF1A | SAMHD1 | MITF | FLRT3 | ST3GAL1 |
| E030037K03RIK | IL1F9 | UPP1 | PELI1 | CD83 |
| CD180 | PSTPIP2 | NUB1 | RNF19B | NFKB1 |
| FABP3 | RGS14 | BPAG1 | PGAP2 | PVRL2 |
| SGMS1 | FCGR4 | IL18BP | CSF1 | SEMA6D |
| STAT1 | AK200837 | IRF7 | UBXN2A | KYNU |
| P4HA1 | MNDAL | ZNFX1 | TNIP1 | BCL2A1A |
| C5AR1 | PLEKHO2 | PNPT1 | OSGIN2 | EIF2C3 |
| CMPK2 | NOTCH2 | AK050909 | JUNB | DENND4A |
| CALCRL | FAM26F | IL12RB2 | H1F0 | IL23A |
| CAV1 | OPTN | DNAJC13 | 1200009I06RIK | CCNG2 |
| FOS | STXBP3A | GTF2B | RAB8B | NFKBIB |
| FAM46C | IFI203 | SETDB2 | MTMR14 | BATF |
| CFB | CCRL2 | SLFN10-PS | FGL2 | PALM2 |
| SLC7A2 | H2-T24 | ISG15 | KPNA3 | EBI3 |
| STK38L | AK042010 | LY75 | CD86 | MMP25 |
| HK3 | TMEM219 | BC006779 | BTG2 | PNRC1 |
| GM14446 | TAP2 | USP12 | MARCKSL1 | CCND2 |
| GPD2 | IFIT1 | NT5C3 | TET2 | FILIP1L |
| IFIT2 | GM6644 | SGCB | BC035044 | EHD1 |
| KLF3 | MERTK | CASP7 | H2-Q7 | SAMSN1 |
| CST7 | MEF2A | TRIM5 | SLC39A14 | AY096003 |
| SLC25A37 | 6330409N04RIK | NMI | BCL2L1 | BCL2A1D |
| CLCN7 | OSBPL3 | ZFP800 | HSD17B11 | CISH |
| CASP1 | LAP3 | F830016B08RIK | AA467197 | NUP62-IL4I1 |
| IL15RA | PLAUR | CCL4 | CCR7 | CCL3 |
| JARID2 | DYNC1H1 | ZUFSP | RNF214 | TBC1D1 |
| EGR1 | P2RY13 | DENND5A | ETV3 | 9030625A04RIK |
| IRF1 | TXNRD1 | HEATR5B | AK139487 | CCL17 |
| D1ERTD622E | ARFGEF1 | RABGEF1 | MARCO | PPP1CB |
| SNX10 | LRP12 | TNFAIP3 | HIST1H4D | TRAF1 |
| CXCL10 | PNP | ZSWIM4 | PMAIP1 | BLNK |
| I830012O16RIK | SAMD9L | AK150559 | TNIP3 | CD80 |
| 2310016C08RIK | OASL1 | TIMP1 | AK052414 | TNFSF15 |
| DRAM1 | 1110038F14RIK | ST3GAL5 | CXCL16 | REL |
| MKIAA1994 | MLKL | MKIAA1823 | GM6377 | BCL2A1B |
| NPY | FRMD4B | TSHZ1 | RGS1 | PDE4B |
| FBXO30 | ARG2 | MAX | SEC24B | FAM177A |
| SLFN3 | GNG12 | PTPRJ | ARF4 | FAM129A |
| ADAP2 | IGTP | PPA1 | 2010106G01RIK | KTELC1 |
| HIST3H2A | P2RY14 | ARL5C | CD14 | RND3 |
| FPR1 | RNF34 | ITGA4 | CD200 | TMEM39A |
| MDM2 | CD44 | AMN1 | A630001G21RIK | GADD45B |
| IL1RN | ASB13 | LYRM1 | TMCC3 | PTGS2 |
| PLEKHF2 | GVIN1 | IL27 | TAPBPL | NFKBIZ |
| TLR7 | ALDH1B1 | GM14047 | SRGN | CCL22 |
| SPATA | ZCCHC6 | TOR1AIP1 | IL18 | STAT5A |
| LGALS3BP | OAS1G | ZBP1 | TAGAP | IL1B |
| XAF1 | RASA4 | FAM108C | GPR85 | IL6 |
| IFI205 | IRAK3 | RNF2 | IFI27L2A | BCL2A1C |
| DAB2 | GBP4 | FBXW17 | CFLAR | IL12B |
| 1600014C10RIK | MAMLD1 | TREM1 | CXCL2 | |
| MMP14 | SVCT2 | IL15 | NCK1 | |
| NRP2 | GBP6 | TNFAIP2 | MS4A6C | |
| OLR1 | HIPK2 | SMIF | AKNA | |

In some embodiments, the target gene is Stat1. In some embodiments, the modulating agent alters the expression, activity and/or function of Stat1. In some embodiments, the modulating agent alters the expression, activity and/or function of a gene that is associated with Stat1, such as, by way of non-limiting example, a gene from those shown in Table 8 below. The underlined genes in Table 8 are genes that are upregulated when Stat1 is absent, e.g., knocked out, and the non-underlined genes are genes that are down-regulated when Stat1 is absent, e.g., knocked out.

TABLE 8

| | | | | |
|---|---|---|---|---|
| RSAD2 | PTTG1 | DCK | ST3GAL1 | RBM7 |
| IFIT2 | OAS1G | RHBDF2 | MAMLD1 | H2-M2 |
| IFI204 | USP25 | IRF1 | TIFA | F10 |
| CMPK2 | IGTP | TMEM2 | FAS | RASA2 |
| IFIT1 | SETDB2 | H2-T10 | SCARF1 | ICOSL |
| IFI203 | PML | CCL3 | NDRG1 | TSHZ1 |
| PYHIN1 | CCL4 | PRPF38A | MED21 | IRG1 |
| RTP4 | DHX58 | TMCC3 | CCNL1 | THBS1 |
| TRIM30D | LAP3 | MOV10 | SLC7A11 | SLC16A10 |
| USP18 | GBP3 | AFF1 | IL12RB2 | GPR84 |
| IFI47 | EHD4 | CFLAR | 2310016C08RIK | MEF2A |
| MNDAL | NMI | AZI2 | SGMS2 | PPP1R15A |
| GM12250 | ETNK1 | MS4A6D | SLC25A25 | CXCL2 |

TABLE 8-continued

| | | | | |
|---|---|---|---|---|
| IFI27L2A | CD69 | ADAP2 | SLC7A2 | CCR7 |
| SLFN8 | TOR1AIP1 | A230046K03RIK | INPP5B | TRAF1 |
| SLFN5 | MTHFR | STARD3 | CDYL2 | 9030425E11RIK |
| IRGM1 | CASP11 | GBP9 | SLC25A37 | SERPINB9 |
| OAS1A | TREX1 | IL18 | SVCT2 | TNIP1 |
| NT5C3 | IRF9 | XKR8 | IL1A | MT2 |
| IFI205 | ATF3 | RNF114 | CD44 | SAMSN1 |
| OASL2 | FRMD4A | TFG | SPIC | PRDX1 |
| PARP14 | 2810474O19RIK | GM5431 | TOP1 | 1200009I06RIK |
| GM4951 | GM14446 | SGCB | FAM129A | LRRK2 |
| MX1 | TMEM106A | TMEM140 | AP4B1 | RPS6KA2 |
| GM8979 | PNP | CISH | TNF | TREM1 |
| IFIT3 | IL27 | FBXW17 | TRMT61B | TNFSF9 |
| XAF1 | LGALS9 | UBA7 | PVR | MMP14 |
| AI607873 | SLFN9 | IRF8 | GPR85 | CXCL3 |
| AK172683 | SLFN1 | AK138792 | HIPK2 | MFLJ00294 |
| GM4902 | DDHD1 | MLKL | EHD1 | MARCKSL1 |
| AA467197 | NOS2 | MITD1 | NFKBIA | TIMP1 |
| TRIM30A | AIDA | SMG7 | ARHGAP31 | TLR6 |
| D14ERTD668E | IFI44 | AK035387 | NFKBID | STK38L |
| IL15 | FNDC3A | MPP1 | AMN1 | PTAFR |
| IRF7 | 9230105E10RIK | NAMPT | 3110043O21RIK | EGR1 |
| CXCL10 | IL18BP | KATNA1 | PIK3AP1 | BPAG1 |
| AK217941 | G530011O06RIK | ISG20 | SKIL | KLF7 |
| IFITM3 | KYNU | TIPARP | CD83 | RNASET2B |
| ZBP1 | SAT1 | TLR3 | DNAJB4 | IRF4 |
| DDX58 | AK142678 | MITF | GTF2B | TXNRD1 |
| GBP2 | MS4A6C | OSM | CCRN4L | NLRP3 |
| H2-T23 | SP140 | TGIF1 | SERPINB2 | ACSL1 |
| MPA2L | TRIM34 | CST7 | CALCRL | SERPINB9B |
| HERC6 | I830012O16RIK | SMIF | CLCN7 | MMP13 |
| IIGP1 | BC147527 | PPP1CB | BRAF | LY6I |
| DAXX | CCND2 | CFB | LY6A | CLEC4D |
| LGALS3BP | BC006779 | RNF2 | PLAGL2 | ST8SIA4 |
| EIF2AK2 | AFTPH | MCMBP | SLC39A14 | BC035044 |
| PARP9 | RASA4 | AOAH | PLA2G4A | ZSWIM4 |
| TAP1 | FGL2 | ARHGEF3 | EBI3 | IER3 |
| SLAMF7 | ISG15 | CCL22 | LMO4 | ATXN7L1 |
| STAT2 | GBP4 | INTS12 | RAB20 | CD14 |
| BST2 | CLIC4 | NCOA7 | NUDT17 | ALDH1A2 |
| AW112010 | SLC25A22 | 1600014C10RIK | METRNL | FOSL2 |
| GVIN1 | AIM1 | FOS | SGK1 | GPD2 |
| SP100 | ADAR | MPP5 | PSTPIP2 | CLEC4E |
| STAT1 | MINPP1 | 1810029B16RIK | FAM108C | SGMS1 |
| GBP6 | PPM1K | ETS2 | PPP1R10 | UBE2Q2 |
| SAMD9L | FAM46A | NUP54 | LASS6 | SERPINB6B |
| MX2 | CD274 | MET | CRBN | CAR2 |
| ZUFSP | F830016B08RIK | MCOLN2 | P2RY13 | EGR2 |
| IFIH1 | SGK3 | AK178429 | BC031781 | GRAMD1B |
| TRIM5 | REL | HIST3H2A | IFRD1 | KLF3 |
| BCL2A1B | PLEKHF2 | SLC3A2 | HMGN3 | CIAPIN1 |
| E030037K03RIK | TMEM184B | PPP2R5A | RALGDS | SPATA13 |
| IFI35 | GNB4 | ARID5B | JARID2 | IRAK3 |
| MS4A4C | LARP1 | RNF19A | PLSCR1 | APOL7C |
| TNFSF15 | PGAP2 | VWA5A | CPD | NIACR1 |
| DTX3L | 5-Mar | ANXA7 | MALT1 | CXCL1 |
| PHF11 | IL7R | RFFL | NFKBIB | PTGES |
| TOR3A | 9930111J21RIK1 | PPAP2B | TPR | LY6C2 |
| RND3 | RIN2 | MARCO | MKI67 | ORAI2 |
| TRIM25 | OAS2 | RAB10 | APBB2 | CLU |
| IRGM2 | MAFK | JHDM1D | FLRT3 | PTPRE |
| PARP12 | PSMB9 | IFT172 | TGM2 | C5AR1 |
| OAS3 | CH25H | RABGEF1 | TARM1 | LCN2 |
| OASL1 | KPNA3 | NRP2 | MKIAA0769 | ARG2 |
| DDX60 | PCGF5 | INHBA | SLC20A1 | SLPI |
| MXD1 | RAP2C | SNX10 | AK042010 | IL1F9 |
| SAMHD1 | MBNL2 | PLK3 | GNG12 | PTX3 |
| RNASET2A | PARP11 | TNFAIP2 | DUSP16 | CD38 |
| NLRC5 | FAM26F | BIRC6 | PILRA | GM6644 |
| ZNFX1 | 4930523C07RIK | PPP4R2 | BHLHE40 | SAA3 |
| BCL2A1D | PELI1 | FPR2 | FPR1 | SOD2 |

In some embodiments, the target gene is interferon production regulator (IFNR). In some embodiments, the modulating agent alters the expression, activity and/or function of IFNR. In some embodiments, the modulating agent alters the expression, activity and/or function of a gene that is associated with IFNR, such as, by way of non-limiting example, a gene from those shown in Table 9 below. The underlined genes in Table 9 are genes that are upregulated when IFNR absent, e.g., knocked out, and the non-underlined genes are genes that are down-regulated when IFNR is absent, e.g., knocked out.

TABLE 9

| | | | | |
|---|---|---|---|---|
| ACSL1 | IRG1 | OSM | FNDC3A | LGALS3BP |
| RPS6KA2 | SGK1 | APBB2 | <u>HSPA5</u> | PRPF38A |
| SLPI | SERPINB9B | GTF2B | <u>IL18</u> | TMCC3 |
| PTPRE | MFSD7 | LCP2 | <u>XRN1</u> | <u>9030625A04RIK</u> |
| PTX3 | KTN1 | SLC3A2 | <u>SAT1</u> | VCAN |
| LYZ1 | TIFA | JARID2 | <u>P4HA1</u> | <u>OAS1G</u> |
| PMP22 | IFNB1 | RCAN1 | <u>USP25</u> | <u>BC147527</u> |
| CXCL2 | LY6C2 | TMEM167B | <u>TMEM184B</u> | <u>HERC6</u> |
| IER3 | ARG2 | FLRT3 | <u>BCL2A1D</u> | <u>CD47</u> |
| CLEC4E | CCL7 | MDM2 | <u>F830016B08RIK</u> | <u>APOBEC3</u> |
| CXCL1 | PIP5K1A | VCAM1 | <u>AZI2</u> | <u>AW112010</u> |
| MALT1 | RGL1 | TLR1 | <u>SLFN2</u> | <u>MXD1</u> |
| LMO4 | NUP54 | ZCCHC2 | <u>MINPP1</u> | <u>IGTP</u> |
| TXNRD1 | HIF1A | CCNL1 | <u>ATF3</u> | <u>BC013712</u> |
| IFRD1 | SH3BP5 | KLF7 | <u>LARP1</u> | <u>PGAP2</u> |
| TNF | PLAT | MFLJ00294 | <u>SP140</u> | <u>SETDB2</u> |
| 9030425E11RIK | 6330409N04RIK | INPP5B | <u>UBE2L6</u> | <u>PML</u> |
| CD38 | GRAMD1B | FAM102B | <u>AK142678</u> | <u>ZNFX1</u> |
| EGR2 | MMP14 | 3110043O21RIK | <u>BFAR</u> | <u>LAP3</u> |
| BC031781 | PPFIA1 | NFKBIA | <u>TRIM5</u> | <u>PARP12</u> |
| SLC20A1 | FAM46C | TNFAIP2 | <u>IRF8</u> | <u>GBP3</u> |
| INHBA | GPR84 | TRIM13 | <u>TFG</u> | <u>ADAP2</u> |
| METRNL | 1200009I06RIK | CRBN | <u>KPNA3</u> | <u>GVIN1</u> |
| PLK2 | ST8SIA4 | PSTPIP2 | <u>ZC3H7A</u> | <u>SLFN9</u> |
| 1190002H23RIK | PLEKHO2 | PLAGL2 | <u>P2RY14</u> | <u>EIF2AK2</u> |
| ZSWIM4 | RFFL | GCNT2 | <u>NAMPT</u> | <u>KYNU</u> |
| LRP12 | DNAJB4 | THBS1 | <u>IKZF1</u> | <u>IRGM2</u> |
| CXCL3 | SLC7A2 | AK200837 | <u>NUB1</u> | <u>ZUFSP</u> |
| CCL2 | FAM108C | TPR | <u>MYD88</u> | <u>AI607873</u> |
| FABP3 | ARHGAP31 | NFKB1 | <u>FAM26F</u> | <u>MPA2L</u> |
| RASA2 | OLR1 | ZEB2 | <u>AFF1</u> | <u>A230046K03RIK</u> |
| MKIAA0769 | RABGEF1 | CDYL2 | <u>PPM1K</u> | <u>OAS3</u> |
| ALDH1A2 | F10 | MED21 | <u>9930111J21RIK1</u> | <u>IFI204</u> |
| SPIC | HIPK2 | STK38L | <u>EHD4</u> | <u>MX2</u> |
| TSHZ1 | UPP1 | ARID5B | <u>BBX</u> | <u>E030037K03RIK</u> |
| MT2 | PVR | MBNL2 | <u>SAMD9L</u> | <u>FGL2</u> |
| PPP1R15A | IRAK-2 | TLR6 | <u>ETV3</u> | <u>DTX3L</u> |
| PRDX1 | SQSTM1 | APPL1 | <u>UBA7</u> | <u>MS4A6C</u> |
| MET | TLR2 | CHAC2 | <u>PLEKHF2</u> | <u>PARP14</u> |
| FBXO30 | AK217941 | DCBLD2 | <u>CCDC86</u> | <u>IFI35</u> |
| MMP13 | PLA2G4A | RNASET2B | <u>TCF4</u> | <u>1110018G07RIK</u> |
| PDPN | CD200 | FRMD4B | <u>IL15RA</u> | <u>IL12B</u> |
| CLEC4D | IL20RB | H3F3B | <u>KTELC1</u> | <u>TOR3A</u> |
| CD44 | H2-M2 | OSBPL3 | <u>I830012O16RIK</u> | <u>NLRC5</u> |
| MCOLN2 | DENND3 | GTPBP2 | <u>LNPEP</u> | <u>TOR1AIP1</u> |
| SGMS1 | RNASET2A | <u>AK163331</u> | <u>DYNC1I2</u> | <u>AK172683</u> |
| TNFAIP3 | JHDM1D | <u>RNF114</u> | <u>ISG15</u> | <u>ETNK1</u> |
| ADORA2B | CLCN7 | <u>BIRC3</u> | <u>MTHFR</u> | <u>LGALS9</u> |
| 2310016C08RIK | ELL2 | <u>TNIP3</u> | <u>RND3</u> | <u>MS4A4C</u> |
| RALGDS | RNF19A | <u>ISG20</u> | <u>GBP4</u> | <u>ZBP1</u> |
| SPATA13 | LASS6 | <u>MORC3</u> | <u>5730508B09RIK</u> | <u>GBP2</u> |
| ORAI2 | IFT172 | <u>KATNA1</u> | <u>TAGAP</u> | <u>SLFN5</u> |
| TNIP1 | H2-Q7 | <u>FRMD4A</u> | <u>SLAMF7</u> | <u>CCND2</u> |
| RBM7 | SLC39A14 | <u>PSMB10</u> | <u>STXBP3A</u> | <u>PTTG1</u> |
| BPAG1 | UBE2Q2 | <u>ANKRD17</u> | <u>RNF19B</u> | <u>TRIM25</u> |
| TOP1 | RAB12 | <u>TLR3</u> | <u>CD86</u> | <u>NMI</u> |
| MAPKAPK2 | CAV1 | <u>BTG2</u> | <u>CD14</u> | <u>DHX58</u> |
| AK050909 | LCN2 | <u>AK035387</u> | <u>PCGF5</u> | <u>GM8979</u> |
| OPTN | ANXA7 | <u>CCL22</u> | <u>GNB4</u> | <u>STAT1</u> |
| TNFSF9 | PPP4R2 | <u>AIDA</u> | <u>CPNE3</u> | <u>DDX58</u> |
| NUPR1 | FPR1 | <u>NFKB2</u> | <u>PARP11</u> | <u>TAP1</u> |
| CLU | PTAFR | <u>SERPINA3G</u> | <u>IFI205</u> | <u>PHF11</u> |
| PPAP2B | CAR2 | <u>SMG7</u> | <u>TRAFD1</u> | <u>IIGP1</u> |
| NRP2 | MKIAA0694 | <u>BCL2A1B</u> | <u>AFTPH</u> | <u>STAT2</u> |
| EGR1 | DENND5A | <u>ZFP800</u> | <u>IFI44</u> | <u>CXCL10</u> |
| SAA3 | TGM2 | <u>BCL2A1A</u> | <u>ZFP36</u> | <u>TRIM30A</u> |
| IRAK3 | NFKBIB | <u>EIF2C3</u> | <u>IL18BP</u> | <u>IRF7</u> |
| IL1A | IL12RB2 | <u>GM6548</u> | <u>WHSC1L1</u> | <u>CD69</u> |
| SOD2 | TIMP1 | <u>MAP2K1</u> | <u>ITGA5</u> | <u>DAXX</u> |
| KLF3 | ZC3H12C | <u>CEPT1</u> | <u>STARD3</u> | <u>SP100</u> |
| PLAUR | CCL3 | <u>GM5431</u> | <u>VCPIP1</u> | <u>XAF1</u> |
| U90926 | GM6377 | <u>TRIM26</u> | <u>MS4A6D</u> | <u>IFIT1</u> |

TABLE 9-continued

| | | | | |
|---|---|---|---|---|
| MARCKSL1 | CLN3 | XKR8 | IRF9 | IFIT3 |
| IRF4 | CAR4 | ITGA4 | TOR1AIP2 | GM4951 |
| SLC25A37 | ETS2 | TAPBP | DDX60 | D14ERTD668E |
| VCL | LRRK2 | TLE3 | ADAR | IRGM1 |
| MPP5 | GNG12 | RNF139 | FBXW17 | BCL2A1C |
| PLSCR1 | NDRG1 | FAM46A | PLA2G16 | SLFN8 |
| PTGES | ENC1 | AK139487 | SGK3 | TRIM30D |
| A130040M12RIK | TLR7 | PSME2 | PSMB9 | IL15 |
| P2RY13 | JUNB | TRA2A | CD80 | PYHIN1 |
| IL1F9 | SLC12A6 | PPA1 | 5-Mar | NT5C3 |
| LZTFL1 | SGMS2 | 4930523C07RIK | TNFSF15 | OASL2 |
| AK042010 | NUDT17 | IL10RA | DCK | IFI27L2A |
| GPD2 | ITGAV | NOD1 | OASL1 | OAS1A |
| SLC39A2 | SLC16A10 | B3GNT2 | 9230105E10RIK | RTP4 |
| FAM20C | RNF2 | MAF | MITD1 | GM12250 |
| ATXN7L1 | CCRL2 | H2-T10 | 2810474O19RIK | RSAD2 |
| AP4B1 | CPD | AIM2 | BST2 | CMPK2 |
| AK163103 | OSGIN2 | PNRC1 | SLC25A22 | IFI47 |
| ACPP | APOL7C | CCNG2 | PARP8 | IFITM3 |
| DAB2 | AK178429 | REL | SAMHD1 | GM4902 |
| SERPINB6B | LY6I | RIN2 | TREX1 | USP18 |
| CALCRL | GM14047 | CASP11 | GM14446 | MX1 |
| GM6644 | FOSL2 | DENND1B | BC006779 | IFIT2 |
| C5AR1 | NFKBID | DYNC1H1 | GBP6 | |
| SERPINB2 | PFKFB3 | GBP9 | SLFN1 | |
| MKI67 | ALCAM | MIER3 | PARP9 | |
| RAB20 | NLRP3 | OAS2 | IFI203 | |

In some embodiments, the target gene is one or more genes from those listed below in Table 10, Table 11 or Table 12. In some embodiments, the modulating agent alters the expression, activity and/or function of the target gene(s). The underlined genes in Table 10, Table 11 and/or Table 12 are genes that are upregulated when a target gene absent, e.g., knocked out, and the non-underlined genes are genes that are down-regulated when the target gene is absent, e.g., knocked out.

TABLE 10

| | | | | |
|---|---|---|---|---|
| IFIT2 | IRGM2 | H2-T23 | CLEC4E | TAPBPL |
| MX1 | SLC7A2 | STAT5A | GPR84 | NFKBIA |
| IFI47 | BC147527 | DENND4A | RHOB | RBM7 |
| TRIM30D | IFIH1 | GCA | RAB9 | RABGEF1 |
| ILI2B | GVIN1 | AK217941 | CSF1 | SOD2 |
| GM12250 | DDHD1 | PLEKHF2 | SMIF | ETS2 |
| PYHIN1 | KTELC1 | GM5431 | SBDS | RILPL2 |
| BTG1 | NAMPT | TNFSF8 | MKI67 | SLC16A10 |
| GM4951 | GM14446 | AK035387 | CASP3 | RHBDF2 |
| IFIT3 | IRF9 | 5-Mar | PFKP | TXNRD1 |
| IFIT1 | SLFN1 | PDZK1IP1 | GM14047 | DAB2 |
| GM4902 | SAMHD1 | MCMBP | TLR7 | BCL2L11 |
| CMPK2 | 1110018G07RIK | SLC25A22 | GRAMD1B | CCL7 |
| IL15 | FAM129A | MCA32 | RASA2 | BHLHE40 |
| NT5C3 | IGTP | PSME2 | UBR4 | KLF3 |
| GBP3 | APOBEC3 | SLC2A6 | CDC42EP4 | UBC |
| RSAD2 | STAT1 | PPM1K | PPP1R15B | NDRG1 |
| GBP5 | RIN2 | GYPC | PRKX | UPP1 |
| SLFN8 | HK2 | ZDHHC21 | GNG12 | FAM46C |
| TRIM30A | MS4A6D | PARP10 | SPATA13 | CLCN7 |
| AW112010 | CXCL16 | PNP2 | MMP14 | TGIF1 |
| CD40 | CD80 | IL6 | RARS | GTF2B |
| DTX3L | H3F3B | ALCAM | RNF31 | CDKN1A |
| USP18 | RND3 | NOD1 | SLC25A25 | SLC11A2 |
| OASL2 | RAB32 | SNX10 | CAV1 | MCOLN2 |
| GBP2 | IRF8 | PARP11 | PI4K2A | PLSCR1 |
| SKIL | ZUFSP | XKR8 | PENK | MALT1 |
| HERC6 | 9030625A04RIK | GBP9 | CLEC4D | CCRL2 |
| STAT2 | PML | P2RY14 | SGK1 | PTAFR |
| D14ERTD668E | MAF | CASP11 | GCNT2 | RGL1 |
| IIGP1 | SGK3 | SERPINB9 | UBE2Q2 | FOSL2 |
| XAF1 | BCL2A1A | CCR7 | METRNL | FABP3 |
| AA467197 | AK139528 | GLIPR2 | PLEKHN1 | NLRP3 |
| CCND2 | TMCC3 | STXBP3A | SPIC | ZFP36 |
| PARP9 | AIDA | FAM177A | HK3 | LCP2 |
| SLFN5 | CEPT1 | MORC3 | BCL2L1 | HIPK2 |

TABLE 10-continued

| | | | | |
|---|---|---|---|---|
| MS4A6C | PPP1CB | TRAFD1 | MKIAA1673 | IL1A |
| DHX58 | BIRC3 | RAP2C | PSTPIP2 | MPP5 |
| PARP12 | GBP4 | 9930111J21RIK1 | AK200837 | SERTAD2 |
| CCL22 | UBE2L6 | CPNE3 | AP4B1 | MAPKAPK2 |
| MS4A4C | VCAN | TMEM184B | SOCS3 | SQSTM1 |
| DDX58 | I830012O16RIK | KPNA3 | PPAP2B | ZCCHC2 |
| PHF11 | PLA2G16 | OAS1G | SLC25A37 | MEF2A |
| RTP4 | TNFAIP2 | CASP7 | MDM2 | CCL4 |
| CXCL10 | 4930523C07RIK | TBC1D1 | SLC3A2 | PLAGL2 |
| GBP6 | AI607873 | ETNK1 | PILRA | ARG2 |
| IFI204 | FPR2 | BC013712 | STAT3 | RPS6KA2 |
| ADAP2 | PTTG1 | IFI203 | ZC3H12C | LRP12 |
| JAK2 | USP25 | AY096003 | LASS6 | NUP54 |
| SDC4 | NOTCH2 | TMEM67 | PRDM1 | NFKBID |
| IFITM3 | NUP62-IL4I1 | 1600014C10RIK | TLR2 | HSPA5 |
| DDX60 | MINA | MTHFR | SLC7A8 | CPEB4 |
| SLFN9 | SLFN2 | MINPP1 | FAM53C | 6330409N04RIK |
| KYNU | BLNK | NCOA7 | ARHGAP31 | CXCL1 |
| NLRC5 | TAGAP | SGCB | SGMS2 | ATF3 |
| MX2 | TNFRSF1B | KATNA1 | VCL | SLC20A1 |
| 9230105E10RIK | OAS3 | XRN1 | SEC24B | TOP1 |
| CD69 | PELI1 | AZI2 | NRP2 | PMP22 |
| PARP14 | TRIM34 | SAMD9L | NFKBIZ | NFKBIB |
| BCL2A1D | AK139487 | IL7R | OSM | INHBA |
| GM8979 | IL27 | ISG15 | IL1F9 | PLEKHO2 |
| IFI205 | ZNFX1 | CCDC25 | IFNB1 | FAM20C |
| BCL2A1B | OAS1A | GPR141 | TNFSF4 | NPY |
| E030037K03RIK | MNDAL | TMCO3 | TNIP1 | SERPINB2 |
| AFTPH | RNASET2A | GBGT1 | OSGIN2 | ZSWIM4 |
| ARL5C | MAP2K1 | 4930453N24RIK | PGF | PLK3 |
| FAM102B | FAM26F | SERTAD3 | SLC39A2 | FBXO30 |
| FGL2 | CD86 | PPFIA1 | MET | PTX3 |
| IRF7 | INSIG1 | F10 | TNFAIP3 | PIP5K1A |
| OASL1 | MARCKSL1 | GNA13 | PVR | IFRD1 |
| AK138792 | IFI44 | GYK | A130040M12RIK | MMP13 |
| CCL5 | DAXX | LGALS9 | PRDX1 | FLRT3 |
| NFKB1 | ST3GAL5 | AIM2 | THBS1 | IRF4 |
| SLCO3A1 | RAB8B | IL20RB | OLR1 | GM6644 |
| TNFSF15 | BIRC6 | REL | MAFK | 2310016C08RIK |
| ITGA4 | EBI3 | 3110001I22RIK | IL12RB2 | PTPRE |
| ZBP1 | BBX | AK042010 | TRIM13 | CISH |
| AK142678 | A230046K03RIK | AKNA | ARID5B | DNAJB4 |
| SP100 | 2010106G01RIK | IRAK3 | MFLJ00294 | TGM2 |
| SMG7 | MTPN | CD38 | TNFSF9 | JUNB |
| TCF4 | NOS2 | TMEM219 | PDPN | MT2 |
| CD47 | CD83 | AK178429 | MAMLD1 | PLK2 |
| NMI | SP140 | P2RY13 | EXPI | BC031781 |
| F830016B08RIK | GNB4 | ELL2 | 9030425E11RIK | CCL3 |
| TAP1 | MITD1 | CD180 | AK050909 | TNF |
| PARP8 | IL18BP | PTGES | IL1RN | RALGDS |
| PCGF5 | IKZF1 | NFIL3 | RCAN1 | CAR2 |
| IL15RA | BST2 | OLFR110 | TRMT61B | PLAUR |
| MPA2L | PVRL2 | PROCR | RNF2 | EGR2 |
| TRIM5 | OAS2 | PHC2 | RAB20 | PPP1R15A |
| TOR1AIP1 | MMP25 | NIACR1 | PIK3AP1 | CXCL2 |
| 9430076C15RIK | ADAR | ZC3HAV1 | CCRN4L | IER3 |
| UBA7 | IL18 | ADORA2B | DUSP1 | CCL2 |
| EIF2AK2 | IFI35 | LY6C2 | OPTN | 1190002H23RIK |
| SAT1 | PSMB9 | INTS12 | TNIP3 | |
| IRGM1 | DRAM1 | ORAI2 | PTGS2 | |
| 2810474O19RIK | TLR3 | NUB1 | SLPI | |
| TOR3A | MOV10 | SERPINB9B | RASGEF1B | |
| TARM1 | ICOSL | ARF4 | SGMS1 | |

TABLE 11

| | | | | |
|---|---|---|---|---|
| SAA3 | H1F0 | DDX60 | IRF4 | GTF2B |
| MARCO | TSHZ1 | APOBEC3 | PRKX | PHC2 |
| LMO4 | TCF4 | RND3 | RAB9 | PFKP |
| BCL2A1C | SWAP70 | SLC12A6 | GBP9 | RANBP2 |
| MS4A6C | MAF | ARHGEF3 | GCNT2 | MCOLN2 |
| HCK | BC147527 | BCL2A1D | MTMR7 | LYZ1 |
| BLNK | TRIM34 | PNPT1 | MEF2A | AMN1 |
| AOAH | IFI205 | VCAN | ARL5C | IL1B |
| NUP62-IL4I1 | PSTPIP2 | DHX58 | TNFSF4 | EHD4 |
| BIRC3 | BC013712 | BC006779 | 6330409N04RIK | ZCCHC2 |
| MX1 | PPP1CB | ORAI2 | SLC11A2 | NAA25 |

TABLE 11-continued

| | | | | |
|---|---|---|---|---|
| 9030625A04RIK | SEMA6D | ZC3H7A | NFKB2 | IFI203 |
| TRIM30A | TARM1 | GM14005 | LRRK2 | MXD1 |
| AW112010 | AK139528 | IRGM2 | SCO1 | NPY |
| MMP14 | JAK2 | SLFN5 | SMIF | REL |
| FPR2 | OAS1A | CFB | SGK1 | CSF1 |
| DRAM1 | UBA7 | ITGAV | CLEC4D | SERPINA3G |
| STAT2 | GM12250 | TMEM106A | FAM53C | IL23A |
| EBI3 | PARP10 | MITF | HSPA5 | PIP5K1A |
| SLFN8 | MINA | ARFGEF1 | HK2 | CCL17 |
| USP18 | IRAK3 | MKI67 | NCK1 | MNDAL |
| OSBPL3 | UBXN2A | BST2 | ZC3HAV1 | TNIP3 |
| ST3GAL5 | IRF9 | NUDT17 | SERPINB2 | MDM2 |
| IKZF1 | AIDA | FNDC3A | CCNG2 | BHLHE40 |
| SLCO3A1 | DYNC1I2 | TAPBP | GNA13 | UBE2Q2 |
| SNX10 | ZEB2 | PYHIN1 | CHD1 | OPTN |
| GPR141 | TLR1 | PPM1K | H2-Q7 | 4930453N24RIK |
| MYD88 | TRIM30D | NAMPT | TTC39B | H3F3B |
| LASS6 | IFIT1 | JHDM1D | STAT5A | 9030425E11RIK |
| PIK3R5 | FILIP1L | CCND2 | GOLGA3 | SAT1 |
| NFKB1 | MTMR14 | TAGAP | OSGIN2 | OSM |
| CPD | AK139487 | GNG12 | METRNL | FBXL3 |
| CD38 | INPP5B | NRP2 | HK3 | RNF2 |
| STAT1 | PCGF5 | CAR13 | PTPRE | PENK |
| A230046K03RIK | 3110043O21RIK | CHAC2 | PLA2G4A | LRP12 |
| RAB10 | SLFN9 | NLRC5 | SGCB | 3110001I22RIK |
| FAM129A | XRN1 | MS4A6B | SLC3A2 | RALGDS |
| RAB32 | ADAR | SP100 | SAMHD1 | KLF6 |
| IL12B | TNFRSFIB | NUP54 | FCGR1 | FBXO30 |
| BATF | IFI47 | PARP8 | ANKRD57 | GM14047 |
| SLC16A10 | MFSD7 | P2RY14 | LYRM1 | RPS6KA2 |
| DTX3L | DDHD1 | IFI35 | IQSEC2 | SLC39A2 |
| FPR1 | PVRL2 | FAM46A | IL18BP | ARG2 |
| STXBP3A | C5AR1 | GBP3 | ANXA7 | MAFK |
| TNIP1 | CLN3 | D14ERTD668E | SLC7A11 | DNAJB4 |
| GPR84 | CASP7 | IL13RA1 | FOS | SLC20A1 |
| 1200009I06RIK | MAP2K1 | GLIPR2 | NFIL3 | MET |
| PARP9 | DENND4A | CLEC4E | HIF1A | MMP13 |
| SLC2A6 | PSME1 | FBXW17 | PLEKHN1 | MT2 |
| PSMB10 | TLR2 | CMPK2 | SLC15A3 | CCRN4L |
| ICOSL | CCL5 | CCR7 | CASP3 | FABP3 |
| PALM2 | ATXN7L1 | CXCL3 | PLEKHO2 | TNF |
| CCDC86 | MS4A4C | TRIM25 | BPAG1 | IL1RN |
| TMCC3 | ZBP1 | PPP4R2 | PTX3 | SLPI |
| CXCL16 | DNAJB6 | TET2 | IFT172 | EGR1 |
| HERC6 | CLIC4 | F10 | CIAPIN1 | SQSTM1 |
| FAM102B | EPSTI1 | SLC39A14 | DCK | ATF3 |
| IRGM1 | TBC1D1 | MKIAA0694 | RCAN1 | CDKN1A |
| PSME2 | MX2 | SP140 | SERPINB9B | PPP1R15A |
| ACPP | BC035044 | ANKRD17 | OLR1 | FAM46C |
| AK150559 | IL6 | CD69 | TRIM13 | AK050909 |
| CD40 | H2-M2 | KYNU | BBX | IFRD1 |
| SAMSN1 | SH3BP5 | PLAT | SGMS1 | TGIF1 |
| NMI | PNP | SEPW1 | MKIAA1673 | NLRP3 |
| RTP4 | TBK1 | SOCS3 | PMAIP1 | FOSL2 |
| LCN2 | IRF7 | SLC25A22 | FAM82A2 | NDRG1 |
| TOR1AIP1 | RNF114 | MED21 | ARID5B | LAP3 |
| GBP5 | APOL7C | RNF34 | CD274 | CCL7 |
| IL18 | EHD1 | PTTG1 | INSIG1 | RGS1 |
| PARP14 | CLCN7 | IL15RA | TIPARP | CXCL1 |
| MARCKSL1 | DDX58 | LRCH1 | SLFN1 | A130040M12RIK |
| TRAF1 | GPD2 | RNASET2B | TOP1 | DUSP1 |
| AKNA | IGTP | AFTPH | AP4B1 | BTG1 |
| FAM20C | TBC1D13 | TFG | ISG20 | A430084P05RIK |
| PTPRJ | TMEM39A | TNFSF9 | CARHSP1 | CAR4 |
| NCOA7 | TRIM26 | RNF135 | MIER3 | ZFP36 |
| GPR85 | FAS | TLE3 | TGM2 | PMP22 |
| USP25 | LY6C2 | PNRC1 | SERTAD2 | BC031781 |
| IFITM3 | PGAP2 | CCNL1 | TIMP1 | SRGN |
| SGK3 | PPP1R15B | AK163331 | SLFN3 | NFKBID |
| TOR3A | MKIAA1994 | RNF19A | PROCR | ZSWIM4 |
| KTELC1 | FTSJD2 | DENND3 | VCAM1 | UPP1 |
| ZNFX1 | ZUFSP | SLFN2 | 1830012O16RIK | JUNB |
| GADD45B | PLAGL2 | IL12RB2 | H2-T24 | CCL4 |
| 2010106G01RIK | XAF1 | PPAP2B | UBC | CAR2 |
| OASL2 | 1110038F14RIK | MCMBP | PRDM1 | EGR2 |
| TAPBPL | IL15 | BRAF | BTG2 | RABGEF1 |
| GBP2 | UBE2L6 | NFKBIB | RASGEF1B | H2-T23 |
| TAP1 | PSMB9 | MFLJ00294 | MERTK | IL1A |
| MTDH | LARP1 | TLR3 | RNF139 | DAB2 |
| EIF2C3 | AK138792 | THBS1 | IL1F9 | PTGS2 |

TABLE 11-continued

| | | | | |
|---|---|---|---|---|
| CD47 | EIF2AK2 | PDE4B | RGL1 | CISH |
| RELA | MCA32 | PFKFB3 | SCARF1 | CXCL2 |
| PARP12 | CD83 | DENND1B | GM6377 | FLRT3 |
| IFIH1 | ARMC8 | SBDS | TMEM67 | CCL2 |
| IRAK-2 | SEC24B | RAB20 | HIST3H2A | PLK3 |
| PILRA | DAXX | ARF4 | AK052414 | PDPN |
| TNFSF15 | MKIAA0769 | AA960436 | RFFL | CCL3 |
| ITGA4 | BCL2A1B | NOD1 | IF127L2A | IER3 |
| CCL22 | GTPBP2 | GNB4 | CPEB4 | G530011O06RIK |
| TRAFD1 | AK217941 | TREM1 | OAS3 | 2310016C08RIK |
| INFAIP2 | LZTFL1 | EXPI | 2810474O19RIK | INHBA |
| MS4A6D | PDZK1IP1 | CH25H | RHOB | PRDX1 |
| KPNA3 | MDFIC | ETS2 | A630001G21RIK | PLAUR |
| TIFA | ETNK1 | CD80 | HIPK2 | 1190002H23RIK |
| KLF7 | MTPN | LY75 | IL7R | PLK2 |
| TREX1 | ZDHHC21 | STAT3 | WARS | |

TABLE 12

| | | | | |
|---|---|---|---|---|
| MX1 | UBA7 | DENND1B | GNA13 | AMN1 |
| GBP3 | BC147527 | BIRC3 | MCOLN2 | SBDS |
| IFIT3 | BC006779 | XAF1 | ITGAV | CD14 |
| IL15 | GBP6 | CCR7 | NFKBID | H2-T23 |
| APOBEC3 | ACSL1 | INPP5B | ARID5B | SLC15A3 |
| CXCL10 | ZUFSP | 9230105E10RIK | SERPINB9B | CAV1 |
| GM12250 | GM4951 | PLEKHF2 | TOP1 | CCL7 |
| ITGA4 | FGL2 | SERPINA3G | RHOB | BCL2L11 |
| PYHIN1 | ZBP1 | P2RY14 | LCP2 | NFIL3 |
| ADAP2 | NOTCH2 | TMEM39A | GCNT2 | DNAJB4 |
| SNX10 | RIN2 | FCGR1 | UPP1 | TRIM13 |
| GBP5 | RTP4 | MXD1 | ALCAM | ETS2 |
| D14ERTD668E | 9030625A04RIK | BLNK | MAMLD1 | FABP3 |
| CMPK2 | APOL7C | CPNE3 | BRAF | HSPA5 |
| PSMB10 | NCOA7 | PML | NDRG1 | MET |
| AW112010 | D1ERTD622E | ETV3 | NLRP3 | CAR4 |
| STAT1 | RAB32 | KATNA1 | RGS1 | TREM1 |
| GM4902 | PCGF5 | DHX58 | CDKN1A | IL1A |
| GBP2 | HERC6 | TAGAP | U90926 | ZSWIM4 |
| IRF1 | MX2 | 5730508B09RIK | APPL1 | IL1RN |
| SLFN8 | XRN1 | RAP2C | MFLJ00294 | CPEB4 |
| TRIM30D | PARP9 | STXBP3A | SERTAD2 | TRMT61B |
| GPR141 | KYNU | CD38 | UBE2Q2 | SLC3A2 |
| ZNFX1 | PIK3R5 | EHD4 | MAP3K8 | LZTFL1 |
| I830012O16RIK | DDHD1 | SGK3 | TLR6 | CCRN4L |
| EPSTI1 | SETDB2 | TRAFD1 | SLC12A6 | SLPI |
| BCL2A1C | TBC1D1 | TOR3A | SLC25A25 | OSGIN2 |
| MS4A6C | H1F0 | GBP4 | TNFSF4 | CCL2 |
| IFI205 | TOR1AIP1 | JAK2 | TET2 | RABGEF1 |
| NLRC5 | RAB10 | C5AR1 | RNF2 | INSIG1 |
| TBC1D13 | PARP12 | MNDAL | 6330409N04RIK | CCL17 |
| USP18 | LRCH1 | RBM43 | DCBLD2 | OSM |
| IFIT2 | IFITM3 | TAPBPL | LRP12 | H2-T24 |
| BC013712 | MMP14 | DDX60 | DUSP1 | ARL5C |
| IKZF1 | DDX58 | BBX | NFKBIB | CAR2 |
| IIGP1 | PTPRJ | SLC25A22 | FSTL1 | CXCL3 |
| FPR2 | SLFN2 | TMEM2 | RAB20 | IRF4 |
| PHF11 | E030037K03RIK | DRAM1 | SCO1 | MMP13 |
| TRIM30A | PSME1 | RAB8B | 4930453N24RIK | PLK2 |
| GM14446 | NT5C3 | SERPINB9 | OLFR110 | MDM2 |
| FAM26F | EXT1 | AIM1 | EGR1 | CCL4 |
| PARP10 | FAM129A | TIFA | MAFK | FLRT3 |
| IFIT1 | GVIN1 | FNDC3A | FBXL3 | CISH |
| STAT2 | CCL5 | TLR3 | CHAC2 | FOSL2 |
| FILIP1L | FPR1 | AKNA | VNN3 | PPP1R15A |
| A230046K03RIK | MITF | TMCC3 | SPIC | BC031781 |
| RSAD2 | IL27 | FOS | GM14047 | ATF3 |
| MARCKSL1 | PPM1K | SP100 | IFRD1 | PRDX1 |
| UBE2L6 | DENND3 | FRMD4A | IFNB1 | NPY |
| NMI | PARP8 | RALGDS | UBC | BTG2 |
| 1600014C10RIK | TOR1AIP2 | MTPN | BPAG1 | 1190002H23RIK |
| IL15RA | GM8979 | RCAN1 | GTF2B | SRGN |
| CD40 | SLFN9 | CSF1 | TTC39B | EGR2 |
| DTX3L | MYD88 | CXCL1 | RND3 | DAB2 |
| IGTP | PSME2 | MTMR7 | NUP54 | PDPN |
| PARP14 | OASL1 | GM6644 | TGIF1 | PTPRE |
| SLFN5 | MOV10 | MPP5 | ARG2 | CXCL2 |
| CD69 | IFI203 | FAM53C | METRNL | PTGS2 |

TABLE 12-continued

| | | | | |
|---|---|---|---|---|
| IFI47 | EIF2AK2 | H3F3B | JUNB | BTG1 |
| LASS6 | AK150559 | NIACR1 | IER3 | IL1F9 |
| HCK | GLIPR2 | 2310004I24RIK | SLC39A2 | G530011O06RIK |
| SLC2A6 | SERPINB6B | MKIAA1673 | EXPI | IL1B |
| OASL2 | FBXW17 | NFKB2 | TIMP1 | A130040M12RIK |
| DAXX | MAF | PPP4R2 | SLC20A1 | FBXO30 |
| TAP1 | SWAP70 | PIP5K1A | PLEKHN1 | SQSTM1 |
| IRGM2 | SVCT2 | HK3 | FAM46C | PROCR |
| IRF8 | ZC3HAV1 | SLC39A14 | SLC11A2 | PLK3 |
| AK217941 | CCND2 | GRAMD1B | A430084P05RIK | CCL3 |
| PSMB9 | CD47 | MINA | RPS6KA2 | PLAUR |
| IRGM1 | MPA2L | MKI67 | CARHSP1 | 2310016C08RIK |
| | | | | INHBA |

The sensitivity of the techniques provided herein allows for the detection and definition of closely related subpopulations of cells. These techniques allow for the identification of gene response modules, e.g., signatures, which are selectively induced in distinct subsets of cells. Correlative analyses between single cells are useful in reconstructing cellular circuits and identifying regulators of these modules.

Recent molecular studies have revealed that, even when derived from a "homogenous" population, individual cells can exhibit significant differences in gene expression, protein levels, and phenotypic output (Spencer, S. L., Gaudet, S., Albeck, J. G., Burke, J. M. & Sorger, P. K. Non-genetic origins of cell-to-cell variability in TRAIL-induced apoptosis. Nature 459, 428-432, doi:10.1038/nature08012 (2009); Cohen. A. A. et al. Dynamic Proteomics of Individual Cancer Cells in Response to a Drug. Science 322, 1511-1516, doi:10.1126/science.1160165 (2008); Niepel, M., Spencer, S. L. & Sorger, P. K. Non-genetic cell-to-cell variability and the consequences for pharmacology. Curr. Opin. Chem. Biol. 13, 556-561, doi:10.1016/j.cbpa.2009.09.015 (2009); Sharma, S. V. et al. A chromatin-mediated reversible drug-tolerant state in cancer cell subpopulations. Cell 141, 69-80, doi:10.1016/j.cell.2010.02.027 (2010); Gascoigne, K. E. & Taylor, S. S. Cancer cells display profound intra- and interline variation following prolonged exposure to antimitotic drugs. Cancer cell 14, 111-122, doi:10.1016/j.ccr.2008.07.002 (2008), with important functional consequences (Spencer, S. L., Gaudet, S., Albeck, J. G., Burke, J. M. & Sorger, P. K. Non-genetic origins of cell-to-cell variability in TRAIL-induced apoptosis. Nature 459, 428-432, doi:10.1038/nature08012 (2009); Sharma, S. V. et al. A chromatin-mediated reversible drug-tolerant state in cancer cell subpopulations. Cell 141, 69-80, doi:10.1016/j.cell.2010.02.027 (2010); Gascoigne, K. E. & Taylor, S. S. Cancer cells display profound intra- and interline variation following prolonged exposure to antimitotic drugs. Cancer cell 14, 111-122, doi:10.1016/j.ccr.2008.07.002 (2008); Feinerman, O. et al. Single-cell quantification of IL-2 response by effector and regulatory T cells reveals critical plasticity in immune response. Molecular Systems Biology 6, 1-16, doi:papers2://publication/doi/10.1038/msb.2010.90 (2010)). Existing studies of cellular heterogeneity, however, have typically measured only a small number of pre-selected RNAs (Yu, M. et al. RNA sequencing of pancreatic circulating tumour cells implicates WNT signalling in metastasis. Nature 487, 510-513, doi:10.1038/nature11217 (2012); Raj, A., Rifkin, S. A., Andersen, E. & Van Oudenaarden, A. Variability in gene expression underlies incomplete penetrance. Nature 463, 913-918, doi:10.1038/nature08781 (2010)) or proteins simultaneously (Spencer, S. L., Gaudet, S., Albeck, J. G., Burke, J. M. & Sorger, P. K. Non-genetic origins of cell-to-cell variability in TRAIL-induced apoptosis. Nature 459, 428-432, doi:10.1038/nature08012 (2009); Cohen. A. A. et al. Dynamic Proteomics of Individual Cancer Cells in Response to a Drug. Science 322, 1511-1516, doi:10.1126/science.1160165 (2008); Niepel, M., Spencer, S. L. & Sorger, P. K. Non-genetic cell-to-cell variability and the consequences for pharmacology. Curr. Opin. Chem. Biol. 13, 556-561, doi:10.1016/j.cbpa.2009.09.015 (2009); Sharma, S. V. et al. A chromatin-mediated reversible drug-tolerant state in cancer cell subpopulations. Cell 141, 69-80, doi:10.1016/j.cell.2010.02.027 (2010); Gascoigne, K. E. & Taylor, S. S. Cancer cells display profound intra- and interline variation following prolonged exposure to antimitotic drugs. Cancer cell 14, 111-122, doi:10.1016/j.ccr.2008.07.002 (2008); Dalerba, P. et al. Single-cell dissection of transcriptional heterogeneity in human colon tumors. Nature Biotechnology 29, 1120-1127, doi:10.1038/nbt.2038 (2011); Bendall, S. C. & Nolan, G. P. Single-Cell Mass Cytometry of Differential Immune and Drug Responses Across a Human Hematopoietic Continuum. Science (New York, N.Y.) 332, 677-678, doi:10.1126/science.1206351 (2011), because genomic profiling method (Bendall, S. C. & Nolan, G. P. Single-Cell Mass Cytometry of Differential Immune and Drug Responses Across a Human Hematopoietic Continuum. Science (New York, N.Y.) 332, 677-678, doi:10.1126/science.1206351 (2011); Altschuler, S. J. & Wu, L. F. Cellular Heterogeneity: Do Differences Make a Difference? Cell 141, 559-563, doi:10.1016/j.cell.2010.04.033 (2010); Kalisky, T., Blainey, P. & Quake, S. R. Genomic Analysis at the Single-Cell Level. Annual review of genetics 45, 431-445, doi:papers2://publication/doi/10.1146/annurev-genet-102209-163607 (2011); Kalisky, T. & Quake, S. R. Single-cell genomics. Nature Methods 8, 311-314 (2011)) could not be applied to single cells until very recently (Islam. S. et al. Characterization of the single-cell transcriptional landscape by highly multiplex RNA-seq. Genome Research, doi:papers2://publication/doi/10.1101/gr.110882.110 (2011); Tang, F. et al. RNA-Seq analysis to capture the transcriptome landscape of a single cell. Nature Protocols 5, 516-535, doi:10.1038/nprot.2009.236 (2010); Tang, F. et al. mRNA-Seq whole-transcriptome analysis of a single cell. Nature Methods 6, 377-382, doi:10.1038/nmeth.1315 (2009); Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012); Hashimshony, T., Wagner, F., Sher, N. & Yanai, I. CEL-Seq: Single-Cell RNA-Seq by Multiplexed Linear Amplification. Cell Reports, doi:10.1016/j.celrep.2012.08.003). Here, single-cell RNA-Seq was used to investigate heterogeneity in the response of a model mammalian system, bone marrow derived dendritic cells (BMDCs) stimulated by lipopolysaccharide (LPS). Extensive, and previously unobserved, bimodal variation was discovered in both the abundance and splicing patterns of RNA transcripts, which were independently validated by RNA-fluorescence in situ hybridization of selected transcripts. In particular, hundreds of key immune genes are bimodally expressed across individual cells, surprisingly even for genes that are very highly expressed at the population average. Moreover, splicing patterns across single cells demonstrate previously unobserved levels of heterogeneity: for genes that have multiple splice isoforms at the population level, individual cells exhibit a bias towards predominant expression of one particular isoform. As shown by the Examples provided herein, these cell-to-cell differences are driven by heterogeneity in both cell state and cell circuit usage. While some of the bimodality reflects the presence of BMDCs in closely related, yet distinct, known maturity states, other bimodal patterns exist even within cells in the same maturity state, reflecting differences in the usage of key regulatory circuits between otherwise identical cells. For example, a module of 137 highly variable, yet co-regulated, antiviral response genes was identified. Using BMDCs from knockout mice, the studies presented herein demonstrate that bimodality in this antiviral module may be propagated through an interferon circuit involving the master antiviral transcriptional regulators Stat2 and Irf7. This study demonstrates the power and promise of unbiased single-cell genomics in uncovering extensive functional diversity between cells and in deciphering cell states and circuits.

Figure 19:
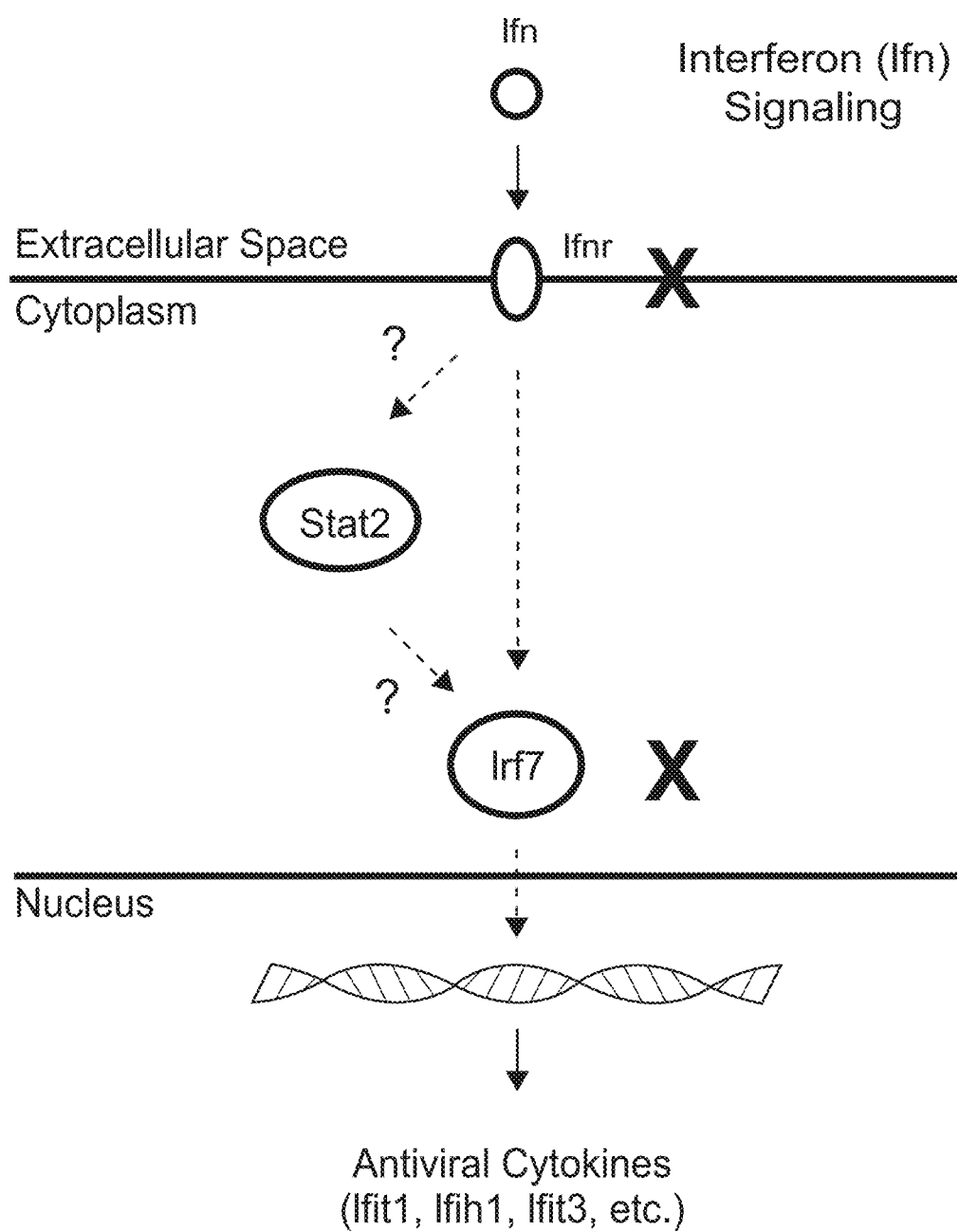
FIG. 19 is an illustration depicting a simple model for the identified antiviral circuit. X's represent points of perturbation. Ifn feedback drives expression of Irf7 and Stat2. Variability in the expression of Irf7 propagates to variability in the expression of antiviral genes, such as Ifit1. Stat2 is implicated as well, though its relation to Irf7 cannot be established by the current experiments.

The above analysis provides a proof-of-concept demonstrating how co-variation between transcripts across single cells in the same condition and overall state can help to identify and assemble regulatory circuits whose differential usage promotes significant cellular heterogeneity. Specifically, in the variable circuit (FIG. 19) interferon signaling is required for induction of Stat2 and Irf7, which, in turn, act to induce the variable antiviral cluster genes. The experiments do not definitively determine, however, which component of the circuit causes the observed heterogeneity per se. One compelling possibility is that upstream noise is propagated from the interferon-signaling pathway first to Stat2 and Irf7 and then to the target genes. This hypothesis is supported by the variation that was observed in Stat protein levels and nuclear localization. It is also supported by recent studies (Zhao, M., Zhang, J., Phatnani, H., Scheu, S. & Maniatis, T. Stochastic Expression of the Interferon-? Gene. PLoS biology 10, e1001249 (2012); Apostolou. E. & Thanos. D. Virus Infection Induces NF-kappaB-dependent interchromosomal associations mediating monoallelic IFN-beta gene expression. Cell 134, 85-96 (2008); Rand, U. et al. Multi-layered stochasticity and paracrine signal propagation shape the type-I interferon response. Molecular Systems Biology 8, doi:10.1038/msb.2012.17 (2012)) demonstrating that over expression of Irf7 during viral replication in mammalian cells reduces heterogeneity in Ifn-β production and that Irf7 translocation correlates with Ifn-β production under a viral stimulus. Notably, variability in the expression of interferon-stimulated genes (e.g., Isg15) and interferon-induced proteins that correlated strongly with the levels of Irf7 and Stat2 was also observed. This was not observed in previous studies with uniform Ifn-β stimulation (Zhao, M., Zhang, J., Phatnani, H., Scheu, S. & Maniatis, T. Stochastic Expression of the Interferon-β Gene. PLoS biology 10, e1001249 (2012)), supporting the hypothesis that variability in interferon feedback drives downstream heterogeneity.

Figure 20:
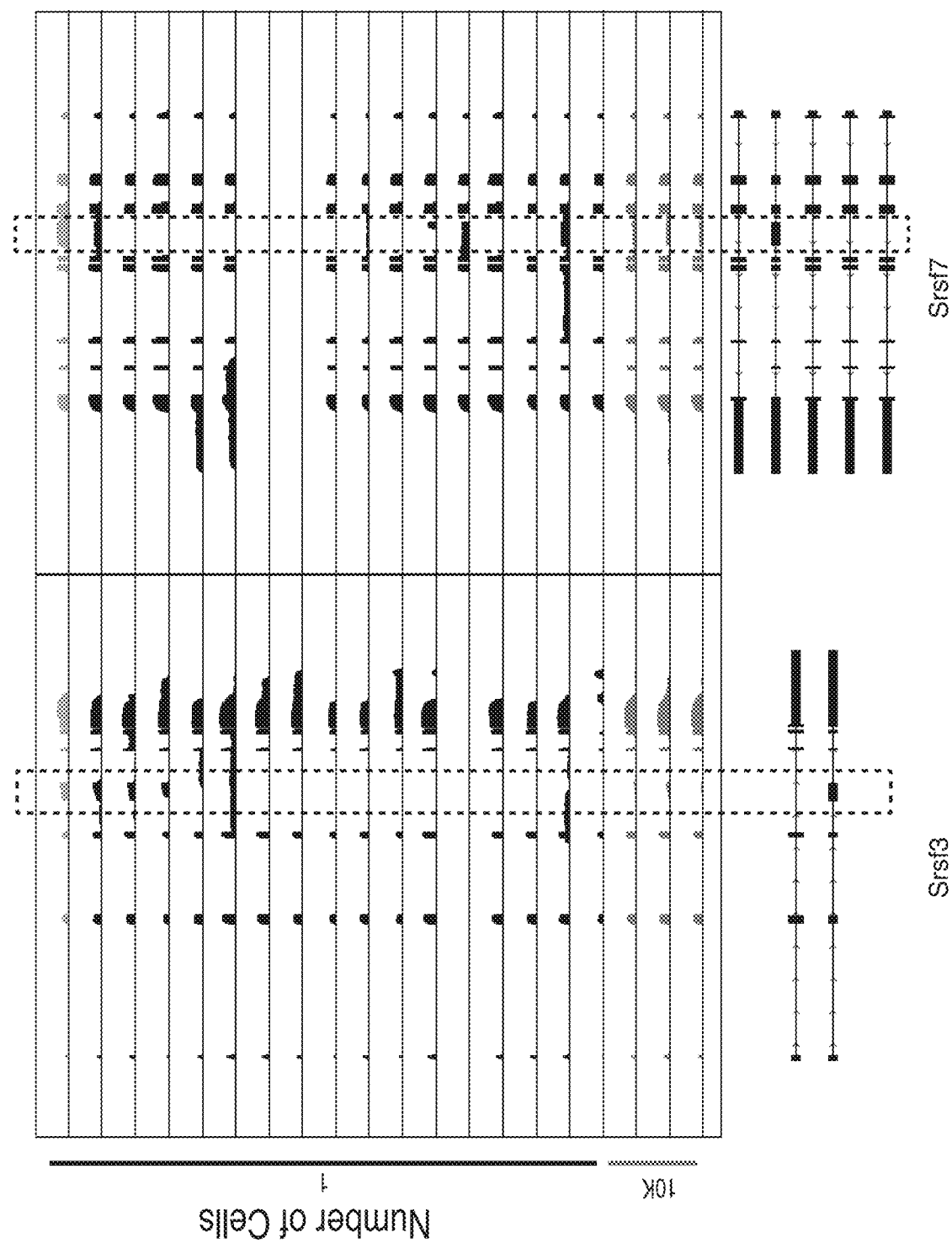
FIG. 20 is a graph depicting splicing patterns for 'poison' cassette exons of the splicing factors Srsf3 and Srsf7. Shown are the RNA-Seq read densities in each individual cell ('1', blue) and the population average ('10,000', grey) for two genes encoding the splicing factors Srsf3 and Srsf7, each of which is known to have an alternatively spliced poison cassette exon (dashed box). The known annotated isoforms for each gene is shown at the bottom. One cell, S13, highlighted in orange at the top, expressed only the Srsf3 and Srsf7 isoforms that contain the 'poisonous' exons. For each gene, 11 cells exclusively expressed the alternative isoform.

A similar strategy could potentially be used to explore the consequences of bimodality in splicing. Even looking at just 18 cells, interesting examples of bimodal splicing patterns were observed for genes whose isoforms have distinct functional consequences. For example, the splicing regulators Srsf3 and Srsf7 are each known to contain a "poison cassette exon", that, when included, targets the RNA for degradation via nonsense-mediated decay (Änkö, M.-L. et al. The RNA-binding landscapes of two SR proteins reveal unique functions and binding to diverse RNA classes. *Genome Biology* 13, doi:10.1186/gb-2012-13-3-r17 (2012)). While these exons are very weakly expressed at a population level, one of the single cells (cell S13, FIG. 20) exclusively expressed the poisoned isoforms at high levels (for both Srsf3 and Srsf7, 11 cells exclusively expressed the other). Since Srsf3 itself is responsible for increasing inclusion of its own poison cassette exon in a negative feedback loop (Änkö, M.-L. et al. The RNA-binding landscapes of two SR proteins reveal unique functions and binding to diverse RNA classes. *Genome Biology* 13, doi:10.1186/gb-2012-13-3-r17 (2012)), S13 may in fact represent the highest levels of Srsf3 activity. When armed with a larger number of cells, correlation analyses could be used to identify potential targets of Srsf3. Splicing differences in other regulatory genes, meanwhile, may further enhance expression diversity: for example, proteins encoded by different isoforms of Irf7—bimodally spliced in the cells (FIG. 3c)—differentially activate interferon-responsive genes in vitro (Ning, S., Huye, L. E. & Pagano, J. S. Regulation of the Transcriptional Activity of the IRF7 Promoter by a Pathway Independent of Interferon Signaling. *Journal of Biological Chemistry* 280, 12262-12270 (2005)). These examples suggest that heterogeneity in splicing may represent another potential layer of response encoding.

Figure 9A:
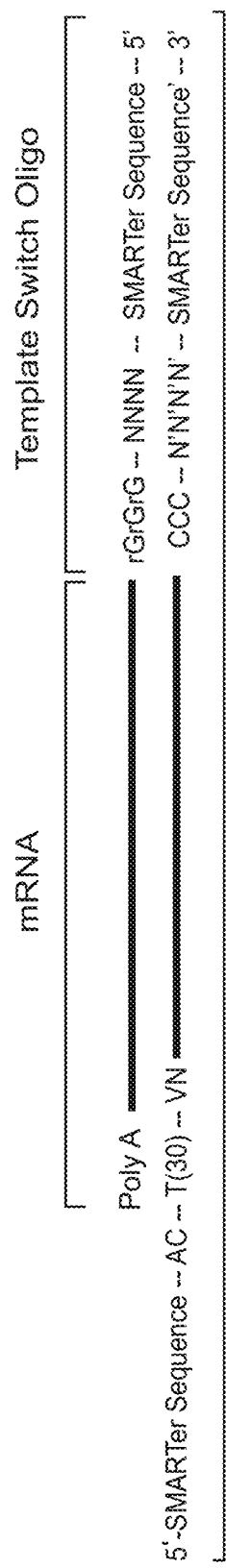
Figure 9B:
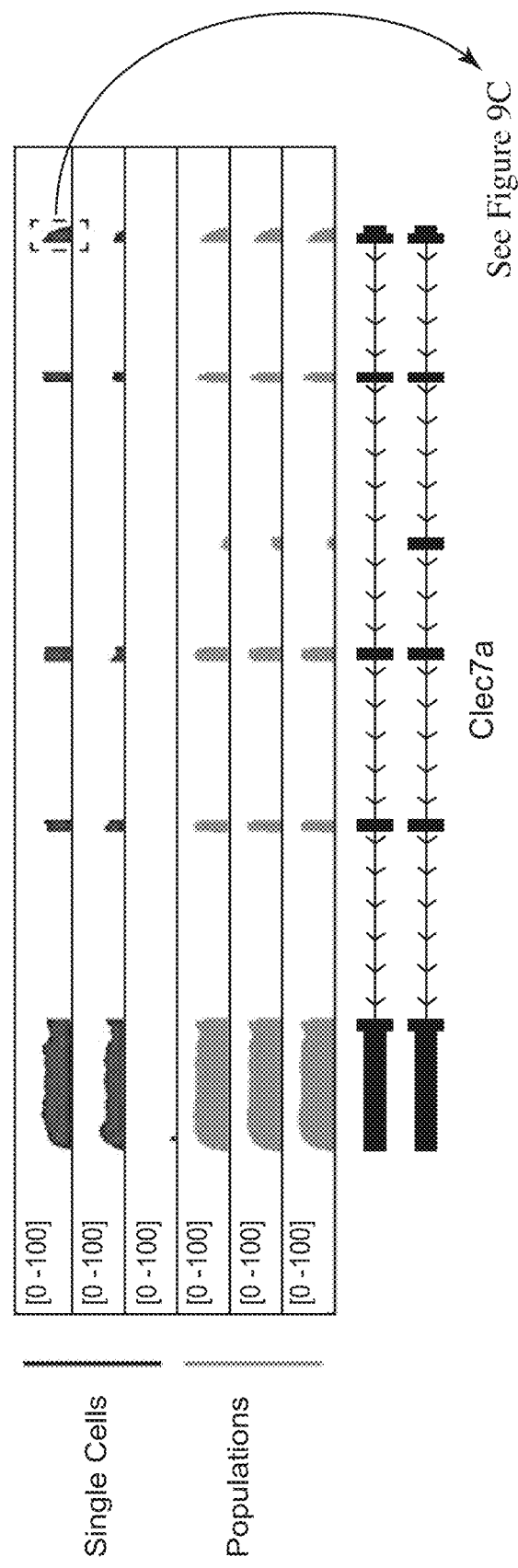
Figure 9D:
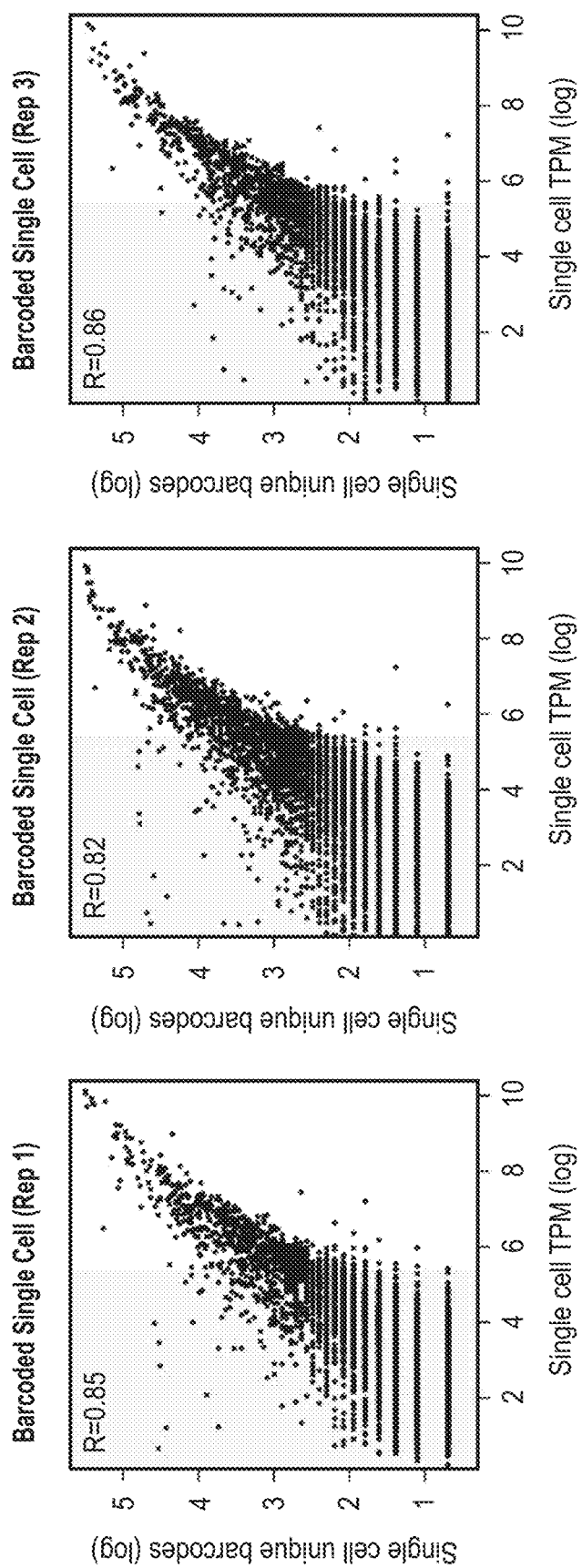
Figure 21:
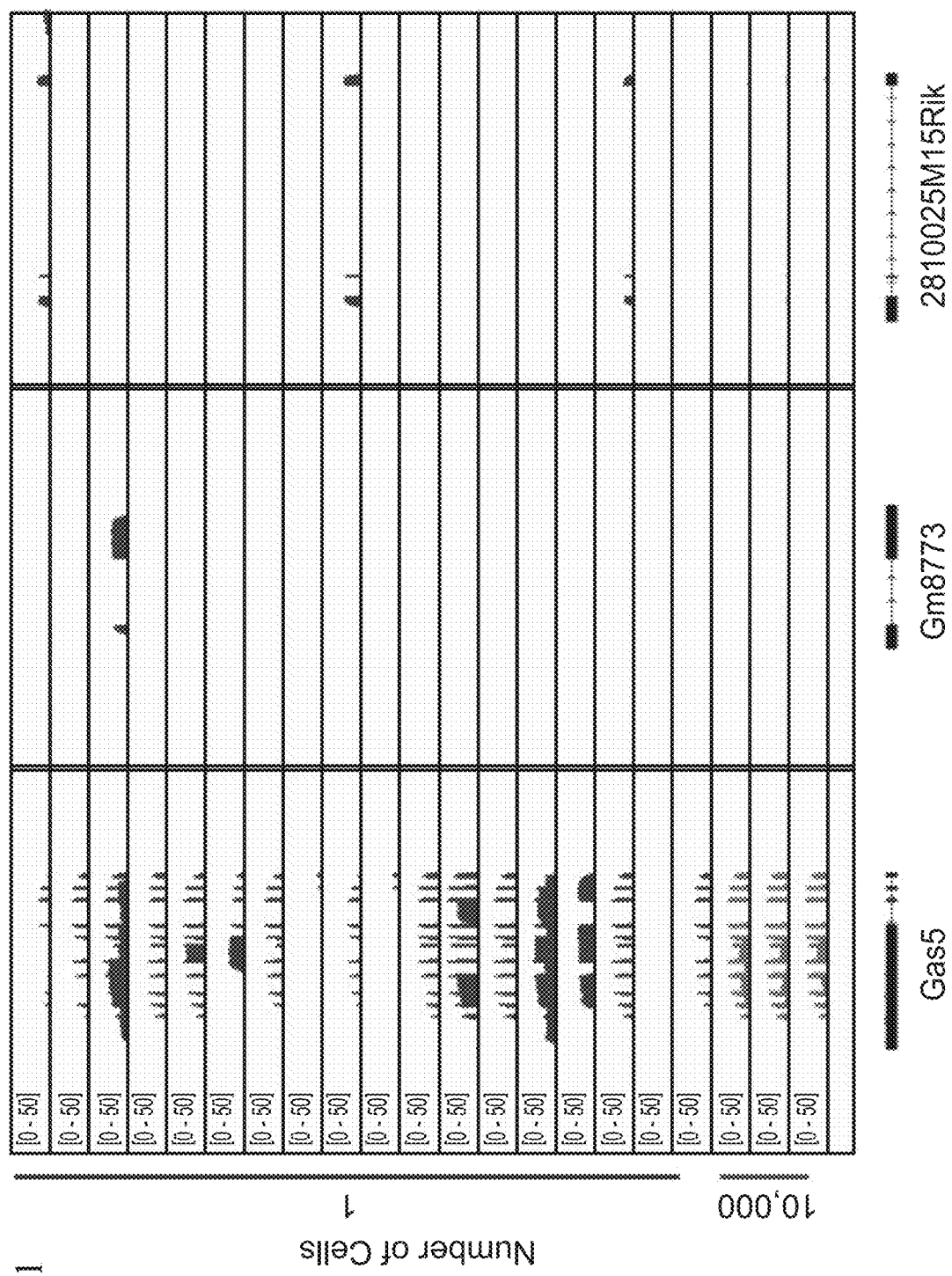
FIG. 21 is a graph depicting expression variation in long non-coding (Inc) RNAs. Shown are the RNA-Seq read densities in each individual cell ('1', blue) and the population average ('10,000', grey) for three previously annotated lncRNA genes. A lncRNA relatively highly expressed at the population level (Gas5, left), is bimodally expressed at the single-cell level. Two lncRNAs lowly expressed or undetectable at the population (Gm8773, 2810025M15Rik) are in fact significantly expressed in some individual cells.
Figure 9C:
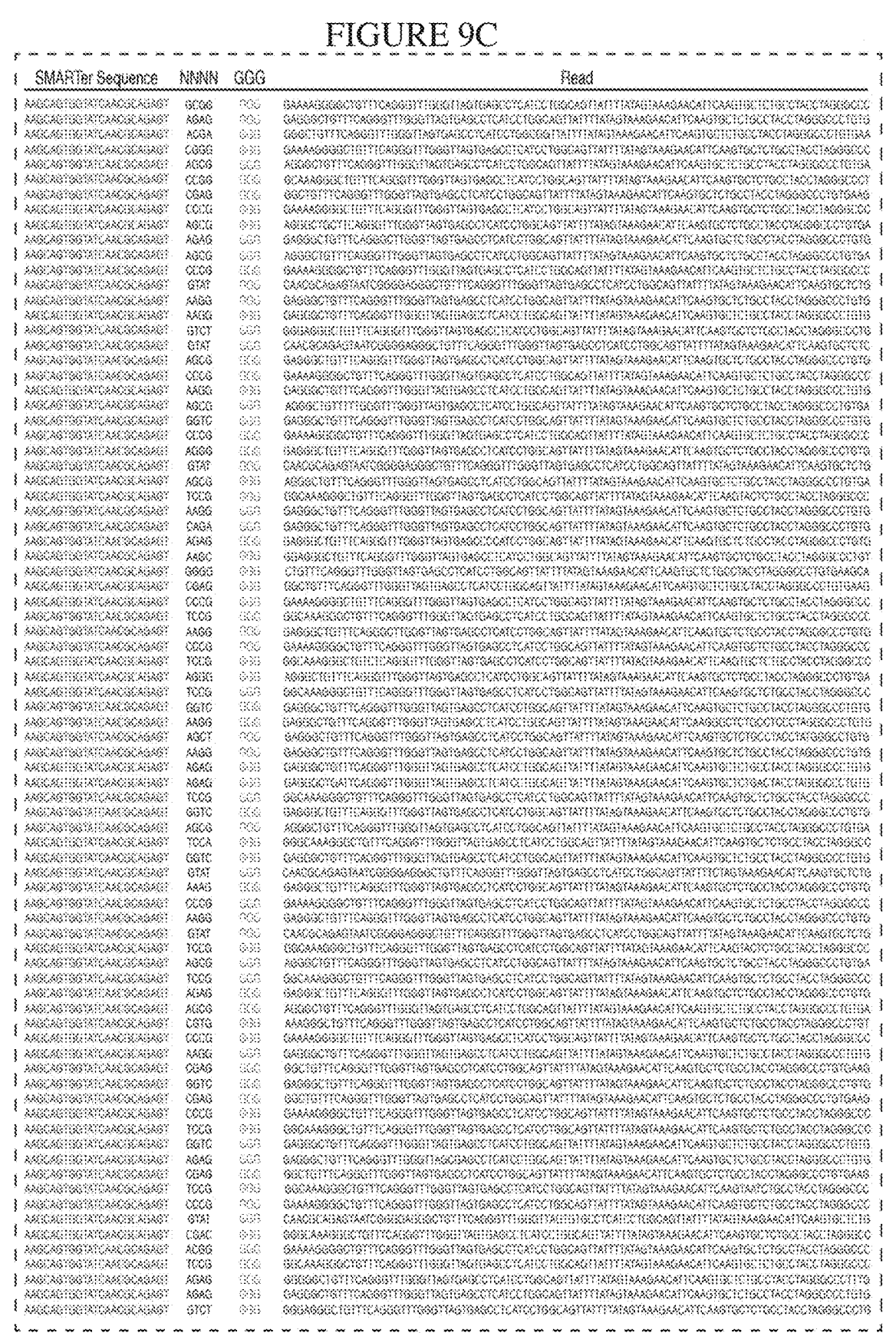

The studies provided herein discover extensive bimodality in the transcriptional response of BMDCs to LPS stimulation, reflected in gene expression, alternative splicing, and regulatory circuit activity. In gene expression, hundreds of bimodally expressed transcripts encoding key immune proteins, including those that are highly expressed in the population average, were found. While variation in some genes is due to a minority sub-population in a different maturation state, others reflect the bimodal activity of an anti-viral regulatory circuit. Co-variation across single cells can help dissect refined functional gene modules that may be indistinguishable in population scale measurements. In particular, in a recent population-scale study (Gather, M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012)), a large cluster of 808 "late-induced" LPS genes that was enriched for maturation genes as well as antiviral genes controlled by STAT proteins was identified. These two subsets could not be teased apart based on population-level data alone, but the single-cell data from a single time point clearly distinguishes them as expressed in different single cells. Similarly, the unexpected and prevalent skewing that was discovered in alternative splicing between single cells revises the molecular view of this process. Both phenomena also allow for the treatment of each cell as a "perturbation system" for reconstructing cell circuits (Angelo, K. et al. A biophysical signature of network affiliation and sensory processing in mitral cells. Nature 488, 375-378, doi:papers2://publication/doi/10.1038/nature1291 (2012); Sachs, K., Perez, O., Pe'er, D. & al, e. Causal protein-signaling networks derived from multiparameter single-cell data. Science (New York, N.Y.) (2005)). Indeed, even with data from just 18 single cells and focusing on induced genes, the studies herein demonstrated as a 'proof of concept' how different regulators could be causally connected to their co-varying targets within an interferon-driven antiviral circuit that was subsequently validated in knockout models. Finally, although many of the analyses focused on highly expressed genes to remove the possible influence of amplification noise, the data also reveal significant bimodality amongst more moderately expressed transcripts, such as large non-coding RNAs (FIG. 21). This observation suggests an intriguing possibility that the lower expression levels of these transcripts in the population (Cabili, M. N. et al. Integrative annotation of human large intergenic noncoding RNAs reveals global properties and specific subclasses. *Genes & development* 25, 1915-1927 (2011)) may be the result of a small number of cells expressing them at high levels rather than all of the cells expressing them at a low level, although further technical improvements will be necessary to disentangle these two hypotheses (FIG. 9). As such, single-cell measurements should help facilitate the discovery, annotation, and analysis of these transcripts.

Comparing these results to other single cell RNA-Seq data sets indicates that the source of the analyzed tissue (in vitro vs. ex vivo), the biological condition of the individual cells (steady state vs. dynamically responding), and the heterogeneity in cellular microenvironment all likely influence the extent of single-cell heterogeneity within any individual system. When applied to complex tissues—such as unsorted bone marrow, different stages of developing embryos, heterogeneous tumors, and rare clinical samples (Spencer, S. L., Gaudet, S., Albeck, J. G., Burke, J. M. & Sorger, P. K. Non-genetic origins of cell-to-cell variability in TRAIL-induced apoptosis. *Nature* 459, 428-432, doi: 10.1038/nature08012 (2009); Todd, R. & Margolin. D. H. Challenges of single-cell diagnostics: analysis of gene expression. *Trends Mol. Med.* 8, 254-257 (2002))—the variability seen through single-cell genomics may help determine new cell classification schemes, identify transitional states, discover previously unrecognized biological distinctions, and map markers that differentiate them. Fulfilling this potential would require novel strategies to address the high levels of noise inherent in single-cell genomics—both technical, due to minute amounts of input material, and biological, e.g., due to short bursts of RNA transcription (Taniguchi, Y. et al. Quantifying *E. coli* Proteome and Transcriptome with Single-Molecule Sensitivity in Single Cells. *Science* 329, 533-538, doi:10.1126/science.1188308 (2010); Cai, L., Dalal, C. K. & Elowitz, M. B. Frequency-modulated nuclear localization bursts coordinate gene regulation. *Nature* 455, 485-490, doi:nature07292 [pii]10.1038/nature07292 (2008)). Future studies that couple technological advances in experimental preparation with novel computational approaches would enable analyses, based on hundreds or thousands of single cells, to reconstruct intracellular circuits, enumerate and redefine cell states and types, and fundamentally transform the understanding of cellular decision-making on a genomic scale.

The studies provided herein also use a microfluidic system to generate and analyze more than 2,000 SMART-Seq (Ramskold, D. et al. Full-length mRNA-Seq from single-cell levels of RNA and individual circulating tumor cells. *Nature Biotechnology* 30, 777-782, doi:papers2:///publication/doi/10.1038/nbt.2282 (2012)) single cell Bone Marrow Dendritic Cell (BMDC) RNA-Seq libraries. BMDCs are an attractive system for studying single cell responses since they are primary, post-mitotic, and, in response to pathogenic components, elicit robust, physiologically relevant transcriptional programs for inflammatory and antiviral cytokines that are well-characterized at the population level (Amit, I. et al. Unbiased reconstruction of a mammalian transcriptional network mediating pathogen responses. *Science* 326, 257-263, doi:10.1126/science.1179050 (2009); Chevrier, N. et al. Systematic Discovery of TLR Signaling Components Delineates Viral-Sensing Circuits. *Cell* 147, 853-867, doi:10.1016/j.cell.2011.10.022 (2011); Garber, M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012); Takeuchi, O. & Akira, S. Pattern Recognition Receptors and Inflammation. *Cell* 140, 805-820, doi:10.1016/j.cell.2010.01.022 (2010); Shalek, A. K. et al. Nanowire-mediated delivery enables functional interrogation of primary immune cells: application to the analysis of chronic lymphocytic leukemia. *Nano Lett.* 12(12):6498-504, doi:10.1021/nl3042917 (2012)). Initially, BMDCs were profiled pre-stimulation and at four time points (1, 2, 4, 6 h) after stimulation with LPS, PAM3CSK, and polyI:C (resp. from gram-negative bacteria, gram-positive bacteria and a synthetic mimic of viral RNA). From these distinct snapshots, the temporal and response-specific structures of single cell noise were examined. To assess changes in single cell variation across stimuli and time points, a new nested statistical model was developed and used to parameterize the single cell expression distributions of each gene. While each pathogen component activates a distinct temporal program at the population level, individual responding cells display dramatically variable behaviors also within each response. In inflammatory circuits, two temporally distinct patterns of expression heterogeneity were found: some circuits are strongly synchronized early and de-phase over time, whereas others are noisily induced. Antiviral gene circuits, meanwhile, onset noisily and become tightly synchronized over time.

In particular, the studies presented herein discovered a rare population of precocious "early anti-viral responders", masked in population measurements, and hypothesize that their response is amplified throughout the population via paracrine signaling. To test this hypothesis, each cell was stimulated individually in a sealed microfluidic chamber, and it was found that most cells fail to induce key antiviral response genes. Surprisingly, however, the inflammatory response is less variable in these isolated cells, demonstrating that intracellular communication can both restrict and increase noise for different circuits. Analyzing DCs lacking the interferon receptor recapitulates many of these findings, showing that interferon feedback in essential for coordinating the antiviral response as well as for cross-inhibition and noise in the inflammatory response. Finally, DCs deleted for key intracellular regulators nominated by the model were tested to verify key circuit component controlling this process. This study demonstrates how to harness variability across single cells for reconstructing inter- and intracellular circuits, and for understanding of cellular decision-making on a genomic scale.

The compositions and methods of the disclosure use a use a microfluidics-based approach to prepare over 1,700 SMART-Seq single cell RNA-Seq libraries, sampling the dynamic response of BMDCs to different pathogen components and related perturbations. (See e.g., Ramskold, D. et al. Full-length mRNA-Seq from single-cell levels of RNA and individual circulating tumor cells. Nature Biotechnology 30, 777-782, doi:10.1038/nbt.2282 (2012). Distinct gene modules are characterized by different temporal variability profiles, arising from changes in both the fraction of cells that express a given mRNA transcript at a detectable level and the mRNA levels within these detectably expressing cells. The average temporal response of the BMDC population arises from an underlying asynchronous, yet continuous, process at the single-cell level: at each sampled time point, and for each module, some cells are more 'advanced' than others on the temporal continuum. In particular, a few "precocious" cells were discovered, masked in population measurements, that produce interferon and activate a core antiviral module early. Without intending to be bound by theory, it is believed that these precocious cells are responsible for driving the antiviral response in the population through interferon-mediated paracrine signaling.

To understand the role of paracrine signaling in coordinating the population response, the studies provided herein developed a new experimental approach to stimulate cells individually in sealed microfluidic chambers, preventing cell-to-cell communication. This blocks the spread and coordination of the antiviral response at later time points, suggesting that these "precocious" cells play a crucial role in initiating and coordinating the native population response. Furthermore, it was found that BMDCs deficient for interferon receptor, or treated with a secretion inhibitor (Brefeldin A, 'GolgiPlug') or a protein synthesis inhibitor (Cycloheximide), failed to induce "core" antiviral response genes when they were stimulated with LPS. Surprisingly, inhibiting paracrine signaling or just interferon signaling also resulted in a significant increase in the fraction of cells expressing an inflammatory response gene module with an early, sharply peaked induction pattern, highlighting how dynamic population-level positive and negative paracrine feedback loops can both promote and restrain variation in the immune response.

The behavior of individual cells within BMDC populations is highly dynamic during the immune response, with both digital and analogue variation changing across various time points, stimuli and modules. These patterns—masked in population-level measurements—reveal principles for how a cell population can use both intra- and inter-cellular control strategies to coordinate a complex dynamic response. The single-cell profiling data sets presented here, obtained in different time points and stimuli, and the associated statistical analyses, and physical, genetic and biochemical perturbations, provide essential input and approaches for dissecting these intra- and intercellular control strategies.

First, the statistical analysis of single-cell expression distributions reveals that during a dynamic response both the fraction of cells expressing a particular transcript at a detectable level as well as the mRNA levels within expressing cells change. The interaction of these two functions can encode a rich diversity of temporal response profiles. For example, late-induced "core" antiviral genes exhibit very weak average expression at early time points, but are highly expressed in a few "precocious" cells. In contrast, the progressive dampening of "peaked" inflammatory genes reflects changes in the fraction of cells expressing these transcripts, rather than a uniform gradual decrease in the expression in all cells. The ubiquity of this behavior challenges conventional computational approaches for circuit reconstruction that tend to implicitly attribute the changes in population expression profiles solely to intra-cellular events. Rather, these observations suggest that cell populations can generate complex average responses not only through intricate intra-cellular circuits, which are common to all cells, but also with inter-cellular feedback mechanisms between heterogeneous single cells. The early changes in bimodality which characterize multiple response programs (FIG. 26f) could suggest that the most efficient way to generate rapid immune responses is to ask more cells to perform a given task rather than to ask any cell to perform it more efficiently.

One example of the importance of such inter-cellular control strategies is the finding that paracrine signaling plays a crucial role in establishing several distinct temporal patterns of single-cell behavior. In particular, the studies herein have uncovered a small number of "precocious" cells that express Ifnb1 and "core" antiviral genes as early as 1 h after LPS stimulation, and through the secretion of IFN-β, help activate "core" antiviral genes in other cells to coordinate the population response. It is noted that these cells are not distinguishable from the rest of the population, except for expression of the approximately one hundred genes in the "core" antiviral module.

Figure 29A:
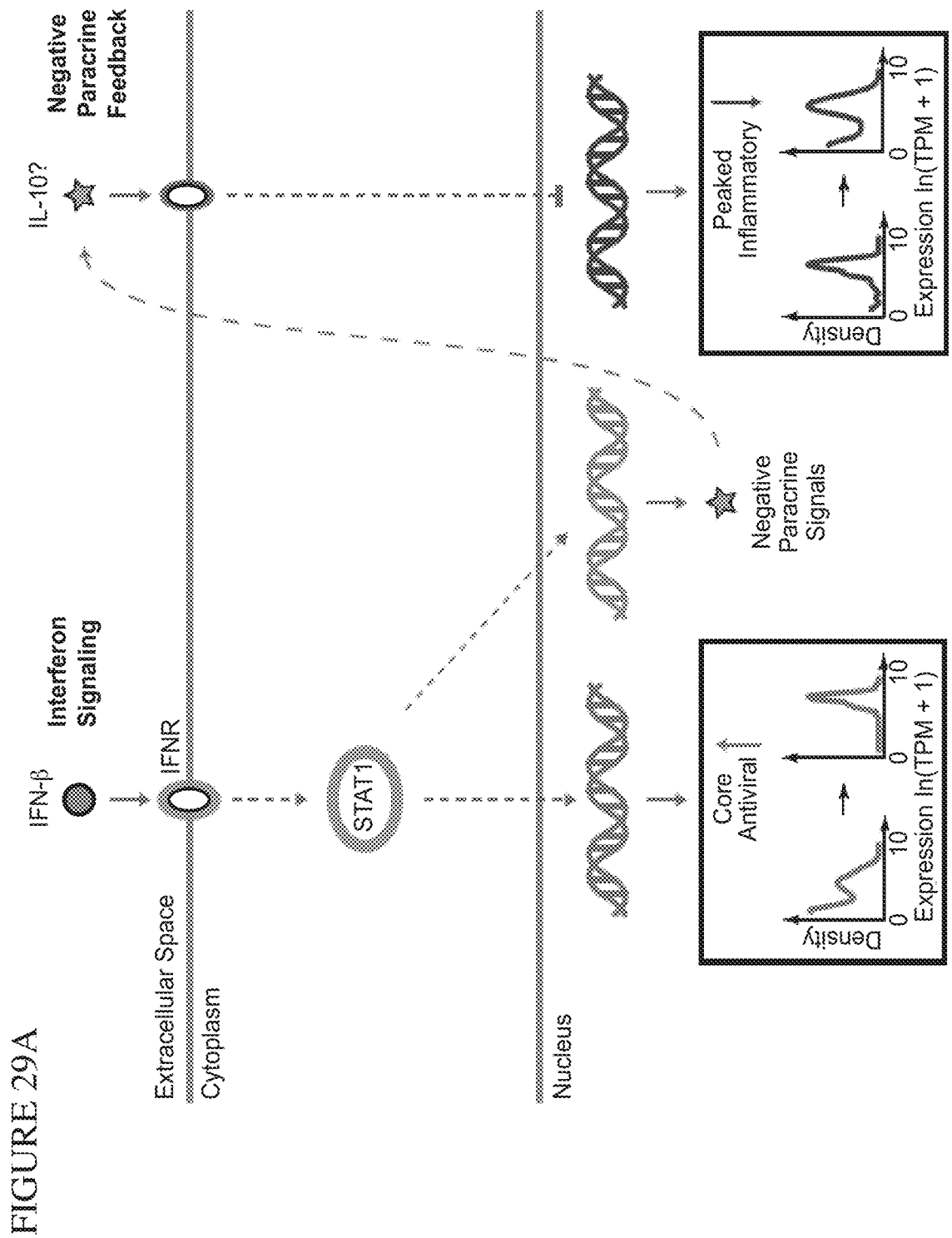
FIGS. 29A and 29B are a series of illustrations and graphs depicting that population-level paracrine signaling enhances and coordinates the "core" antiviral response while dampening and desynchronizing the "peaked" inflammatory ones.
Figure 29B:
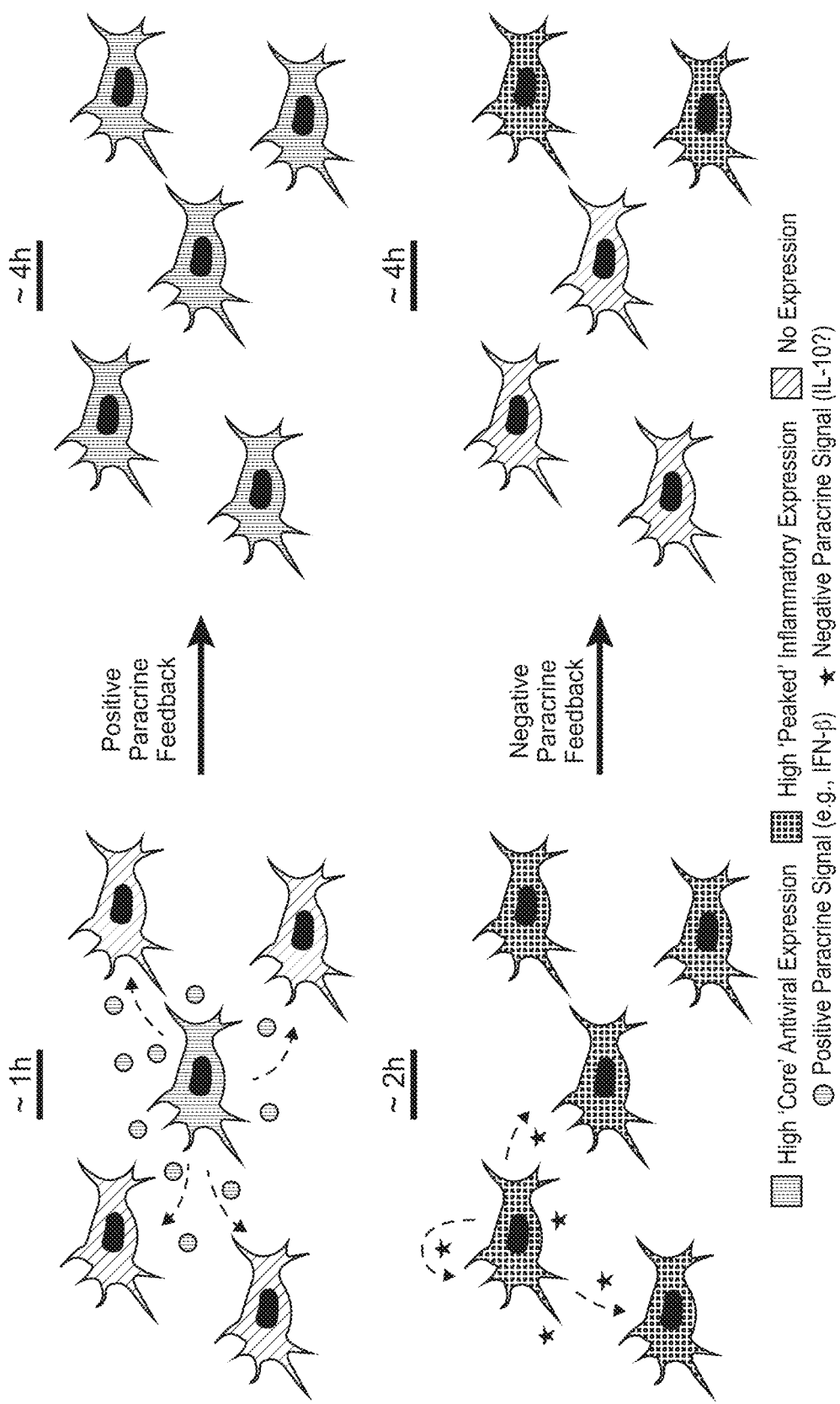

The experimental data presented herein do suggest that the "precocious" cells that were observed are likely to be primed initiators that are crucial in enabling the efficient, and timely, population response. First, the Brefeldin A (GolgiPlug) experiment inhibiting secretion at different time points after addition of LPS suggests that the key paracrine signal acting on the "core" antiviral response is secreted early, around 1 h. More importantly, the "on-chip" isolation experiment shows that, without paracrine signaling from these "precocious" cells, only a small portion (20%) of cells can initiate a diminished "core" antiviral response to LPS by themselves even after 4 h of incubation. These data therefore suggest that the "precocious" cells may represent cells in a special, possibly stochastically defined, epigenetic state that are primed to express Ifnb1 in response to LPS as early as 1 h. Paracrine signaling, including interferon-mediated communication, also acts to dampen a subset of induced genes ("peaked" inflammatory) at later time points. Taken together, these observations suggest a model (FIG. 29) for the cross-inhibition between the antiviral and inflammatory pathways that was observed in "on-chip", knockout and chemical modulatory experiments. In this model, anti-viral feedback from a small number of cells induces the expression and secretion of anti-inflammatory cytokines from a subset of cells, which, in turn, attenuate the inflammatory responses of nearby cells. Importantly, this model also suggests alternative therapeutic strategies that target the balance between distinct response subsets rather than presenting uniform excess extracellular signaling molecules (e.g., IFN-β) (see e.g., Banchereau, J. & Pascual, V. Type I Interferon in Systemic Lupus Erythematosus and Other Autoimmune Diseases. Immunity 25, 383-392, doi:http://dx.doi.org/10.1016/j.immuni.2006.08.010 (2006); Hall, J. C. & Rosen, A. Type I interferons: crucial participants in disease amplification in autoimmunity. Nature Reviews Rheumatology 6, 40-49, doi:http://dx.doi.org/10.1038/nrrheum.2009.237 (2010)).

Automated Procedure for Selection of Signature Genes

The invention also provides methods of determining gene signatures that are useful in various therapeutic and/or diagnostic indications. The goal of these methods is to select a small signature of genes that will be informative with respect to a process of interest. The basic concept is that different types of information can entail different partitions of the "space" of the entire genome (>20 k genes) into subsets of associated genes. This strategy is designed to have the best coverage of these partitions, given the constraint on the signature size. For instance, in some embodiments of this strategy, there are two types of information: (i) temporal expression profiles; and (ii) functional annotations. The first information source partitions the genes into sets of co-expressed genes. The information source partitions the genes into sets of co-functional genes. A small set of genes is then selected such that there are a desired number of representatives from each set, for example, at least 10 representatives from each co-expression set and at least 10 representatives from each co-functional set. The problem of working with multiple sources of information (and thus aiming to "cover" multiple partitions) is known in the theory of computer science as Set-Cover. While this problem cannot be solved to optimality (due to its NP-hardness) it can be approximated to within a small factor. In some embodiments, the desired number of representatives from each set is one or more, at least 2, 5 or more, 10 or more, 15 or more, 20 or more, 25 or more, 30 or more, 35 or more, 40 or more, 50 or more, 60 or more, 70 or more, 80 or more, 90 or more, or 100 or more.

An important feature of this approach is that it can be given either the size of the signature (and then find the best coverage it can under this constraint); or the desired level of coverage (and then select the minimal signature size that can satisfy the coverage demand).

An exemplary embodiment of this procedure is the selection of the various gene signatures presented in Tables 1, 1A, 2, 2A, 3, 3A, 4, 4A, 5 and/or 5A.

Use of Signature Genes

The invention provides dendritic cell related gene signatures for use in a variety of diagnostic and/or therapeutic indications, as well as in a variety of methods of screening for or otherwise identifying therapeutic molecules. "Signatures" in the context of the present invention encompasses, without limitation nucleic acids, together with their polymorphisms, mutations, variants, modifications, subunits, fragments, and other analytes or sample-derived measures.

Exemplary signatures are shown in Tables 1, 1A, 2, 2A, 3, 3A, 4, 4A, 5 and 5A and are collectively referred to herein as, inter alia, "dendritic cell-associated genes," "dendritic cell-associated nucleic acids," "signature genes," or "signature nucleic acids."

These signatures are useful in methods of diagnosing, prognosing and/or staging an immune response and/or aberrant dendritic cell response in a subject by detecting a first level of expression, activity and/or function of one or more signature genes or one or more products of one or more signature genes selected from those listed in Tables 1, 1A, 2, 2A, 3, 3A, 4, 4A, 5 and/or 5A and comparing the detected level to a control of level of signature gene or gene product expression, activity and/or function, wherein a difference in the detected level and the control level indicates that the presence of an immune response and/or aberrant dendritic cell response in the subject.

These signatures are useful in methods of monitoring an immune response and/or aberrant dendritic cell response in a subject by detecting a level of expression, activity and/or function of one or more signature genes or one or more products of one or more signature genes selected from those listed in Tables 1, 1A, 2, 2A, 3, 3A, 4, 4A, 5 and/or 5A at a first time point, detecting a level of expression, activity and/or function of one or more signature genes or one or more products of one or more signature genes selected from those listed in Tables 1, 1A, 2, 2A, 3, 3A, 4, 4A, 5 and/or 5A at a second time point, and comparing the first detected level of expression, activity and/or function with the second detected level of expression, activity and/or function, wherein a change in the first and second detected levels indicates a change in the immune response and/or aberrant dendritic cell response in the subject.

These signatures are useful in methods of identifying patient populations at risk or suffering from an immune response, e.g., an aberrant immune response, an autoimmune response, and/or an inflammatory response, and/or aberrant dendritic cell response based on a detected level of expression, activity and/or function of one or more signature genes or one or more products of one or more signature genes selected from those listed in Tables 1, 1A, 2, 2A, 3, 3A, 4, 4A, 5 and/or 5A. These signatures are also useful in monitoring subjects undergoing treatments and therapies for aberrant immune response(s) and/or aberrant dendritic cell response(s) to determine efficaciousness of the treatment or therapy. These signatures are also useful in monitoring subjects undergoing treatments and therapies for aberrant immune response(s) and/or aberrant dendritic cell response(s) to determine whether the patient is responsive to the treatment or therapy. These signatures are also useful for selecting or modifying therapies and treatments that would be efficacious in treating, delaying the progression of or otherwise ameliorating a symptom of an aberrant immune response and/or aberrant dendritic cell response. The signatures provided herein are useful for selecting a group of patients at a specific state of a disease with accuracy that facilitates selection of treatments.

These signature genes are also useful in methods of monitoring patient response to a therapy, vaccine, transplant or other therapeutic intervention. For example, the expression level of one or more signature genes can be detected at a variety of timepoints pre- and post-administration, and these levels can be analyzed using the single cell methods provided herein. By determining which genes are being expressed in cohorts or other coherent groups and/or which subpopulations of cells are exclusively expressing these genes, a practitioner will be able to determine which cohort(s) and/or which pathway(s) are responsible for generating an immune response and/or an aberrant dendritic cell response.

The present invention also comprises a kit with a detection reagent that binds to one or more signature nucleic acids. Also provided by the invention is an array of detection reagents, e.g., oligonucleotides that can bind to one or more signature nucleic acids. Suitable detection reagents include nucleic acids that specifically identify one or more signature nucleic acids by having homologous nucleic acid sequences, such as oligonucleotide sequences, complementary to a portion of the signature nucleic acids packaged together in the form of a kit. The oligonucleotides can be fragments of the signature genes. For example the oligonucleotides can be 200, 150, 100, 50, 25, 10 or fewer nucleotides in length. The kit may contain in separate container or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art. The kit may for example include reagents and instructions for carrying out any of the methods described herein, including PCR, nucleic acid sequencing, etc. Alternatively, the kit contains a nucleic acid substrate array comprising one or more nucleic acid sequences.

Dendritic Cells and Uses Thereof

Dendritic cells (DCs) are involved in a number of immune responses including and/or contributing to resistance to infection and modulating tolerance to self. DCs have the capacity to control T-cell recognition and/or responsiveness.

DCs are known to induce resistance to infection, as they mature in distinct ways in response to different pathogens, e.g., microbial components, and can therefore initiate different host immunity responses. (See e.g., Steinman & Banchereau. "Taking dendritic cells into medicine." Nature, vol. 449: 419-426 (2007); doi:10.1038/nature06175). The modulating agents provided herein can be used to disrupt these immune responses. For example, the modulating agents modulate the expression, activity, and/or function of one or more genes from Tables 1-5A. In some embodiments, these modulating agents block or otherwise inhibit DC maturation. In some embodiments, these modulating agents alter or otherwise influence one or more functions of DCs, thereby modulating T-cell responses, for example, from a protective $T_H1$ phenotype to a non-protective $T_H2$ phenotype.

DCs are also useful in the design and creation of a variety of vaccine indications to treat and prevent infection by enhancing immunogenesis. In these indications, the vaccine can include one or more modulating agents. For example, in some embodiments, the vaccine delivers a modulating agent that controls or otherwise influences dendritic cell maturation. In some embodiments, the vaccine delivers a modulating agent that alters or otherwise influences one or more T-cell responses, for example, induction of the protective $T_H1$ phenotype.

DCs are also useful in the design and creation of a variety of therapeutic vaccines against cancer due to their capacity to regulate T cell immunity (see e.g., Banchereau & Palucka. Dendritic Cells as Therapeutic Vaccines Against Cancer. Nature, vol. 5: 296-306 (2005); doi:10.1038/nril592); see also, Palucka et al. "Building on dendritic cell subsets to improve cancer vaccines." Curr Op Immunol, 22: 258-63 (2010); doi:10.1016/j.coi.2010.02.010).

For example, DCs are used as adjuvants in the vaccines. Immature DCs are known to induce tolerance, while mature DCs induce immunity. Immature DCs function mainly as antigen-capturing cells, while mature DCs mainly function as antigen-presenting cells. Thus, the modulating agents can be used to modulate the maturity of a DC or population of DCs, for example, to shift the balance between mature and immature DCs based on the desired outcome. For example, the modulating agent can be used to shift toward an immature DC phenotype where tolerance is desired, and in indications where immunity is desired, the modulating agent can be used to shift toward a mature DC phenotype. In some embodiments, the modulating agent is used to modulate the plasticity of a DC or population of DCs. For example, the modulating agent can be used to shift a DC or population of DCs toward a particular subset of DCs, e.g., toward or away from Langerhans cells, interstitial DCs and plasmacytoid DCs; or toward a particular pathway of DC differentiation, e.g., toward or away from the myeloid pathway and/or toward or away from the lymphoid pathway.

The invention provides compositions and methods for modulating one or more dendritic cell responses. As used herein, the term "modulating" includes up-regulation of, or otherwise increasing, the expression of one or more genes, down-regulation of, or otherwise decreasing, the expression of one or more genes, inhibiting or otherwise decreasing the expression, activity and/or function of one or more gene products, and/or enhancing or otherwise increasing the expression, activity and/or function of one or more gene products.

As used herein, the term "modulating a response of dendritic cells" includes the modulation of any of a variety of dendritic cell functions and/or activities, including by way of non-limiting example, controlling or otherwise influencing the networks that regulate dendritic cell maturation; controlling or otherwise influencing the networks that regulate an immune response of a dendritic cell; controlling or otherwise influencing the networks that regulate an antiviral immune response of a dendritic cell, for example, an antiviral immune response of a dendritic cell including a core antiviral response and/or a secondary antiviral response; controlling or otherwise influencing the networks that regulate an inflammatory immune response of a dendritic cell, for example, an induced inflammatory response and/or a sharped peak inflammatory response; controlling or otherwise influencing the networks that regulate a Toll-like receptor (TLR) response of dendritic cells; controlling or otherwise influencing the networks that regulate T cell and B cell recruitment; controlling or otherwise influencing the networks that regulate DC promotion of $T_H1$-cell response(s); controlling or otherwise influencing the networks that regulate DC induction of $T_H2$-cell response(s); controlling or otherwise influencing the networks that regulate DC induction, impact or other effect on any cell that is downstream of the D; controlling or otherwise influencing the networks that regulate DC induction of T cells including regulatory T cells (Tregs), Th17 cells, memory T cells and other T cells; controlling or otherwise influencing the networks that regulate a shift in a DC phenotype, for example, between a mature and immature phenotype and/or between subsets of DCs; manipulating or otherwise influencing at least one function or biological activity of a dendritic cell; manipulating or otherwise influencing dendritic cell control of pathogen-drive T cell polarization; and/or manipulating or otherwise influence the production of cytokines, chemokines and other molecules secreted by the DC.

The invention provides modulating agents that modulate one or more dendritic cell response(s). Suitable modulating agents include an antibody, a soluble polypeptide, a polypeptide agent, a peptide agent, a nucleic acid agent, a nucleic acid ligand, or a small molecule agent.

In some embodiments, the modulating agent is used to modulate the expression of one or more genes from the "Core Antiviral" gene signature, e.g., one or more genes from those listed in Tables 1 and 1A. These modulating agents are referred to herein as "core antiviral modulating agent(s)."

For example, in some embodiments the core antiviral modulating agent is a kinase, such as, by way of non-limiting example, a kinase selected from the group consisting of: MAPK1, EIF2AK2, TBK1, PLK4, IKBKE, PLK2, MAP3K7, CHUK, JAK1, CRKL, MKNK2, TYK2, RPS6KB2, IKBKB, MKNK1, NEK7, PIK3R2, IKBKG, RIPK2, MAP2K6, MET, RPS6KB1, MARK2, DGKA, and BUB1B.

For example, in some embodiments, the core antiviral modulating agent is a transmembrane receptor, such as, by way of non-limiting example, a transmembrane receptor selected from the group consisting of: IFNAR1, TLR3, TLR4, IL28RA, TLR9, IFNAR2, COLEC12, SCARA3, MSR1, FCER1G, and KIR2DS4.

For example, in some embodiments, the core antiviral modulating agent is a mammalian endogenous chemical drug, such as, by way of non-limiting example, tretinoin, or a non-mammalian endogenous chemical drug such as, by way of non-limiting example, a non-mammalian endogenous chemical drug selected from the group consisting of: salmonella minnesota R595 lipopolysaccharides, mezerein, 3-deoxy-2-octulosonic acid(2)-lipid A. *E. coli* B5 lipopolysaccharide, and bafilomycin A1.

For example, in some embodiments, the core antiviral modulating agent is a chemical drug, such as, by way of non-limiting example, a chemical kinase inhibitor drug such as SB203580 or H-7, or another chemical drug such as a chemical reagent, toxicant or other chemical drug selected from the group consisting of: lipopolysaccharide, poly rI:rC-RNA, *E. coli* B4 lipopolysaccharide, stallimycin, bromodeoxyuridine, 2-aminopurine, ribavirin, CpG ODN 1668, pristane, imiquimod, decitabine, *Salmonella enterica* serotype abortus equi lipopolysaccharide, CpG ODN 1826, concanamycin A, poly dA-dT, ionomycin, fucoidan, CpG ODN 2216, AL 108, 4,4'-diaminodiphenylmethane, epigallocatechin-gallate, chloroquine, 3M-011, carbimazole, 3M-001, Pam3-Cys, rosiglitazone, and lipid A.

For example, in some embodiments, the core antiviral modulating agent is a biologic drug, such as, by way of non-limiting example, a biologic drug selected from the group consisting of: pegintron, fontolizumab and interferon beta-1a.

In some embodiments, the modulating agent is used to modulate the expression of one or more genes from the "Secondary Antiviral" gene signature, e.g., one or more genes from those listed in Tables 2 and 2A. These modulating agents are referred to herein as "second antiviral modulating agents."

For example, in some embodiments the secondary antiviral modulating agent is a kinase, such as, by way of non-limiting example, a kinase selected from the group consisting of: MAPK9, EIF2AK2, CRKL, MET, TBK1, MAP3K7, and JAK1.

For example, in some embodiments, the secondary antiviral modulating agent is a transmembrane receptor, such as, by way of non-limiting example, a transmembrane receptor selected from the group consisting of: TLR4, TLR3, and IFNAR2.

For example, in some embodiments, the secondary antiviral modulating agent is a non-mammalian endogenous chemical drug such as, by way of non-limiting example, salmonella minnesota R595 lipopolysaccharides.

For example, in some embodiments, the secondary antiviral modulating agent is a chemical drug, such as, by way of non-limiting example, a chemical kinase inhibitor drug such as LFM-A13, or another chemical drug such as a chemical reagent, toxicant or other chemical drug selected from the group consisting of: poly rI:rC-RNA, lipopolysaccharide, and R-WIN 55,212.

In some embodiments, the modulating agent is used to modulate the expression of one or more genes from the "Maturation" gene signature, e.g., one or more genes from those listed in Tables 3 and 3A. These modulating agents are referred to herein as "maturation modulating agents."

For example, in some embodiments the maturation modulating agent is a kinase, such as, by way of non-limiting example, a kinase selected from the group consisting of: IKBKB, MAP2K4, PRKCD, MTOR, MAPKAPK2, PRKCB, LYN, MAPK14, DDR1, TGFBR1, PRKCA, AKT1, RAF1, SHC1, CSF1R, IRAK4, PRKCQ, SPHK1, MAP4K1, RPS6KB1, GSK3B, FES, MAP3K7, MAP3K8, SRC, CHUK, PTK2, PIK3R1, MAP2K7, MAPK9, RPS6KA5, MAPK8, BTK, EGFR, MAP2K6, PDPK1, PRKG1, FLT3, TYK2, CDK9, ACVR2B, CDK10, MAST2, MAPK11, FGFR3, PIM1, ACVRL1, FGFR2, MARK2, PBK, PLK3, MAP3K14, NME1, HIPK2, and ERBB2.

For example, in some embodiments, the maturation modulating agent is a transmembrane receptor, such as, by way of non-limiting example, a transmembrane receptor selected from the group consisting of: CD40, TLR4, TLR9, FAS, TLR7, CD5, IL27RA, TLR2, TLR3, CD28, ICAM1, LTBR, TLR8, FCGR2A, TYROBP, TNFRSF10A, TLR5, TREM2, IGHM, CD2, TNFRSF8, IL6R, CLEC7A, CHRNA1, ITGB3, AGER, TNFRSF6B, TLR6, TNFRSF11A, TRA@ (also known as TRA, T cell receptor alpha locus), FCGR2B, NGFR, IGF1R, TNFRSF1A, IL1RL2, CD300C, CD86, and MS4A2.

For example, in some embodiments, the maturation modulating agent is a mammalian endogenous chemical drug such as, by way of non-limiting example, a mammalian endogenous chemical drug selected from the group consisting of prostaglandin E2, hyaluronic acid, ATP, tretinoin, ethanol, hydrogen peroxide, butyric acid, arachidonic acid, uric acid, chondroitin sulfate A, adenosine, heparin, Ca2+, histamine, L-methionine, carbon monoxide, cyclic AMP, lauric acid, epinephrine, 11,12-epoxyeicosatrienoic acid, beta-estradiol, lipoxin A4, L-glutamic acid, dihydrotestosterone, progesterone, kynurenic acid, mevalonic acid, 5,6-epoxyeicosatrienoic acid, L-ornithine, malonic acid, elaidic acid. N(omega)-hydroxyarginine, dimethylglycine, 17-epi-estriol, D-galactosamine, hydrocortisone, folic acid, hemin, glucosamine, platelet activating factor, glycosylphosphatidylinositol, palmitoleic acid, and glutathione.

For example, in some embodiments, the maturation modulating agent is a non-mammalian endogenous chemical drug such as, by way of non-limiting example, a non-mammalian endogenous chemical drug selected from the group consisting of *E. coli* lipopolysaccharide, lipoteichoic acid, *E. coli* B5 lipopolysaccharide, N-acetylmuramyl-L-alanyl-D-isoglutamine, zymosan A, 15-deoxy-delta-12,14-PGJ 2, peptidoglycan, ursolic acid, ganglioside GD3, zymosan, hemozoin, prostaglandin A1, mezerein, *E. coli* serotype 0127B8 lipopolysaccharide, salmonella minnesota R595 lipopolysaccharides, ricinoleic acid, tunicamycin, and apigenin.

For example, in some embodiments, the maturation modulating agent is a chemical drug, such as, by way of non-limiting example, a chemical kinase inhibitor drug such as SB203580, wortmannin, PD98059, SP600125, Sb202190, U0126, LY294002, AG490, KN 93, bisindolylmaleimide I, Ro31-8220, staurosporine, Bay 11-7082, H89, Go 6976, tyrphostin AG 1478, PD 169316, PP1, 8-bromoguanosine 3',5'-cyclic monophosphate, 1-o-hexadecyl-2-o-methyl-rac-glycerol, myristoylated PKCzeta pseudosubstrate peptide inhibitor, KT 5926, and 8-chlorophenylthio-adenosine 3',5'-cyclic monophosphate.

For example, in some embodiments, the maturation modulating agent is a chemical drug, such as, by way of non-limiting example, another chemical drug such as a chemical reagent, chemical toxicant or other chemical drug selected from the group consisting of: lipopolysaccharide, ssRNA40, N-nitro-L-arginine methyl ester, caffeic acid phenethyl ester, S-nitrosoglutathione, W7, *E. coli* B4 lipopolysaccharide, phorbol myristate acetate, CpG ODN 2006, CpG ODN 1826, poly rI:rC-RNA, ATP-gamma-S, simvastatin, EGTA, nystatin, N-acetyl-L-cysteine, 3M-001, tranilast, thapsigargin, Pam3-Cys-Ser-Lys4, DETA-NONOate, resiquimod, CpG ODN 1668, *Salmonella enterica* serotype abortus equi lipopolysaccharide, 3-methyladenine, murabutide. CpG oligonucleotide, R5020, lovastatin, sirolimus, bucladesine, epigallocatechin-gallate, melphalan, 3M-011, imatinib, zVAD-FMK, Pam3-Cys, aspirin, bleomycin, dexamethasone, sanglifehrin A, methoxsalen, bortezomib, camptothecin, monophosphoryl lipid A, 3M-002, paclitaxel, pyrrolidine dithiocarbamate, nickel, trichostatin A, docosahexaenoic acid, curcumin, dextran sulfate, resveratrol, forskolin, suramin, pristane, 7-ethyl-10-hydroxy-camptothecin, Ni2+, trovafloxacin, phenanthridine, bryostatin 1, UCN-01, vinblastine, etoposide, cycloheximide, oxaliplatin, [Lys15,Arg16,Leu27]VIP(1-7)GRF(8-27), fluvastatin, ciglitazone, nicotine, eicosapentaenoic acid, rosiglitazone, ionomycin, pentoxifylline, niflumic acid, [Ac-His1, D-Phe2,Lys15,Arg16,Leu27]VIP-(3-7)-GRF-(8-27), mifepristone, gliotoxin, flavopiridol, tanespimycin, rotenone, GCS-100, midazolam, 1-alpha, 25-dihydroxy vitamin D3, decitabine, 3,3'-diindolylmethane, A23187, entinostat, zidovudine, cytidylyl-3'-5'-guanosine, tetrandrine, valproic acid, cisplatin, toremifene, quinacrine, vitamin E, vorinostat, GW3965, isobutylmethylxanthine, fulvestrant, Sn50 peptide, clobetasol propionate, D609, benzene, epothilone B, spermine nitric oxide complex, methylselenic acid, deferoxamine, troglitazone, 1'-acetoxychavicol acetate, paricalcitol, arsenic, imiquimod, GLP-1-(7-34)-amide, S-(2,3-bispalmitoyloxypropyl)-cysteine-GDPKHPKSF, 9-cis-retinoic acid, cadmium, sulindac sulfide, rottlerin, 13-cis-retinoic acid, nitrofurantoin, N-Ac-Leu-Leu-norleucinal, dacinostat, Ro41-5253, tosylphenylalanyl chloromethyl ketone, raloxifene, cerivastatin, panobinostat, fisetin, trinitrobenzenesulfonic acid, CpG ODN 2216, ochratoxin A, azoxymethane, epicatechin gallate, phorbol esters, MALP-2s, S-nitroso-N-acetyl-DL-penicillamine, rolipram, lactacystin, reactive oxygen species, carbon tetrachloride, phorbol 12,13-didecanoate, polyethylene glycol, diisopropanolnitrosamine, N(1)-guanyl-1,7-diaminoheptane, aldesleukin, 4-hydroxytamoxifen, thalidomide, doxorubicin, sulforaphane, methylnitronitrosoguanidine, SU6656, CGS 21680, daunorubicin, omega-N-methylarginine, linsidomine, fasudil, 5-fluorouracil, diethylstilbestrol, morphine, mitomycin C, ribavirin, S-nitroso-N-acetylpenicillamine, sodium orthovanadate, Am 580, prednisolone, chloroquine, galactosylceramide-alpha, gemcitabine, 9,10-dimethyl-1,2-benzanthracene, BAPTA-AM, methylprednisolone, indomethacin, CP-55940, docetaxel, memantine, arbutin, moxestrol, 2,2,2-trichloroethanol, danusertib, anastrozole, perifosine, bisphosphonate, mefenamic acid, glutathione ethyl ester, vinflunine, polyinosinic acid, sparfosic acid, retinoid, vincristine, phenacetin, lipid, dimethylnitrosamine, genistein, 2-deoxyglucose, pioglitazone, O6-benzylguanine, beryllium sulfate, benzo(a)pyrene 7,8-dihydrodiol, methylamphotericin B, riociguat, O-(chloroacetylcarbamoyl)fumagillol, dephostatin, atrasentan, tipifarnib, bongkrekic acid, natamycin, 10-decarbamoylmitomycin C, phenoxodiol, potassium cyanide, 3,4-methylenedioxyamphetamine, (–)-gallocatechin gallate, 1beta,25-dihydroxyvitamin D3, 17-alpha-ethinylestradiol, salicylic acid, 3-deazaneplanocin, and doxycycline.

For example, in some embodiments, the maturation modulating agent is a biologic drug, such as, by way of non-limiting example, a biologic drug selected from the group consisting of: cyclosporin A, hemocyanin, etanercept, enterotoxin B, romidepsin, adalimumab, interferon beta-1b, atosiban, and defibrotide.

In some embodiments, the modulating agent is used to modulate the expression of one or more genes from the "Peaked Inflammatory" gene signature, e.g., one or more genes from those listed in Tables 4 and 4A. These modulating agents are referred to herein as "peaked inflammatory modulating agents."

For example, in some embodiments the peaked inflammatory modulating agent is a kinase, such as, by way of non-limiting example, a kinase selected from the group consisting of: IRAK4, CHUK, IKBKG, IKBKB, MAP2K1, MARK2, MAP3K14, TBK1, IRAK3, TGFBR2, LYN, EIF2AK2, MAPK8, KIT, RIPK2, PRKCA, CDK9, SPHK1, PRKCD, EGFR, MAP3K7, TXK, MAP3K8, MAPKAPK2, MAPK10, IRAK2, IKBKE, RAF1, JAK2, ADRBK1, TEK, MAPK9, MET, MAPK14, ITK, BMPR2, FLT3, PRKD1, TYK2, PRKCQ, MERTK, MAPK1, AKT2, MAPKAPK5, JAK1, and PIK3CG.

For example, in some embodiments, the peaked inflammatory modulating agent is a transmembrane receptor, such as, by way of non-limiting example, a transmembrane receptor selected from the group consisting of: TLR4, IL28RA, IFNAR1, FAS, TLR7, CD14, TLR3, TNFRSF1A, TLR5, CD40, ICAM1, TLR9, SIGIRR, MSR1, IL10RA, FCGR2B, FCGR2A, IL27RA, TLR2, CD28, PLAUR, MARCO, UNC5B, THBD, IFNGR1, IL10RB, CD86, IL1R1, FCGR1A, IL1RL1, IL6R, TNFRSF18, RARRES2, TNFRSF1B, EPOR, TRA@, IL17RA, TRB@ (also known as TRB, T cell receptor beta locus), and CD300C.

For example, in some embodiments, the peaked inflammatory modulating agent is a mammalian endogenous chemical drug, such as, by way of non-limiting example, a mammalian endogenous chemical drug selected from the group consisting of hyaluronic acid, beta-estradiol, prostaglandin E2, uric acid, neuroprotectin D1, platelet activating factor, stearic acid, tretinoin, palmitic acid, progesterone, D-sphingosine, spermine, hydrogen peroxide, leukotriene D4, hydrocortisone, lauric acid, fatty acid, 11,12-epoxyeicosatrienoic acid, chenodeoxycholic acid, linolenic acid, ATP, lithocholic acid, lipid, arachidonic acid, aldehyde, methyl palmitate, L-cystine, L-tartaric acid, arginine, butyric acid, D-glucose, L-ornithine, 1,4-glucan, taurolithocholic acid, globotriaosylceramide, cerotic acid, D-erythro-C16-ceramide, dimethylglycine, 22(R)-hydroxycholesterol, L-triiodothyronine, mevalonic acid, alcohol, beta-carotene, and D-galactosamine.

For example, in some embodiments, the peaked inflammatory modulating agent is a non-mammalian endogenous chemical drug such as, by way of non-limiting example, a non-mammalian endogenous chemical drug selected from the group consisting of: salmonella minnesota R595 lipopolysaccharides, *E. coli* B5 lipopolysaccharide, zymosan, N-acetylmuramyl-L-alanyl-D-isoglutamine, *E. coli* serotype 0127B8 lipopolysaccharide, lipoteichoic acid, *E. coli* lipopolysaccharide, peptidoglycan, mezerein, mannan, carrageenan, ubiquinone 9, brefeldin A, polyamines, mannosylated lipoarabinomannan, isoquercitrin, cyclomaltodextrin, cyclopiazonic acid, 2-mercaptoacetate, bafilomycin A1, hemozoin, lipoarabinomannan, MALP-2R, Silybum marianum extract, polysaccharide, 15-deoxy-delta-12,14-PGJ 2, phorbol 12,13-dibutyrate, syringin, isobutylamine, and glucuronoxylomannan.

For example, in some embodiments, the peaked inflammatory modulating agent is a chemical drug, such as, by way of non-limiting example, a chemical kinase inhibitor selected from the group consisting of SP600125, U0126, SB203580, LY294002, PD98059, PP1, wortmannin, Bay 11-7082, Go 6976, PS-1145, JAK inhibitor I, merck C, bisindolylmaleimide 1, and tyrphostin B56.

For example, in some embodiments, the peaked inflammatory modulating agent is another chemical drug such as a chemical reagent, toxicant or other chemical drug selected from selected from the group consisting of: lipopolysaccharide, *Salmonella enterica* serotype abortus equi lipopolysaccharide, trovafloxacin, resiquimod, dexamethasone, cycloheximide, trinitrobenzenesulfonic acid, MALP-2s, *E. coli* B4 lipopolysaccharide, poly rI:rC-RNA, camptothecin, Pam3-Cys, Pam3-Cys-Ser-Lys4, CpG ODN 1668, CpG oligonucleotide, simvastatin, paclitaxel, genistein, phorbol myristate acetate, N-nitro-L-arginine methyl ester, triamcinolone acetonide, thapsigargin, picryl chloride, 1-alpha, 25-dihydroxy vitamin D3, 5-N-ethylcarboxamido adenosine, pyrrolidine dithiocarbamate, ceruletide, magnesium sulfate, GW3965, cortisone acetate, ranitidine, roflumilast, 3-methyladenine, Ni2+, dextran sulfate, glucocorticoid, epigallocatechin-gallate, ozone, gemfibrozil, triciribine, famotidine, tranexamic acid, grepafloxacin, acetaminophen, daidzein, bepafant, IDN-6556, ZFA-fmk, BQ 123, pentoxifylline, zinc, chloroquine, alpha-tocopherol, triamcinolone hexacetonide, edaravone, rabeprazole, okadaic acid, CP-55940, ionomycin, caffeic acid phenethyl ester, Z-DEVD-FMK, polymyxin B, palmitoyl-Cys((RS)-2,3-di (palmitoyloxy)-propyl)-Ala-Gly-OH, cytidylyl-3'-5'-guanosine, BQ-788, melphalan, N-acetyl-L-cysteine, stallimycin, 25-hydroxycholesterol, bucladesine, A23187, sunitinib, lactacystin, actinomycin D, methylprednisolone, docosahexaenoic acid, SR 144528, vitamin E, clarithromycin, salmeterol, mevastatin, bromodeoxyuridine, CpG ODN 1826, monophosphoryl lipid A, 2,4-dinitrofluorobenzene, vorinostat. TO-901317, erythromycin, misoprostol, PD184352, diethylmaleate, ammonium chloride, 1-methyl-4-phenyl-1,2,3,6-tetrahydropyridine, bleomycin, alendronic acid, parthenolide, tosylphenylalanyl chloromethyl ketone, nifedipine, rosiglitazone, desipramine, ilomastat, nicotine, 13-cis-retinoic acid, trichostatin A, cis-urocanic acid, rosuvastatin, mycophenolic acid, cyclophosphamide, 8-bromo-cAMP, eicosapentaenoic acid, estrogen, oleoyl-estrone, 8-cyclopentyl-1,3-dipropylxanthine, carteolol, N-formyl-Nle-Leu-Phe, NSC 270012, dalcetrapib, MK2206, GSK2118436, dexamethasone/tobramycin, deoxyspergualin. RP 48740, fosfomycin, NSC 95397, bacitracin, tirofiban, dexanabinol, rolipram, curcumin, diclofenac, N-formyl-Met-Leu-Phe, reactive oxygen species, omega-N-methyl-arginine, tacrolimus, pirinixic acid, valproic acid, thioacetamide, cisplatin, propylthiouracil, 5-azacytidine, galactosylceramide-alpha, diphosphoryl lipid A, gentamicin C1, CpG ODN M362, PF-251802, PF-4308515, GTS 21, compound 48/80, vesnarinone, glyoxal, 2,4-dinitrothiocyanatobenzene, enalaprilat, trehalose dimycolate, bis-pompmea, BAPTA-AM, resveratrol, S-nitrosoglutathione, lovastatin, and chlorpromazine.

For example, in some embodiments, the peaked inflammatory modulating agent is a biologic drug, such as, by way of non-limiting example, a biologic drug selected from the group consisting of: cyclosporin A, enterotoxin B, lisinopril, abciximab, and eptifibatide.

In some embodiments, the modulating agent is used to modulate the expression of one or more genes from the "Induced Inflammatory" gene signature, e.g., one or more genes from those listed in Tables 5 and 5A. These modulating agents are referred to herein as "induced inflammatory modulating agents."

For example, in some embodiments the induced inflammatory modulating agent is a kinase, such as, by way of non-limiting example, a kinase selected from the group consisting of: CHUK, IKBKB, TBK1, MAP2K1, MAPK1, LYN, IKBKG, MAP3K8, IKBKE, MAP3K7, NEK7, AKT1, GSK3B, MAPKAPK2, INSR, LRRK2, PRKCB, JAK2, CARD11, MET, MAPK9, IRAK4, MAPK14, EGFR, MAP3K14, RET, MAP2K4, PIK3R1, RIPK2, PRKCE, MAPK8, MAP2K6, ERBB2, CSF1R, PLK4, PLK2, PRKCD, SPHK1, MAPK11, EIF2AK3, PIK3CA, MERTK, SYK, KDR, MARK2, JAK1, and RAF1.

For example, in some embodiments, the induced inflammatory modulating agent is a transmembrane receptor, such as, by way of non-limiting example, a transmembrane receptor selected from the group consisting of: TLR4, TLR3, IFNAR1, TLR9, CD40, IL28RA, TNFRSF1A, TLR2, CD14, MRC1, CD244, NCR1, KLRC4-KLRK1/KLRK1, FAS, FCER1G, IL1R1, LEPR, PGRMC1, MSR1, TNFRSF18, Klra4 (includes others), ITGB3, IL4R, FCGR2A, TNFRSF1B, TREM2, NCR3, TLR5, TLR7, ICAM1, TLR8, IGF1R, FCER2, IL6R, AGER, CD28, IL11RA, ITGB1, SIGLEC7, TYROBP, and GFRA1.

For example, in some embodiments, the induced inflammatory modulating agent is a mammalian endogenous chemical drug, such as, by way of non-limiting example, a mammalian endogenous chemical drug selected from the group consisting of: ATP, prostaglandin E2, progesterone, hyaluronic acid, beta-estradiol, superoxide, lauric acid, uric acid, palmitic acid, hydrogen peroxide, tretinoin, histamine, benzylamine, poly(ADP-ribose), ethanol, oleic acid, glutathione, carbon monoxide, cholesterol, sphingosine-1-phosphate, arginine, N-acetylglucosamine, testosterone, phosphatidic acid, niacinamide, UDP, nitric oxide, ganglioside GD1a, gamma-linolenic acid, 8-oxo-7-hydrodeoxyguanosine, melatonin, alcohol, D-galactosamine, ganglioside, iron, leukotriene D4, leukotriene C4, 5'-methylthioadenosine, glycochenodeoxycholate, linoleic acid, neuroprotectin D1, hydrocortisone, sodium chloride, heparin, prostaglandin E1, 4-phenylbutyric acid, cyclic AMP, fatty acid, chenodeoxycholic acid, UTP, cholecalciferol, lipoxin A4, thromboxane A2, acyl-coenzyme A, geranylgeranyl pyrophosphate, arachidonic acid, formaldehyde, taurine, prostaglandin D2, L-glutamic acid, anandamide, 2-methoxyestradiol, advanced glycation end-products, D-glucose, sepiapterin, vanillic acid, D-erythro-C16-ceramide, citrulline, mevalonic acid, and beta-carotene.

For example, in some embodiments, the induced inflammatory modulating agent is a non-mammalian endogenous chemical drug such as, by way of non-limiting example, a non-mammalian endogenous chemical drug selected from the group consisting of: peptidoglycan, salmonella minnesota R595 lipopolysaccharides, E. coli serotype 0127B8 lipopolysaccharide, E. coli lipopolysaccharide, zymosan, phospholipid, bafilomycin A1, luteolin, E. coli B5 lipopolysaccharide, carrageenan, ursolic acid, apigenin, 2-cyclohexen-1-one, lipoteichoic acid, geldanamycin, manganese, N-acetylmuramyl-L-alanyl-D-isoglutamine, isoliquiritigenin, cyclomaltodextrin, benzyl isothiocyanate, piceatannol, naringenin, hemozoin, prostaglandin A1, honokiol, pregna-4,17-diene-3,16-dione, lipoarabinomannan. D-cysteine, 8-prenylkaempferol, sinapinic acid, (S)-norcoclaurine, fumagillin, 15-deoxy-delta-12,14-PGJ 2, bile acid, prostaglandin J2, isoleucine, and ginsenoside Rg1.

For example, in some embodiments, the induced inflammatory modulating agent is a chemical drug, such as, by way of non-limiting example, a chemical kinase inhibitor selected from the group consisting of Bay 11-7082, PD98059, U0126, SB203580, LY294002. JAK inhibitor 1, 1L-6-hydroxymethyl-chiro-inositol 2-(R)-2-O-methyl-3-O-octadecylcarbonate, tyrphostin AG 1296, wortmannin, Ro31-8220, SC68376, PS-1145, SP600125, PP2/AG1879 tyrosine kinase inhibitor, AG490, PP1, bisindolylmaleimide I, tyrphostin AG 127, herbimycin, Go 6976, Sb202190, H89, calphostin C, Rp-cAMPS, Tp12 kinase inhibitor, CGP77675, Ro 31-7549, tyrphostin AG 1288, 8-bromoguanosine 3',5'-cyclic monophosphate, SB 220025, AR-12, erbstatin, KT 5926, tyrphostin 47, and staurosporine.

For example, in some embodiments, the induced inflammatory modulating agent is another chemical drug, such as, by way of non-limiting example, a chemical reagent, chemical toxicant or other chemical drug selected from the group consisting of: lipopolysaccharide, poly rI:rC-RNA, resiquimod, CpG oligonucleotide, E. coli B4 lipopolysaccharide, lipid A, CpG ODN 1826, Pam3-Cys-Ser-Lys4, dexamethasone, CEP-1347, phorbol myristate acetate, rosiglitazone, *Salmonella enterica* serotype abortus equi lipopolysaccharide, ciglitazone, MALP-2s, trinitrobenzenesulfonic acid, CpG ODN 1668, CGS 21680, methyl 2-cyano-3,12-dioxoolean-1,9-dien-28-oate, cycloheximide, pyrrolidine dithiocarbamate, lonafarnib, ferrous sulfate, lysophosphatidylcholine, Pam3-Cys, picolinic acid, tacrolimus, aspirin, dextran sulfate, carbon tetrachloride, resveratrol, 2-aminopurine, curcumin, bleomycin, 3-methyladenine, GW3965, camptothecin, methotrexate, bortezomib, celecoxib, tributyrin, cigarette smoke, arachidonyltrifluoromethane, simvastatin, thioacetamide, epigallocatechin-gallate, lipooligosaccharide, amphotericin B, triamcinolone acetonide, pioglitazone, nystatin, 3M-002, peroxynitrite, S-(2,3-bispalmitoyloxypropyl)-cysteine-GDPKHPKSF, fish oils, indomethacin, salicylic acid, arsenite, pirinixic acid, quercetin, parthenolide, fenretinide, paclitaxel, A23187, temozolomide, tetrachlorodibenzodioxin, atorvastatin, docosahexaenoic acid, N-acetyl-L-cysteine, lansoprazole, rutin, rimonabant, selenium, isoproterenol, actinomycin D, ATP-gamma-S, vinblastine, bucladesine, cinnamaldehyde, tempol, thalidomide, topotecan, diethylstilbestrol, fluvastatin, 13-cis-retinoic acid, proteasome inhibitor PSI, ferric nitrilotriacetate, N-Ac-Leu-Leu-norleucinal, etoposide, mycophenolic acid, chloroquine, tannic acid, rabeprazole, 3M-011, forskolin, okadaic acid, doxorubicin, SB 216763, 2',3'-dialdehyde ATP, NCX-4040, capsazepine, 5-aminosalicylic acid, hexamethoxyflavone, tosyllysine chloromethyl ketone, corticosteroid, 3M-001, cytochalasin D, cisplatin, cryptotanshinone, methylene blue, L-N6-(1-iminoethyl)-lysine, nitroprusside, N-acetylsphingosine, mifepristone, 5-azacytidine, telmisartan, ebselen, prostaglandin, capsaicin, doxycycline. SR 144528, piperine, pravastatin, carbonyl cyanide m-chlorophenyl hydrazone, ethyl pyruvate, clenbuterol, auranofin, tamoxifen, minocycline, TGAL copolymer, cannabidiol, Sn50 peptide, benzo(a)pyrene, silibinin, 1'-acetoxychavicol acetate, nimesulide, rofecoxib, isobutylmethylxanthine, diethylmaleate, tranilast, dipyridamole, 1-methyl-4-phenyl-1,2,3,6-tetrahydropyridine, fulvestrant, imiquimod, 17-alpha-ethinylestradiol, triflusal, tosylphenylalanyl chloromethyl ketone, captopril, fluticasone, fisetin, nicotine, benzyloxycarbonyl-Leu-Leu-Leu aldehyde, cis-urocanic acid, fucoidan, N-nitro-L-arginine methyl ester, genistein, azoxymethane, epicatechin gallate, ionomycin, troglitazone, NS-398, cerivastatin, allopurinol, 8-chloroadenosine, AZD8055, chlorpheniramine, diethylthiocarbamate, LY311727, BN 50730, 1-(1-glycero)dodeca-1,3,5,7,9-pentaene, bisperoxo(picolinato)oxovanadate, ethyl vanillin, benznidazole, CE-2072, metaproterenol sulfate, n-6 docosapentaenoic acid, AGN194204, choline fenofibrate, eicosapentaenoic acid, losartan potassium, vancomycin, bryostatin 1, urethane, estrogen, methylprednisolone. U73122, metformin, bezafibrate, diclofenac, crocidolite asbestos, acetovanillone, N-formyl-Met-Leu-Phe, reactive oxygen species, SU6656, 2-cyano-3,12-dioxoolean-1,9-dien-28-oic acid, semaxanib, streptozocin, green tea polyphenol, S-nitroso-N-acetylpenicillamine, 5-N-ethylcarboxamido adenosine, lactacystin, N-(3-(aminomethyl)benzyl)acetamidine, pentoxifylline, tanespimycin, medroxyprogesterone acetate, sulforaphane, propranolol, alpha-tocopherol, arbutin, transcinnamaldehyde, hesperidin, sitagliptin, des-Arg(10)-kallidin, lysine clonixinate, bafilomycin A, soy isoflavones, hydroxyl radical, marimastat, zileuton, bumetanide, oxazepam, metastat, felodipine, gamma tocopherol, pyrilamine, microcystin, epoxyeicosatrienoic acid, remifentanil, laminaran, flunisolide, ibuprofen, 9,10-dimethyl-1,2-benzanthracene, morphine, pimagedine, zVAD-FMK, and S-nitrosoglutathione.

For example, in some embodiments, the induced inflammatory modulating agent is a biologic drug, such as, by way of non-limiting example, a biologic drug selected from the group consisting of: cyclosporin A, infliximab, interferon beta-1a, NF-kappaB decoy, enterotoxin B, fontolizumab, anakinra, hemocyanin, grape seed extract, and etanercept.

Use of Modulating Agents

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug. Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a modulating agent, are used to treat or alleviate a symptom associated with an immune-related disorder, an aberrant immune response, and/or an neoplastic condition such as, for example, cancer. The present invention also provides methods of treating or alleviating a symptom associated with an immune-related disorder or an aberrant immune response. A therapeutic regimen is carried out by identifying a subject, e.g., a human patient suffering from (or at risk of developing) an immune-related disorder or aberrant immune response, using standard methods. For example, modulating agents are useful therapeutic tools in the treatment of autoimmune diseases and/or inflammatory disorders. In certain embodiments, the use of modulating agents is contemplated, for example, against certain pathogens and other infectious diseases. The modulating agents are also useful therapeutic tools in various transplant indications, for example, to prevent, delay or otherwise mitigate transplant rejection and/or prolong survival of a transplant. The modulating agents are also useful in patients who have genetic defects that exhibit aberrant dendritic cell response.

The modulating agents are also useful in vaccines and/or as vaccine adjuvants, against autoimmune disorders, inflammatory diseases, proliferation disorders including cancers, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis herpetiformis; chronic fatigue immune dysfunction syndrome (CFIDS), chronic inflammatory demyelinating polyneuropathy (CIDP), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

In some embodiments, modulating agents are useful in treating, delaying the progression of, or otherwise ameliorating a symptom of an autoimmune disease having an inflammatory component such as an aberrant inflammatory response in a subject. In some embodiments, modulating agents are useful in treating an autoimmune disease that is known to be associated with an aberrant dendritic cell response.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the modulating agent confers a clinical benefit.

Administration of a modulating agent to a patient suffering from an immune-related disorder or aberrant immune response is considered successful if any of a variety of laboratory or clinical objectives is achieved. For example, administration of a modulating agent to a patient is considered successful if one or more of the symptoms associated with the immune-related disorder or aberrant immune response is alleviated, reduced, inhibited or does not progress to a further, i.e., worse, state. Administration of modulating agent to a patient is considered successful if the immune-related disorder or aberrant immune response enters remission or does not progress to a further, i.e., worse, state.

A therapeutically effective amount of a modulating agent relates generally to the amount needed to achieve a therapeutic objective. The amount required to be administered will furthermore depend on the specificity of the modulating agent for its specific target, and will also depend on the rate at which an administered modulating agent is depleted from the free volume other subject to which it is administered.

Modulating agents can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton. Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences. Vol. 4), 1991, M. Dekker, New York.

Where polypeptide-based modulating agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Materials and Methods

Cell Culture, Sorting, and Lysis:
Cultures of bone marrow derived dendritic cells (BMDCs) from 6-8 week old female B6 mice were prepared as previously described (Amit, I. et al. Unbiased reconstruction of a mammalian transcriptional network mediating pathogen responses. Science 326, 257-263, doi:10.1126/science.1179050 (2009); Chevrier, N. et al. Systematic Discovery of TLR Signaling Components Delineates Viral-Sensing Circuits. Cell 147, 853-867, doi:10.1016/j.cell.2011.10.022 (2011)). At 9 days of in vitro culture, the cells were stimulated with lipopolysaccharide (LPS, Invivogen) as previously described (Ibid) for 4 h, transferred the cells to a 15 mL conical tube on ice, added 5 µM Calcein AM and 5 µM Ethidium Homodimer (EthD-1, Invitrogen), and then sorted single Calcein-positive, EthD-1-negative cells into individual wells of a 96-well plate, each containing 5 µl TCL buffer supplemented with 1% 2-mercaptoethanol (Qiagen, Valencia, Calif.). After centrifuging, the plates were frozen immediately at −80° C. The total time elapsed between removal from the incubator and lysis was less than 15 minutes. Right before cDNA synthesis, the cells were thawed on ice and purified them with 2.2× RNAClean SPRI beads (Beckman Coulter Genomics, Danvers, Mass.) without final elution. The beads with captured RNA were air-dried and processed immediately for cDNA synthesis. Wells with no cells were also prepared as negative controls and extracted total RNA from ensembles of 10,000 cells as population samples (see below).

cDNA Synthesis and Amplification:
The SMARTer Ultra Low RNA Kit (Clontech. Mountain View, Calif.) was used to prepare amplified cDNA. 1 µl of 12 µM 3' SMART primer (5'-AAGCAGTGGTAT-CAACGCAGAGTACT$_{(30)}$N-1N (N=A, C, G, or T; N−1=A, G, or C), SEQ ID NO: 273), 1 µl of H$_2$O, and 2.5 µl of Reaction Buffer were added onto the RNA-capture beads. The beads were mixed well by pipetting. The mixture was heated at 72° C. for 3 minutes and then placed on ice. First-strand cDNA was synthesized with this RNA primer mix by adding 2 µl of 5× first-strand buffer, 0.25 µl of 100 mM DTT, 1 µl of 10 mM dNTPs, 1 µl of 12 µM SMARTer II A Oligo (5'-AAGCAGTGGTAT-CAACGCAGAGTACXXXXX (X=undisclosed base in the proprietary SMARTer oligo sequence), SEQ ID NO: 274), 100 U SMARTScribe RT, and 10 U RNase Inhibitor in a total volume of 10 µl and incubating at 42° C. for 90 minutes followed by 10 minutes at 70° C. The first strand cDNA was purified by adding 25 µl of room temperature AMPure XP SPRI beads (Beckman Coulter Genomics, Danvers, Mass.), mixing well by pipetting, incubating at room temperature for 8 minutes. The supernatant was removed from the beads after a good separation was established. All of the above steps were carried out in a PCR product-free clean room. The cDNA was amplified by adding 5 µl of 10× Advantage 2 PCR Buffer, 2 µl of 10 mM dNTPs, 2 µl of 12 µM IS PCR primer (5'-AAGCAGTGGTATCAACGCAGAGT, SEQ ID NO: 275), 2 µl of 50× Advantage 2 Polymerase Mix, and 39 µl H$_2$O in a total volume of 50 µl. The PCR was performed at 95° C. for 1 minute, followed by 21 cycles of 15 seconds at 95° C., 30 seconds at 65° C. and 6 minutes at 68° C., followed by another 10 minutes at 72° C. for final extension. The amplified cDNA was purified by adding 90 µl of AMPure XP SPRI beads and washing with 80% ethanol. For molecule counting (see Kivioja, T. et al. Counting absolute numbers of molecules using unique molecular identifiers. Nature Methods 9, 72-74, doi:10.1038/nmeth.1778 (2011) (as in FIGS. 9 & 10), the SMARTer II A Oligo was replaced with a custom RNA oligonucleotide containing four random bases (Barcoded SMARTer II A Oligo: 5'-AAGCAGTGGTATCAACGCAGAGTNNNNrGrGrG-3', SEQ ID NO: 276).

cDNA Shearing and Library Construction:
The purification buffer (Clontech) was added to the amplified cDNA to make a total volume of 76 µl. The cDNA was sheared in a 100 µl tube with 10% Duty Cycle, 5% Intensity and 200 Cycles/Burst for 5 minutes in the frequency sweeping mode (Covaris S2 machine, Woburn, Mass.). The sheared cDNA was purified with 2.2 volumes AMPure XP SPRI beads.

Indexed paired-end libraries for Illumina sequencing were prepared as described (see Levin, J. Z. et al. Comprehensive comparative analysis of strand-specific RNA sequencing methods. Nature Methods 7, 709-715 (2010), with the following modifications. First, a different indexing adaptor (containing an 8-base barcode) was used for each library. Second, the ligation product was size-selected by using two rounds of 0.7 volume of AMPure XP SPRI bead cleanup with the first round starting volume at 100 µl. Third, PCR was performed with Phusion High-Fidelity DNA polymerase with GC buffer and 2 M betaine. Fourth, 55° C. was used as the annealing temperature in PCR with the universal indexing primers (forward primer 5'-AATGA-TACGGCGACCACCGAGATCTACACTCTTTCCCTA-CACGAC (SEQ ID NO: 277), reverse primer 5'-CAAGCAGAAGACGGCATACGAGAT (SEQ ID NO: 278)). Fifth, 12 cycles of PCR were performed. Sixth, PCR primers were removed using two rounds of 1.0 volume of AMPure beads.

Population Controls and Negative Controls:
For positive (population) controls, 13.8 ng of total RNA was isolated, as measured by BioAnalyzer (Agilent, Santa Clara, Calif.), from 10,000 cells using PrepEase RNA Spin Kit (Affymetrix, Santa Clara, Calif.). 1 ng of total RNA was used in the above processes except that only 12 cycles were used in the cDNA amplification step. For negative controls, all of the above processes were carried out starting with zero sorted cells in TCL-buffer-containing wells. 18 cycles in the final PCR of Illumina library construction was used.

Read Trimming and Mapping:
During reverse transcription, the SMART polymerase adds short (SMARTer II A Oligo) and long (SMART primer oligo) adapters to the beginning of the second read for fragments originating from the 5' and 3' ends of the transcript, respectively. Before mapping reads, these adapter sequences were removed using Btrim64 with command line arguments −1 1 −e 100 −v 1 −b 28 −a −100. Adapter sequences were trimmed from approximately a third of the second reads. Trimmed reads were mapped to the mm9 version of the mouse genome using Tophat v1.4.1 (Trapnell, C., Pachter, L. & Salzberg, S. L. TopHat: discovering splice junctions with RNA-Seq. Bioinformatics 25, 1105-1111, doi:10.1093/bioinformatics/btp120 (2009)) with default parameters. Genome mappings were used to visualize data in the Integrative Genome Viewer (Robinson, J. T. et al. Integrative genomics viewer. Nature Biotechnology 29, 24-26, doi:10.1038/nbt.1754 (2011)), and to compute a set of library quality metrics, as described below.

Reads where the short adapter (5' end) was trimmed mapped at approximately equal rates to untrimmed reads. However, read pairs where the long adapter (3' end) was trimmed often contained polyA stretches even after trimming, and mapped at extremely low rates (<1%). Since these reads should originate from the 3' end of the transcript, this low mapping percentage results in a depletion of reads from the 3' end of the transcript. This depletion may cancel out the 3' coverage bias that is a byproduct of the SMART protocol (see below) (Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012)).

Quantifying Unique mRNA Molecules:

When processing the three single-cell libraries where the SMARTer oligo was modified to include a four-nucleotide random barcode sequence, reads containing the SMARTer II A Oligo were isolated and trimmed as described above. Four additional bases (corresponding to the barcode) were then trimmed and maintained for later processing. Trimmed reads were mapped to the mouse mm9 genome as described above. For each gene, the subset of these reads that mapped to exonic sequence on the correct strand was then identified, and their original four-nucleotide barcodes were retrieved. The unique number of barcodes for each gene was counted and used as an alternative quantification of single-cell gene expression. Both unique molecular barcode counts and TPM estimates were provided for all three cells.

Figure 22:
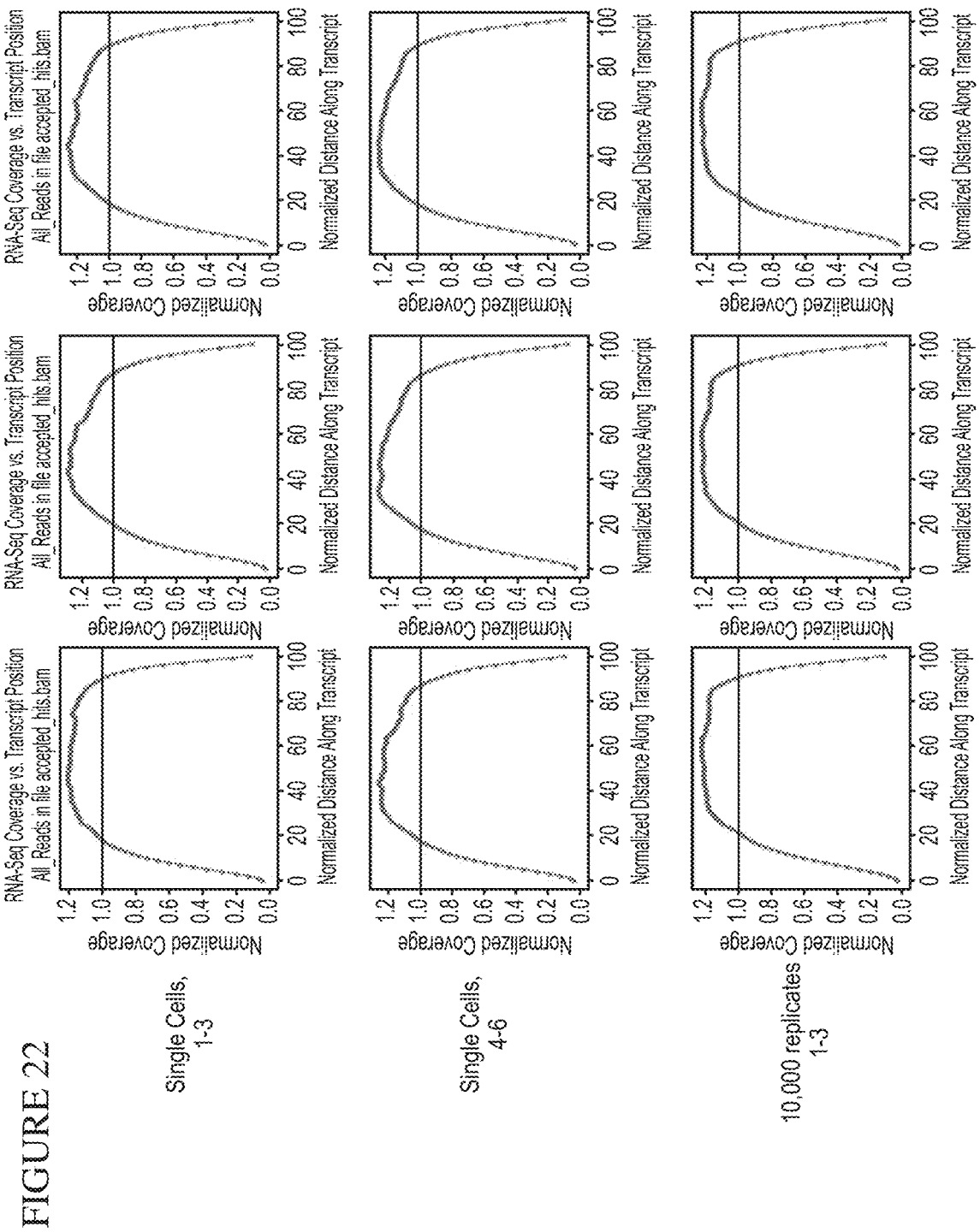
FIG. 22 is a series of graphs depicting quality control for 3' bias. Shown are plots of normalized RNA-Seq coverage at each normalized transcript position from 5' (left) to 3' (right) for 6 single cells (top two rows) and all three 10,000 populations (bottom row). Both the single cells and the populations show little 3' bias.

Library Quality Metrics:

Library quality metrics, including genomic mapping rates, coefficients of variation of coverage of each transcript, the fraction of ribosomal RNA in each library, and positional coverage biases, were calculated using PicardTools version 1.42 (picard.sourceforge.net). Less 3' bias was observed in this data, compared to previous reports (Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012)), likely due to the differences in library construction noted above (FIG. 22).

Expression Level Calculation:

A Bowtie index (Langmead, B., Trapnell, C., Pop, M. & Salzberg, S. Ultrafast and memory-efficient alignment of short DNA sequences to the human genome. Genome Biology 10, doi:10.1186/gb-2009-10-3-r25 (2009)) was created based on the UCSC known Gene transcriptome (Fujita, P. A. et al. The UCSC Genome Browser database: update 2011. Nucleic Acids Research, doi:10.1093/nar/gkq963 (2010)), and paired-end reads were aligned directly to this index using Bowtie v 0.12.7 with command line options -q —phred33-quals -n 2 -e 99999999 -1 25-I 1 -X 1000 -a -m 200. Next, RSEM v1.11 (Li, B. & Dewey, C. RSEM: accurate transcript quantification from RNA-Seq data with or without a reference genome. BMC Bioinformatics 12, doi:10.1186/1471-2105-12-323 (2011)) was ran with default parameters on these alignments to estimate expression levels. RSEM's gene level expression estimates (tau) were multiplied by 1.000,000 to obtain transcript per million (TPM) estimates for each gene. To transform expression levels to log-space, the ln(TPM+1) was taken. When calculating the "average" single-cell expression level, TPM levels from each of the 18 single cells were first averaged, and then this average estimate was transformed into log space.

Identical procedures were applied to a previously published dataset (Garber, M. et al. A High-Throughput Chromatin Immunoprecipitation Approach Reveals Principles of Dynamic Gene Regulation in Mammals. Molecular Cell 47, 810-822, doi:10.1016/j.molcel.2012.07.030 (2012)), consisting of an RNA-Seq time course after LPS stimulation of BMDCs. This dataset was used to identify a set of 632 genes that were induced at least two-fold in the population at 4 h following LPS stimulation as compared to pre-stimulation. These genes were analyzed in FIG. 2a, FIG. 2d, and FIG. 4b.

RNA Fluorescence In Situ Hybridization (FISH):

The expression levels were measured for 25 different mRNA transcripts in situ using RNA-FISH probes (Panomics). Briefly, BMDCs were sorted on Cd11c (Miltenyi Biotech) at 8 days in vitro and plated on poly-l-lysine coated glass coverslips. The following morning, some cells were stimulated with LPS as previously described (Amit, I. et al. Unbiased reconstruction of a mammalian transcriptional network mediating pathogen responses. Science 326, 257-263, doi:10.1126/science.1179050 (2009); Chevrier, N. et al. Systematic Discovery of TLR Signaling Components Delineates Viral-Sensing Circuits. Cell 147, 853-867, doi: 10.1016/j.cell.2011.10.022 (2011)). Ten minutes prior to fixation, cell culture media was replaced with a 1:500 dilution of Alexa-350 Wheat Germ Agglutinin (WGA, Invitrogen) in HBSS. Subsequently, cells were fixed and stained according to the manufacturer's recommendations. After curing overnight, Slowfade (Invitrogen) mounted coverslips were raster scanned at 60× magnification (1.42 NA, oil immersion) in x, y, and z using an epifluorescence microscope (Olympus) outfitted with Metamorph software. On average, 100 individual 3-dimensional stacks were taken for each sample. For all samples, four-color imaging was performed to obtain the following information: excitation (ex) 405 nm—WGA & DAPI stains; ex 488 nm, ex 546 nm, ex 647 nm—Probes 1, 2, and 3, respectively.

The obtained images were processed in two phases. First, CellProfiler (Carpenter, A. et al. CellProfiler: image analysis software for identifying and quantifying cell phenotypes. Genome Biology 7, doi:10.1186/gb-2006-7-10-r100 (2006)) was used to determine cell numbers and locations for each stack of images taken using the UV filter set (ex405 nm). Brightly stained nuclear regions (DAPI) were used to identify individual nuclei and were then used as seeds for determining the extents of each cell from the duller membrane outlines (WGA). The locations and extents of individual cells were then extracted for each imaging condition using the software. Next, for each color channel, individual mRNAs were identified and counted in Matlab using a previously described analysis package (Raj, A., Van Den Bogaard, P., Rifkin, S. A., Van Oudenaarden, A. & Tyagi, S. Imaging individual mRNA molecules using multiple singly labeled probes. Nature Methods 5, 877-879, doi:10.1038/nmeth.1253 (2008)). Identified mRNAs were then allotted to individual cells using the output of CellProfiler. Final analysis and plotting was also performed using Matlab. The displayed RNA-FISH images were false-colored and overlaid using Adobe Photoshop.

Figure 23:
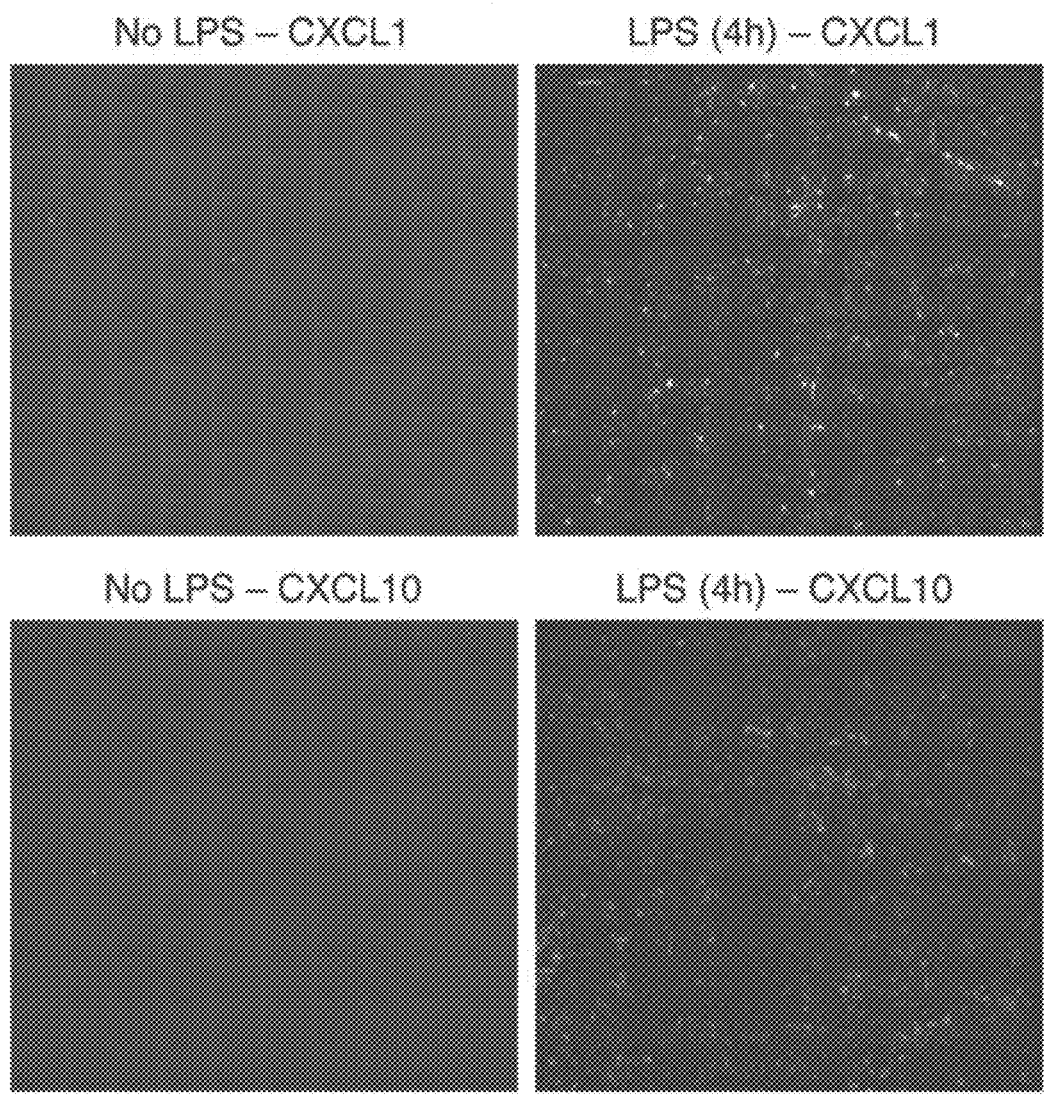
FIG. 23 is a series of photographs depicting RNA-FISH of the immune-response genes Cxcl1 (Top) and Cxcl10 (Bottom) in the absence of LPS stimulation (left) and after 4 h of an LPS stimulus (right). Cxcl10 and Cxcl1, although expressed at negligible levels prior to stimulation, are strongly induced by LPS.

For all RNA FISH histograms, counts were binned (n=50) and smoothed with a window of 5 bins in Matlab. As controls, BMDCs that were not stimulated with LPS were also analyzed to ensure the specificity of the induced-gene RNA-FISH probes (FIG. 23).

Figure 3A:
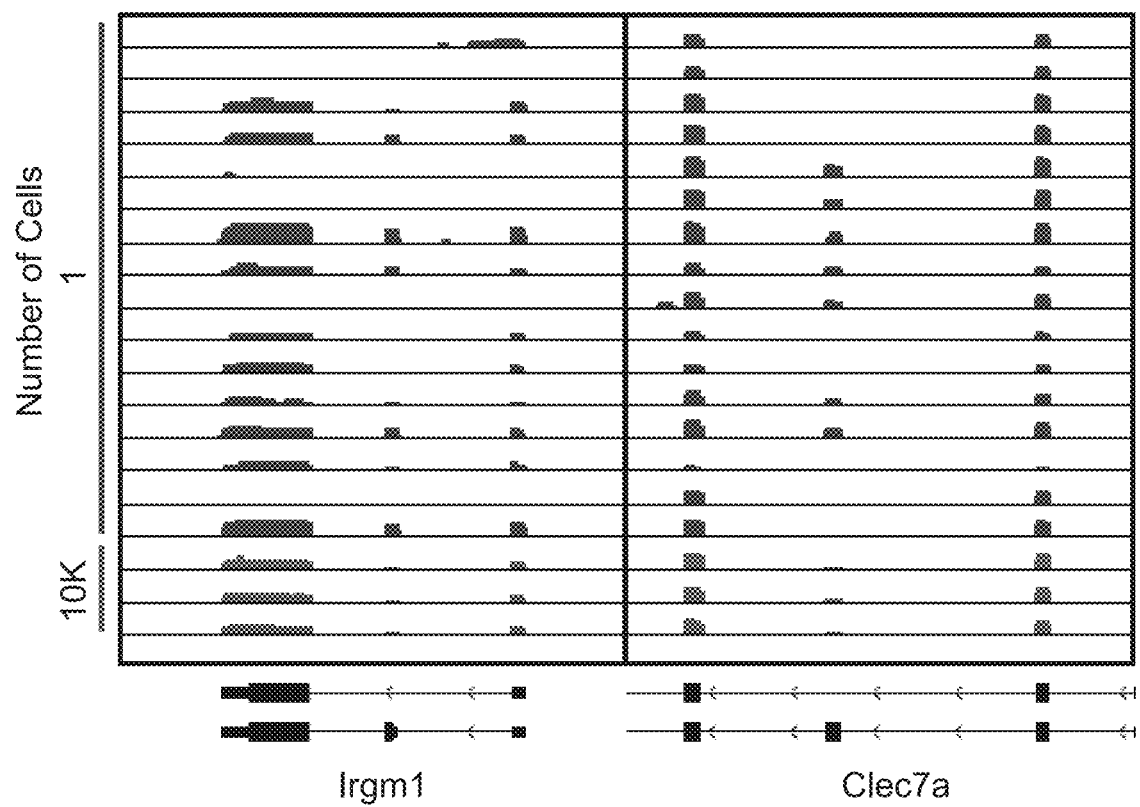
FIGS. 3A-3D are a series of graphs and illustrations depicting variation in isoform usage between single cells. A color version of these figures can be found in Shalek et al., "Single-cell transcriptomics reveals bimodality in expression and splicing in immune cells." Nature 498(7453):236-
Figure 3B:
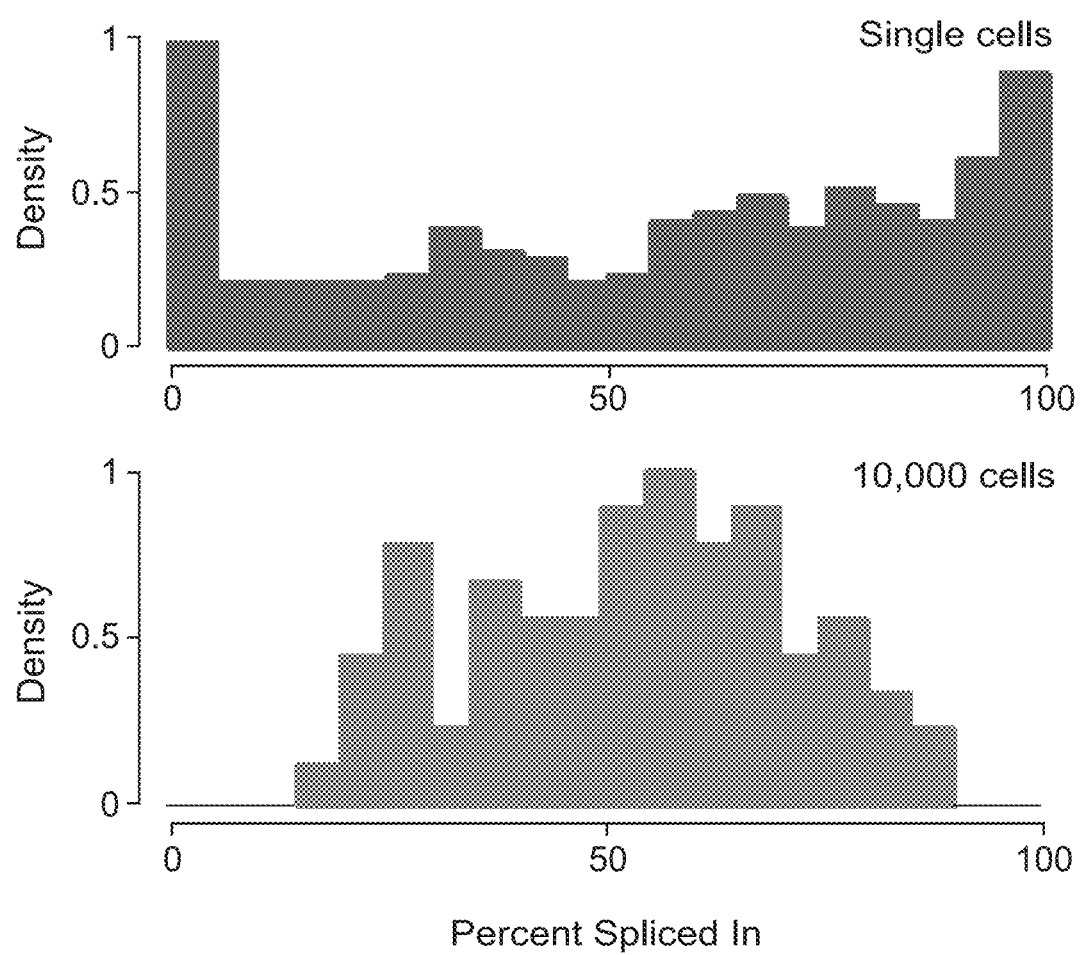
Figure 3C:
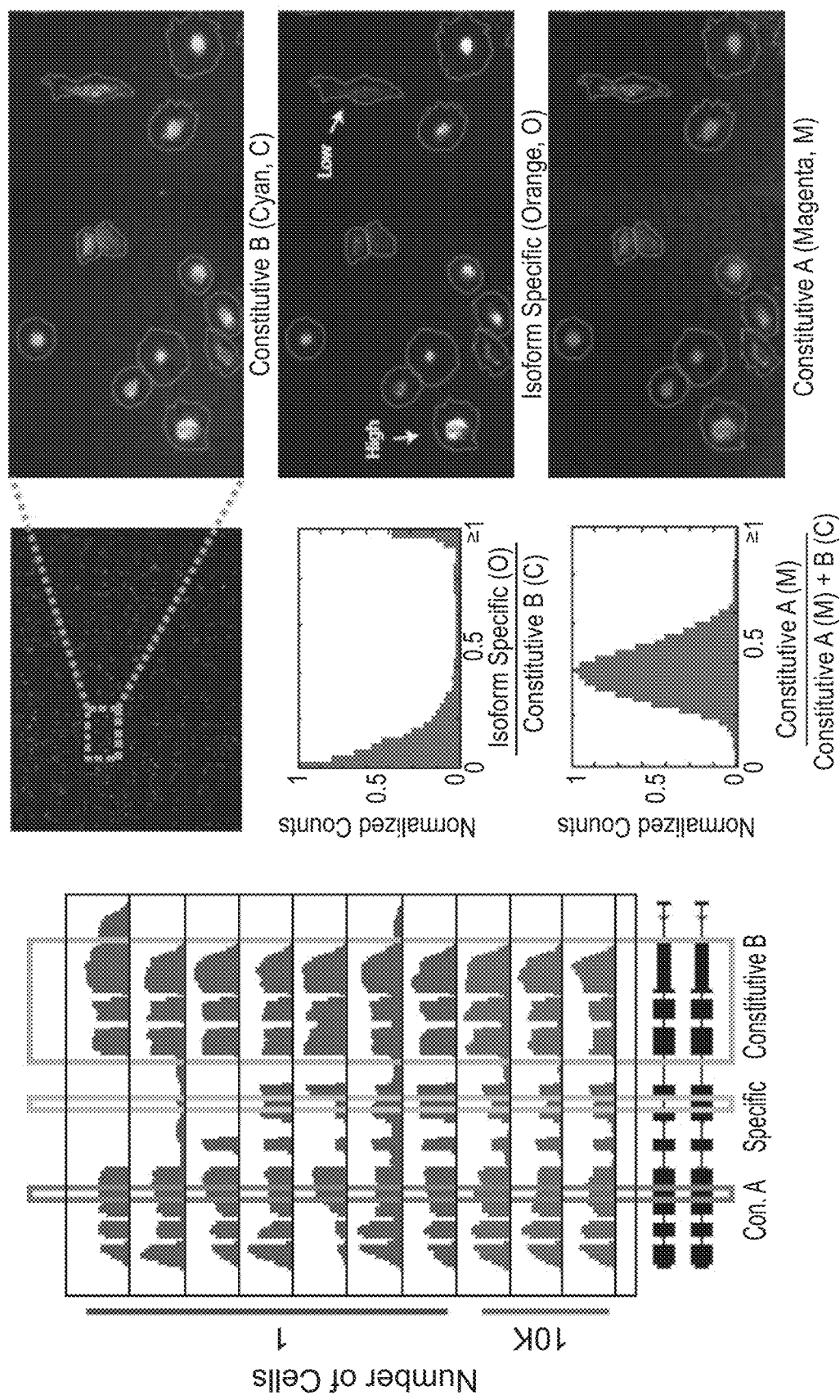

For splicing analyses, custom RNA fish probes (Panomics) were designed to either Irf7 or Acpp as follows:

| # | Accession | Target | Start | Stop | Length | Approx. bDNAs | Name and color in FIG. 3c,d |
|---|-----------|--------|-------|------|--------|---------------|------------------------------|
| 1 | NM_019807.2 | Acpp | 1199 | 2667 |  | 20 | Exon A (Orange, O) |
| 2 | NM_207668.2 | Acpp | 1199 | 4488 |  | 20 | Exon B (Magenta, M) |
| 3 | NM_016850 | Irf7 | 891 | 992 | 101 | 3 | Isoform Specific (Orange, O) |
| 4 | NM_016850 | Irf7 | — | — |  | 20 | Constitutive B (Cyan, C) |
| 5 | NM_016850 | Irf7 | 1461 |  |  | 3 | Constitutive A (Magenta, M) |

The difference in the number of bDNAs between the two constitutive Irf7 probes led to slightly better binding and thus higher counts for the constitutive probe B. As a result, the metric, probe A counts/(probe A counts+probe B counts) (used in the histogram in FIG. 3c), is normally distributed with a mean of ~0.45 (instead of ~0.5). Plotting the isoform-specific probe over constitutive probe B gave a similar curve (compare FIG. 3c with FIG. 15). A cell was only included if the number of counted mRNAs for the constitutive probe (Irf7) was at least 5 or if the sum of alterative exon counts was at least 5. For Acpp, n=615 cells; for Irf7, n=490.

Figure 17A:
FIGS. 17A and 17B are a series of photographs and graphs depicting RNA-FISH and Immunofluorescence co-staining.
Figure 17B:
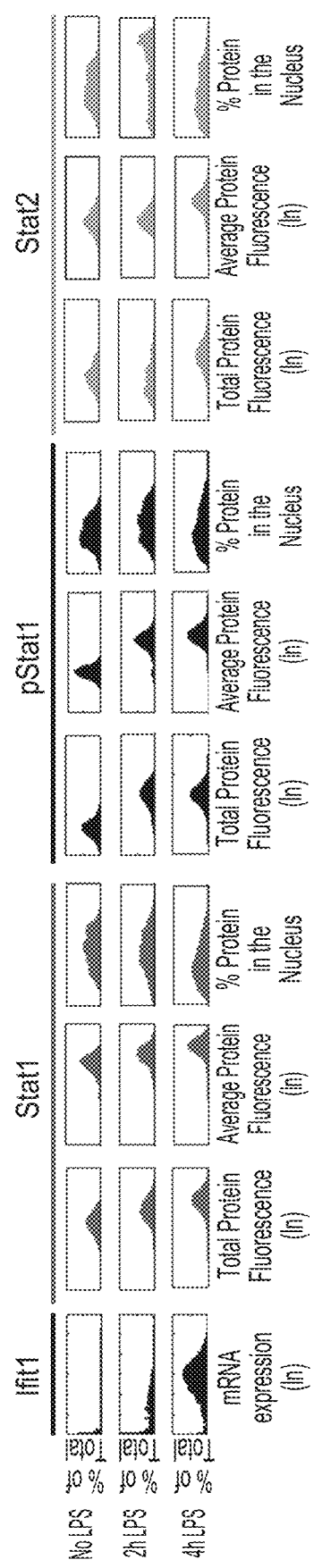
Figure 18A:
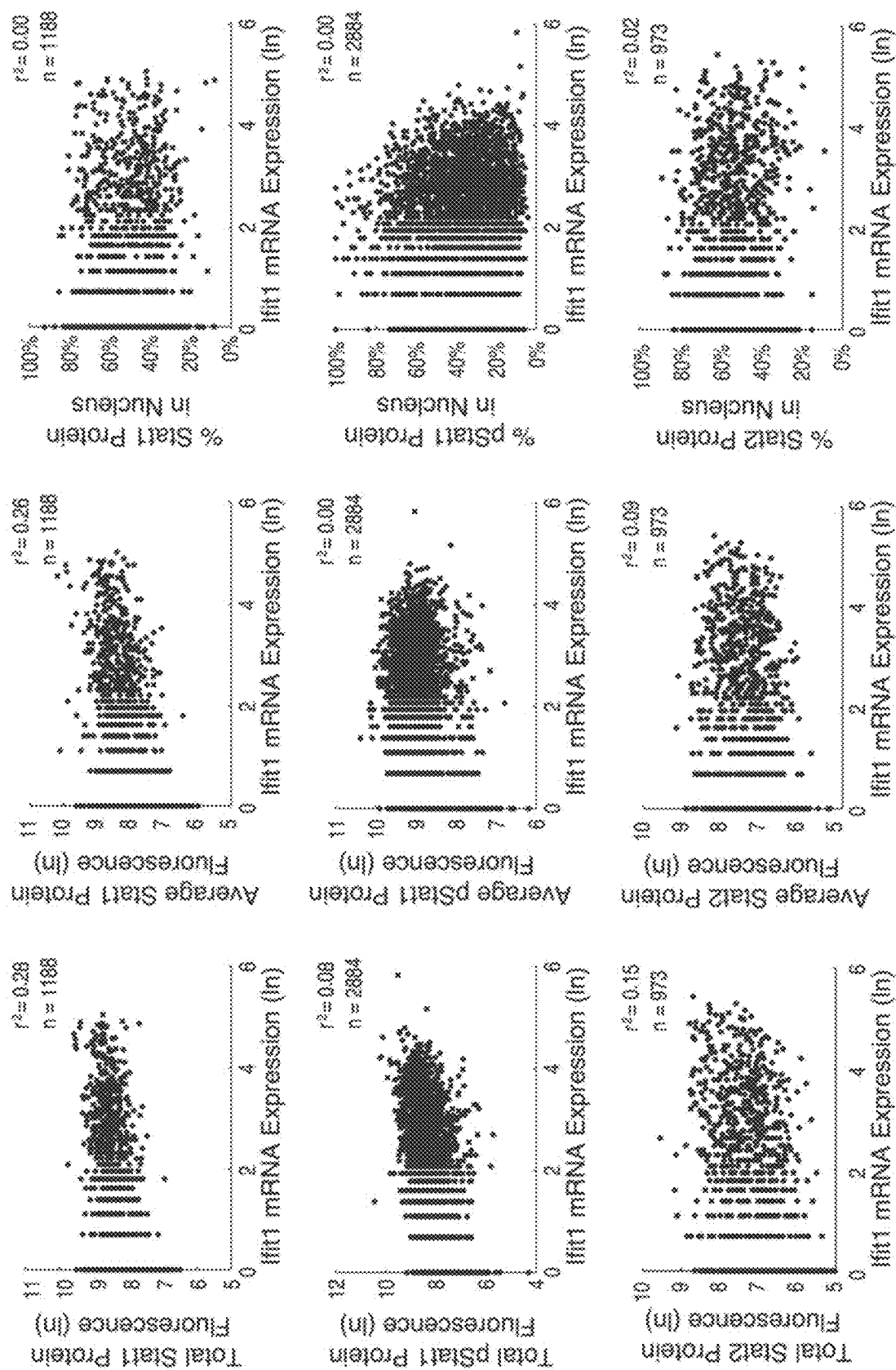
FIGS. 18A and 18B are a series of graphs depicting correlation between Stat protein and Ifit1 mRNA expression.
Figure 18B:
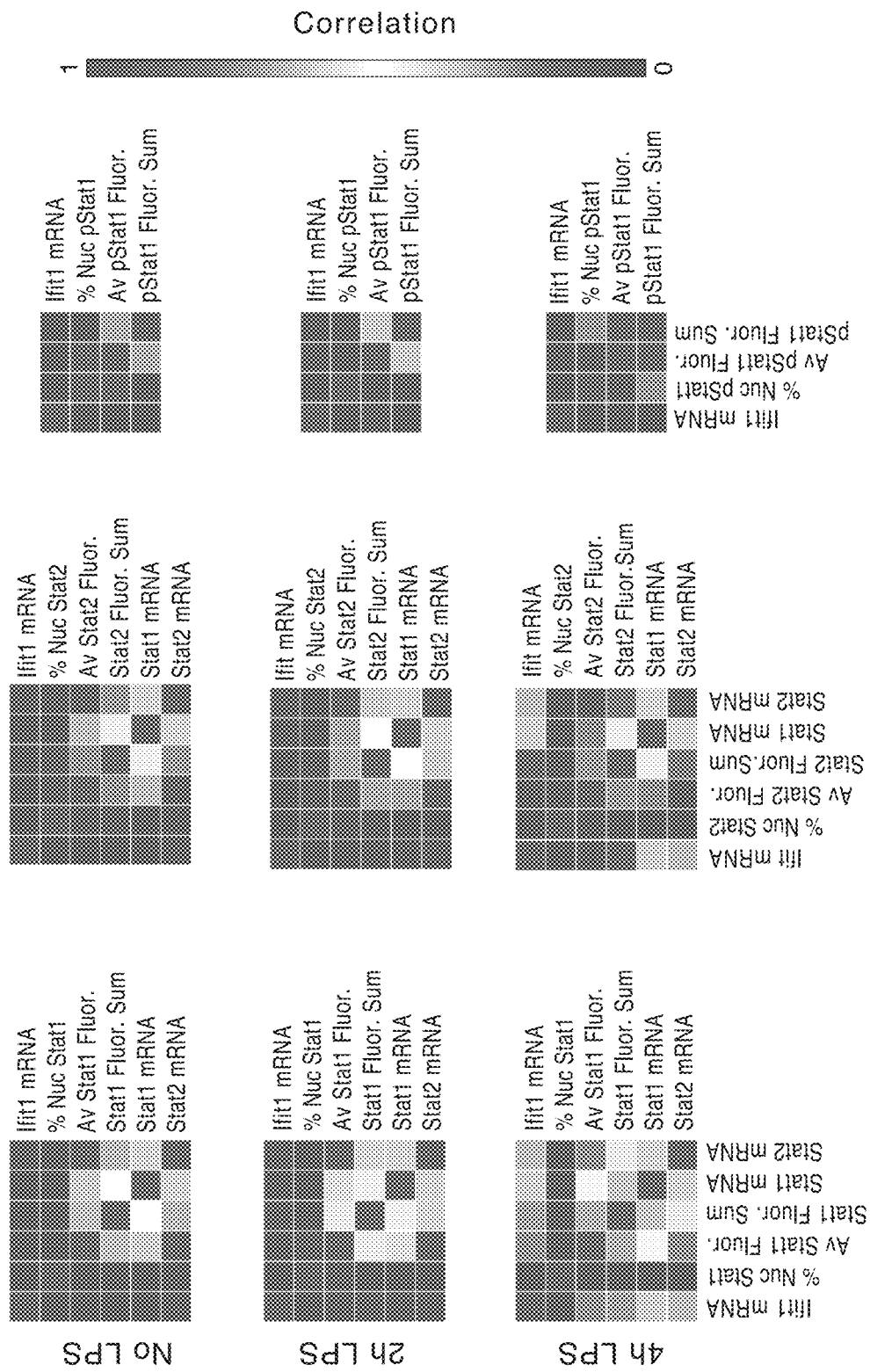

Immunofluorescence (IF) Measurements:

IF co-staining was performed as previously described (Chevrier, N. et al. Systematic discovery of TLR signaling components delineates viral-sensing circuits. Cell 147, 853-867, doi:10.1016/j.cell.2011.10.022 (2011); Shalek, A. K. et al. Nanowire-Mediated Gene Silencing in Primary Immune Cells: Identification of Patient-Specific Responses in Chronic Lymphocytic Leukemia. In Review (2012)) directly after RNA-FISH staining. Stat1, pStat1, and Stat2 antibodies, all used at 1:200, were obtained from Santa Cruz Biotechnology. Average and total fluorescence levels, as well as the percentage of the fluorescence localized to the nucleus, were quantified from epifluorescence images using locations and extents of individual cells and their nuclei, as above (FIGS. 17 & 18). For all protein histograms, counts were binned (n=100) and smoothed with a window of 5 bins in Matlab. Single-plane and 3-dimensional scans yielded similar results (data not shown).

Single-Cell qRT-PCR:

Single BMDCs were prepared for qRT-PCR using the Single-Cell-to-Ct kit (Ambion) with minor modifications. Namely, individual BMDCs were sorted into one-fourth of the recommended lysis buffer volume and all subsequent steps were scaled to match. After specific target amplification, an exonuclease I digestion (NEB) was performed by adding 0.5 µL Exonuclease 1, 0.25 µL Exonuclease I Reaction Buffer, and 1.75 µL water to each sample, vortexing, centrifuging, and heating to 37° C. for 30 minutes. After an 80° C. heat inactivation for 15 minute, samples were diluted 1:5 in Buffer TE. Single cells, negative controls, and population controls (prepared equivalently using extracted total RNA) were analyzed using 96×96 gene expression chips (Fluidigm Biomark) (Dalerba, P. et al. Single-cell dissection of transcriptional heterogeneity in human colon tumors. Nature Biotechnology 29, 1120-1127, doi:10.1038/nbt.2038 (2011)).

Fano Factor Calculation:

The Fano factor (normalized standard deviation) was calculated as the ratio of the standard deviation of gene expression values (log space) across single cells and the average single cell expression level (log space, see above). The dashed grey lines in FIGS. 2a,b represent a constant Fano factor of 0.25, and broadly separate highly expressed genes into two groups of variable and non-variable genes, as shown below in Table S3. Functional enrichment analysis of these two gene sets (see below) was highly robust to small changes in the Fano factor threshold (between 0.2 and 0.3) that was used.

TABLE S3

| Highly Expressed Genes Based On Averages In Cell Populations ||||||
|---|---|---|---|---|---|
| ATPASE6 | RPL6 | CCRL2 | ATP5O | RBM3 | PCNA |
| BCL2A1B | ANXA2 | TXN1 | ATOX1 | SKAP2 | MAPKSP1 |
| COX2 | SH3BGRL3 | COPE1 | RAC2 | RGS1 | NUPR1 |
| UBB | CTSS | CD74 | PSME1 | S100A1 | CCR1 |
| DQ539915 | BTF3 | RPSA | ATP5C1 | TUBB6 | NCK1 |
| CYTB | NPM1 | PSMA3 | TMSB10 | MDH1 | LY6E |
| TMSB4X | RPS6 | CSF2RB | RPL26 | IL1RN | CRIP1 |
| CYBA | S100A10 | TNFAIP2 | SEC11A | SNX2 | SNAP23 |
| CDC42 | RPL11 | FTH1 | CD14 | VDAC3 | TRF |
| MYL12B | PLEK | CCL3 | CANX | GPNMB | PSMA5 |
| UBC | CD9 | RASSF4 | BCAP31 | CNDP2 | CXCL3 |
| AK018753 | RPS13 | SLC7A11 | CLEC4E | TECR | ITGAM |
| RPS3A | ACTB | CTSB | PSMA4 | ATP6AP2 | TCEB1 |
| RPL23A | CSDE1 | BHLHE40 | FIS1 | CISH | CCL7 |
| RPL10 | RPL18A | RPS16 | PTGES3 | RPS15 | 0610031-J06RIK |
| RPL41 | GLIPR1 | H3F3B | ATP6V1D | TUBA1C | TREM2 |
| HNRNPK | RAB8B | ARL6IP1 | GPX4 | PDIA6 | RTP4 |
| PPIA | RPL9 | RPLP0 | HNRNPA2B1 | USP18 | F10 |
| B2M | CAPG | ATP6V0C | LRPAP1 | SDC4 | P2RY14 |
| LAPTM5 | SLC25A5 | ID2 | IFITM2 | SRP14 | MORF4L2 |
| SEPT2 | PSMB3 | RPS24 | VPS28 | CTSL | MRPL42 |
| FCER1G | PRR13 | M6PR | SPP1 | SARNP | PLP2 |
| BCL2A1D | HSP90B1 | GABARAP | PLSCR1 | FABP5 | CD200R4 |
| PSMB6 | HSP90AB1 | LPL | NFKBIZ | TRAF1 | BCL2L1 |
| RPL19 | SELK | EHD1 | PLK2 | SLAMF7 | FCGR3 |
| RPS3 | SLC2A6 | CXCL2 | ANXA1 | ARHGEF3 | POLR2G |
| POL | LSP1 | CCL4 | TSPAN31 | ATP6V0B | CCL17 |

TABLE S3-continued

| Highly Expressed Genes Based On Averages In Cell Populations | | | | | |
|---|---|---|---|---|---|
| RPL3 | NACA | SHISA5 | SP140 | C5AR1 | PTGS2 |
| RPL4 | RPL13A-PS1 | SLFN2 | EMP3 | FAS | GSTM1 |
| RPL7 | UBA52 | YWHAE | IL12B | CD68 | H2-AA |
| TAGLN2 | RPS11 | H2-DMB1 | RPL8 | FCGR2B | TGIF1 |
| ACTR2 | PTPRC | AKR1A4 | COX6B1 | COX7A2L | 1600029-D21RIK |
| 2900073-G15RIK | ACAD9 | CCL5 | CLEC4N | IFI204 | PILRB1 |
| ATP5L | SUMO1 | TYROBP | CHMP2A | PSMC4 | MPP1 |
| SHFM1 | PSME2 | H3F3A | RPL17 | PLA2G7 | PTGS1 |
| GHITM | CAPZA1 | HMGB1 | CD274 | PLD3 | MGL2 |
| BC071253 | RPL14 | CD63 | LGALS3 | PRDX2 | ATP6V0D2 |
| AK163440 | 6720456-B07RIK | IL1B | IL6 | FAM96A | TARM1 |
| GU332589 | VAMP8 | TNFAIP3 | ANXA3 | GTF2B | CXCL1 |
| DAZAP2 | C920009-B18RIK | CDKN1A | IFITM3 | MSR1 | RSAD2 |
| FTL1 | MALAT1 | CNBP | MMP12 | DAD1 | THBS1 |
| RPS19 | GPI1 | PRDX5 | ECH1 | IDH1 | EMR1 |
| CALM2 | LITAF | EIF3E | A130040-M12RIK | VPS29 | RBM7 |
| BCL2A1A | IL2RG | CCL6 | MGST1 | INHBA | TUBA1B |
| ATP6V0E | RPL37A | HNRNPC | ARPC1B | PFDN5 | IFI205 |
| RPL35 | TPM3 | FXYD5 | IRG1 | CFP | MMP13 |
| MT-ND4 | PTAFR | HN1 | LDHA | GRN | SIRPB1B |
| RPL23 | PPIB | RPL30 | DLD | TCP1 | AW112010 |
| MSN | SAT1 | PSAP | CCL2 | PRDX6 | TBXAS1 |
| AK140265 | TMBIM6 | LILRB4 | SH3BGRL | LIPA | KLK1B11 |
| ATP6AP1 | PSMB1 | ANXA4 | PSMA6 | SCPEP1 | LY6C2 |
| CD52 | BTG1 | SAMSN1 | ALOX5AP | SERPINB2 | GLIPR2 |
| RPS27A | RPL34 | AKAP13 | SDHD | IGSF6 | CD86 |
| ALDOA | RPL7A | ISG15 | SDHA | NME2 | C1QB |
| SUB1 | RPS29 | CYBB | H2-DMA | LGALS9 | H2-M2 |
| TALDO1 | CCDC72 | PTP4A2 | CLEC7A | CORO1A | ACSL1 |
| CFL1 | ITGB2 | RPL27 | RPL10A | RPS27L | IFNB1 |
| CLIC1 | HNRNPF | NFE2L2 | TNIP3 | LCP2 | FPR1 |
| RPS18 | BRP44L | H2-K1 | PILRA | TNFSF15 | FPR2 |
| ANXA5 | EIF3K | SBDS | CXCL10 | IFIT1 | LGALS1 |
| GM15450 | CD44 | CTSD | NAPSA | CLEC4D | CCR7 |
| ARHGDIB | RPS7 | UQCRB | EIF4A1 | HPRT | OASL1 |
| S100A11 | IQGAP1 | H2AFV | PFKP | TTC35 | GLRX |
| RPL32 | DSTN | CYB5 | UBE2L6 | ATP5H | CHI3L3 |
| SRGN | BZW1 | MT1 | LAMP2 | LGMN | FLRT3 |
| ARPC3 | AA467197 | PLD4 | ALAS1 | ESD | TMEM39A |
| RPS9 | WDR1 | TREX1 | ATP6V1F | IDI1 | PF4 |
| 3110003-A17RIK | ATP6V1E1 | IL1A | ARL5C | PSMA1 | AK041746 |
| LCP1 | RPS8 | H1F0 | LYZ1 | SEC13 | EAR2 |
| MYL6 | RPS27 | CD48 | PLIN2 | SUMO2 | IL23A |
| AK141672 | ATP5G2 | RPS26 | LGALS3BP | OAZ1 | SAA3 |
| CSTB | CCL9 | ASS1 | PGK1 | RSU1 | CD82 |
| COPZ1 | RPS17 | LYZ2 | TFEC | PLAUR | ZFP263 |
| RPS14 | ENO1 | ASAH1 | ATP5J | GBP2 | LY86 |
| CAPZA2 | ERH | COX4I1 | RNH1 | CCL22 | UPP1 |
| ATP6V1G1 | PRDX1 | POMP | PGD | PSMD14 | TMEM176B |
| RPL24 | RPL15 | TMEM50A | PSMB2 | GYG | IFIT2 |
| EEF1A1 | MBNL1 | MAP1LC3B | 2900010-J23RIK | MYO1F | CD69 |
| CFLAR | CTSC | CTSZ | PSMA2 | CD38 | GPR84 |
| NPC2 | VPS35 | ARF1 | EEF1G | DPEP2 | TNFSF4 |
| SRSF5 | ACTG1 | RPL28 | TNFSF9 | GM6644 | STMN1 |
| TANK | LILRB3 | AP2M1 | TLR2 | CD80 | GM6377 |
| RPS25 | RPS20 | COX6C | 1810029-B16RIK | DAB2 | IL1R2 |
| FAU | UQCRH | TNF | CTSA | CCT5 | TUBA1A |
| EIF4G2 | GNB2L1 | SDCBP | GM11428 | ETFB | CD40 |
| EEF2 | HSPA8 | RASGEF1B | CD53 | MMP8 | NIACR1 |
| RPS5 | AY096003 | PKM2 | HSPA5 | EVI2A | |

Figure 2A:
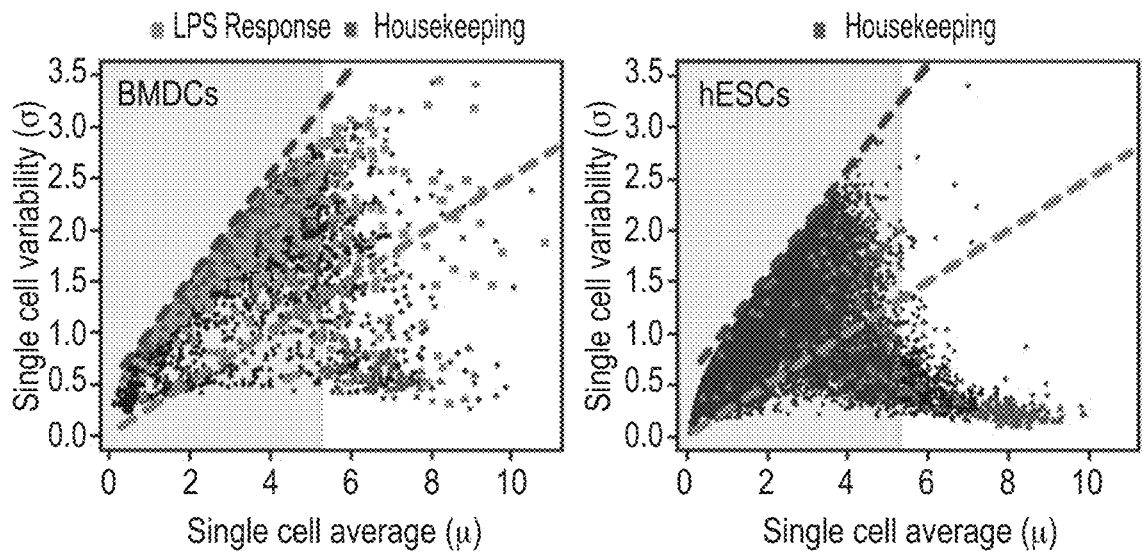
FIGS. 2A-2C are a series of graphs and illustrations depicting bimodal variation in expression levels across single cells. A color version of these figures can be found in Shalek et al., "Single-cell transcriptomics reveals bimodality in expression and splicing in immune cells." Nature 498 (7453):236-40 (2013).

The dashed blue line in FIG. 2a represents the maximum theoretical standard deviation for the 18 single cells given their single cell average. This theoretical maximum occurs when the cells are perfectly bimodally distributed about a value of $(\mu+\log(2))/2$ and is represented by the relationship: $\sigma_{max}=\text{sqrt}(18/17)*(\mu+\log(2))/2)$.

Functional Enrichment of Variable/Non-Variable Gene Sets:

Functional enrichment (GO annotation) of non-variable highly expressed gene sets was performed using DAVID v6.7 (Huang, D. W., Sherman, B. T. & Lempicki, R. A. Bioinformatics enrichment tools: paths toward the comprehensive functional analysis of large gene lists. Nucleic Acids Research 37, 1-13, doi:10.1093/nar/gkn923 (2009); Huang, D. W., Sherman, B. T. & Lempicki, R. A. Systematic and integrative analysis of large gene lists using DAVID bioinformatics resources. Nature Protocols 4, 44-57, doi:10.1038/nprot.2008.211 (2009)). The full list of 522 highly expressed genes was used as the background set. For FIG. 2a and Table S3, two lists were combined to form a set of housekeeping genes. The first list is a set of ribosomal subunit proteins defined in GO annotations (Huang, et al., Nucleic Acids Research 2009; Huang, et al., Nature Protocols 2009) and the second list is taken from a table of commonly used mouse housekeeping genes that were downloaded from the Qiagen website.

Correlation Matrix and Principal Component Analysis (PCA):

PCA for 632 induced genes was performed in R using the prcomp function. The expression values of each gene were transformed to have zero mean and unit variance across single cells in order to appropriately compare variability patterns across genes with different overall abundance in the population.

A correlation matrix was calculated based on the log-scale (but non-transformed) gene-expression estimates, and clustered the matrix using k-means. A parameter of five clusters based on the "elbow method" (Diday, E. New approaches in classification and data analysis. (Springer-Verlag, 1994)) (data not shown) were chosen, but the identification of a strongly enriched antiviral cluster (and its high degree of overlap with PC2) was highly robust to the parameter choice or stochasticity of k-means.

In the set of 632 genes, a set of antiviral gene targets from previous work (Amit, I. et al. Unbiased reconstruction of a mammalian transcriptional network mediating pathogen responses. Science 326, 257-263, doi:10.1126/science.1179050 (2009)) were annotated. Stat2 targets were annotated from a previously defined set of "promoter ChIP peaks" (Garber, M. et al. A High-Throughput Chromatin Immunoprecipitation Approach Reveals Principles of Dynamic Gene Regulation in Mammals. Molecular Cell 47, 810-822, doi:10.1016/j.molcel.2012.07.030 (2012)) on a set of identically stimulated (at 4 h) BMDCs. Cluster-specific enrichment analyses were performed using a hypergeometric test in R, using the full set of 632 induced genes as a background set.

Figure 15:
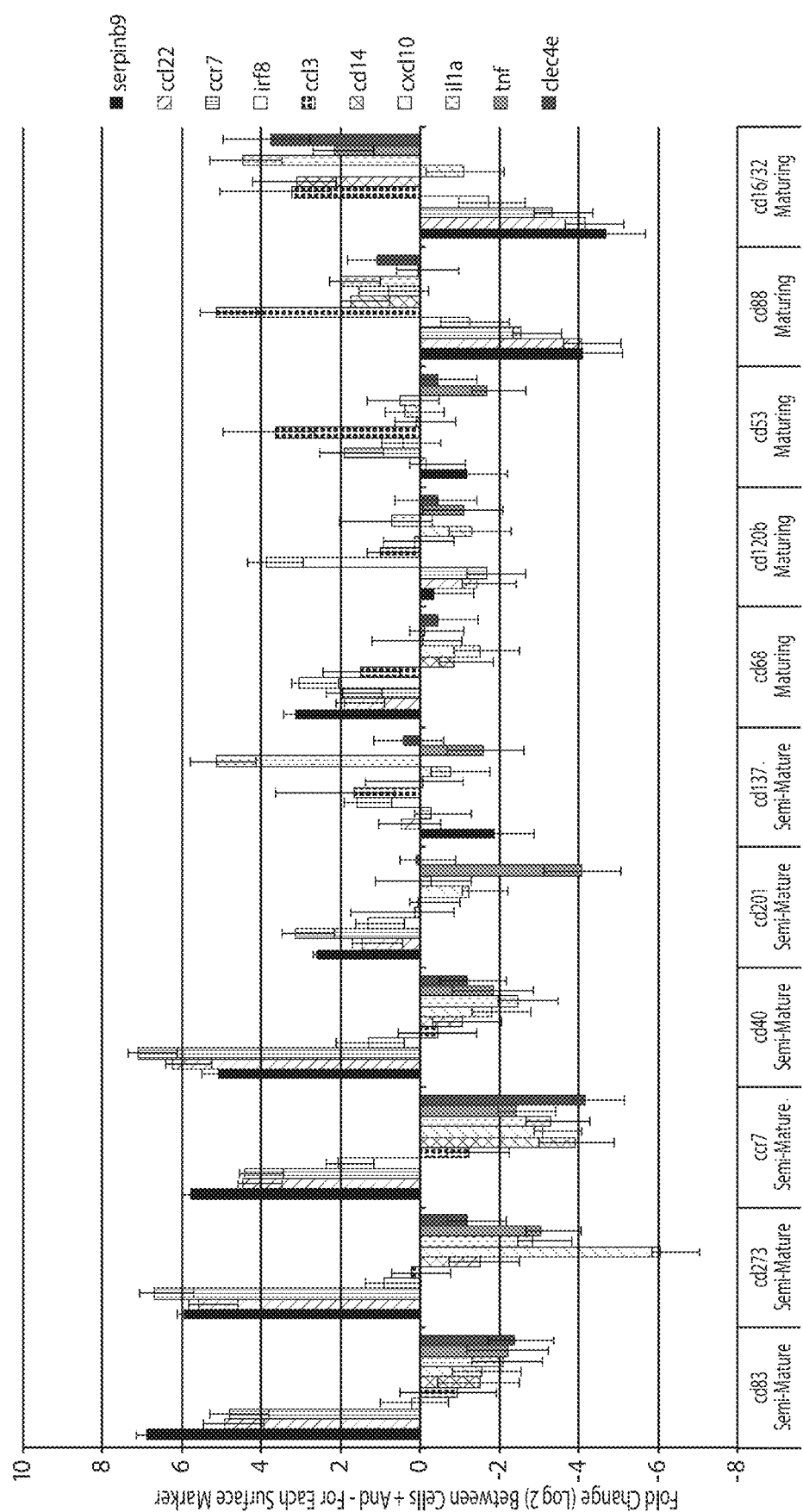
FIG. 15 is a graph depicting differences in expression levels of key markers between subpopulations that are positive and negative for different semi-mature and maturing cell surface markers. Shown are the differential expression levels (Y axis) of each of 10 marker genes (bars, color legend, right) measured by qRT-PCR between cells positively and negative sorted for each marker (X axis). The markers were chosen based on their ability to discriminate the 'maturing' (Red) and 'semi-mature' (Blue) subpopulations in the RNA-Seq data.

Population Fluorescence-Activated Cell-Sorting (FACS) Analysis and Quantitative Reverse Transcription Polymerase Chain Reaction (qRT-PCR):

BMDCs were stimulated with LPS for 4 h. Fifteen minutes prior to sorting, cells were stained with each of 11 antibodies from Biolegend that defined the semi-mature (S) or maturing (M) cells: Cd83 (S), Cd273 (S), Ccr7 (S), Cd40 (S), Cd201 (S), Cd137 (S), Cd68 (M), Cd120b (M), Cd53 (M), Cd88 (M), and Cd16/32 (M). Three groups of 1,000 cells either positive or negative for each of the tested surface markers were sorted in 100 µL of buffer TCL supplemented with 1% 2-mercaptoethanol. Total RNA was then extracted from each of the 20 samples using an RNeasy Mini Kit (Qiagen) and cDNA was prepared using Sensiscript RT (Qiagen) as previously described (Shalek, A. K. et al. Vertical silicon nanowires as a universal platform for delivering biomolecules into living cells. Proceedings of the National Academy of Sciences 107, 1870-1875, doi: 10.1073/pnas.0909350107 (2010)). Population-wide expression levels for different transcripts were then analyzed relative to GAPDH using qRT-PCR, as previously described (Shalek, A. K. et al. Vertical silicon nanowires as a universal platform for delivering biomolecules into living cells. Proceedings of the National Academy of Sciences 107, 1870-1875, doi:10.1073/pnas.0909350107 (2010)) (FIG. 15). Primers for qRT-PCR are presented below in Table S6.

TABLE S6

Gene List, PCR Primer Pairs For Fluidigm Single Cell qPCR Codeset

| Gene Name | Forward Primer | SEQ ID NO: | Reverse Primer | SEQ ID NO: |
|---|---|---|---|---|
| 18s | gcaattattccccatgaacg | 1 | gggacttaatcaacgcaagc | 137 |
| 28s | tcatcagacccagaaaagg | 2 | gattcggcaggtgagttgtt | 138 |
| Actb |ctaaggccaaccgtgaaaag | 3 | accagaggcatacagggaca | 139 |
| Anxa7 | gaacgtctcctcgtgtccat | 4 | ggccatctggtggttcac | 140 |
| Arbp/RPLP0 | actggtctaggacccgagaag | 5 | tcccaccttgtctccagtct | 141 |
| Arf4 | gatgcgcattttgatggtt | 6 | ttcagtttatacagaattgtcgtcttg | 142 |
| Arg2 | tatggtccagctgccattc | 7 | ccaaagtcttttaggtggcatc | 143 |
| Atf3 | gctggagtcagttaccgtcaa | 8 | cgcctcctttcctctcat | 144 |
| Atf4 | atgatggcttggccagtg | 9 | ccattttctccaacatccaatc | 145 |
| B2m | ttctggtgcttgtctcactga | 10 | cagtatgttcggcttccattc | 146 |
| Calcrl | ctcctgagactattcccacagaa | 11 | caagatgttgctgtatcatcatagg | 147 |

TABLE S6-continued

Gene List, PCR Primer Pairs For Fluidigm Single Cell qPCR Codeset

| Gene Name | Forward Primer | SEQ ID NO: | Reverse Primer | SEQ ID NO: |
|---|---|---|---|---|
| cav1 | ccagggaaacctcctcaga | 12 | ccggatgggaacagtgtaga | 148 |
| Ccl2 | catccacgtgttggctca | 13 | gatcatcttgctggtaatgagt | 149 |
| Ccl3 | tgcccttgctgttcttctct | 14 | gtggaatcttccggctgtag | 150 |
| Ccl7 | ttctgtgcctgctgctcata | 15 | ttgacatagcagcatgtggat | 151 |
| Ccnd2 | ctgtgcatttacaccgacaac | 16 | cactaccagttcccactccag | 152 |
| Ccr7 | ctccttgtcattttccaggtg | 17 | tggtattctcgccgatgtagt | 153 |
| Cd14 | aaagaaactgaagcctttctcg | 18 | agcaacaagccaagcacac | 154 |
| Cebpb | tgatgcaatccggatcaa | 19 | cacgtgtgttgcgtcagtc | 155 |
| Cited2 | atcgcaaagacggaagga | 20 | tgctgctggtgatgatgc | 156 |
| Clec4e | gcctccatcctgtttctcag | 21 | tgagagctgcgatatgttacg | 157 |
| Cxcl1 | ctgggattcacctcaagaacatc | 22 | cagggtcaaggcaagcctc | 158 |
| Cxcl10 | gccgtcattttctgcctca | 23 | cgtccttgcgagagggatc | 159 |
| Cxcl2 | aaaatcatccaaaagatactgaacaa | 24 | ctttggttcttccgttgagg | 160 |
| DDX58 | gaagattctggaccccaccta | 25 | tgaatgtactgcacctcctca | 161 |
| Dnmt3a | acacagggcccgttacttct | 26 | tcacagtggatgccaaagg | 162 |
| ets2 | cagttttcgtgggacactca | 27 | aagggagcacagcaaacaga | 163 |
| Gnb4 | ttgggatagctatacgacaaataaga | 28 | ggcgtaggcacaggtcat | 164 |
| Hmgn2 | gctcccagcgctataaaaact | 29 | tgagcacggggatacagc | 165 |
| Hprt | tcctcctcagaccgctttt | 30 | cctggttcatcatcgctaatc | 166 |
| Ifih1 | ctattaaccgtgttcaaaacatgaa | 31 | cacctgcaattccaaaatctta | 167 |
| Ifit1 | tctaaacagggccttgcag | 32 | gcagagcccttttgataatgt | 168 |
| Ifit2 | gcaagatgcaccaagatgag | 33 | cttctaatgaagtgctccagacc | 169 |
| Ifit3 | tgaactgctcagcccaca | 34 | tcccggttgacctcactc | 170 |
| Ifnb1 | ctggcttccatcatgaacaa | 35 | agagggctgtggtggagaa | 171 |
| Ikbke | gggagagtctttgcctgattc | 36 | atctcctgggcttggctatc | 172 |
| Il12b | gattcagactccaggggaca | 37 | tggttagcttctgaggacacatc | 173 |
| Il15 | cagctcagagaggtcaggaaa | 38 | catgaagaggcagtgctttg | 174 |
| IL15ra | ccagtgccaacagtagtgaca | 39 | ttgggagagaaagcttctgg | 175 |
| Il1a | ttggttaaatgacctgcaaca | 40 | gagcgctcacgaacagttg | 176 |
| Il1b | acctgtcctgtgtaatgaaagacg | 41 | tgggtattgcttgggatcca | 177 |
| Il6 | gctaccaaactggatataatcagga | 42 | ccaggtagctatggtactccagaa | 178 |
| inhba | atcatcacctttgccgagtc | 43 | tcactgccttccttggaaat | 179 |
| Irf1 | gagctgggccattcacac | 44 | tccatgtcttgggatctgg | 180 |
| Irf4 | acagcacctatggctctctg | 45 | atggggtggcatcatgtagt | 181 |
| Irf7 | cttcagcactttcttccgaga | 46 | tgtagtgtggtgacccttgc | 182 |
| Irf8 | gagccagatcctccctgact | 47 | ggcatatccggtcaccagt | 183 |
| Irf9 | tgaggccaccattagagagg | 48 | agcagcagcgagtagtctga | 184 |

TABLE S6-continued

Gene List, PCR Primer Pairs For Fluidigm Single Cell qPCR Codeset

| Gene Name | Forward Primer | SEQ ID NO: | Reverse Primer | SEQ ID NO: |
|---|---|---|---|---|
| Irg1 | gcttttgttaatggtgttgctg | 49 | ggcttccgatagagctgtga | 185 |
| Isg15 | agtcgacccagtctctgactct | 50 | ccccagcatcttcaccttta | 186 |
| Jak2 | aagattgccaaggccaga | 51 | tgttgttccagcactagtca | 187 |
| Jarid2 | gcacttgtgctacctgtcca | 52 | tccaggcagaacacgacat | 188 |
| Lgals9 | gcattggttcccctgagata | 53 | tccagtaaaggggatgatcg | 189 |
| mapkapk2 | cagcaaaaattcgccctaaa | 54 | agtgcagctccacctctctg | 190 |
| Mt2 | catggaccccaactgctc | 55 | agcaggagcagcagcttt | 191 |
| Mx1 | ttcaaggatcactcatacttcagc | 56 | gggaggtgagctcctcagt | 192 |
| Mx2 | cagttcctctcagtcccaagat | 57 | tgcggttgtgagcctctt | 193 |
| Myd88 | tggccttgttagaccgtga | 58 | aagtatttctggcagtcctcctc | 194 |
| Nfe2l2 | catgatggacttggagttgc | 59 | cctccaaaggatgtcaatcaa | 195 |
| Nfkb1 | cactgctcaggtccactgtc | 60 | ctgtcactatcccggagttca | 196 |
| Nfkbia | acgagcaaatggtgaaggag | 61 | atgattgccaagtgcagga | 197 |
| Nfkbiz | cagctggggaagtcattttt | 62 | ggcaacagcaatatggagaaa | 198 |
| Pa2g4 | ggtcgtgaccaagtataagatgg | 63 | cagacacacctgagctggaa | 199 |
| Peli1 | ctgatcaagaaaatcatccttcc | 64 | accgtttgggagagatccat | 200 |
| pgk1 | tacctgctggctggatgg | 65 | cacagcctcggcatatttct | 201 |
| Plek | agtggatcaaagccatccag | 66 | tcagtgattctcggtgtcctc | 202 |
| Plk1 | ttgtagttttggagctctgtcg | 67 | agtgccttcctcctcttgtg | 203 |
| Plk2 | catcaccaccattcccact | 68 | tcgtaacactttgcaaatcca | 204 |
| Pml | aggaaccctccgaagactatg | 69 | ttcctcctgtatggcttgct | 205 |
| Pnrc2 | tgtgctgaggagactcgatg | 70 | tgagccagtctgctgatttc | 206 |
| Ppia | acgccactgtcgctttc | 71 | gcaaacagctcgaaggagac | 207 |
| Ptgs2 | gatgacttccgagctgtg | 72 | ggattggaacagcaaggattt | 208 |
| ptx3 | cgctgtgctggaggaact | 73 | gggaagaaaattgctgtttcac | 209 |
| Rel | ttgcagagatggatactatgaagc | 74 | caccgaatacccaaattttgaa | 210 |
| Rpl13a | atccctccaccctatgacaa | 75 | gccccaggtaagcaaactt | 211 |
| Rsad2 | gcttcaacgtggacgaagac | 76 | cctcaattaggaggcactgg | 212 |
| Serpinb9 | tgtggacctcagcaaggtg | 77 | cctcaacatcagtgctcttcat | 213 |
| Sfpi1 | ggagaagctgatggcttgg | 78 | caggcgaatcttttcttgc | 214 |
| Slc7a11 | tgggtggaactgctcgtaat | 79 | aggatgtagcgtccaaatgc | 215 |
| slfn1 | cgtgctcagtagagcagcttag | 80 | catcggtgatgttcattttcc | 216 |
| Slfn2 | aggcaactgagcaaagcaac | 81 | ttgcattttccagctgaatg | 217 |
| Socs3 | atttcgcttcgggactagc | 82 | aacttgctgtgggtgaccat | 218 |
| Stat1 | gcagcacaacatacggaaaa | 83 | tctgtacgggatcttcttgga | 219 |
| Stat2 | ggaacagctggaacagtggt | 84 | gtagctgccgaaggtgga | 220 |
| Tank | attccccaggaaaggctgt | 85 | ttggttaagaaaaggcttccaa | 221 |

TABLE S6-continued

Gene List, PCR Primer Pairs For Fluidigm Single Cell qPCR Codeset

| Gene Name | Forward Primer | SEQ ID NO: | Reverse Primer | SEQ ID NO: |
|---|---|---|---|---|
| Tapbp | cagcactctcttcagcctctc | 86 | tatgggtgaggacggtcag | 222 |
| Tbk1 | cctcggaggaacaaagaagtaa | 87 | tccagatattgcaccagacg | 223 |
| Tmem39a | gacgggcttgaggaacag | 88 | cctggggtaattaaggctgtg | 224 |
| Tnf | tcttctcattcctgcttgtgg | 89 | ggtctgggccatagaactga | 225 |
| Tnfaip2 | ggagcctttgaaagacctcaa | 90 | gaacttcttaaacagcggcttc | 226 |
| Tnfrsf1b | gaggcccaagggtttcag | 91 | ggcttccgtgggaagaat | 227 |
| tnfsf4 | aaaggaccctccaatccaaa | 92 | agttgcccatcctcacatct | 228 |
| Trex1 | cagggcagaccaagaattg | 93 | ggtctgtgagcccatgct | 229 |
| Trim12a | agcaccgtggtcacaaaac | 94 | cagcctttgcagaactacctg | 230 |
| Ywhaz | aacagctttcgatgaagccat | 95 | tgggtatccgatgtccacaat | 231 |
| Zfp36l1 | ttcacgacacaccagatcct | 96 | tgagcatcttgttacccttgc | 232 |
| Arid5a | cagagcaggagccagagc | 97 | gccaagttcatcatacacgttc | 233 |
| Bat5 | acattgctgctgctacttgc | 98 | gtactggggggttggtccag | 234 |
| Bcl3 | gaacaacagcctgaacatgg | 99 | tctgagcgttcacgttgg | 235 |
| Cbx4 | gtgggaaccagaggagaaca | 100 | tcagctgctcctgcctttt | 236 |
| Clic4 | act gtaacctgctgcccaag | 101 | aggaatatcaaagttgcggtattt | 237 |
| Crkl | cgccaggtttgattcttcag | 102 | cctcctggcgagtcactg | 238 |
| E2f5a | aaccccagatgctgacaaag | 103 | ccacctttattttaggtttcttgg | 239 |
| Fos | gggacagccttttcctactacc | 104 | gatctgcgcaaaagtcctgt | 240 |
| Fus | aaggcctaggcgagaatgtt | 105 | cataggctgtccagttttcttgt | 241 |
| Gapdh | ggcaaattcaacggcacagt | 106 | agatggtgatgggcttccc | 242 |
| Hhex | tcagaatcgccgagctaaat | 107 | ctgtccaacgcatcctttt | 243 |
| Ifna2 | atgaggaggctcccctttc | 108 | accttctccaggggaatc | 244 |
| Ifna4 | tcaagccatccttgtgctaa | 109 | gtcttttgatgtgaagaggttcaa | 245 |
| Il12a | ccatcagcagatcattctagacaa | 110 | cgccattatgattcagagactg | 246 |
| isg20 | ttggtgaagccaggctagag | 111 | cttcagggcattgaagtcgt | 247 |
| Jun | ccagaagatggtgtggtgttt | 112 | ctgaccctctcccccttgc | 248 |
| Junb | ccacggagggagagaaaatc | 113 | agttggcagctgtgcgtaa | 249 |
| Lcp2 | ccaacaggcaggaatcactc | 114 | cttctgctgggctcttcgt | 250 |
| Map3k7 | ccatcccaatggcgtatc | 115 | ccatggattctttggagtttg | 251 |
| Mapk9 | acgttaccagcaactgaaacc | 116 | gaactgtatcaaaagcagcacaa | 252 |
| Nfkb2 | tggaacagcccaaacagc | 117 | cacctggcaaacctccat | 253 |
| Parp14 | tggagatcctagtgacaaaaatcc | 118 | ctggaaaggctcccatagatac | 254 |
| Phlpp1 | cttgccctggaccacaaa | 119 | gtcaatcttgaagcagcgaat | 255 |
| Plagl2 | catccggagcagagacca | 120 | atgcactggtggggtttc | 256 |
| Plk3 | ggctggcagctcgattag | 121 | gttgggagtgccacagatg | 257 |
| Plk4 | gaaaaccaaaaaggctgtgg | 122 | tccttcagacgcacactctc | 258 |

TABLE S6-continued

Gene List, PCR Primer Pairs For Fluidigm Single Cell qPCR Codeset

| Gene Name | Forward Primer | SEQ ID NO: | Reverse Primer | SEQ ID NO: |
|---|---|---|---|---|
| Rbl1 | gcggcaactacagcctagag | 123 | tgcggcaagcaacatataaa | 259 |
| Rela | cccagaccgcagtatccat | 124 | gctccaggtctcgcttctt | 260 |
| Relb | gtgacctctcttccctgtcact | 125 | tgtattcgtcgatgatttccaa | 261 |
| Runx1 | ctccgtgctacccactcact | 126 | atgacggtgaccagagtgc | 262 |
| Sap30 | cggtgcagtgtcagcttc | 127 | ctcccgcaaacaacagagtt | 263 |
| Sbds | ggtggtggagagtgaggact | 128 | gctcatcaatttctctgaagca | 264 |
| Sfrs1 | ggtccgagaacagagtggtt | 129 | cctttaagtcctgccagcttc | 265 |
| Sfrs3 | tcgtcgtcctcgagatgatt | 130 | ctccttcttggggatctgc | 266 |
| Snx10 | gccagggcttggaagatt | 131 | cagatggctctgcaggaag | 267 |
| Stat4 | cggcatctgctagctcagt | 132 | tgccatagtttcattgttagaagc | 268 |
| Timeless | gagtcctcagcgagaccttg | 133 | tgtcttcttcttgccgatcc | 269 |
| Tmod3 | ccaagagcgttttcccaat | 134 | gttggatttggtggctcatc | 270 |
| Zc3h12a | gcgaggccacacagatattac | 135 | cgaaggatgtgctggtctg | 271 |
| Zc3h12c | agcgtaatgcgagaaacctc | 136 | ttctttgtttccatggctca | 272 |

Splicing Analysis:

A set of ~67,000 previously annotated alternatively spliced events (skipped exons, mutually exclusive splice events) were downloaded (Wang, E. T. et al. Alternative isoform regulation in human tissue transcriptomes. Nature 456, 470-476, doi:10.1038/nature07509 (2008)). MISO (Katz, Y., Wang, E. T., Airoldi, E. M. & Burge, C. B. Analysis and design of RNA sequencing experiments for identifying isoform regulation. Nature Methods 7, 1009-1015, doi:10.1038/nmeth.1528 (2010)) was run with default parameters to estimate the percent spliced in (PSI) for every event in each of the single cells and population replicates. The vast majority of events were not expressed at sufficient depth in any of the samples to be analyzed by MISO. For the remaining 4,338 events it was noted that PSI estimates derived from 10,000 cell replicates were tightly correlated (mean r=0.91). The PSI values for the three population replicates were averaged and focused the remainder of the analyses on the 352 "alternatively spliced" events (20%<population PSI average<80%) in 322 genes (28 genes had at least two alternative splicing events).

The PSI distribution of these 352 alternative splicing events across single cells was then examined (FIG. 3b). To ensure that only reliable splicing events from highly expressed transcripts were examined, only PSI estimates for single cell/splice event pairs where the alternatively spliced gene was expressed at high levels (single-cell TPM>250) within that single cell were considered. This resulted in 89 unique alternative splice events from 79 genes. After applying this filter, a histogram of PSI estimates across single cells (FIG. 3b, top) was plotted. FIG. 3b (bottom) shows a histogram of PSI estimates from the first 10,000-cell replicate for the same 89 splice events from FIG. 3b (top).

Mice:

For the high throughput Examples provided herein, 6-8 week old female C57BL/6 wild-type (wt), Tnfrsf1a$^{-/-}$ x Tnfrsf1b$^{-/-}$ (Tnfr, Irf1$^{-/-}$, Tirap$^{-/-}$, Il1rn$^{-/-}$, Ikbke$^{-/-}$, Cxcr2$^{-/-}$, Egr1$^{-/-}$, Fas$^{-/-}$, NZBWF1/J and Ifnβ1-eYFP reporter mice were obtained from Jackson Laboratory (Bar Harbor, Me.). Stat1$^{-/-}$ and 129/Sv control mice were purchased from Taconic (Hudson, N.Y.). Irf7$^{-/-}$ bone marrow (BM) was provided by Kate Fitzgerald from University of Massachusetts Medical School. Ifnr$^{-/-}$ BM was provided by Nir Hacohen from Massachusetts General Hospital. ZFP36$^{-/-}$ (TTP$^{-/-}$) and control BM were provided by Perry Blackshear from NIH/NIEHS. Ifnar1-/- (Ifnr KO) bone marrow Nir Hacohen (Massachusetts General Hospital); Il27-/- (Il27r KO) bone marrow as provided by Vijay Kuchroo (Brigham and Women's Hospital).

All animals were housed and maintained in a conventional pathogen-free facility at the MIT in Cambridge, Mass. (IACUC protocol: 0609-058015). All experiments were performed in accordance to the guidelines outlined by the MIT Committee on Animal Care (Cambridge, Mass.).

Cell Culture, Sorting, and Lysis:

For the high throughput Examples provided herein, cultures of bone marrow derived dendritic cells (BMDCs) from 6-8 week old female B6 mice were prepared as previously described (Amit, I. et al. Unbiased reconstruction of a mammalian transcriptional network mediating pathogen responses. Science 326, 257-263, doi:10.1126/science.1179050 (2009); Chevrier, N. et al. Systematic Discovery of TLR Signaling Components Delineates Viral-Sensing Circuits. Cell 147, 853-867, doi:10.1016/j.cell.2011.10.022 (2011)), with minor modification. Namely, isolated bone marrow was frozen down at 5 million (M) cells per mL in pure fetal bovine serum supplemented with 10% DMSO. For each run, a single vial was thawed and cultured as previously described (Ibid). At 9 days of in vitro culture, the cells were labeled with anti-Cd11c antibodies (Miltenyi Biotech) and flow-sorted, retaining the top 10% of positive cells. Subsequently, the cells were spun down and resuspended in a 15 mL conical tube at a concentration of $2 \times 10^5$ cells per mL in media supplemented with the relevant stimulus and placed in the incubator with the cap slightly ajar. Stimulants—PAM3CSK (Invivogen), Poly(I:C) [PIC] (Enzo Life Sciences, 10 μg/mL), LPS (Invivogen, 100 ng/mL), and Interferon-β (Ifn-β) (R&D Systems, 1000 units/mL)—were used as previously described (Ibid). 45 minutes prior to the specific time point, cells were spun down, resuspended at a concentration of $3 \times 10^5$ M cell per mL of complete media supplemented with Hoechst 34580 dye (Life Technologies, according to the manufacturer's recommendations), mixed 7:3 with $C_1$ suspension reagent (Fluidigm), and loaded onto $C_1$ microfluidic chips. After loading, each of the C, microfluidic chip's capture ports were optically inspected for the presence of a cell. The number of cells present in each chamber was determined by counting the number of nuclei. The average single cell capture rate was 72 (average)±13 (standard deviation) per chip. The average number of chambers with two or more cells was 8±7. Although rare multiple capture events were not filtered out automatically (i.e., by computational analysis) in the presented analyses, any specific finding (e.g., 'precocious cells') was confirmed by manual inspection, to ensure that no cell doublet or other cell capture concerns were involved. Similarly, it was explicitly confirmed that the addition of Hoechst 34580 does not alter gene expression in the system provided herein.

Whole Transcriptome Amplification:

After cell isolation, cells were lysed and SMART-Seq (See Ramskold, 2011). Whole Transcriptome Amplified products (WTA) were prepared using the SMARTer Ultra Low RNA Kit for Illumina Sequencing (Clontech) in conjunction with the mRNA-Seq protocol was run on the C1 with the following modifications:

Cell Lysis Mix:

| Composition | Stock Conc. | Volume |
|---|---|---|
| C1 Loading Reagent | 20X | 0.60 ul |
| SMARTer Kit RNase Inhibitor | 40 x | 0.30 ul |
| SMARTer Kit 3' SMART CDS Primer II A | 12 μM | 4.20 ul |
| SMARTer Kit Dilution Buffer | 1X | 6.90 ul |

Cycling Conditions I:
 a) 72° C., 3 min
 b) 4° C., 10 min
 c) 25° C., 1 min
Reverse Transcription (RT) Reaction Mix:

| Composition | Stock Conc. | Volume |
|---|---|---|
| C1 Loading Reagent | 20.0 x | 0.45 ul |
| SMARTer Kit 5X First-Strand Buffer (RNase-Free) | 5.0 x | 4.20 ul |
| SMARTer Kit Dithiothreitol | 100 mM | 0.53 ul |
| SMARTer Kit dNTP Mix (dATP, dCTP, dGTP, and dTTP, each at 10 mM) | 10 mM | 2.10 ul |
| SMARTer Kit SMARTer II A Oligonucleotide | 12 uM | 2.10 ul |
| SMARTer Kit RNase Inhibitor | 40 x | 0.53 ul |
| SMARTer Kit SMARTScribe™ Reverse Transcriptase | 100.0 x | 2.10 ul |

Cycling Conditions II:
 a) 42° C. 90 min
 b) 70° C., 10 min
PCR Mix:

| Composition | Stock Conc. | Volume |
|---|---|---|
| PCR Water | — | 35.2 ul |
| 10X Advantage 2 PCR Buffer | 10.0 x | 5.6 ul |
| 50X dNTP Mix | 10 mM | 2.2 ul |
| IS PCR primer | 12 uM | 2.2 ul |
| 50X Advantage 2 Polymerase Mix | 50.0 x | 2.2 ul |
| C1 Loading Reagent | 20.0 x | 2.5 ul |

Cycling Conditions III:
 a) 95° C., 1 min
 b) 5 cycles of:
  i) 95° C., 20 s
  ii) 58° C. 4 min
  ii) 68° C., 6 min
 c) 9 cycles of:
  i) 95° C., 20 s
  ii) 64° C., 30 s
  ii) 68° C., 6 min
 d) 7 cycles of:
  i) 95° C., 30 s
  ii) 64° C., 30 s
  ii) 68° C. 7 min
 e) 72° C., 10 min Library Preparation and RNA-Seq:

The WTA products were harvested from the C1 chip and cDNA libraries were prepared using Nextera XT DNA Sample preparation kit (Illumina) as per the manufacturer's recommendations, with minor modifications. Namely, reactions were run at one-fourth the recommended volume and the tagmentation step was extended to 10 minutes. After the PCR step, all 96 samples were pooled without library normalization, cleaned twice with 0.9× AMPure XP SPRI beads (Beckman Coulter), and eluted in buffer TE. Finally, the pooled libraries were quantified using Quant-IT DNA High-Sensitivity Assay Kit (Invitrogen), examined using a high sensitivity DNA chip (Agilent), and run on a MiSeq (Illumina). Finally, samples were sequenced deeply using either a HiSeq 2000 or a HiSeq 2500.

RNA-Seq of Population Controls:

Population controls were generated by extracting total RNA using RNeasy plus Micro RNA kit (Qiagen) according to the manufacturer's recommendations. Subsequently, 1 μL of RNA in water was added to 2 μL of lysis reaction mix, thermocycled using cycling conditions I (as above). Next, 4 μL of the RT Reaction Mix were added and the mixture was thermocycled using cycling conditions II (as above). Finally, 1 μL of the total RT reaction was added to 9 μL of PCR mix and that mixture was thermocycled using cycling conditions III (as above). Products were quantified, diluted to 0.125 ng/μL and libraries were prepared, cleaned, and tested as above.

RNA Fluorescence In Situ Hybridization (RNA-Fish):

RNA-FISH (FIG. 27) for Ifit1, Tnf, Il6, B2m, and Ifnb1 were performed as previously described using probes from Panomics (see e.g., Shalek, A. K. et al. "Single-cell transcriptomics reveals bimodality in expression and splicing in immune cells." Nature 498, 236-240, doi:10.1038/nature12172 (2013)).

On-Chip Cell Isolation and Simulation:

To block cell-to-cell communication, individual BMDCs were stimulated in the C1 chip after capture. First, prior to loading the cells, the C1 chip was pre-blocked with C1 blocking reagent and then with complete culture media for 2 h. Next, unstimulated BMDCs were loaded and then washed with complete media supplemented with the appropriate stimulus. After introduction of the stimulus-laced complete media, the chip was maintained at 37° C. within the C1 System until 30 minutes prior to the specific assay time point (i.e., for 3.5 hours for the 4 h stimulation time point). The cells were then washed on chip with media containing Hoechst (Invitrogen), and the chip was removed from the C1 System, imaged and run as above at 4 h. The 30-minute interval at room temperature (equivalent to our timing of loading of "in tube" samples) accounts for cell wash (15 minutes), imaging (5 minutes), and reagent loading (10 minutes) prior to lysis. Lastly, a mock "on-chip" experiment was performed by loading cells as above and then introducing complete media without LPS as above.

Cytokine Addition, GolgiPlug, and Cycloheximide Experiments:

Recombinant IL-4 (Miltenyi Biotec), IL-6 (Miltenyi Biotec), IL-10 (R&D Systems), IL-12 (Miltenyi Biotec), IL-15 (Miltenyi Biotec), IL-27 (R&D Systems), IL-35 (AdipoGen) were added as described at 200 ng/mL. GolgiPlug (BD Biosciences) was added at a 1:1,000 dilution at various time points. Finally, Cycloheximide was added at 100 μg/mL from a 500× ethanolic stock at the time of stimulation or during a standard 4 h LPS control.

Processing RNA-Seq Data:

Raw sequencing data were processed as previously described (Shalek, Nature 2013), except that there was no need to trim SMARTer short and long adapter sequences due to the Nextera library preparation (see e.g., Ramskold, D. et al. Full-length mRNA-Seq from single-cell levels of RNA and individual circulating tumor cells. Nature Biotechnology 30, 777-782, doi:10.1038/nbt.2282 (2012). Short sequencing reads were aligned to the UCSC mm9 transcriptome (see e.g., Fujita, P. A. et al. The UCSC Genome Browser database: update 2011. Nucleic Acids Research, doi:10.1093/nar/gkq963 (2010). These alignments were used to estimate transcriptomic alignment rates, and were also used as input in RSEM v 1.12 (Li, B. & Dewey. C. RSEM: accurate transcript quantification from RNA-Seq data with or without a reference genome. BMC Bioinformatics 12, doi:10.1186/1471-2105-12-323 (2011)) to quantify gene expression levels (transcripts per million; TPM) for all UCSC mm9 genes in all samples. Genomic mappings were performed with Tophat v. 1.41 (Trapnell, C., Pachter, L. & Salzberg, S. L. TopHat: discovering splice junctions with RNA-Seq. Bioinformatics 25, 1105-1111, doi:10.1093/bioinformatics/btp120 (2009)), and the resulting alignments were used to calculate genomic mapping rates, rRNA contamination, and 3' and 5' positional bias (PicardTools). All genes that were not expressed at appreciable levels (ln (TPM+1)>1) in at least 1% of all single cells were discarded, leaving 10,313 genes for all further analyses.

Determining Statistically Significant Associations Between Clusters and Principal Components (PCs):

In order to determine which modules were significantly associated with the primary sources of variability in the data as defined by the PCs, a recently developed statistical resampling approach (Chung, N. C. & Storey, J. D. Statistical significance of variables driving systematic variation. arXiv, doi: uuid/22B6DA41-E02D-423F-87BC-211091235A51 (2013)) was used to determine genes which were associated with the first three PCs. Briefly, F-statistics were calculated for each immune response gene by independently zeroing out the contribution of each gene to the first three PCs, and examining the change in variance explained by the modified PCs. Then, a small number of random rows (n=5) in the matrix were permuted, and F-statistics were calculated for these synthetic null variables. This procedure was repeated 1,000 times to generate a set of null statistics. To assess the statistical significance of each module, a one sided Mann-Whitney test was performed.

Figure 26B:
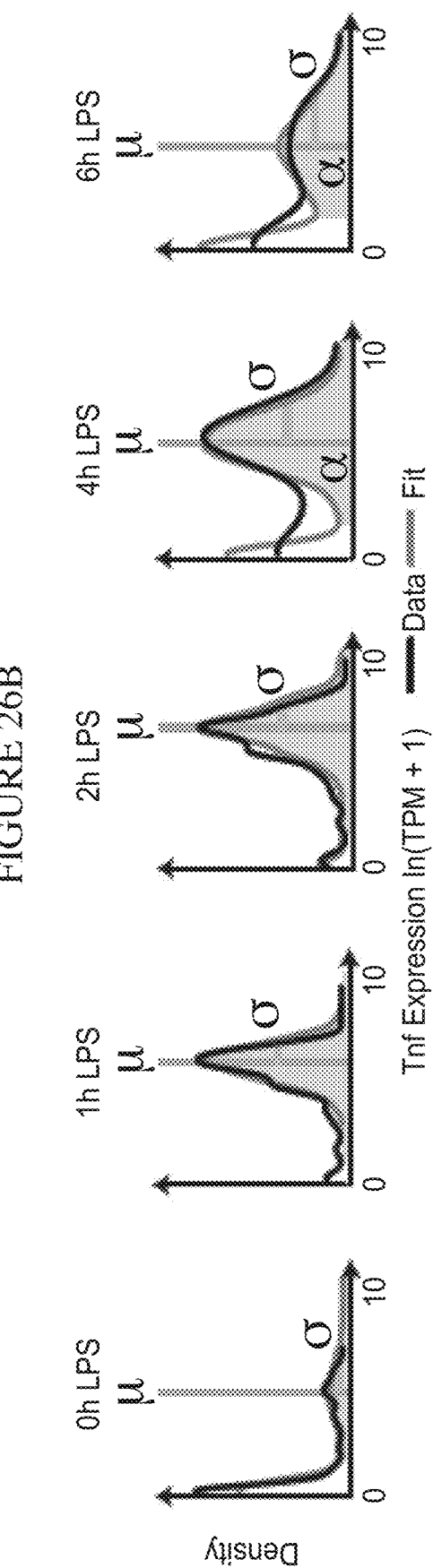
Figure 26C:
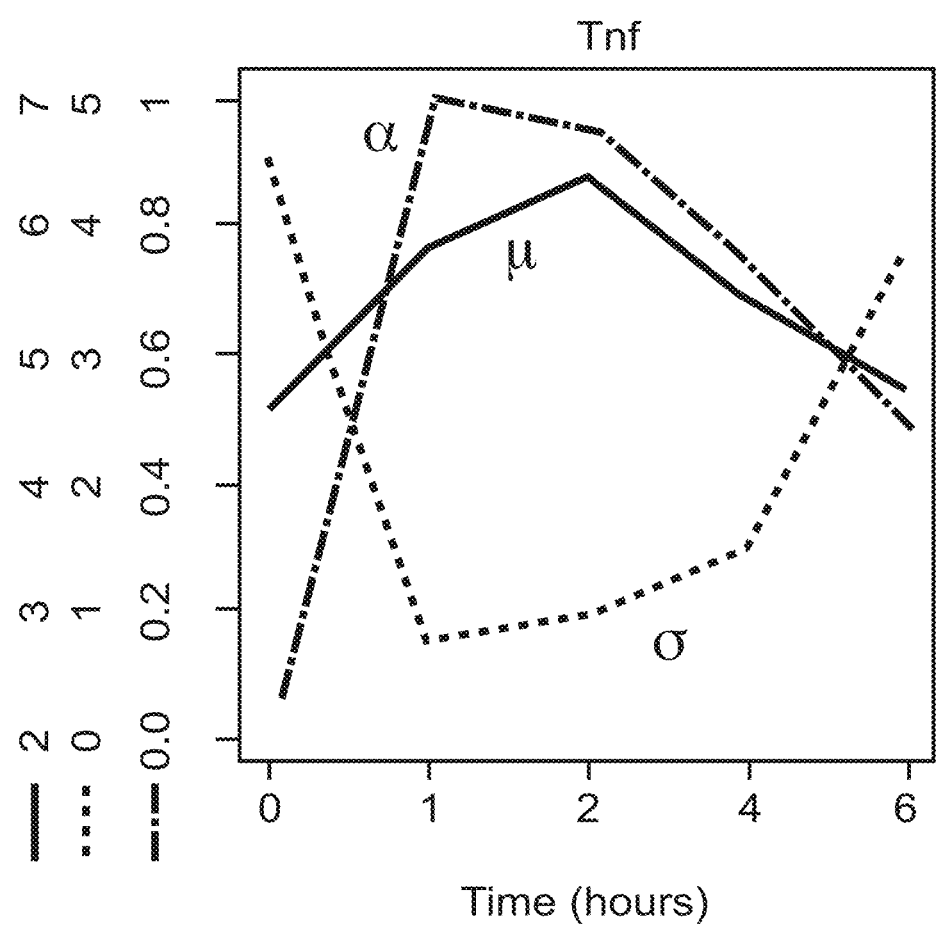
Figure 26D:
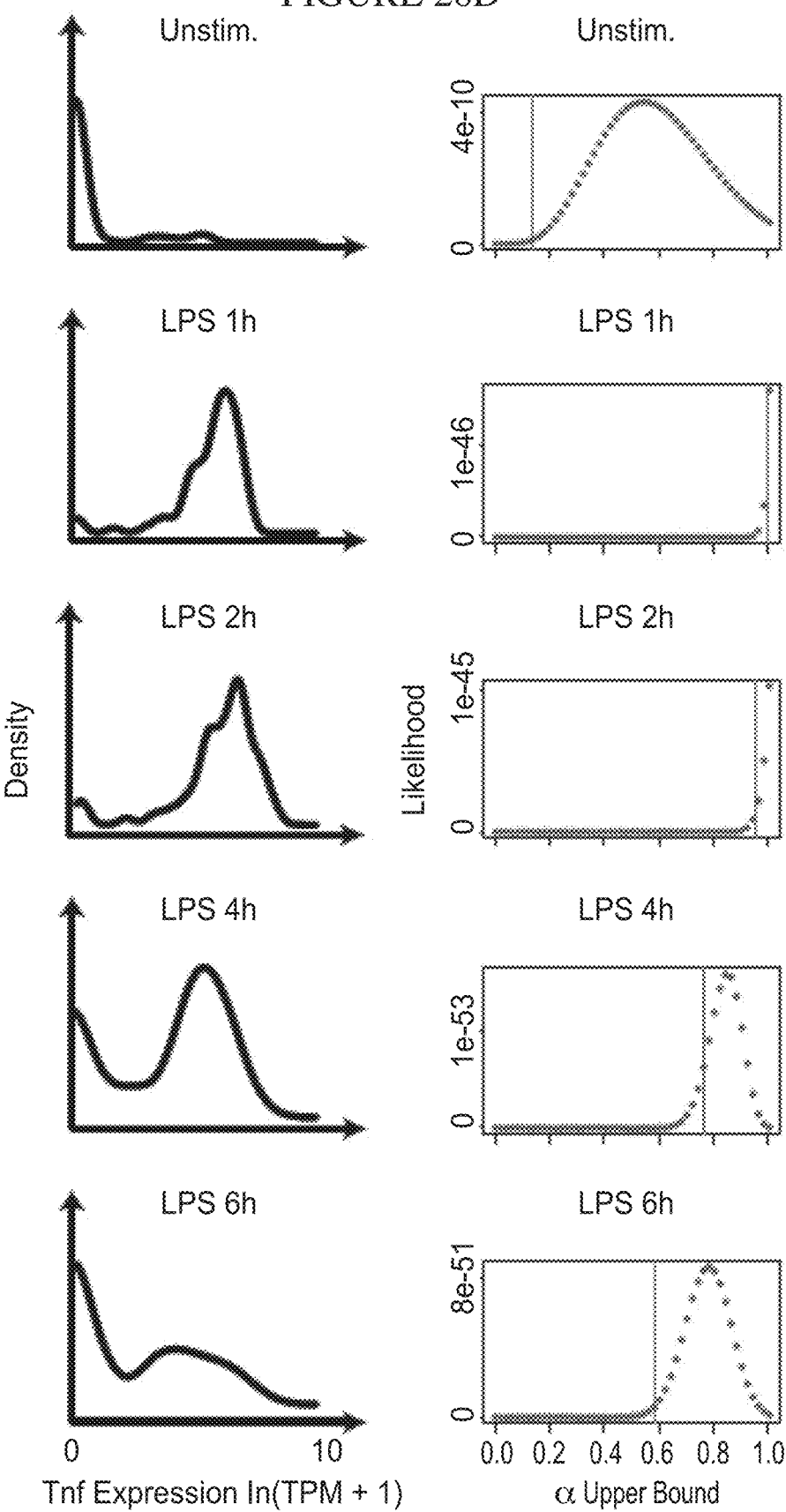
Figure 26E:
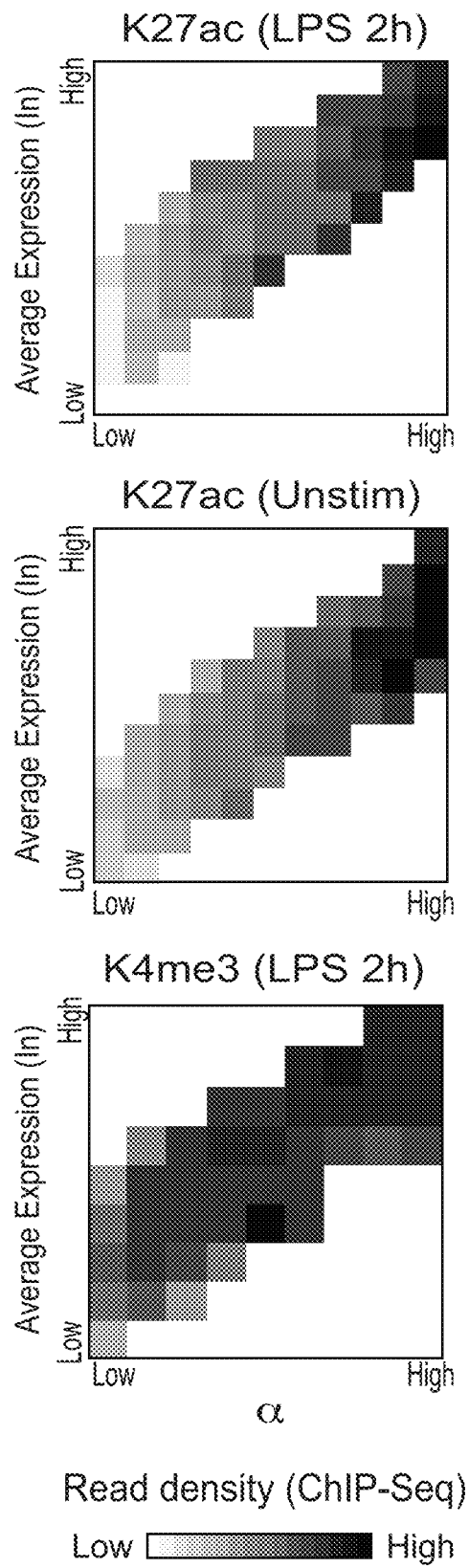
Figure 26F:
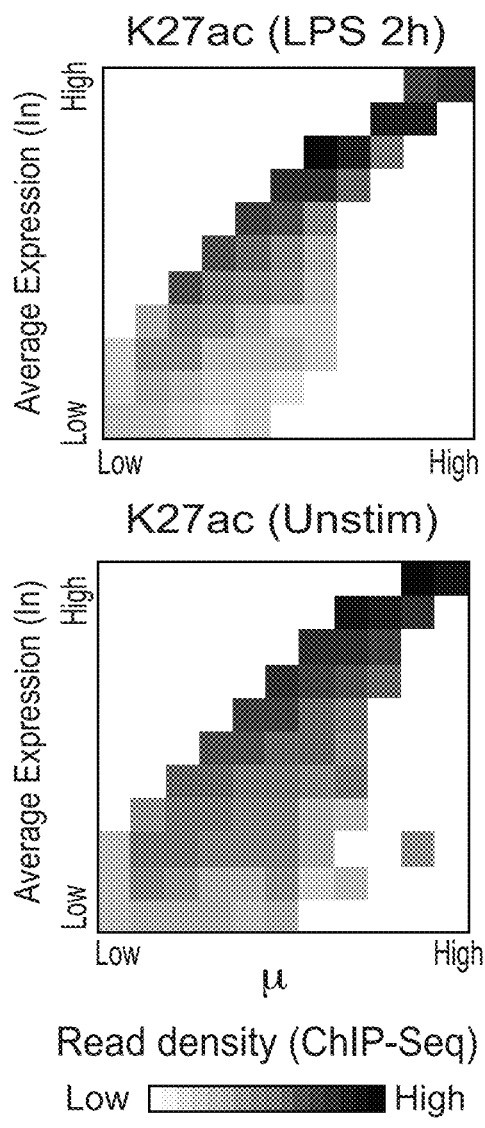
Figure 26G:
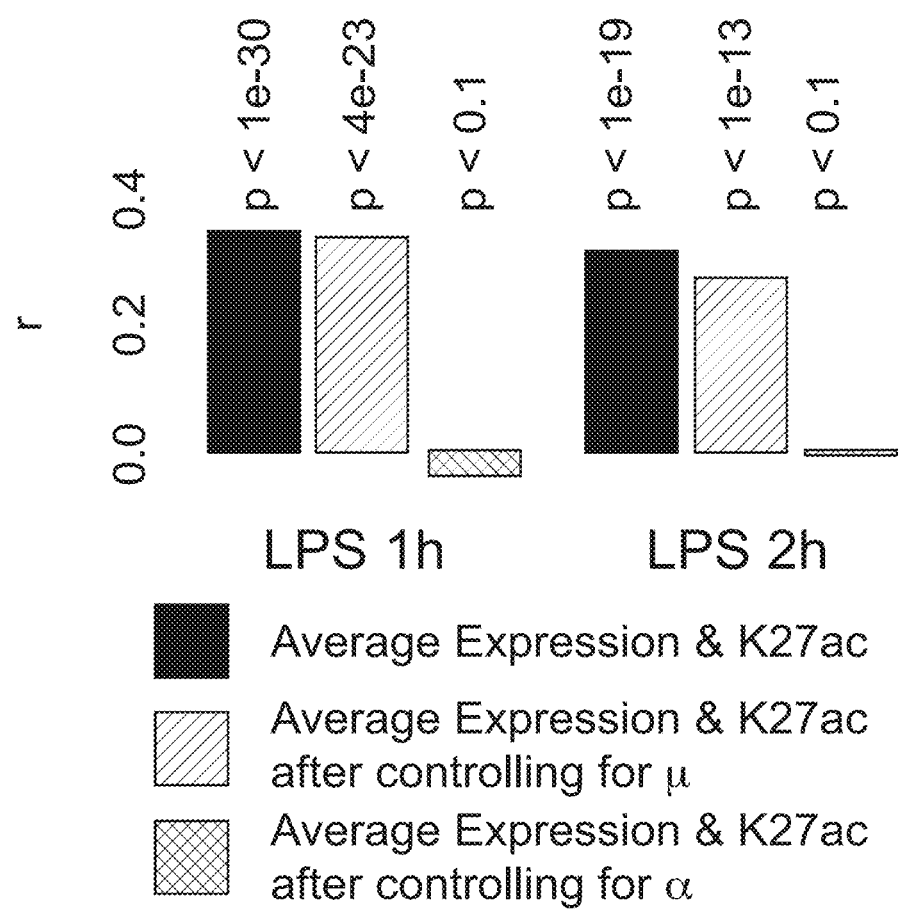
Figure 26H:
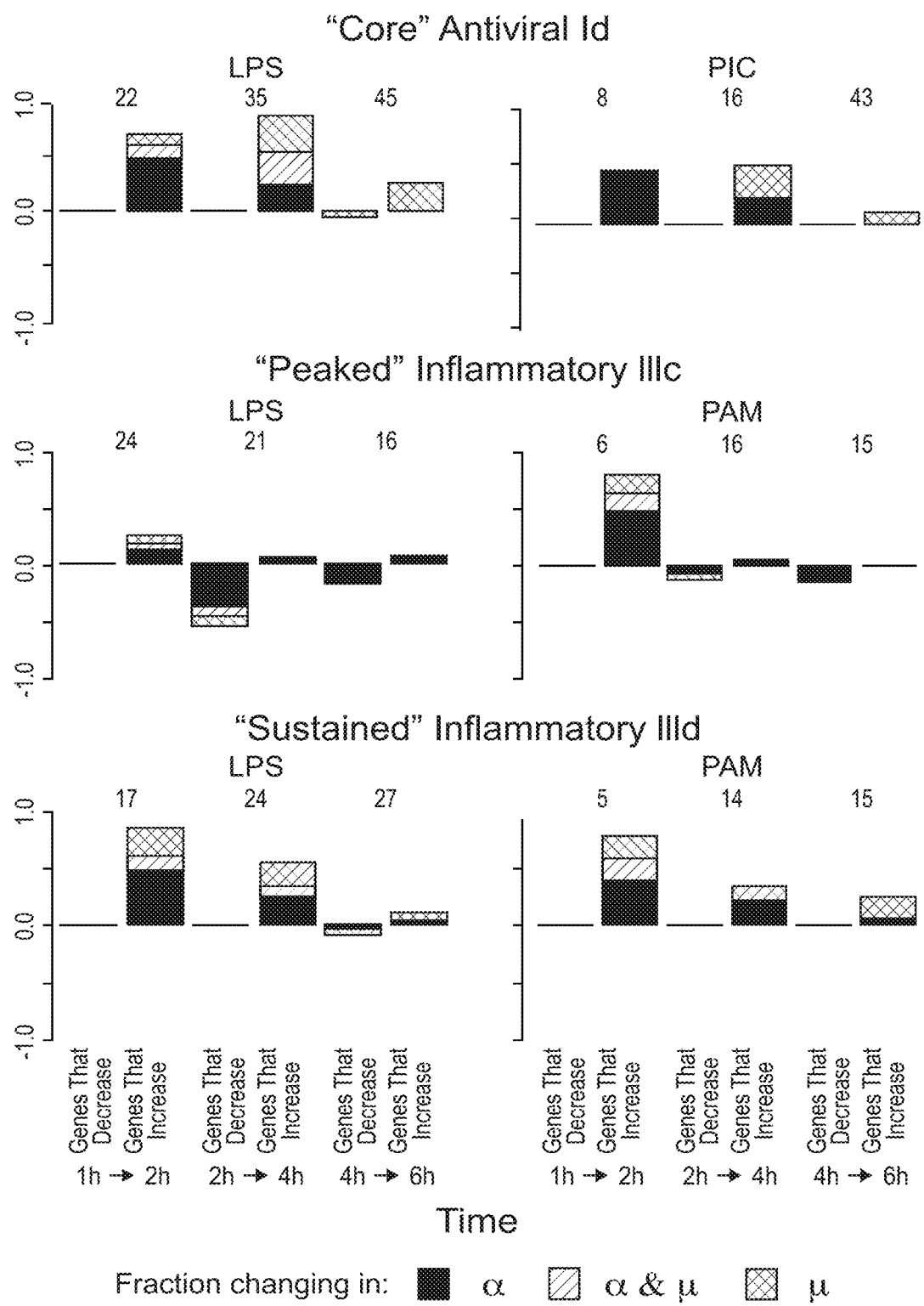
Figure 27A:
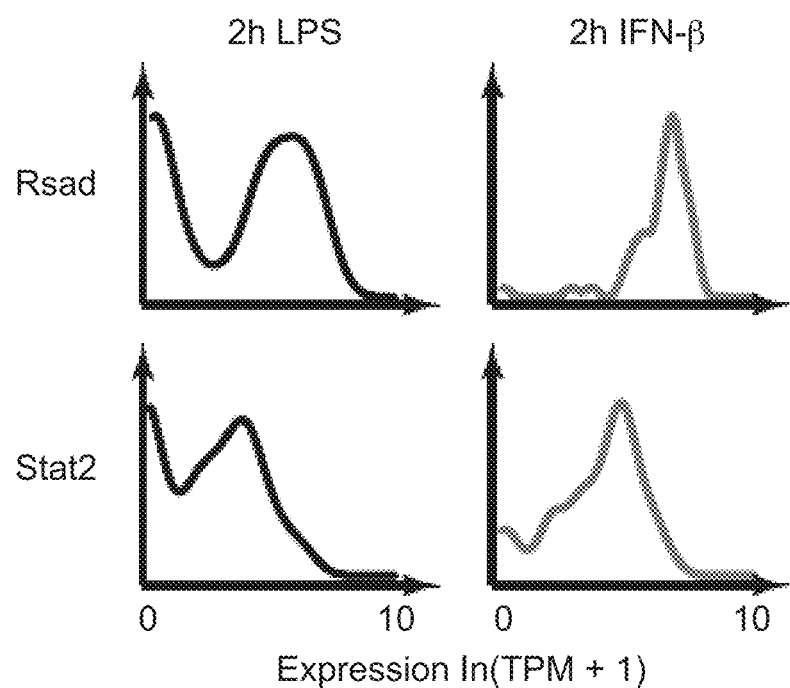
FIGS. 27A-27F are a series of graphs and illustration depicting that IFN-β feedback drives heterogeneity in expression of "core" antiviral targets.
Figure 27B:
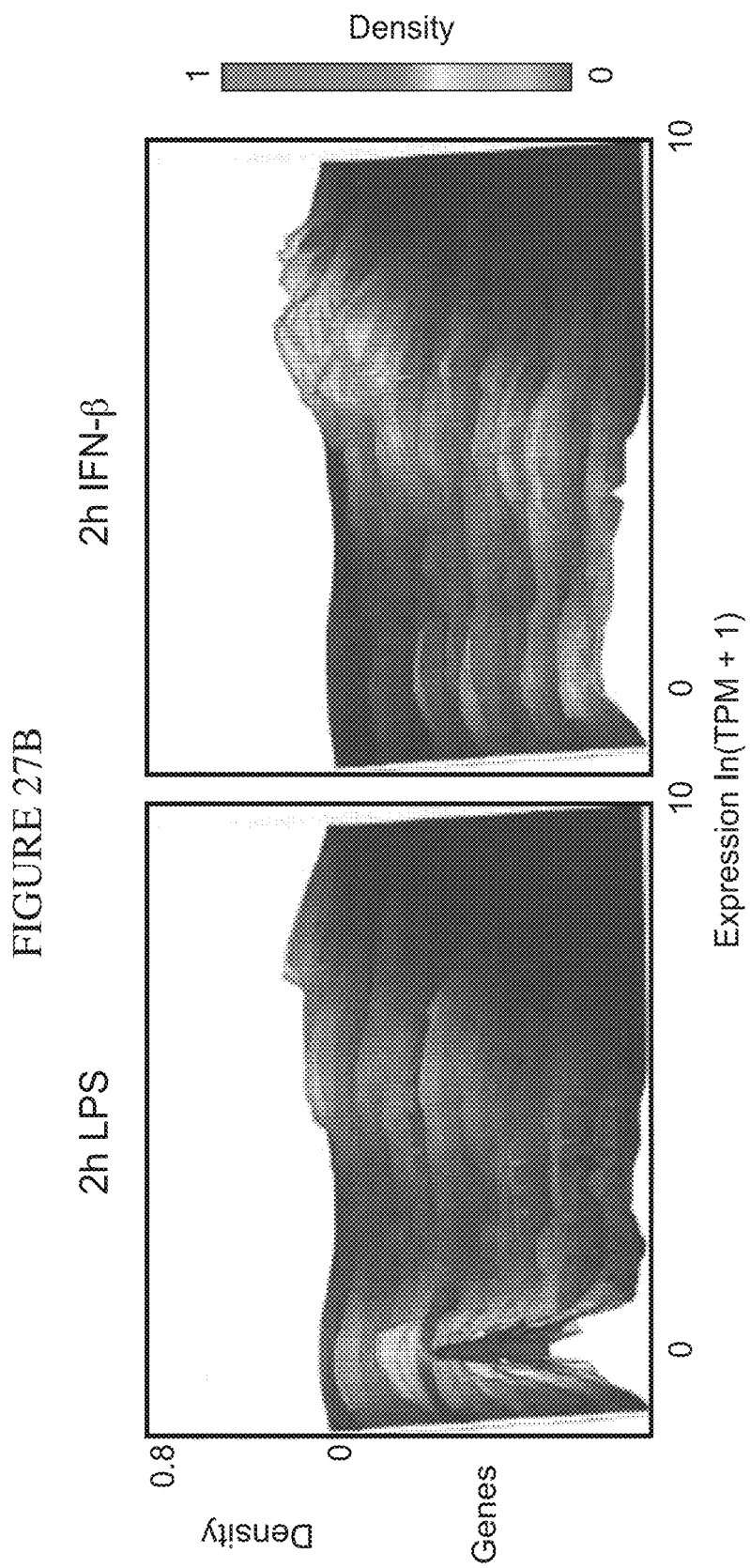
Figure 27C:
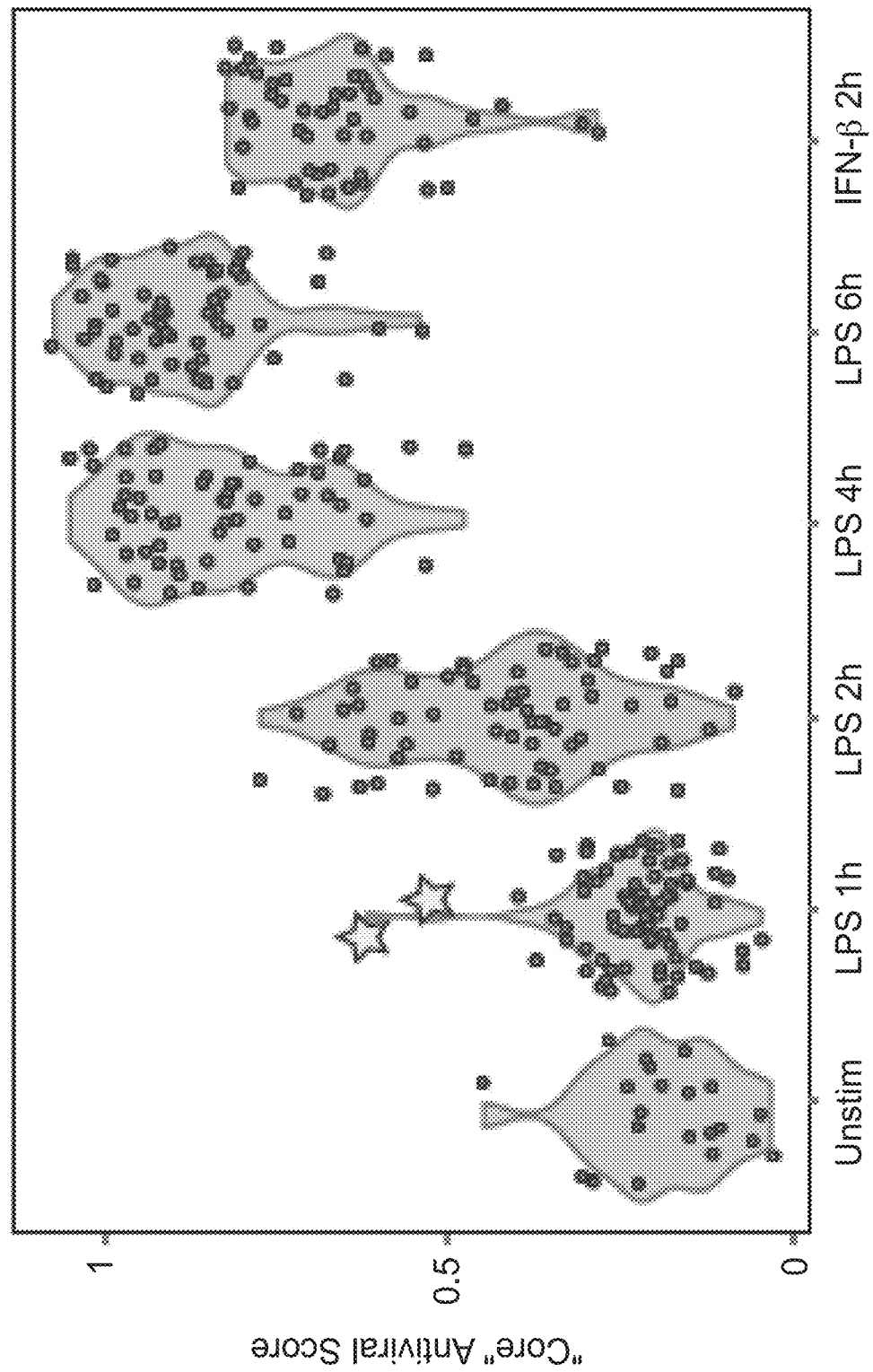
Figure 27D:
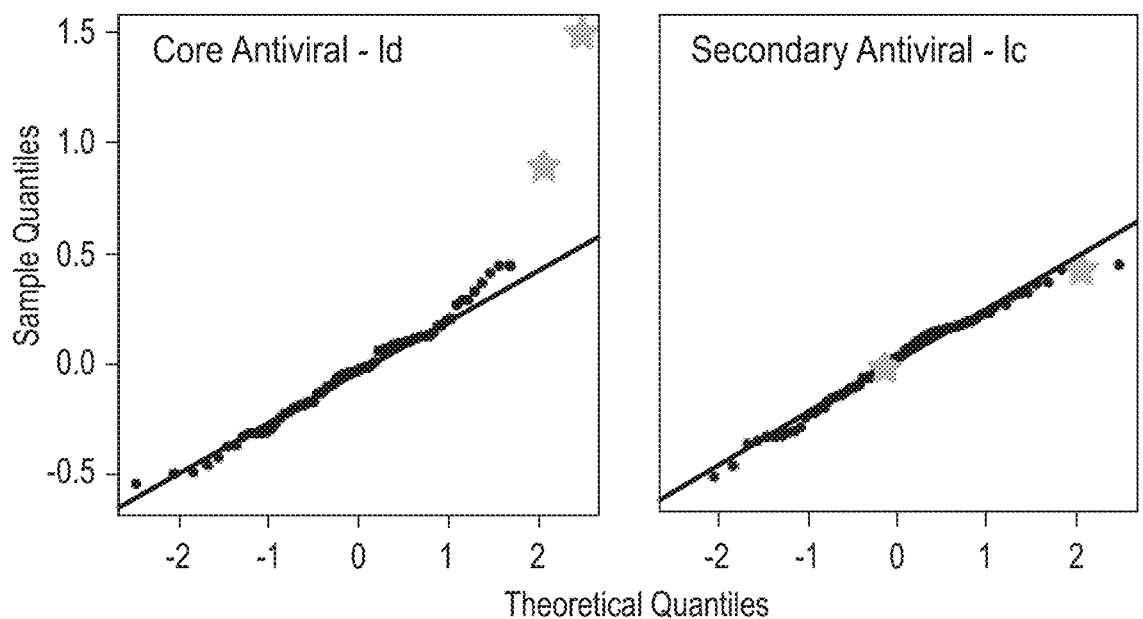
Figure 27E:
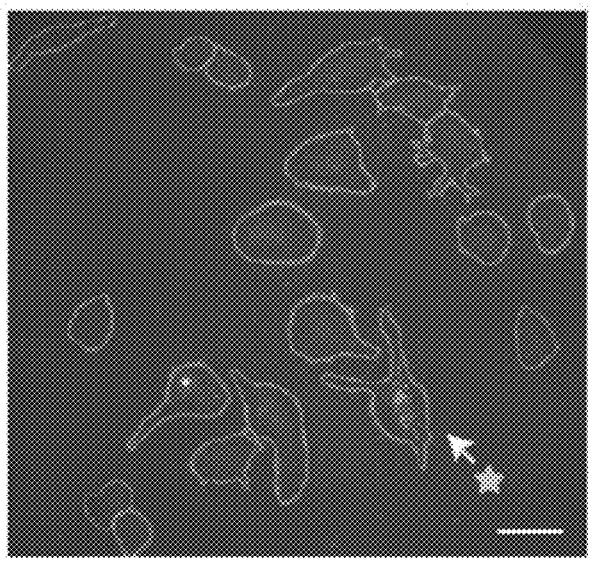
Figure 27F:
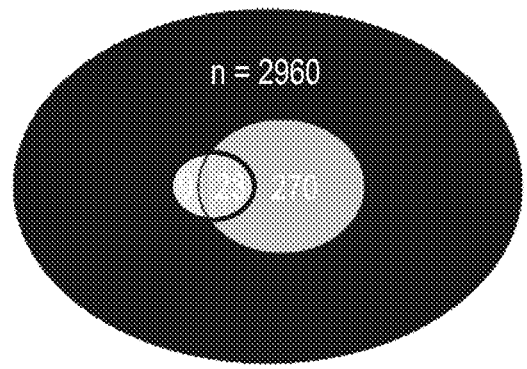
Figure 28A:
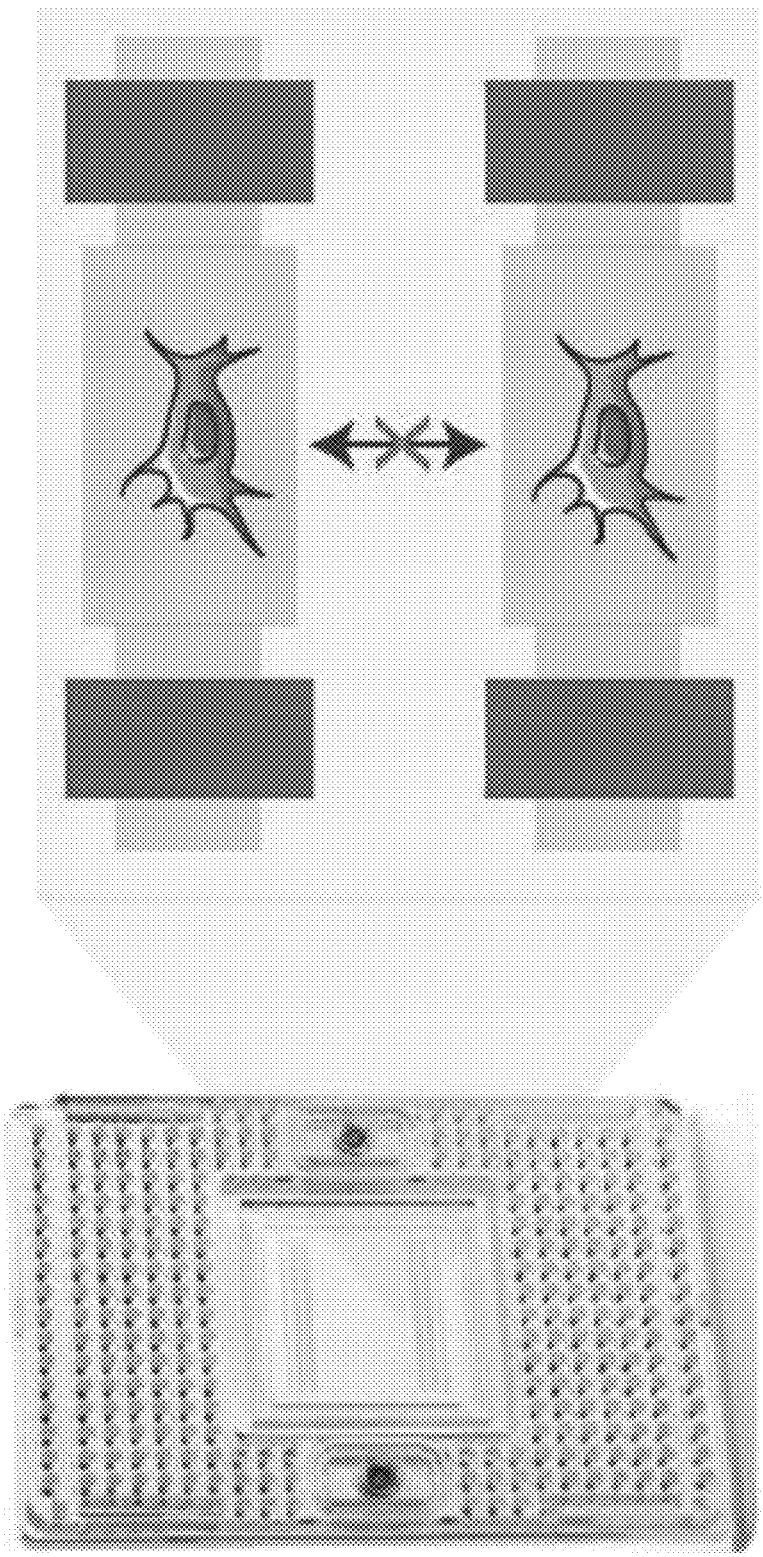
FIGS. 28A-28D are a series of illustrations and graphs depicting microfluidic blocking of cell-to-cell signaling affects response heterogeneity in antiviral and inflammatory modules.
Figure 28B:
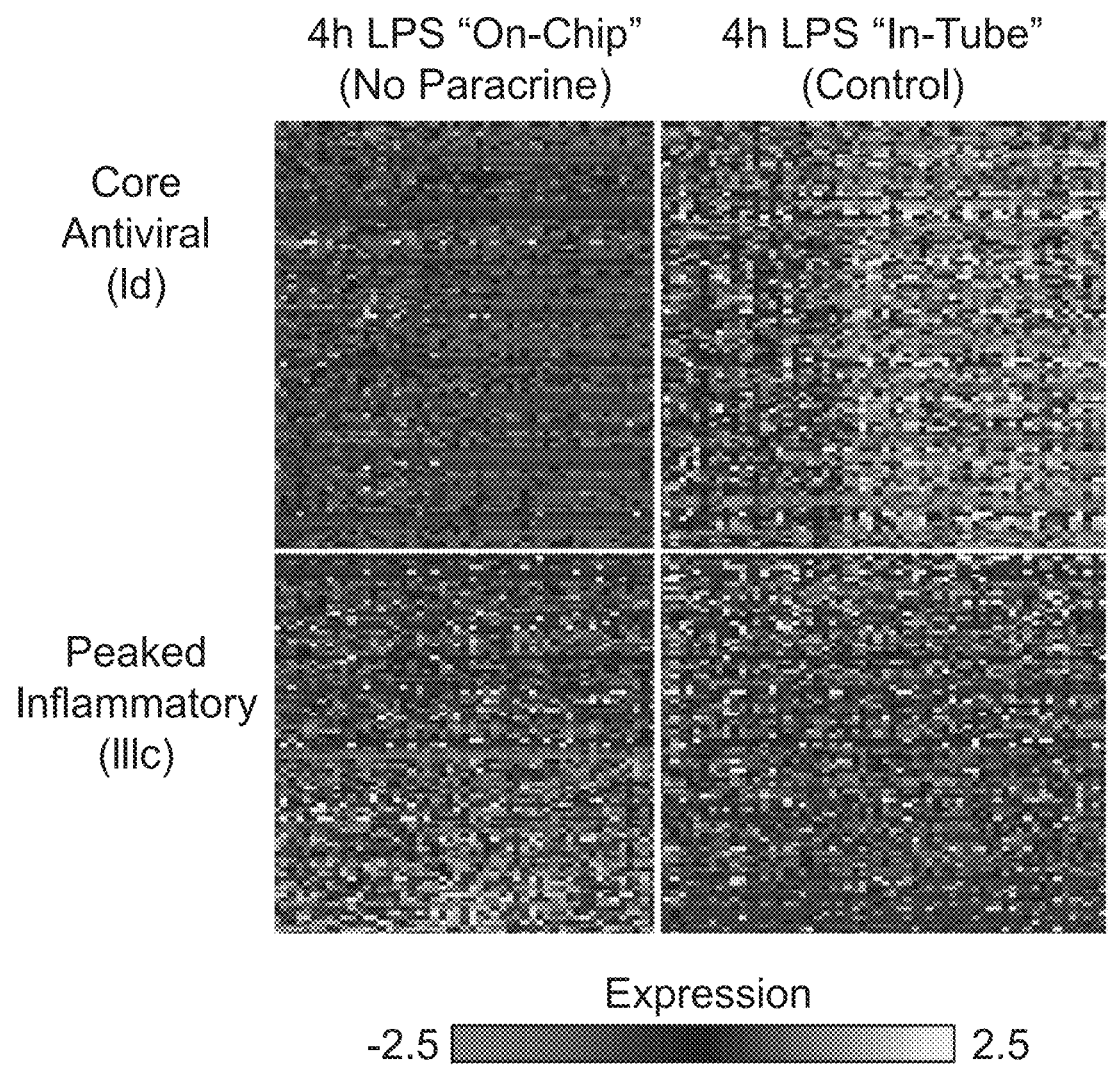
Figure 28C:
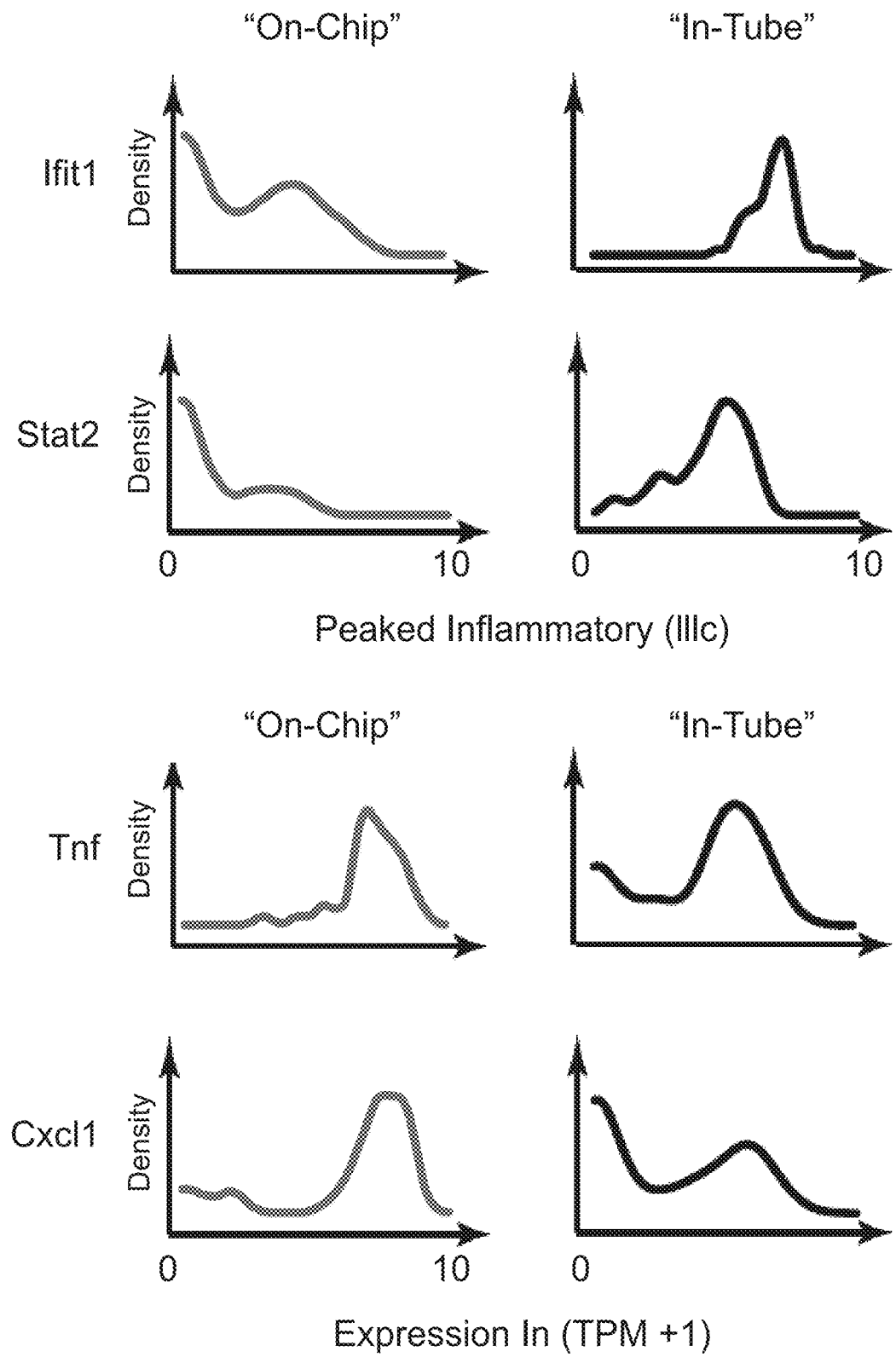
Figure 28D:
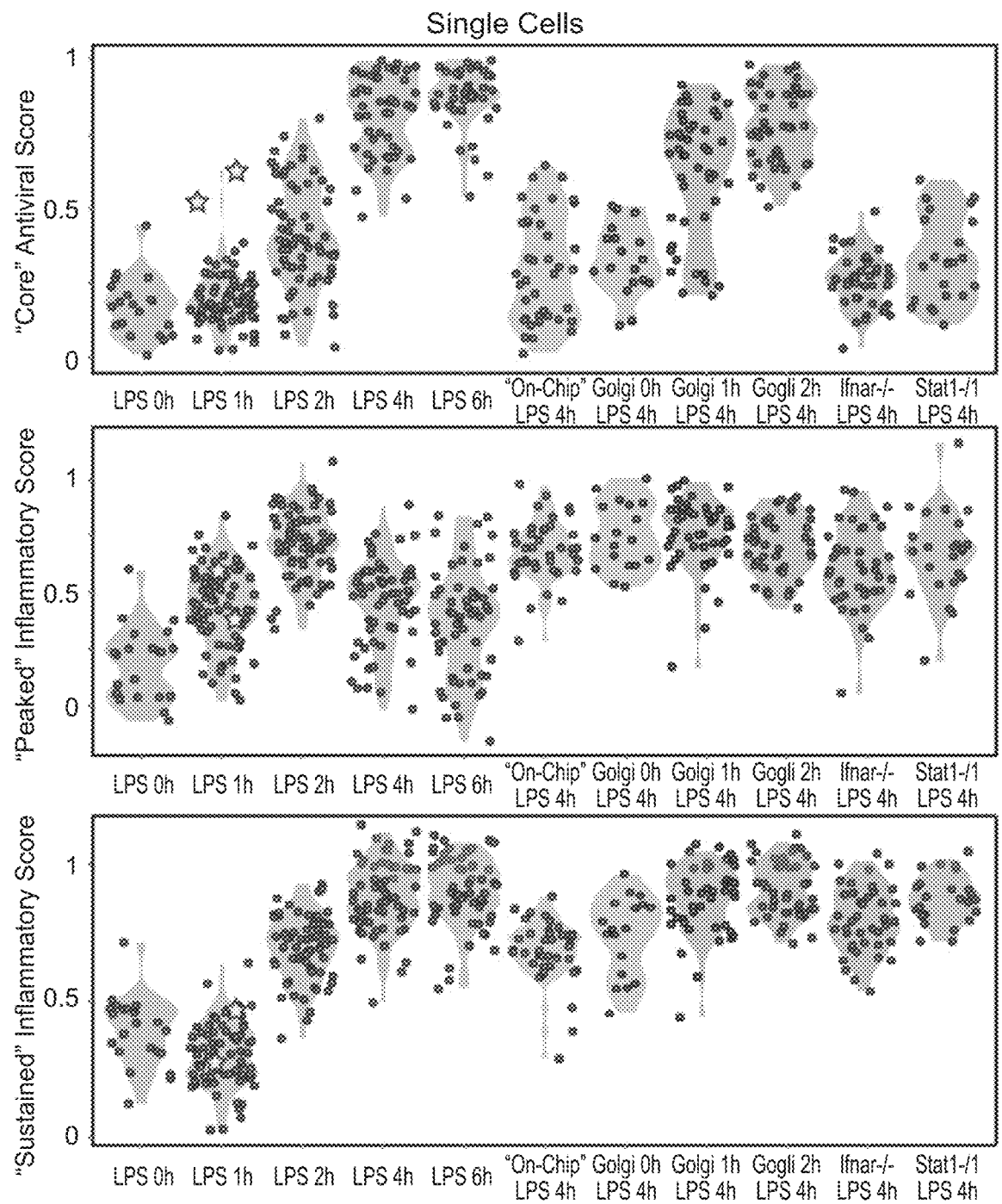

Fitting Parametric Models of Gene Expression Variation:

The nominal parameters α, σ2, and μ were estimated for each gene in each condition by fitting a series of nested statistical models to its expression distribution (FIGS. 26a,b). All presentations were focused on the LPS response, where genes from the most modules are induced. First, it was tested whether the single cell expression distribution of immune response genes was compatible with a $(\mu, \sigma^2)$ unimodal lognormal distribution, as has been previously used in the literature to describe single-cell distributions of gene expression (see e.g., Raj, A., Peskin, C. S., Tranchina, D., Vargas, D. Y. & Tyagi, S. in PLoS Biol Vol. 4 e309 (2006)). For each gene in each condition, the mean and variance of all log(TPM+1) values was calculated, and a goodness-of-fit test was used to test a lognormal distribution with these parameters. Only a very small minority (2.5%) of distributions was well described by the two-parameter model, primarily due to the inflation of zero values in our single cell data.

Next, each single-cell gene expression distribution was parameterized by estimating values for α, $\sigma^2$, and μ. Each distribution corresponds to the observed expression values across single cells for a given gene in a given condition. The expression threshold was set at ln(TPM+1)>1, as it was observed that levels of expression in the range 0<ln (TPM+1)<1 typically reflected very few reads that mapped to exonic sequences, and these could likely signify small amounts of contamination. Thus a values were estimated as the proportion of cells where transcript expression was detected at levels (ln(TPM+1)>1). The mean (μ) and variance ($\sigma^2$) was then calculated in log-space of all expression values where ln(TPM+1)>1. The fit of this three-parameter model was assessed using an additional goodness-of-fit test. It was found that the majority (92%) of distributions were well described by the three-parameter $(\mu, \sigma^2, \alpha)$ model (p<0.01, goodness of fit test).

Example 2

Stimulation of Bone Marrow Derived Dendritic Cells (BMCDs) with Lipopolysaccharide (LPS)

To characterize the extent of expression variability on a genomic scale and decipher its regulatory and functional implications, single-cell RNA-Seq was used to study heterogeneity in the response of BMDCs to LPS stimulation.

BMDCs are an attractive model system for single-cell analyses for several reasons. First, LPS, a component of gram-negative bacteria and a ligand of Toll-like receptor 4, is a physiologically relevant, uniform stimulus that synchronizes cellular responses and mitigates temporal phasing (Tay, S. et al. Single-cell NF-κB dynamics reveal digital activation and analogue information processing. Nature 466, 267-271, doi:papers2://publication/doi/10.1038/nature09145 (2010)). Second, activation by LPS evokes a robust transcriptional program for inflammatory and antiviral cytokines, and many of the components controlling this response are known from 'population-wide' studies (Takeuchi, O. & Akira, S. Pattern Recognition Receptors and Inflammation. Cell 140, 805-820, doi:10.1016/j.cell.2010.01.022 (2010)). Third, LPS stimulation should increase the synchronization between mRNA and protein levels for induced genes, reducing a potentially confounding factor for single-cell analyses (Taniguchi, Y. et al. Quantifying E. coli Proteome and Transcriptome with Single-Molecule Sensitivity in Single Cells. Science 329, 533-538, doi:10.1126/science.1188308 (2010), Li, G.-W. & Xie, X. S. Central dogma at the single-molecule level in living cells. Nature 475, 308-315 (2011)). Lastly, differentiated DCs from bone marrow cultures are post-mitotic, largely removing the effects of the cell cycle (Kalisky, T., Blainey, P. & Quake. S. R. Genomic Analysis at the Single-Cell Level. Annual review of genetics 45, 431-445, doi:papers2://publication/doi/10.1146/annurev-genet-102209-163607 (2011); Ramos, C. A. et al. Evidence for Diversity in Transcriptional Profiles of Single Hematopoietic Stem Cells. PLoS Genetics 2, e159, doi:papers2://publication/doi/10.1371/journal.pgen.0020159.st008 (2006)).

BMDCs with LPS were stimulated and single cells were harvested after four hours (Amit, I. et al. Unbiased reconstruction of a mammalian transcriptional network mediating pathogen responses. Science 326, 257-263, doi:10.1126/science.1179050 (2009); Chevrier, N. et al. Systematic Discovery of TLR Signaling Components Delineates Viral-Sensing Circuits. Cell 147, 853-867, doi:10.1016/j.cell.2011.10.022 (2011)) (Example 1). Using SMART-Seq (Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012)), cDNA libraries derived from 18 single BMDCs (S1-S18) were constructed, three replicate populations of 10,000 cells, and two negative controls (empty wells). Each of these libraries was sequenced to an average depth of 27-million read-pairs per sample. As expected, less than 0.25% of reads from the negative control libraries aligned to the mouse genome, and these samples were discarded from all further analyses. Library quality metrics (Levin. J. Z. et al. Comprehensive comparative analysis of strand-specific RNA sequencing methods. Nature Methods 7, 709-715 (2010)), such as alignment rates to the genome, ribosomal RNA contamination, and 3' or 5' coverage bias, were similar across all single-cell libraries and 10,000-cell replicates. For each sample, expression levels were calculated for all UCSC-annotated genes (Hsu, F. et al. The UCSC Known Genes. Bioinformatics (Oxford, England) 22, 1036-1046, doi:10.1093/bioinformatics/bt1048 (2006)) using RSEM (Li, B. & Dewey, C. N. RSEM: accurate transcript quantification from RNA-Seq data with or without a reference genome. BMC Bioinformatics 12, 323-323 (2011)) (Example 1), and discarded all genes that were not expressed at appreciable levels (transcripts per million (TPM)>1) in at least three individual cells, retaining 6,313 genes for further analysis.

Figure 1B:
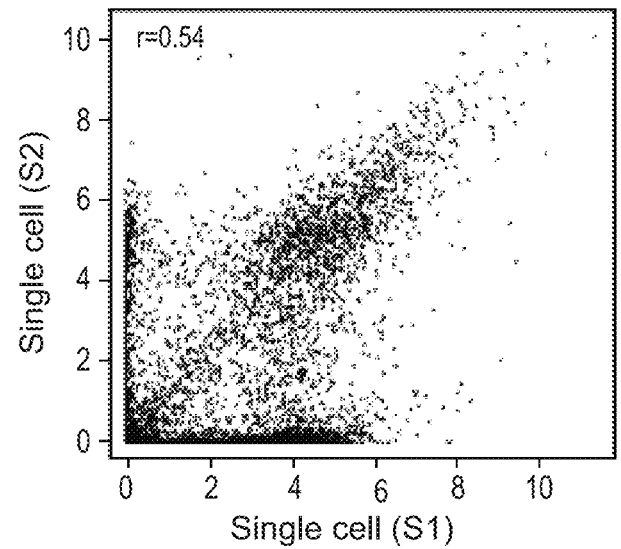
Figure 1C:
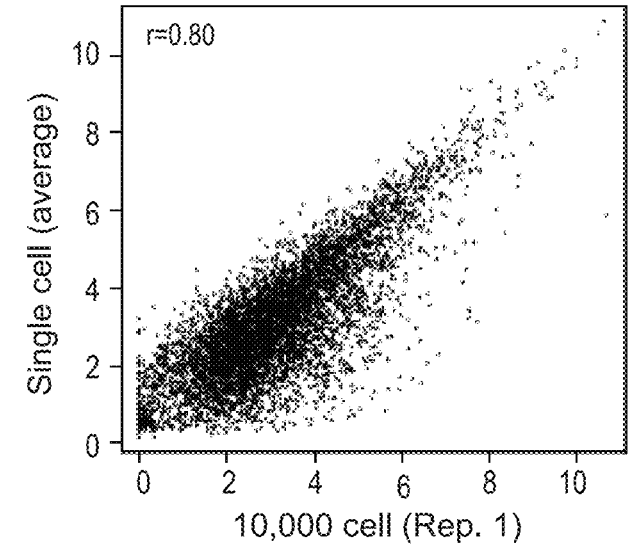
Figure 1D:
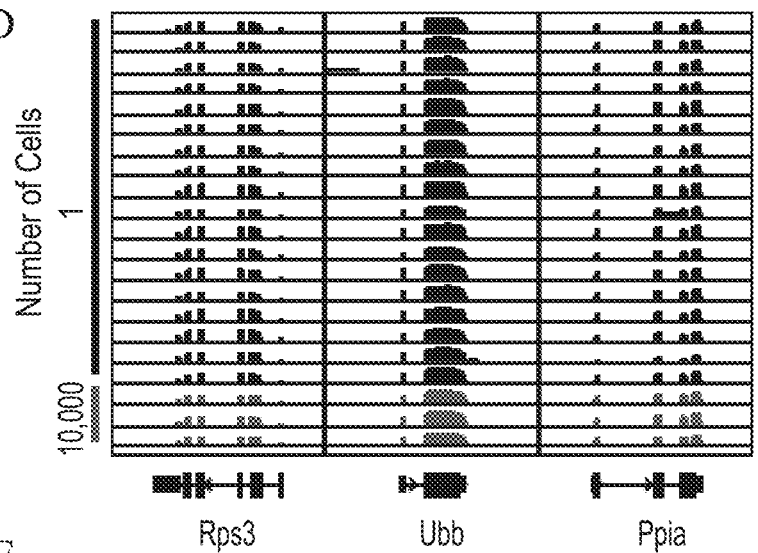
Figure 1E:
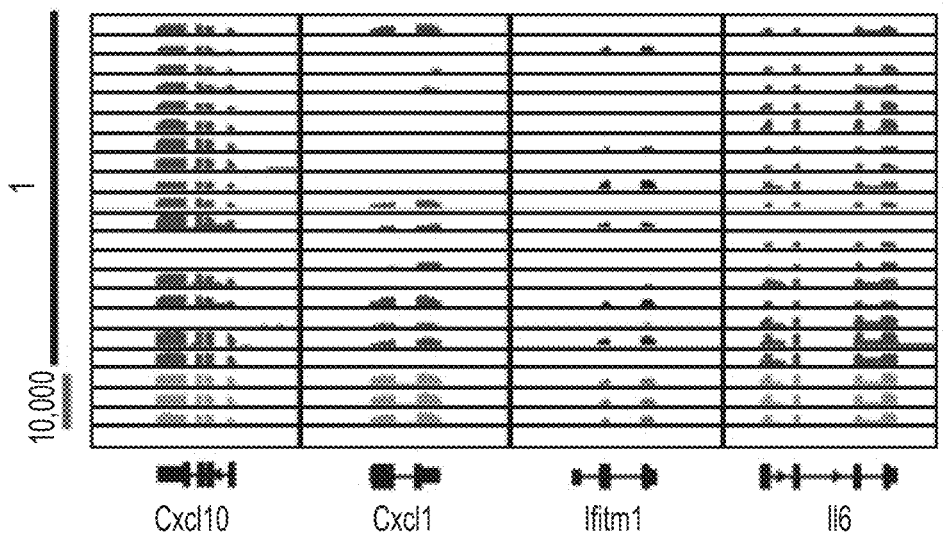
Figure 1F:
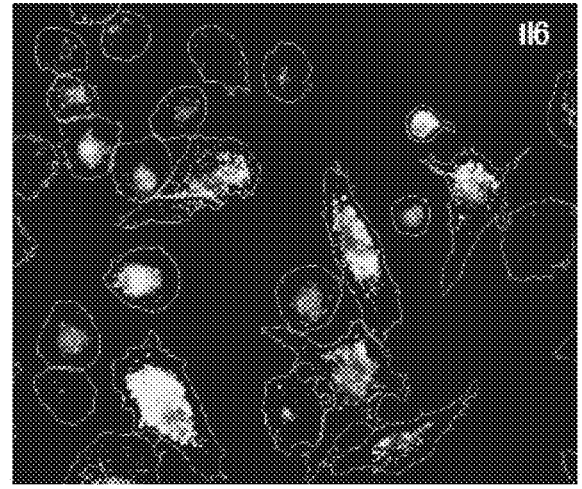
Figure 1G:
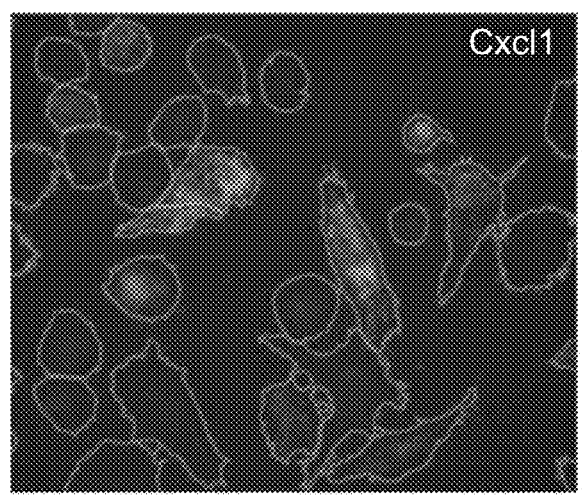
Figure 1H:
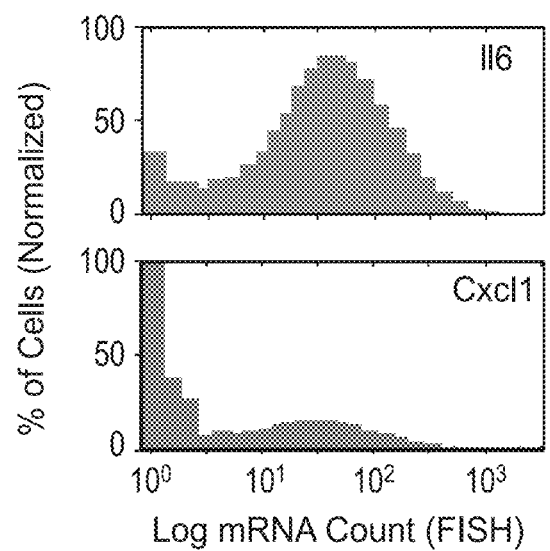
Figure 5:
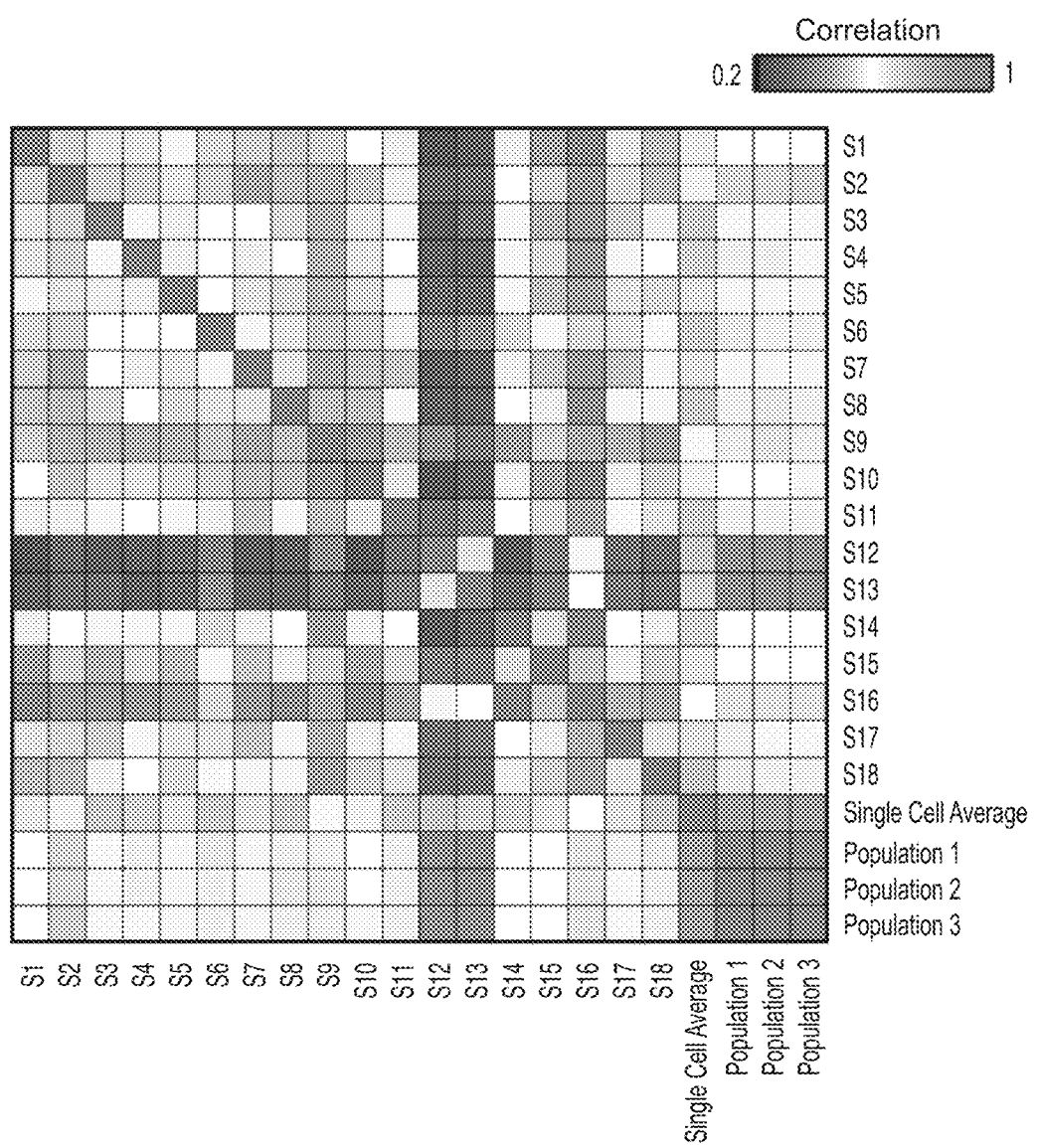

While gene expression levels of population replicates were tightly correlated with one another (Pearson r>0.98, log-scale, FIG. 1a), there was substantial variation in gene expression profiles between individual cells (0.29<r<0.62, mean: 0.48, FIG. 1b, FIG. 5). Despite this extensive cell-to-cell variation, expression levels for an "average" single cell—derived by averaging transcript expression levels over all 18 single cells—correlated well (0.79<r<0.81) with the population samples (FIG. 1c, FIG. 5). This observation confirms that the significant gene expression differences observed between single cells do average together to form the population profile.

RNA-fluorescence in situ hybridization (FISH), a single molecule imaging technique that does not require amplification (Yu, M. et al. RNA sequencing of pancreatic circulating tumour cells implicates WNT signalling in metastasis. Nature 487, 510-513, doi:10.1038/nature11217 (2012); Raj, A., Rifkin, S. A., Andersen, E. & Van Oudenaarden, A. Variability in gene expression underlies incomplete penetrance. Nature 463, 913-918, doi:10.1038/nature08781 (2010)), was used to verify that the heterogeneity in single-cell expression reflects true biological differences, rather than technical noise associated with the amplification of a small amount of cellular RNA. For 25 genes, selected to cover a wide range of expression levels, variation in gene expression levels detected by RNA-FISH closely mirrored the heterogeneity observed in the sequencing data (FIGS. 1d-h, FIG. 6). For example, the expression of classical housekeeping genes (e.g., Beta-Actin (Actb), Beta-2-microglobulin (B2m)) matched a log-normal distribution in both single-cell RNA-Seq and RNA-FISH measurements, consistent with previous studies (Bengtsson, M. Gene expression profiling in single cells from the pancreatic islets of Langerhans reveals lognormal distribution of mRNA levels. Genome Research 15, 1388-1392, doi:papers2://publication/doi/10.1101/gr.3820805 (2005)). In contrast, many genes involved in the BMDC response to LPS, although highly expressed on average, exhibited significantly greater levels of heterogeneity that do not fit a log-normal distribution. In extreme cases, the expression levels of these genes varied up to ~1,000 fold between individual cells (FIGS. 1e-h). More generally, it was found that high levels of variability in single-cell gene expression persisted across a wide range of population expression levels (FIG. 2a).

Figure 2B:
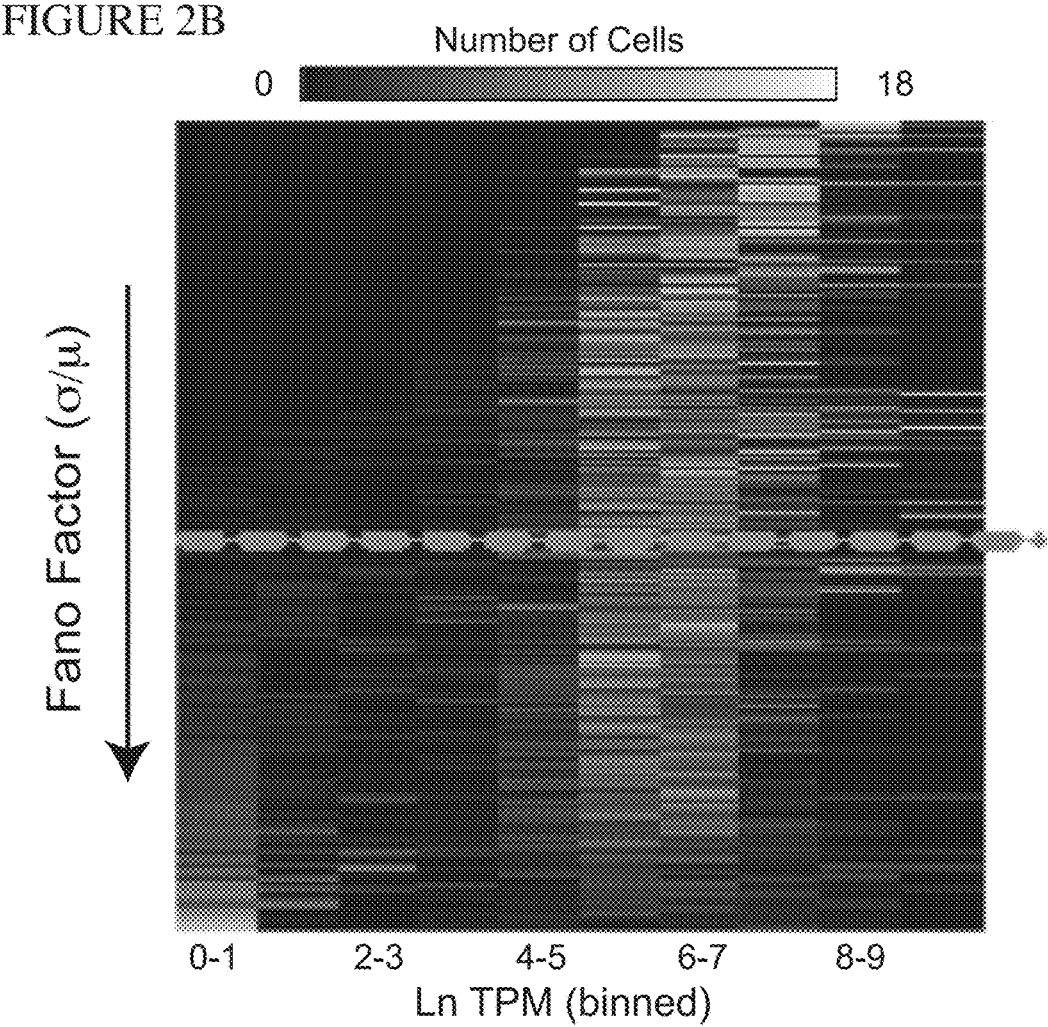
Figure 6:
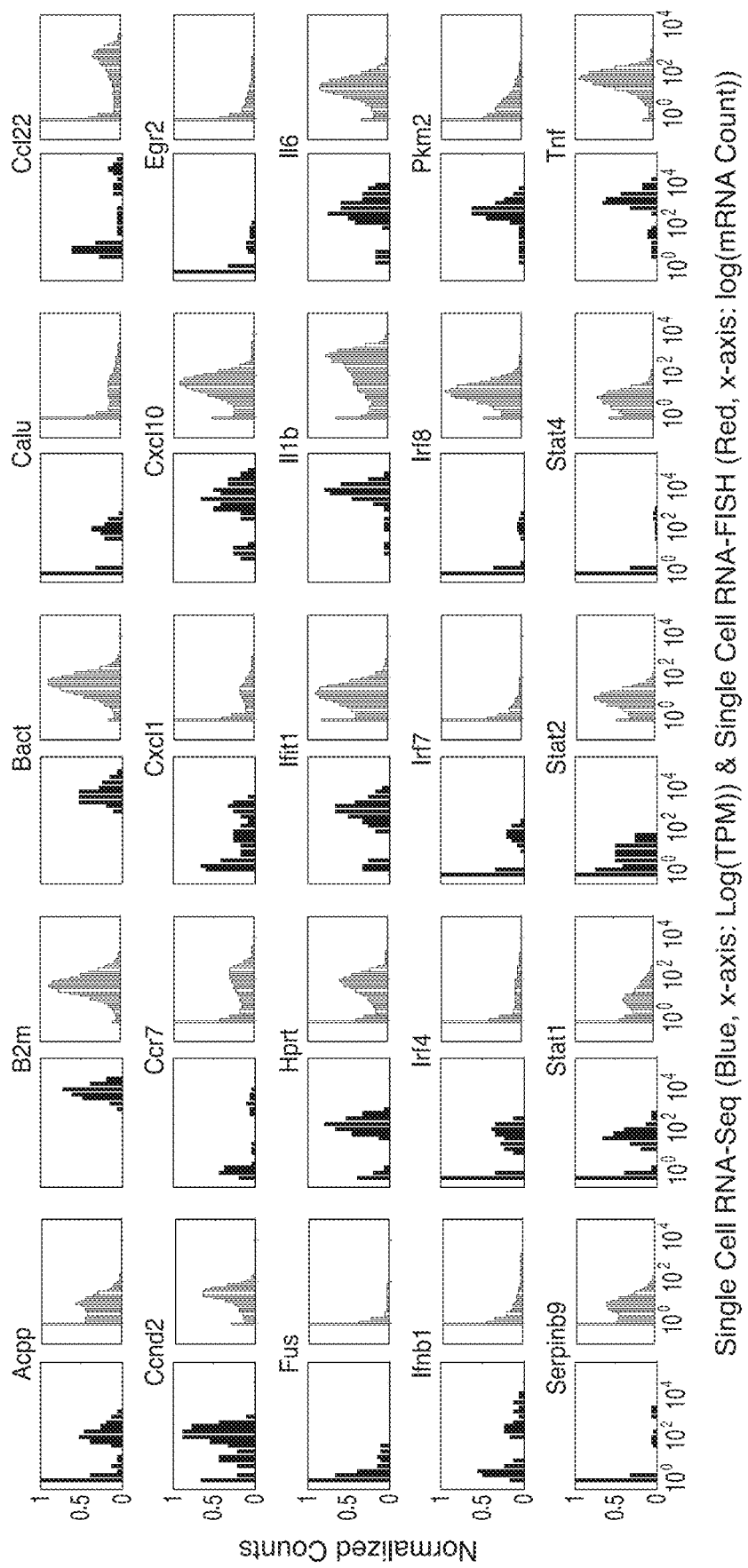
FIG. 6 is a series of graphs depicting agreement between single-cell RNA-Seq and RNA-FISH for 25 different transcripts. Shown are the distributions of gene expression levels for each of 25 transcripts in single-cell RNA-Seq of 18 cells (left, blue) and in single-cell RNA-FISH of, on average, 1600 cells (right, red).

In particular, 281 of the 522 most highly expressed genes (single-cell average TPM>250, Table S3) exhibited low variability, and their expression levels were well described by log-normal distributions across single cells (RNA-Seq: FIGS. 2b,c top. RNA-FISH (Actb, B2m): FIG. 6). These 281 genes are enriched for housekeeping genes, encoding ribosomal and other structural proteins (Bonferroni-corrected p=1.5×10). This is consistent with previous observations in yeast (Newman, J. R. S. & Weissman, J. S. Systems biology: many things from one. Nature 444, 561-562 (2006); Bar-Even, A. et al. Noise in protein expression scales with natural protein abundance. Nature Genetics 38, 636-643 (2006)) and human (Ram. O. et al. Combinatorial Patterning of Chromatin Regulators Uncovered by Genome-wide Location Analysis in Human Cells. Cell 147, 1628-1639 (2011)) cells that highly expressed housekeeping and 'growth' genes are less variable between cells.

Figure 7:
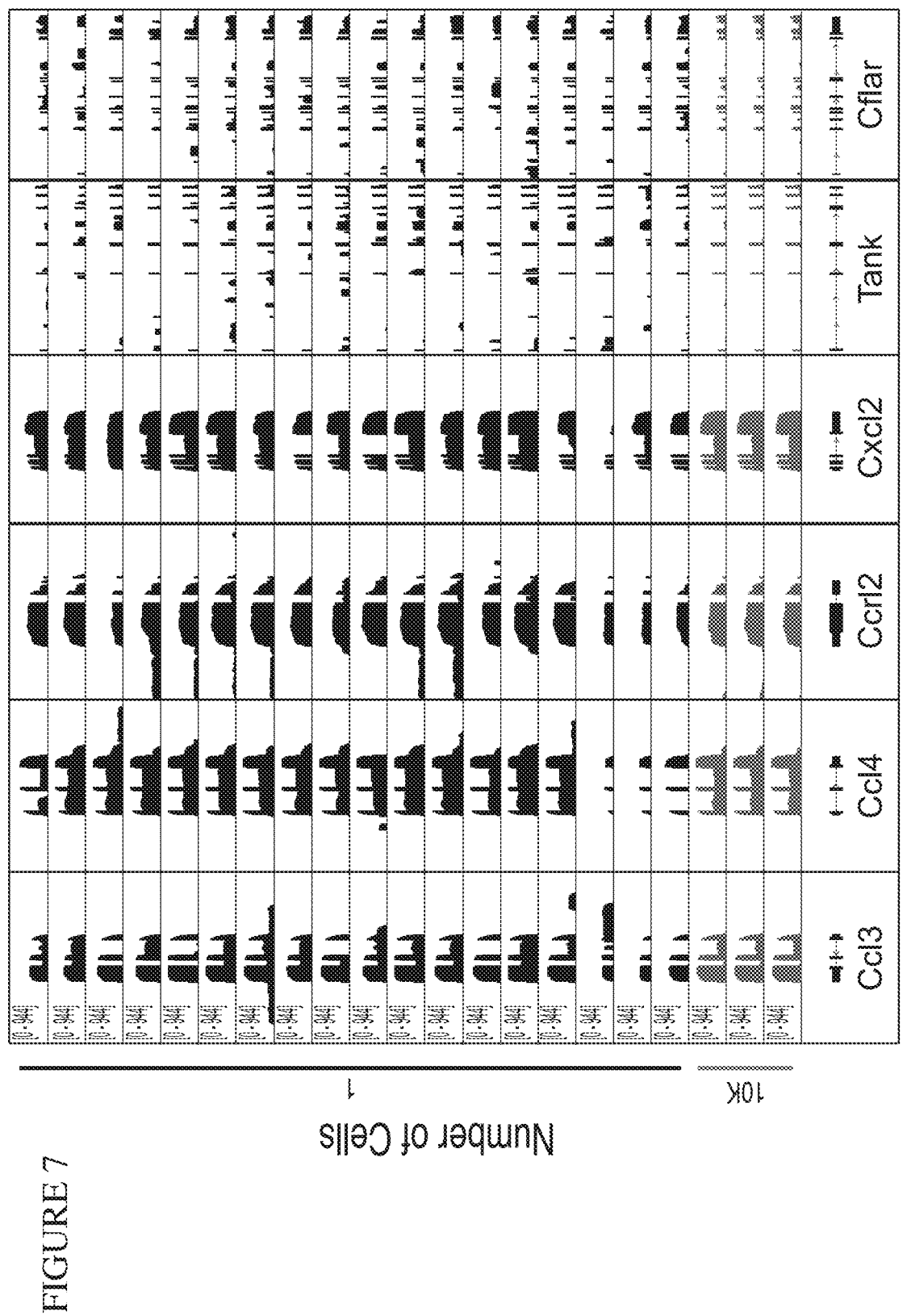
FIG. 7 is a graph depicting robust LPS response across all cells. Shown are tracks of RNA-Seq reads from the Integrative Genomics Viewer for the levels of key response genes (columns, gene name at bottom) in each single cell (blue) and the population average (grey). The genes include key chemokines and chemokine receptors (Ccl3, Ccl4, Ccr12), cytokines (Cxc12), and other important components of the LPS response (Tank, Cflar).

Surprisingly, however, most of the other highly expressed genes exhibited a bimodal expression pattern (185 of 241 highly variable genes, FIGS. 2b,c bottom): mRNA levels for these genes were high in many of the cells, but were at least an order of magnitude lower than the single-cell average in at least three cells, where abundances were often very low or undetectable. This variation was independently verified by RNA-FISH (e.g., Cxc11, Cxc110, Ifit1, and others: FIG. 6), confirming that it is not a result of technical noise. This variable set was highly enriched for genes that were induced by at least two-fold upon LPS stimulation at the population level (Garber, M. et al. A High-Throughput Chromatin Immunoprecipitation Approach Reveals Principles of Dynamic Gene Regulation in Mammals. Molecular Cell 47, 810-822, doi:10.1016/j.molcel.2012.07.030 (2012)) ($p=2.7 \times 10^{-7}$; hypergeometric test), and included both antiviral and inflammatory response elements, suggesting that such widespread variability amongst highly expressed genes might be a feature of the immune response. While bimodal expression patterns characterize many immune response transcripts, some immune response genes were highly expressed in every cell (FIG. 7), demonstrating that all cells robustly responded to LPS. These include key chemokines and chemokine receptors (Cc13, Cc14, Ccr12), cytokines (Cxc12), and other important components of the LPS response (Tank).

Figure 8:
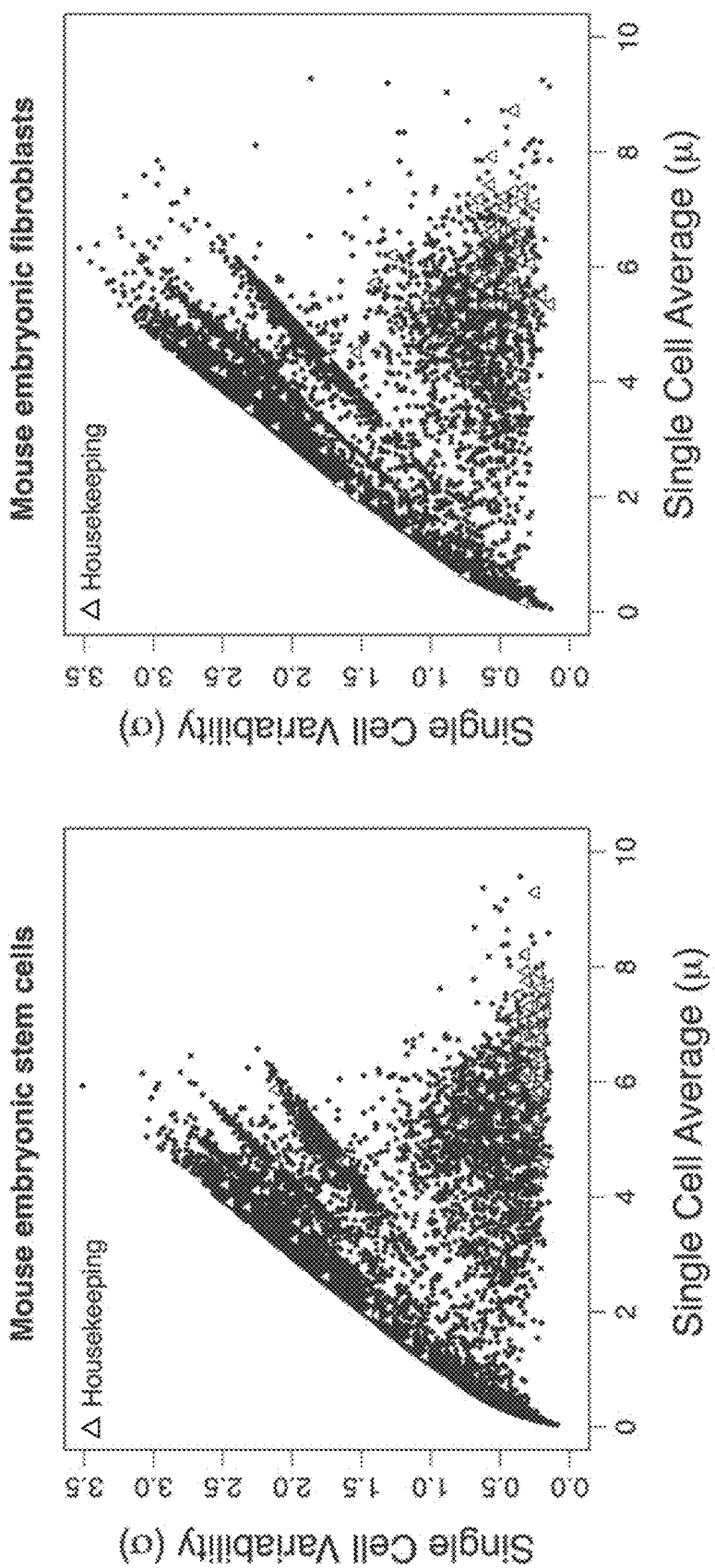
FIG. 8 is a series of graphs depicting variation in gene expression from single-cell RNA-Seq in other cell types. Shown is the relationship between the single cell expression average ($\mu$, X axis) and single cell variability (standard deviation, $\sigma$, Y axis) in mouse embryonic stem cells (left) and mouse embryonic fibroblasts (right). These figures show a re-analysis of previously published single cell RNA-seq data (Hashimshony. T., Wagner, F., Sher, N. & Yanai, I. CEL-Seq: Single-Cell RNA-Seq by Multiplexed Linear Amplification. Cell Reports, doi:10.1016/j.celrep.2012.08.003). Housekeeping genes are green. In both cases substantially less variability in single-cell gene expression was found compared to LPS-stimulated BMDCs (FIG. 2a).

This degree of variation in highly expressed transcripts has not been observed in previous studies (Islam, S. et al. Characterization of the single-cell transcriptional landscape by highly multiplex RNA-seq. Genome Research, doi:papers2://publication/doi/10.1101/gr.110882.110 (2011); Tang, F. et al. RNA-Seq analysis to capture the transcriptome landscape of a single cell. Nature Protocols 5, 516-535, doi:10.1038/nprot.2009.236 (2010); Tang, F. et al. mRNA-Seq whole-transcriptome analysis of a single cell. Nature Methods 6, 377-382, doi:10.1038/nmeth.1315 (2009); Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012); Hashimshony, T., Wagner, F., Sher, N. & Yanai, I. CEL-Seq: Single-Cell RNA-Seq by Multiplexed Linear Amplification. Cell Reports, doi: 10.1016/j.celrep.2012.08.003). For example, far less heterogeneity was found in expression for highly abundant (population average) genes in a published SMART-Seq dataset of eight human embryonic stem cells (Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012)) (FIG. 2a), or in single cell RNA-Seq datasets from terminally differentiated mouse embryonic fibroblasts and mouse embryonic stem cells (Hashimshony, T., Wagner, F., Sher, N. & Yanai, I. CEL-Seq: Single-Cell RNA-Seq by Multiplexed Linear Amplification. Cell Reports, doi: 10.1016/j.celrep.2012.08.003) (FIG. 8). In addition, such bimodality in (on average) highly expressed genes was not observed in genome-scale studies of variation in protein expression in mid-log yeast cells and dividing human cell lines (Newman. J. R. S. & Weissman, J. S. Systems biology: many things from one. Nature 444, 561-562 (2006); Bar-Even, A. et al. Noise in protein expression scales with natural protein abundance. Nature Genetics 38, 636-643 (2006); Sigal, A. et al. Variability and memory of protein levels in human cells. Nature 444, 643-646, doi:10.1038/nature05316 (2006)). It was thus hypothesized that the observed bimodality may reflect functionally important differences in the stimulated BMDC population.

Furthermore, splicing patterns across single cells also show previously unobserved levels of heterogeneity: for genes that have multiple splice isoforms at the population level, individual cells predominantly express one particular isoform. The frequency (percent spliced in, PSI) of previously annotated splicing events in each of the samples was calculated using MISO (Katz, Y., Wang, E. T., Airoldi, E. M. & Burge, C. B. Analysis and design of RNA sequencing experiments for identifying isoform regulation. Nature Methods 7, 1009-1015 (2010)), a Bayesian framework for calculating isoform ratios. Surprisingly, although the population-derived estimates were highly reproducible, single cells exhibited significant variability in exon-inclusion frequencies (FIGS. 3a,b).

The possibility that the PCR amplification steps (intrinsic to the library preparation process) could potentially result in an overestimation of isoform regulation variability, particularly for weakly expressed transcripts, due to 'jackpot effects' (Shiroguchi, K., Jia, T. Z., Sims, P. A. & Xie, X. S. Digital RNA sequencing minimizes sequence-dependent bias and amplification noise with optimized single-molecule barcodes. Proceedings of the National Academy of Sciences of the United States of America 109, 1347-1352 (2012)) was carefully considered. However, it was found that, even when the analysis was limited to 89 alternatively spliced exons (0.2<population PSI<0.8) that were very highly expressed within a single cell (single cell TPM>250), the same bimodality in splicing patterns amongst individual cells was still observed, with highly skewed expression of one or the other splice variant instead of simultaneous expression of both at comparable levels (FIG. 3b).

Figure 10A:
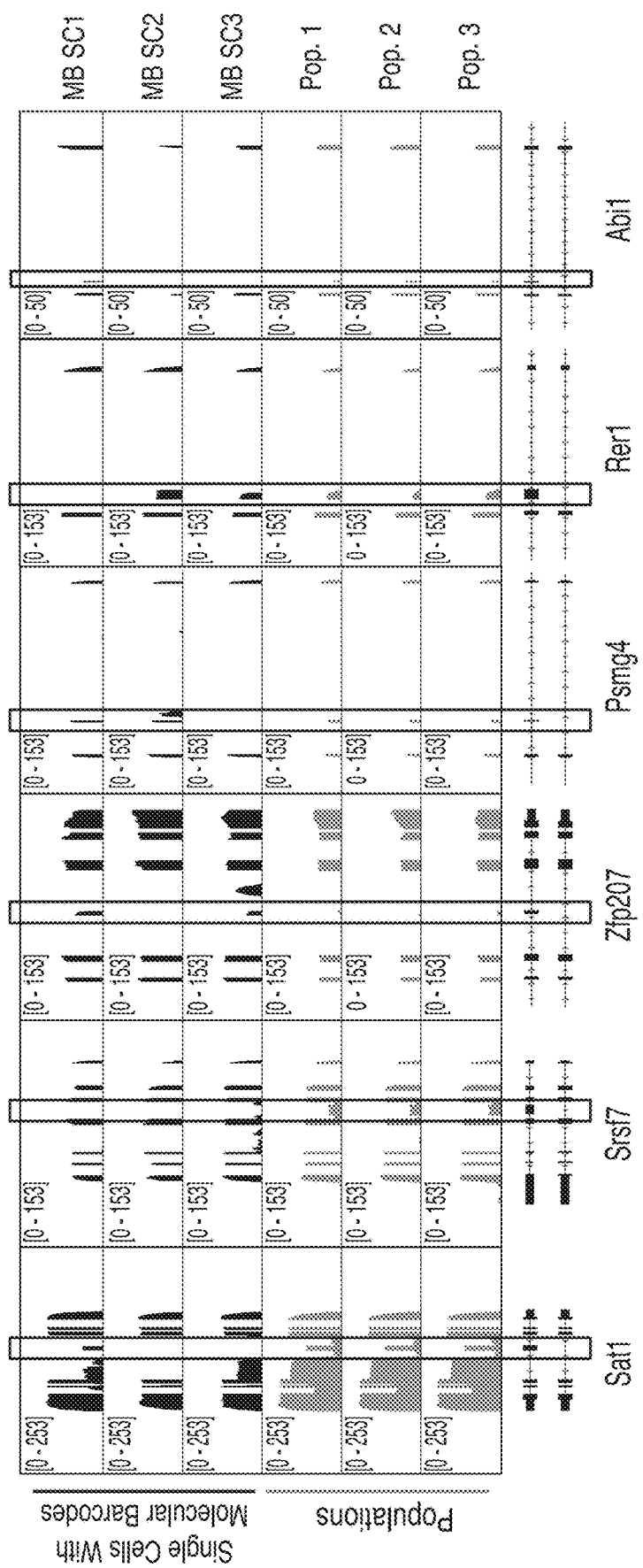
FIGS. 10A-10C are a series of graphs and a table depicting variation in isoform expression between single cells based on the 3 barcoded single-cell libraries.
Figures 10B, 10C:
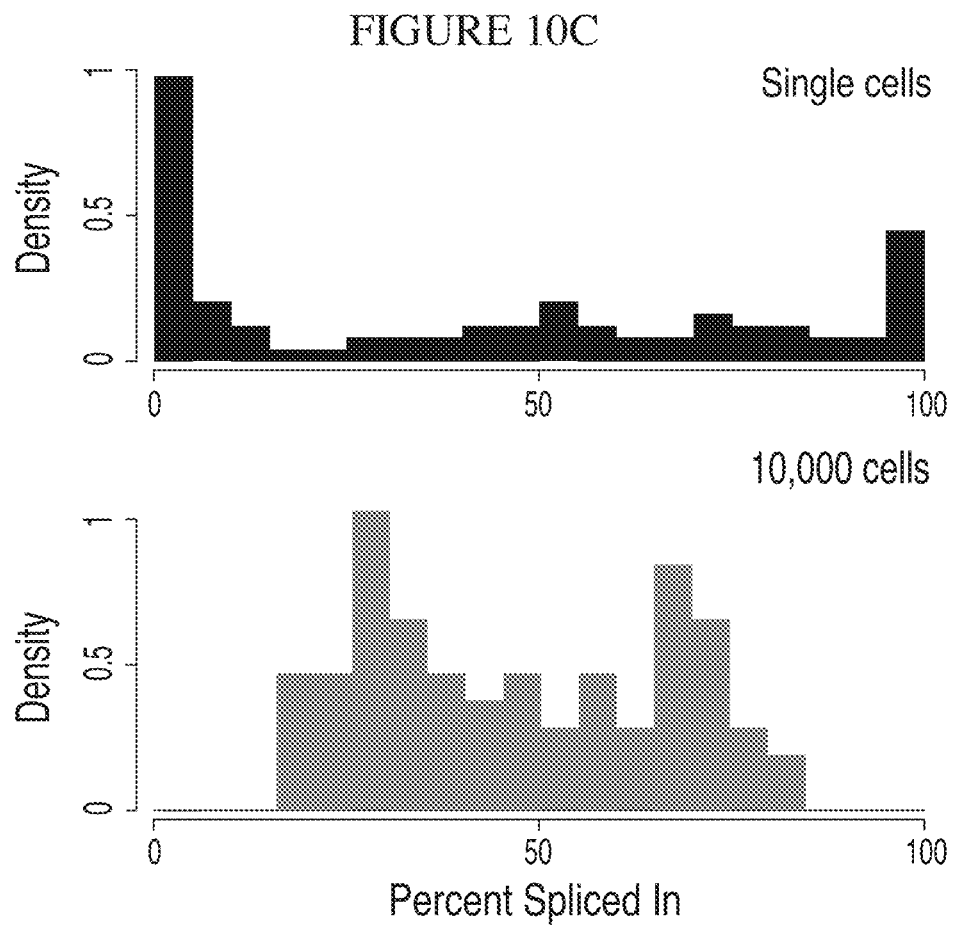

To further control for the possibility that stochastic over-amplification of a few molecules could confound the splicing analyses, three additional single cell cDNA libraries were created using a slightly modified SMART-Seq protocol (Example 1) in which a four nucleotide barcode was introduced onto each RNA molecule during reverse transcription. This barcode was retained through PCR amplification and library preparation, allowing us to quantify the number of unique RNA transcripts that are represented in the sequencing library (FIG. 9 and Example 1). Even when limiting the splicing analyses to genes that were represented by at least 15 unique barcodes, a strong bias in isoform expression in single cells was observed compared to population averages (FIG. 10).

To date, single-cell variation in splicing patterns has rarely been studied even for single genes, and never analyzed at a genomic scale. One recent report (Waks, Z., Klein, A. M. & Silver, P. A. Cell-to-cell variability of alternative RNA splicing. Molecular Systems Biology 7, 1-12, doi: papers2://publication/doi/10.1038/msb.2011.32 (2011)) used RNA-FISH to study variation in alternative isoforms in two genes, and observed lower levels of isoform variability across single cells (the levels of heterogeneity differed in different cell types). Another study using fluorescent reporters to quantify single-cell exon inclusion levels observed highly variable and bimodal splicing patterns for one gene (Gurskaya, N. G. et al. Analysis of alternative splicing of cassette exons at single-cell level using two fluorescent proteins. Nucleic Acids Research 40, doi:10.1093/nar/gkr1314 (2012)).

Figure 3D:
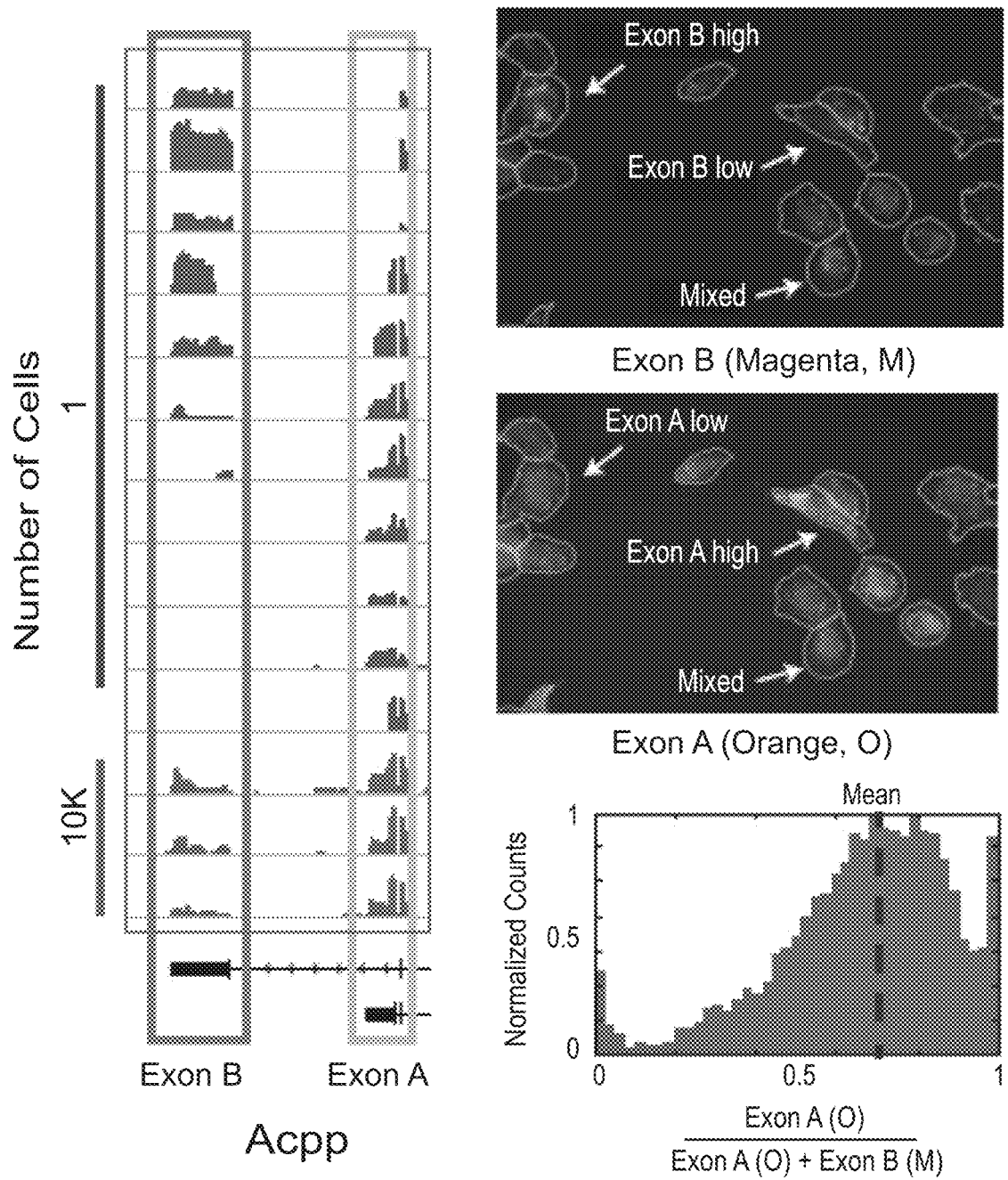
Figure 11:
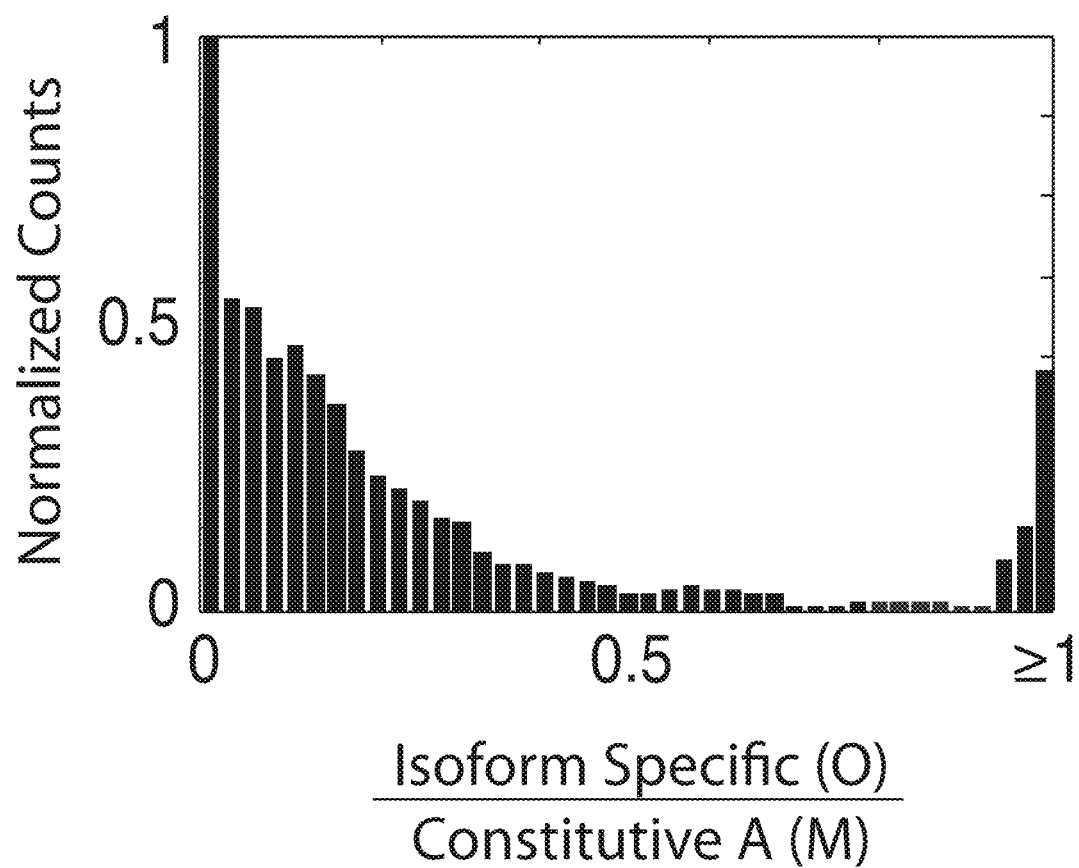
FIG. 11 is a graph depicting RNA-FISH validation of splicing variation in Irf7 in single cells. Shown is the distribution across cells of the ratio of Irf7 transcripts displaying the isoform specific Irf7 probe (Orange, FIG. 3c) relative to the shorter constitutive probe (Magenta, FIG. 3c). The distribution is similarly bimodal to that obtained when calculating the ratio of the specific probe to the longer constitutive probe (FIG. 3c).

To independently verify the extensive differences in isoform ratios between cells, RNA-FISH probes targeting constitutive and isoform-specific exons in two genes (Irf7 and Acpp, FIGS. 3c,d) (Waks, Z., Klein, A. M. & Silver, P. A. Cell-to-cell variability of alternative RNA splicing. Molecular Systems Biology 7, 1-12, doi:papers2://publication/doi/10.1038/msb.2011.32 (2011)) were designed. Substantial expression variability in overall Irf7 levels was found between individual cells (as reflected by the 'constitutive' probes, FIG. 3c, bottom and top panels), mirroring the single-cell sequencing results (and further explored below). Additionally, within each Irf7-expressing cell, a bias toward either the inclusion or exclusion of the specific exon (FIG. 3c, FIG. 11, middle panel, e.g., compare 'high' and 'low' marked cells) was observed. Similar results were obtained using two probes designed to detect mutually exclusive alternative final exons for Acpp (FIG. 3d). Thus, these studies demonstrate that splicing heterogeneity is a common mode of variation between single cells, a phenomenon often masked by the 'simultaneous expression' of alternative isoforms observed in population studies.

Example 3

Sources and Implications of Observed Bimodalities

The studies described herein were designed to explore the sources and functional implications of the observed bimodalities. The enrichment in immune response genes amongst highly (on average), yet bimodally, expressed genes may reflect either distinct functional states (e.g., cell subtypes) or stochastic differences in the activation of signaling circuits (Tay, S. et al. Single-cell NF-κB dynamics reveal digital activation and analogue information processing. *Nature* 466, 267-271, doi:papers2://publication/doi/10.1038/nature09145 (2010)), in promoter events (Sanchez, A., Garcia, H. G., Jones, D., Phillips, R. & Kondev, J. Effect of Promoter Architecture on the Cell-to-Cell Variability in Gene Expression. *PLoS Comput Biol* 7, e1001100-e1001100 (2011)), or in response timing (Nachman, I., Regev, A. & Ramanathan, S. Dissecting timing variability in yeast meiosis. *Cell* 131, 544-556 (2007)). First, it was hypothesized that at least some of the variation may reflect distinct cell states in the in vitro differentiated BMDCs. In particular, it has been previously reported that BMDCs can acquire distinct maturation states through a developmental process in which BMDCs switch from antigen-capturing to antigen-presenting cells in order to prime the adaptive immune system (Banchcreau, J. et al. Immunobiology of Dendritic Cells. *Annual Review of Immunology* 18, 767-811 (2000)). Maturation can occur either in response to pathogen-derived ligands, such as LPS, or as a result of disrupting clusters of DCs in culture (Jiang, A. et al. Disruption of E-Cadherin-Mediated Adhesion Induces a Functionally Distinct Pathway of Dendritic Cell Maturation. *Immunity* 27, 610-624, doi: papers2://publication/doi/10.1016/j.immuni.2007.08.015 (2007)), both leading to up-regulation of specific cell surface markers. The induction of cytokines that occurs in response to LPS represents an even more mature state of BMDCs.

Figure 4A:
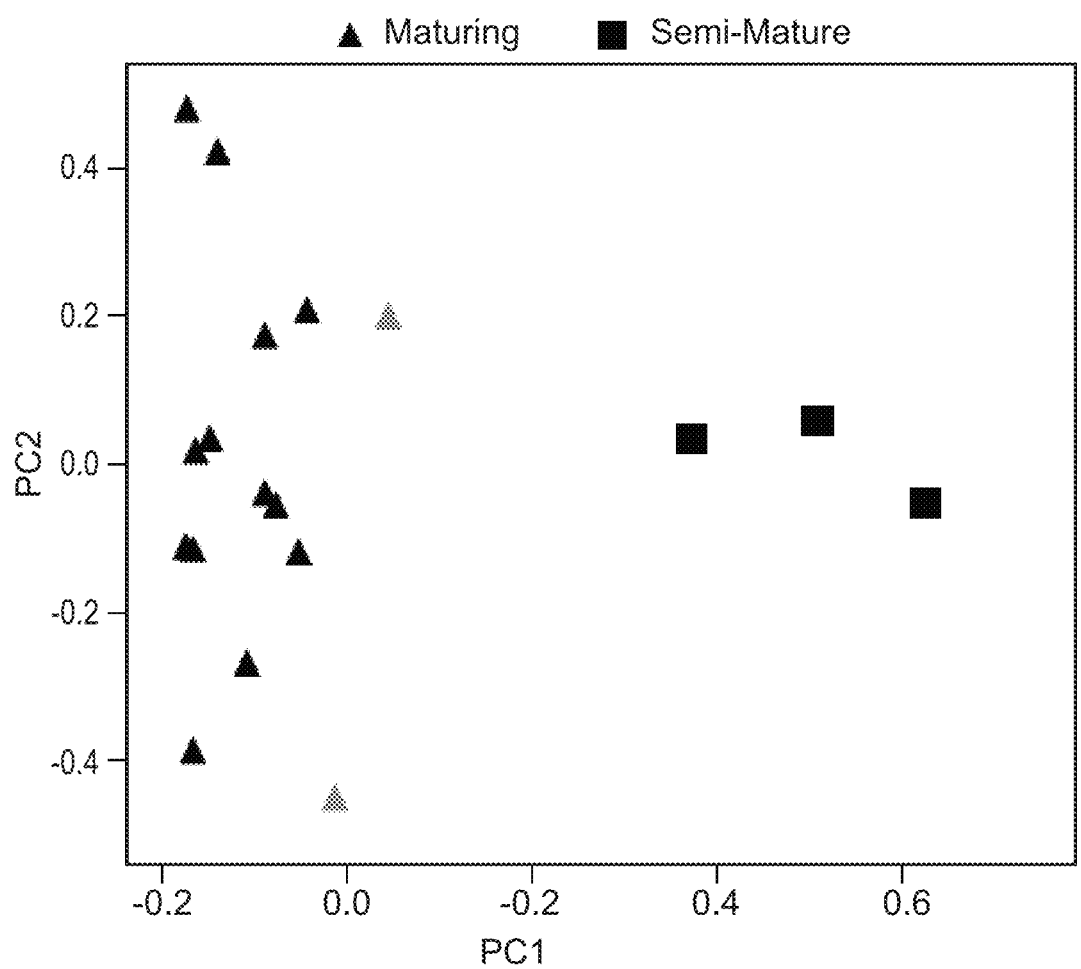
FIGS. 4A-4F are a series of graphs and illustrations that depict how analysis of co-variation in single cell mRNA expression levels revealed distinct maturity states and an antiviral cell circuit. A color version of these figures can be found in Shalek et al., "Single-cell transcriptomics reveals bimodality in expression and splicing in immune cells." Nature 498(7453):236-40 (2013).
Figure 4B:
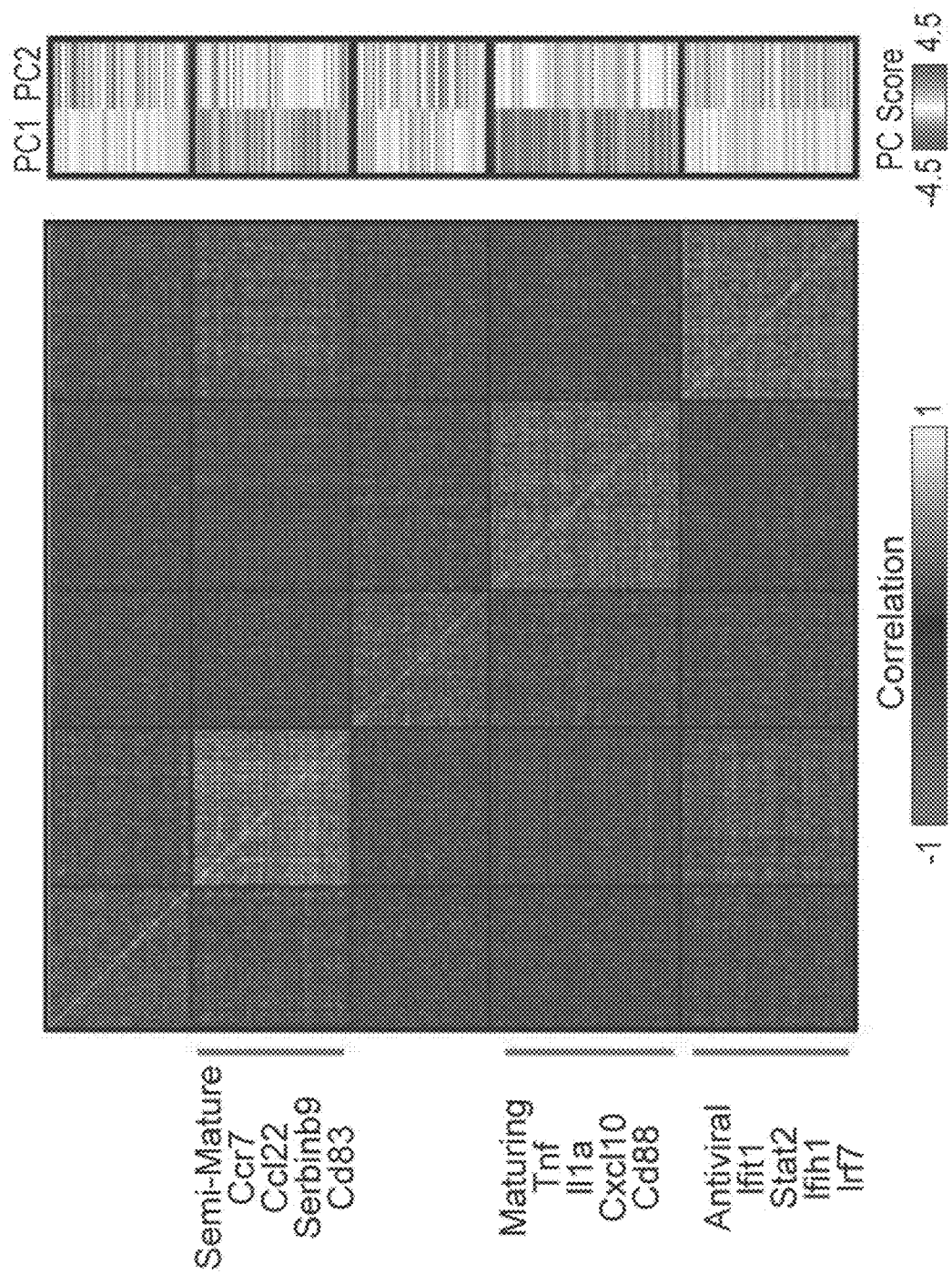
Figure 12:
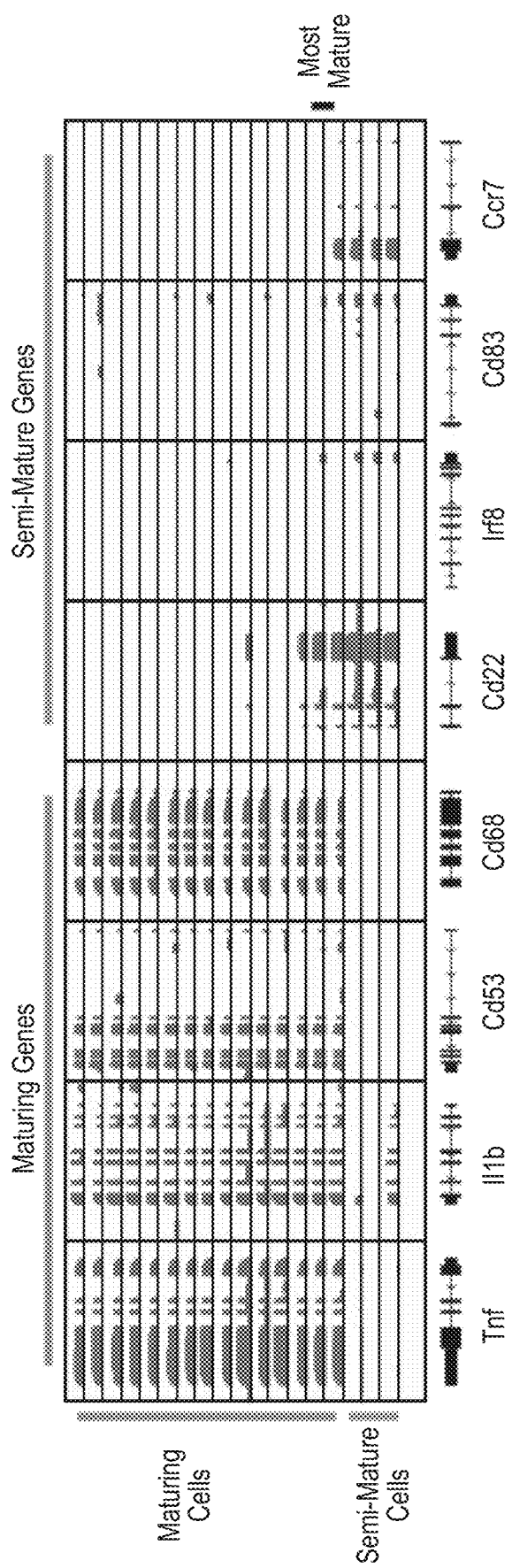
FIG. 12 is a graph depicting IGV screenshots exhibiting the separation between semi-mature and maturing cells. These genes have either very high (positive) or low (negative) projection scores for PC1. A black vertical bar on the right highlights two cells that express both mature and maturing markers, suggesting that they are, in fact, the most mature of the maturing cells.
Figure 13A:
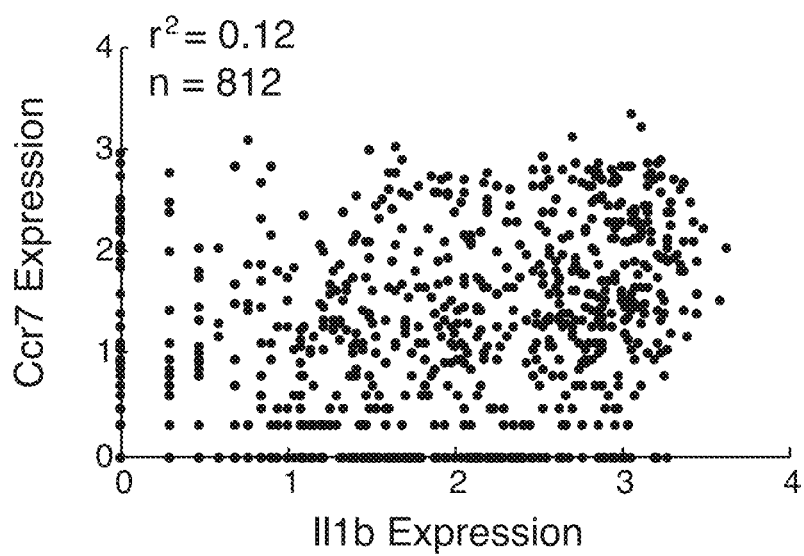
FIGS. 13A-13E are a series of graphs depicting confirmation of co-variation patterns by RNA-FISH. Shown are the relationships in expression levels (log (Count+1)) for pairs of transcripts simultaneously measured by RNA-FISH.
Figure 13B:
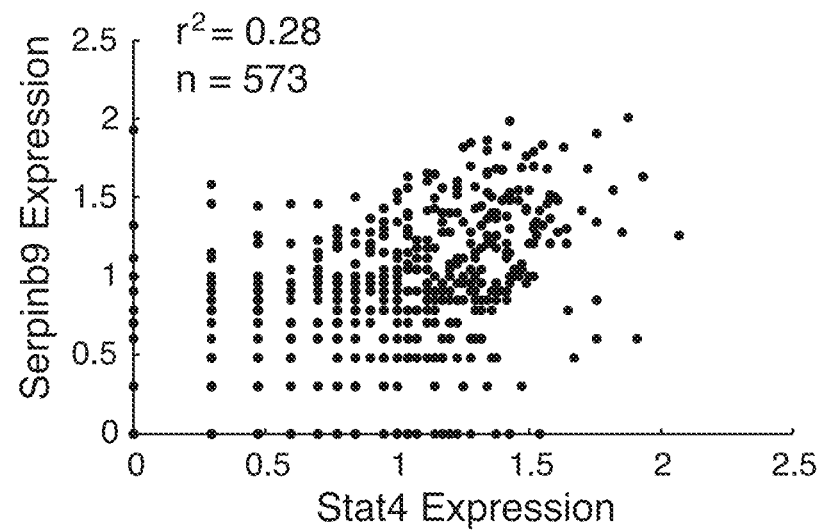
Figure 13C:
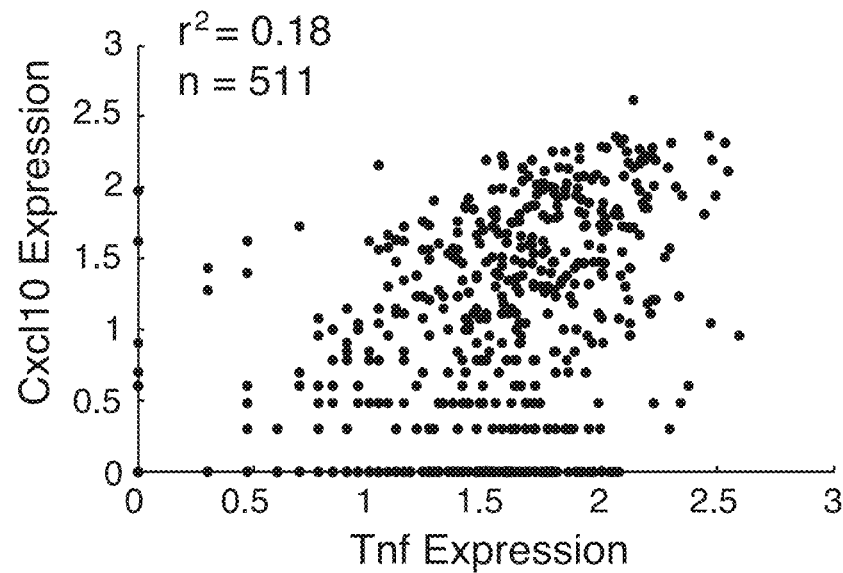
Figure 13D:
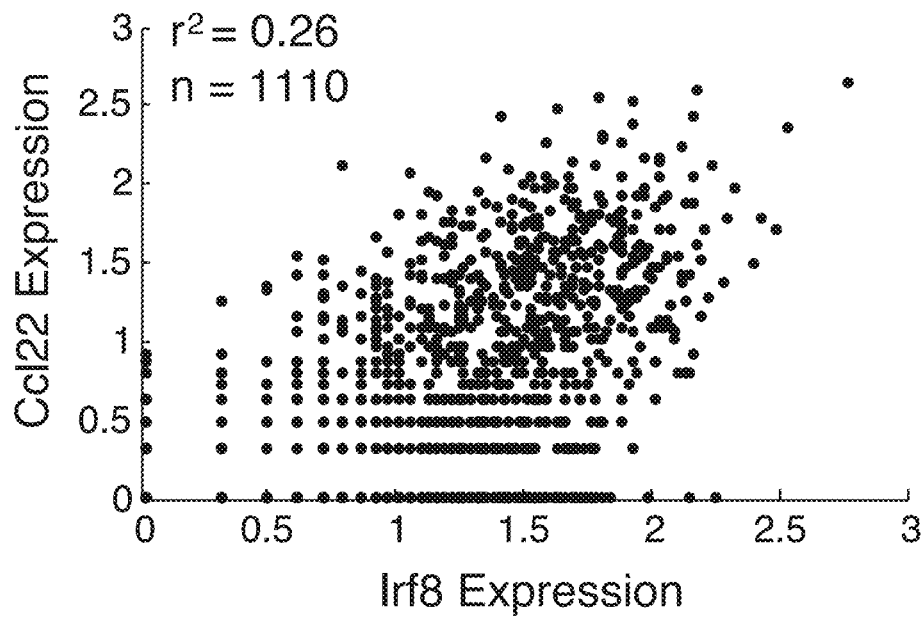
Figure 13E:
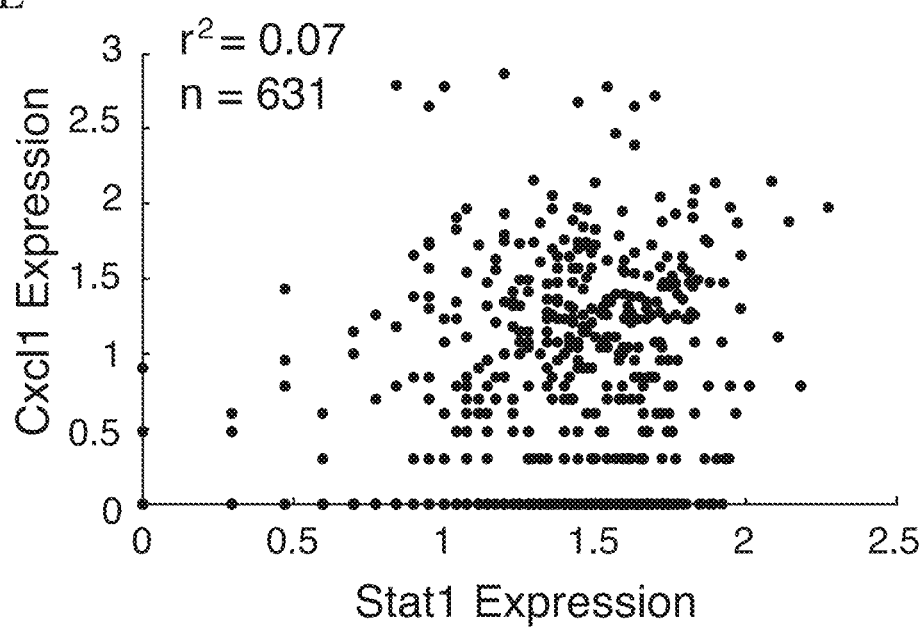
Figure 14:
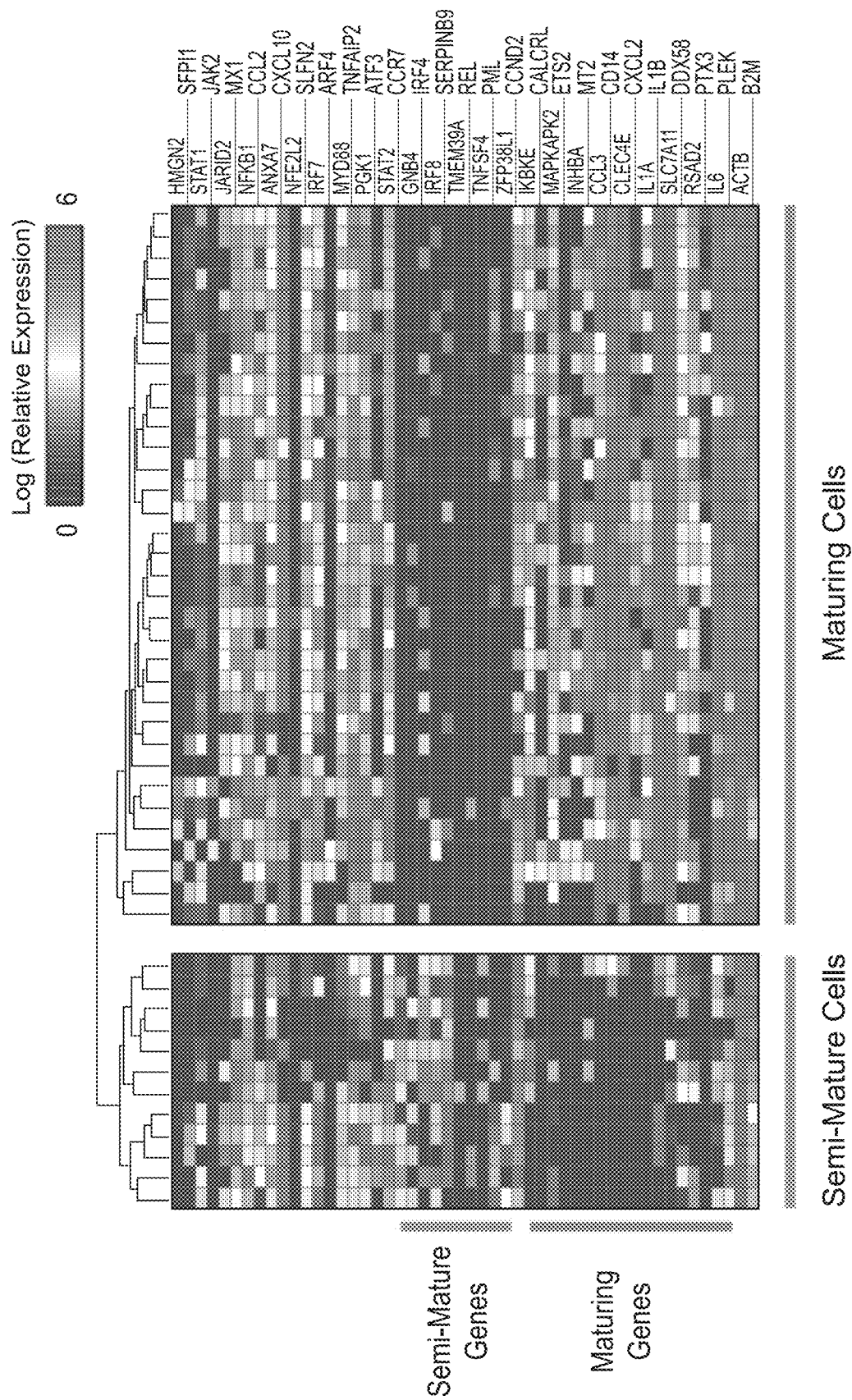
FIG. 14 is a graph depicting that individual LPS-stimulated BMDCs cluster into two distinct populations by single-cell qRT-PCR. Shown are the normalized expression levels (red: high; blue: low, scale on top) from single-cell qRT-PCR (Fluidigm) for 50 genes (rows) in each of 46 individual cells (columns). The cells were clustered by hierarchical agglomerative clustering based on their expression profiles (dendrogram, top) and form two main clusters (semi-mature and maturing, bottom).

To test how much, if any, of the transcriptional variation in immune response genes is due to distinct maturity states, an unbiased principal components analysis (PCA, FIG. 4a) was performed on the single-cell expression profiles, focusing on the 632 genes that were induced at least two-fold in the population-wide response to LPS (Garber. M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012)). At least two distinct subpopulations of cells were found within the dataset, clearly distinguishable by the first principal component (PC1, 15% of the total variation, FIG. 4a). One group of fifteen cells expressed a set of both antiviral and inflammatory cytokines (including: Tnf, Il1a, Il1b, and Cxcl10) at extremely high levels (TPM>1,000), whereas a second group of three cells expressed far lower, albeit detectable, levels of each of these genes (TPM<50). Other markers, such as Ccr7, Cd83, Serpinb9, and Cc122, showed the opposite expression pattern (FIG. 4b, FIG. 12). Many of the genes that distinguish these two groups encode cell surface proteins (e.g., Cd83, Cd86, and Ccr7) that have been previously identified as markers of BMDC maturation. These observations suggest that the two subpopulations of 15 and 3 cells represent distinct stages of DC maturation: cells with high expression of Cd83, Cd86 and Ccr7 and low expression of cytokines resemble 'semi-mature DCs' or cluster-disrupted DCs (Jiang, A. et al. Disruption of E-Cadherin-Mediated Adhesion Induces a Functionally Distinct Pathway of Dendritic Cell Maturation. *Immunity* 27, 610-624, doi:papers2://publication/doi/10.1016/j.immuni.2007.08.015 (2007); Lutz, M. B. Therapeutic potential of semi-mature dendritic cells for tolerance induction. Frontiers in immunology 3, 123, doi: papers2://publication/doi/10.3389/fimmu.2012.00123 (2012)), while those with high expression of cytokines represent 'maturing or mature DCs'. In addition, two of the 15 maturing cells (FIG. 12) express higher levels of transcripts encoding both cytokines and surface markers, suggesting that these cells are the most mature DCs (FIG. 5).

The existence of semi-mature and maturing BMDCs in the single cells were validated in several ways. First, the same semi-mature/maturing groupings were verified with RNA-FISH (FIG. 13), and also with single-cell quantitative reverse-transcription polymerase chain reaction (qRT-PCR: Fluidigm BioMark HD) using a signature of 96 genes selected to cover different expression levels and each of the first two principal components (FIG. 11, Table S6) (Dalerba. P. et al. Single-cell dissection of transcriptional heterogeneity in human colon tumors. *Nature Biotechnology* 29, 1120-1127, doi:10.1038/nbt.2038 (2011)). Second, subsets of Cd11c+ BMDCs were sorted based on the presence or absence of each of 11 cell surface markers whose mRNA levels in the single cell RNA-Seq discriminate between the maturing and semi-mature groups. qRT-PCR was then used in each pair of sorted populations to measure mRNA levels for the ten marker genes that also discriminate the two groups in the sequencing data, for example, Tnf and Cxcl10 (highly expressed in the maturing subpopulation) and Cc122 and Serpinb9 (highly expressed in the semi-mature subpopulation). Indeed, for pairs of populations sorted by 8 of 11 cell surface markers, the expected differences in marker expression levels were detected, confirming the sequencing-based classification (FIG. 15). These results further validate the sensitivity of single-cell RNA-Seq, demonstrating how it can effectively distinguish between closely related, yet distinct, maturity states, even within the same cell type.

Example 4

Role of Variation in Regulatory Circuits Amongst Cells in the Same Cell State

Since distinct maturity states explain only a small portion of the observed heterogeneity and bimodality, the role of variation in regulatory circuits amongst cells in the 'same' cell state (e.g., the 15 maturing cells) was examined next. It was reasoned that if such variable circuits exist, co-variation across single cells between the mRNA levels of a transcription factor and the expression of its targets would represent a potential regulatory interaction, and furthermore, would suggest that the variation in the regulator's expression underlies the variability of its targets. Such a correlative approach has successfully identified regulatory connections from population-level transcription profiles measured in different conditions (Amit, I. et al. Unbiased reconstruction of a mammalian transcriptional network mediating pathogen responses. *Science* 326, 257-263, doi:10.1126/science.1179050 (2009); Nachman, I., Regev, A. & Friedman, N. in *Bioinformatics* Vol. 20 i248 (2004)). Here, the studies were designed to apply it to multiple single cells in the same condition.

Figure 2C:
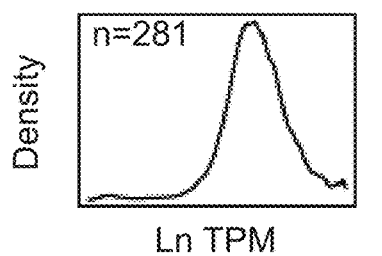
Figure 2C:
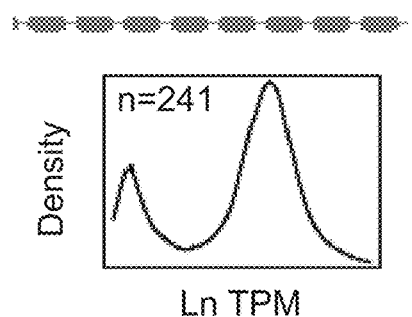
Figure 4C:
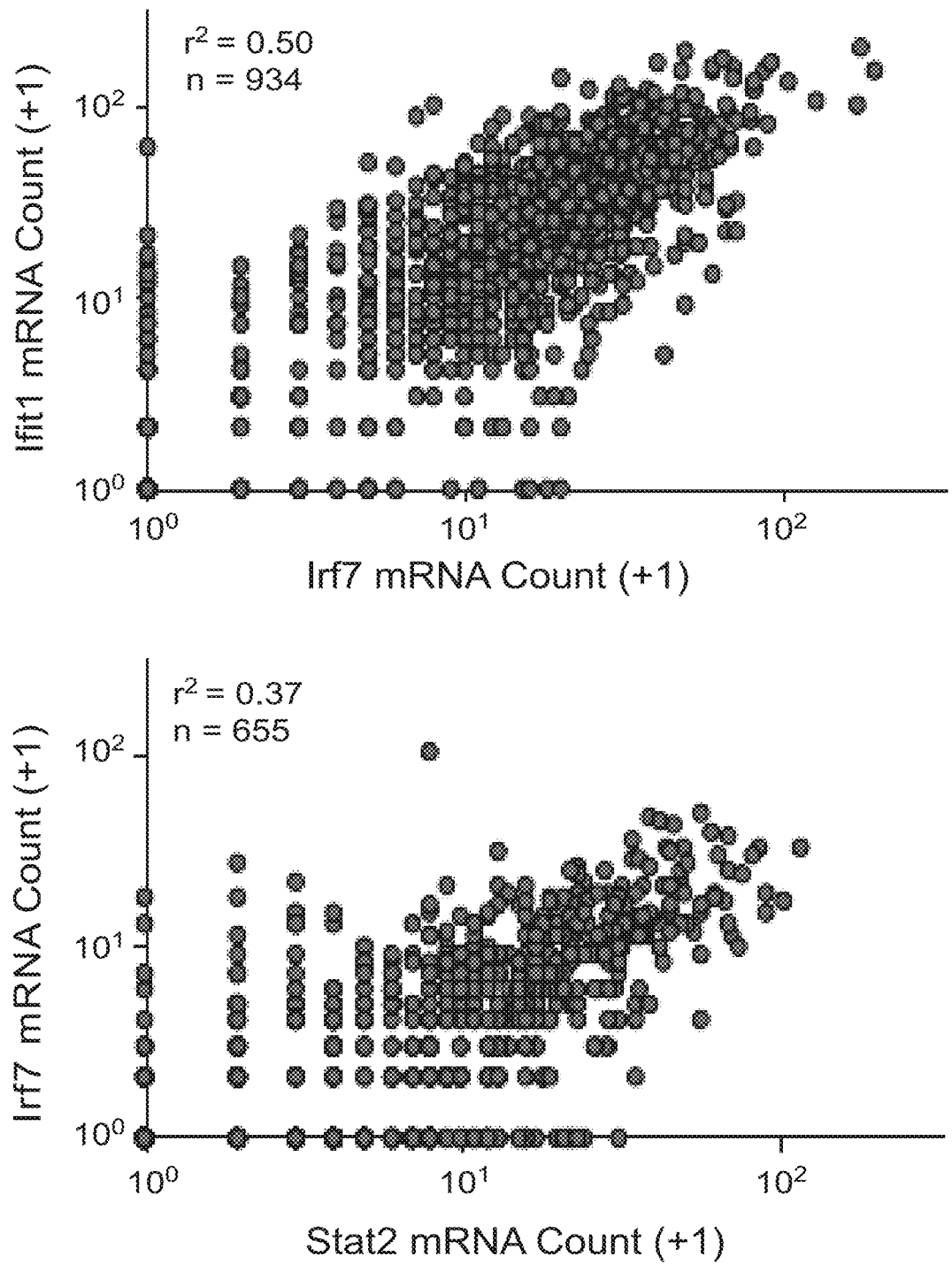
Figure 4D:
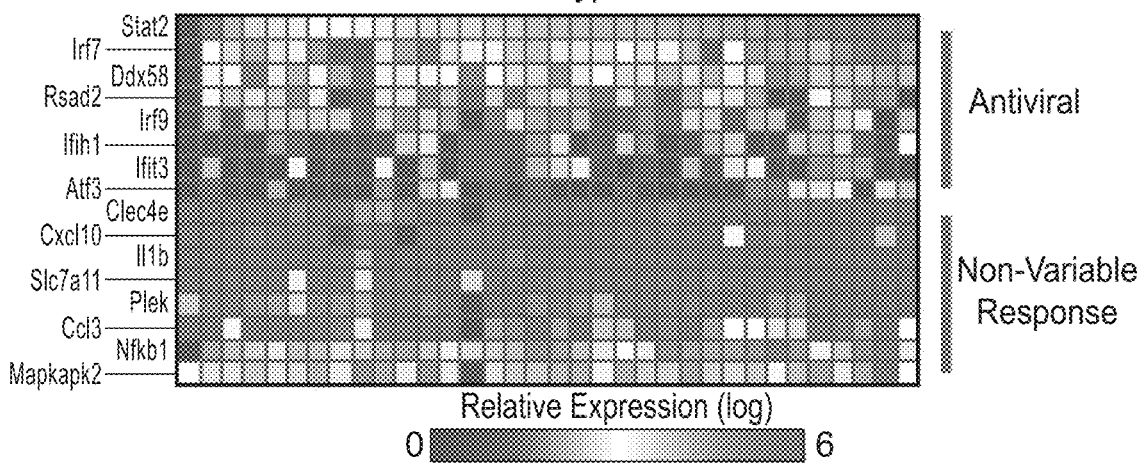

To this end, the correlation in expression profiles between every pair of induced genes across all single cells was calculated, and a cluster of 137 genes that varied in a correlated way across the cells was identified (FIG. 4b). The cluster's genes were highly enriched for members of the antiviral response (Amit, I. et al. Unbiased reconstruction of a mammalian transcriptional network mediating pathogen responses. *Science* 326, 257-263, doi:10.1126/science.1179050 (2009)) (60 of 137 genes, $p=2.5 \times 10^{-3}$, hypergeometric test) and included the transcripts encoding two known master regulators of the antiviral response, Stat2 and Irf7. The cluster was also enriched for Stat2 targets, as were previously determined by ChIP-Seq in DCs stimulated with LPS (Garber, M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012)) (73/137 genes, $p=4.5 \times 10^{-5}$, hypergeometric test). Genes in this 'antiviral cluster' were strongly discriminated by the second principal component of the PCA (PC2, 8% of the variation, FIG. 4a,b). The correlations between these antiviral genes were validated using both single-cell qRT-PCR (the same 96 gene signature as above) and RNA-FISH (FIG. 4c,d). Notably, most (100/137) of the cluster's genes exhibited bimodal expression across the cells (FIG. 2c, bottom) and were strongly expressed at the population level (13 genes TPM>250; 53 genes TPM>50).

Figure 16A:
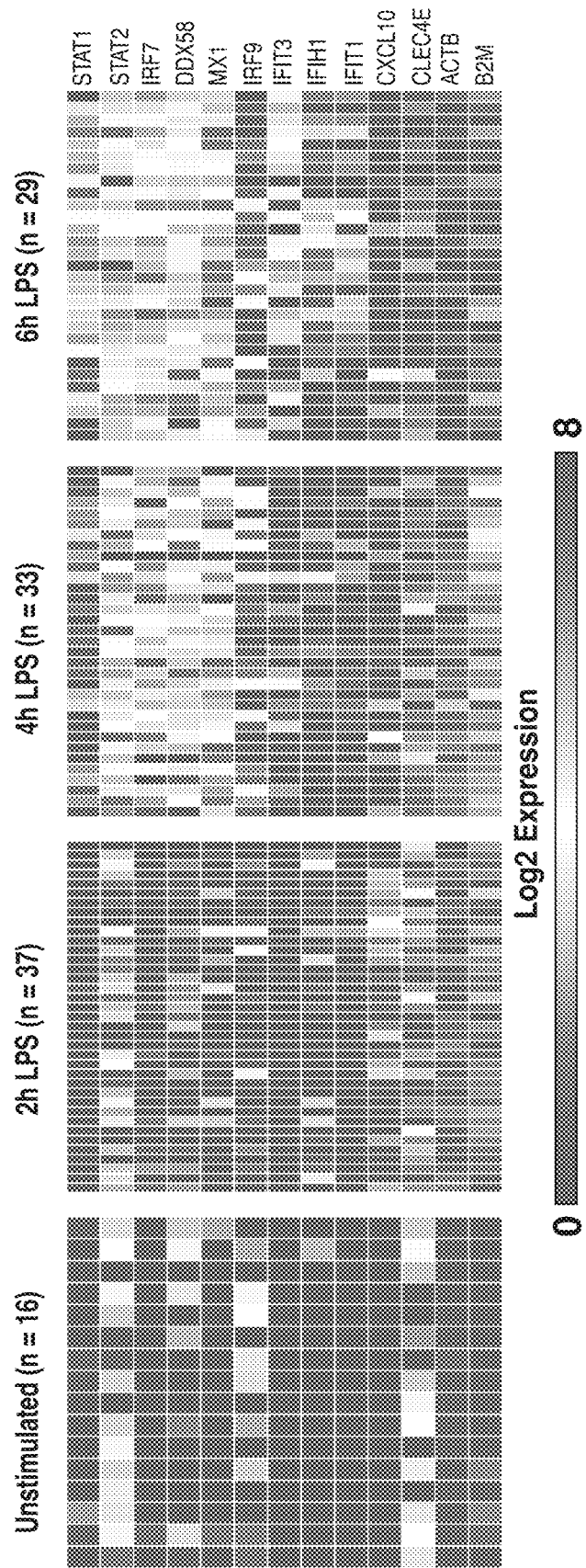
FIGS. 16A and 16B are a series of graphs depicting single-cell qPCR expression profiling for a signature of 13 genes along an LPS response time course.
Figure 16B:
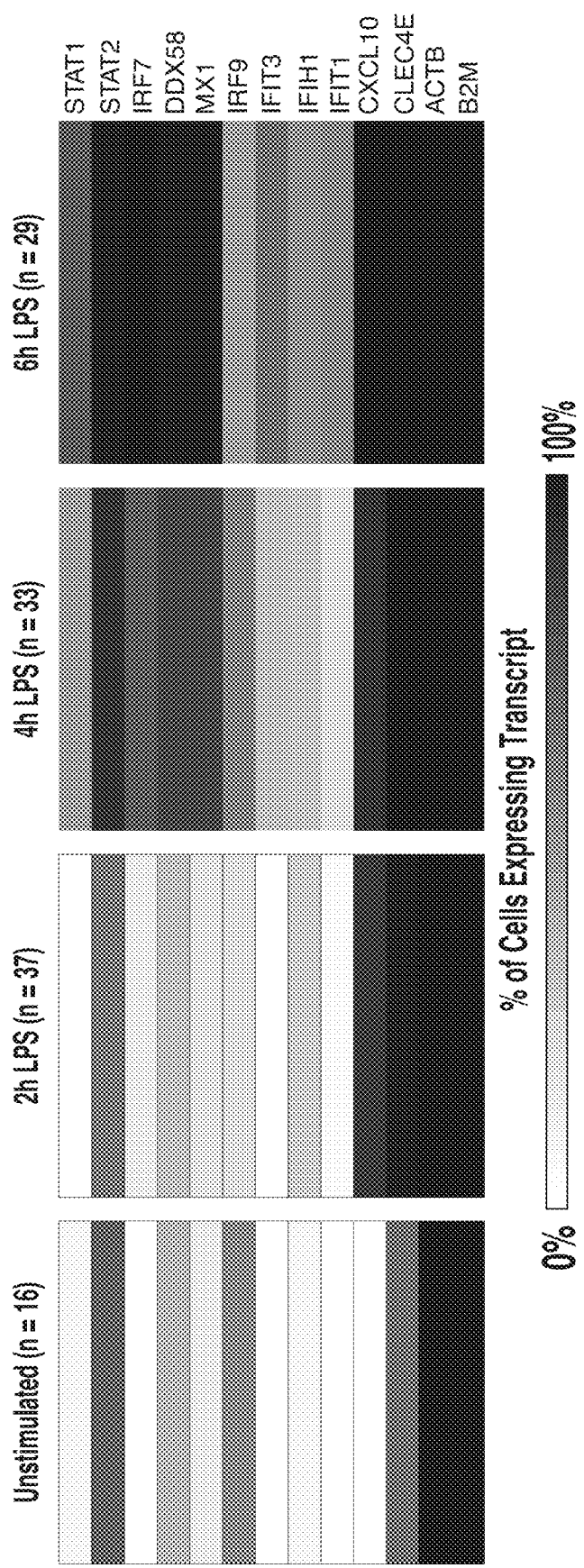

To further characterize how the variation in the antiviral circuit may change during the response, single-cell qPCR expression profiling was performed for a signature of 13 genes (nine antiviral cluster genes, two uniformly induced genes, and two housekeeping controls) in unstimulated BMDCs and at 2 h, 4 h, and 6 h post-LPS stimulation (FIG. 16). The percentage of cells expressing the antiviral cluster genes increased in a time-dependent manner (FIG. 16), and was mirrored by changes in the fraction of cells that exhibit high mRNA levels for antiviral master regulators. In contrast, the uniformly induced genes (Cxcl10, Clec4e) were robustly induced after two hours in all cells. Importantly, the quantitative correlations between the expression levels of the transcripts encoding master regulators and the downstream target genes existed in both the 4 h and 6 h time points.

Example 5

Differences in Levels of Stat2 and Irf7

Figure 4E:
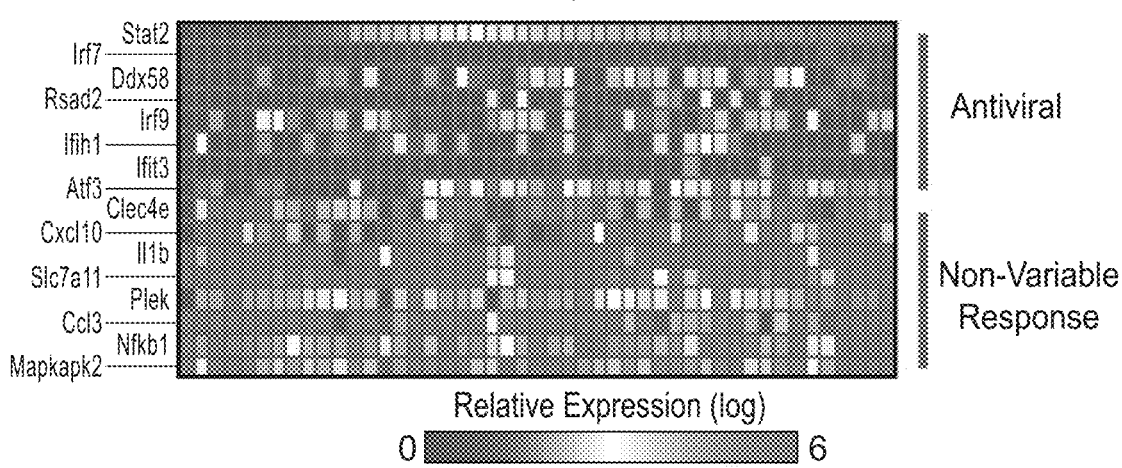
Figure 4F:
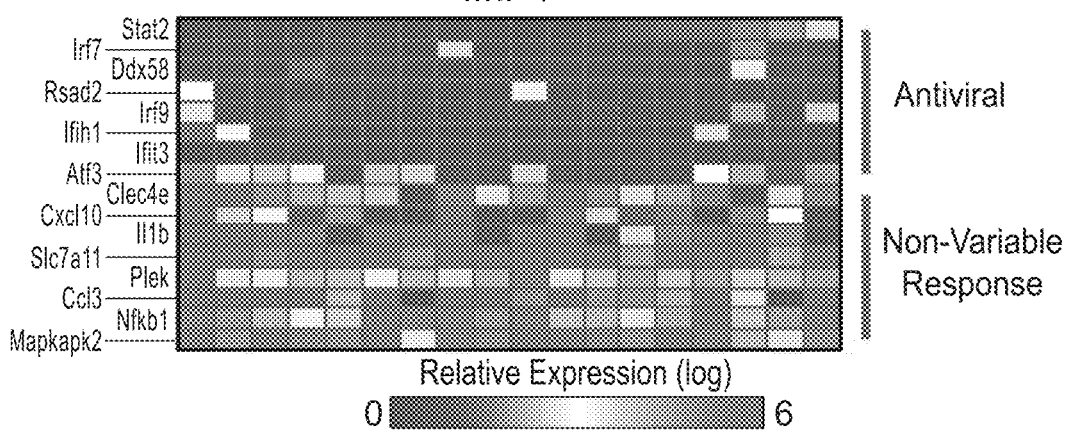

Having observed that the use of this anti-viral response circuit is highly variable between BMDCs of the same maturity state, it was hypothesized that bimodal variation in the expression of the cluster's genes may be related to differences in the levels of Stat2 and Irf7. In this case, it would be expected that perturbing these master regulators in BMDCs would result in reduced expression and variation in their targets. To test this hypothesis, expression of the signature genes was measured using single-cell qRT-PCR in LPS-stimulated cells from Irf7 knockout (Irf7−/−) mice. As expected, this perturbation ablated the transcription of most signature genes in the variable antiviral cluster, while leaving constitutive elements of the antiviral response relatively unaffected (FIG. 4e). However, Stat2 expression and variability levels were unaffected by the Irf7 knockout, implying that Stat2 may act either upstream or in parallel to Irf7 during the response (Ning, S., Huye, L. E. & Pagano, J. S. Regulation of the Transcriptional Activity of the IRF7 Promoter by a Pathway Independent of Interferon Signaling. Journal of Biological Chemistry 280, 12262-12270 (2005); Ousman, S. S., Wang, J. & Campbell, I. L. Differential regulation of interferon regulatory factor (IRF)-7 and IRF-9 gene expression in the central nervous system during viral infection. Journal of Virology 79, 7514-7527 (2005)). Because both Stat2 and Irf7 are targets of the interferon-signaling pathway, the effect of interferon feedback on the expression and variation of Stat2, Irf7 and the cluster genes were tested next. Indeed, when BMDCs from interferon receptor knockout (Ifnr−/−) mice (Darnell, J. E., Jr., Kerr, I. M. & Stark, G. R. Jak-STAT pathways and transcriptional activation in response to IFNs and other extracellular signaling proteins. Science (New York, N.Y.) 264, 1415-1421 (1994); Gough, D. J. et al. Functional crosstalk between type I and II interferon through the regulated expression of STAT1. PLoS biology 8, e1000361-e1000361 (2010)) were stimulated, drastically reduced expression for both Stat2 and Irf7, as well as all other cluster genes was observed (FIG. 4f).

One possibility is that earlier variation in Stat2 levels underlies the extensive variation in the anti-viral cluster at 4 hours, including in the Stat2 transcript itself (via autoregulation (Garber, M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012))). For example, while the majority of immune response genes (e.g., Ifit1) were not expressed in unstimulated cells, the Stat2 transcript is variably expressed even prior to LPS stimulation (FIG. 16). Cells with high levels of Stat2 prior to stimulation may be the most likely to express the antiviral cluster at the 4 h time point.

To further examine this link, cells were co-stained for Ifit1, Stat1, and Stat2 mRNAs and Stat1, pStat1, and Stat2 proteins (Example 1, FIGS. 17 & 18), and quantified these mRNA/protein levels and protein localization in BMDCs simulated with LPS for 0, 2, and 4 hrs. While overall protein levels increased in all cases throughout the time course, substantial heterogeneity was found in the induction of Stat1, pStat1, and Stat2 (FIG. 17). At 2 hr, all three proteins showed heterogeneity in both their expression and nuclear translocation. By 4 hr, protein levels were more homogeneous, and nuclear translocation was less pronounced. Ifit1 mRNA distributions displayed highly similar patterns, exhibiting more bimodal expression at early time points that became more uniform by 4 h. However, Stat protein and Ifit1 mRNA levels within individual cells were not correlated early ($0.00 < r^2 < 0.12$), and only very weakly correlated at four hours ($0.00 < r^2 < 0.28$). This may be due to the fact that a target's mRNA accumulation reflects the integrated spatiotemporal activity of a transcriptional regulator, which may not be well represented by a single temporal snapshot (Cai, L., Dalal, C. K. & Elowitz. M. B. Frequency-modulated nuclear localization bursts coordinate gene regulation. *Nature* 455, 485-490, doi:nature07292 [pii]10.1038/nature07292 (2008)). Thus, in cells with high Ifit1 mRNA levels, Stat proteins may already have left the nucleus. Validating such a hypothesis requires real-time tracing of protein and multiple transcripts simultaneously (Cohen, A. A. et al. Dynamic Proteomics of Individual Cancer Cells in Response to a Drug. *Science* 322, 1511-1516, doi:10.1126/science.1160165 (2008)), a task significantly complicated by difficulties of adding endogenous fluorescent tags in primary immune cells (Shalek, A. K. et al. Nanowire-Mediated Delivery Enables Functional Interrogation of Primary Immune Cells: Application to the Analysis of Chronic Lymphocytic Leukemia. *Nano Lett* 12, 6498-6504, doi: papers2://publication/doi/10.1021/nl13042917 (2012)), and to the Stat proteins specifically (Meyer, T., Begitt, A. & Vinkemeier, U. Green fluorescent protein-tagging reduces the nucleocytoplasmic shuttling specifically of unphosphorylated STAT1. GFP-tagging of STAT1 274, 815-826, doi: papers2://publication/doi/10.1111/j.1742-4658.2006.05626.x (2007)). Conversely, even at 4 h, Ifit1 mRNA levels correlated better with Stat1 and Stat2 mRNA than their protein levels (FIG. 18). Since Stat proteins autoregulate their own gene expression (Garber, M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012)), this is consistent with the hypothesis of an earlier regulatory event.

Example 6

High Throughput Microfluidic-Enabled Single Cell RNA-SEQ

The trillions of cells in complex eukaryotes are canonically grouped in tissues and organs, and further subdivided into types that share molecules, structures and functions. In recent years, however, it has become increasingly apparent that even functionally 'identical' cells can be markedly different in their component molecules (Taniguchi, Y. et al. Quantifying *E. coli* Proteome and Transcriptome with Single-Molecule Sensitivity in Single Cells. Science 329, 533-538, doi:10.1126/science.1188308 (2010); Tay, S. et al. Single-cell NF-κB dynamics reveal digital activation and analogue information processing. Nature 466, 267-271, doi: papers2://publication/doi/10.1038/nature09145 (2010); Raj, A. & Van Oudenaarden, A. Single-Molecule Approaches to Stochastic Gene Expression. Annual Review of Biophysics 38, 255-270, doi:10.1146/annurev.biophys.37.032807.125928 (2009); Cohen, A. A. et al. Dynamic Proteomics of Individual Cancer Cells in Response to a Drug. Science 322, 1511-1516, doi:10.1126/science.1160165 (2008); Altschuler. S. J. & Wu, L. F. Cellular Heterogeneity: Do Differences Make a Difference? Cell 141, 559-563, doi:10.1016/j.cell.2010.04.033 (2010); Warren, L., Bryder, D., Weissman, I. L. & Quake, S. R. Transcription factor profiling in individual hematopoietic progenitors by digital RT-PCR. Proceedings of the National Academy of Sciences of the United States of America 103, 17807-17812, doi:10.1073/pnas.0608512103 (2006); Paszek, P. et al. Population robustness arising from cellular heterogeneity. Proceedings of the National Academy of Sciences of the United States of America 107, 11644-11649, doi:10.1073/pnas.0913798107 (2010); Slack, M. D., Martinez, E. D., Wu, L. F. & Altschuler, S. J. Characterizing heterogeneous cellular responses to perturbations. Proceedings of the National Academy of Sciences 105, 19306-19311, doi: 10.1073/pnas.0807038105 (2008); Niepel, M., Spencer, S. L. & Sorger, P. K. Non-genetic cell-to-cell variability and the consequences for pharmacology. Curr. Opin. Chem. Biol. 13, 556-561, doi:10.1016/j.cbpa.2009.09.015 (2009); Sharma, S. V. et al. A chromatin-mediated reversible drug-tolerant state in cancer cell subpopulations. Cell 141, 69-80, doi:10.1016/j.cell.2010.02.027 (2010); Gascoigne, K. E. & Taylor, S. S. Cancer cells display profound intra- and interline variation following prolonged exposure to antimitotic drugs. Cancer cell 14, 111-122, doi:10.1016/j.ccr.2008.07.002 (2008) and that this heterogeneity can result in substantially different responses to external stimuli (Cohen, A. A. et al. Dynamic Proteomics of Individual Cancer Cells in Response to a Drug. Science 322, 1511-1516, doi:10.1126/science.1160165 (2008); Niepel, M., Spencer, S. L. & Sorger, P. K. Non-genetic cell-to-cell variability and the consequences for pharmacology. Curr. Opin. Chem. Biol. 13, 556-561, doi:10.1016/j.cbpa.2009.09.015 (2009); Sharma, S. V. et al. A chromatin-mediated reversible drug-tolerant state in cancer cell subpopulations. Cell 141, 69-80, doi:10.1016/j.cell.2010.02.027 (2010); Gascoigne, K. E. & Taylor, S. S. Cancer cells display profound intra- and interline variation following prolonged exposure to antimitotic drugs. Cancer cell 14, 111-122, doi:10.1016/j.ccr.2008.07.002 (2008); Spencer, S. L., Gaudet, S., Albeck, J. G., Burke, J. M. & Sorger, P. K. Non-genetic origins of cell-to-cell variability in TRAIL-induced apoptosis. Nature 459, 428-432, doi: 10.1038/nature08012 (2009)). While such variability can prove detrimental in the case of therapeutic intervention (Cohen, A. A. et al. Dynamic Proteomics of Individual Cancer Cells in Response to a Drug. Science 322, 1511-1516, doi:10.1126/science.1160165 (2008); Altschuler, S. J. & Wu, L. F. Cellular Heterogeneity: Do Differences Make a Difference? Cell 141, 559-563, doi:10.1016/j.cell.2010.04.033 (2010); Spencer, S. L., Gaudet, S., Albeck, J. G., Burke, J. M. & Sorger, P. K. Non-genetic origins of cell-to-cell variability in TRAIL-induced apoptosis. Nature 459, 428-432, doi:10.1038/nature08012 (2009); Spencer. S. L. & Sorger, P. K. Measuring and Modeling Apoptosis in Single Cells. Cell 144, 926-939, doi:10.1016/j.cell.2011.03.002 (2011)) it likely plays an important functional role by increasing the diversity of potential population-level responses (Feinerman, O. et al. Single-cell quantification of IL-2 response by effector and regulatory T cells reveals critical plasticity in immune response. Molecular Systems Biology 6, 1-16, doi:papers2://publication/doi/10.1038/msb.2010.90 (2010); Veening, J.-W., Smits, W. K. & Kuipers, O. P. Bistability, Epigenetics, and Bet-Hedging in Bacteria. Annual Review of Microbiology 62, 193-210, doi:papers2://publication/doi/10.1146/annurev.micro.62.081307.163002 (2008); Locke, J. C. & Elowitz, M. B. Using movies to analyse gene circuit dynamics in single cells. Nature reviews. Microbiology 7, 383-392, doi: 10.1038/nrmicro2056 (2009); Thattai, M. & van Oudenaarden, A. Stochastic gene expression in fluctuating environments. Genetics 167, 523 (2004); Beaumont, H. J., Gallie, J., Kost, C., Ferguson, G. C. & Rainey. P. B. Experimental evolution of bet hedging. Nature 462, 90-93, doi:10.1038/nature08504 (2009); Chalancon, G. et al. Interplay between gene expression noise and regulatory network architecture. Trends in genetics: TIG 28, 221-232, doi: 10.1016/j.tig.2012.01.006 (2012)).

The immune system is a well-established example of this: although immune cells are notoriously heterogeneous in their types and functions (Bendall, S. C. & Nolan, G. P. Single-Cell Mass Cytometry of Differential Immune and Drug Responses Across a Human Hematopoietic Continuum. Science (New York, N.Y.) 332, 677-678, doi: 10.1126/science.1206351 (2011); Hashimoto. D., Miller, J. & Merad, M. Dendritic Cell and Macrophage Heterogeneity In Vivo. Immunity 35, 323-335, doi:papers2://publication/doi/10.1016/j.immuni.2011.09.007 (2011)), they must collectively generate appropriate responses to pathogens. Understanding the strategies used to encode population-level behaviors, as well as when they fail and at what expense, is a fundamental biological problem with substantial clinical relevance. Recent molecular studies have demonstrated the potential for single cell approaches to unveil the informing mechanisms, normally masked by technical and biological noise, with sufficient sampling (Cohen. A. A. et al. Dynamic Proteomics of Individual Cancer Cells in Response to a Drug. Science 322, 1511-1516, doi:10.1126/science.1160165 (2008); Altschuler, S. J. & Wu, L. F. Cellular Heterogeneity: Do Differences Make a Difference? Cell 141, 559-563, doi:10.1016/j.cell.2010.04.033 (2010); Niepel, M., Spencer, S. L. & Sorger, P. K. Non-genetic cell-to-cell variability and the consequences for pharmacology. Curr. Opin. Chem. Biol. 13, 556-561, doi:10.1016/j.cbpa.2009.09.015 (2009); Sharma, S. V. et al. A chromatin-mediated reversible drug-tolerant state in cancer cell subpopulations. Cell 141, 69-80, doi:10.1016/j.cell.2010.02.027 (2010); Spencer, S. L., Gaudet, S., Albeck, J. G., Burke, J. M. & Sorger, P. K. Non-genetic origins of cell-to-cell variability in TRAIL-induced apoptosis. Nature 459, 428-432, doi:10.1038/nature08012 (2009); Feinerman, O. et al. Single-cell quantification of IL-2 response by effector and regulatory T cells reveals critical plasticity in immune response. *Molecular Systems Biology* 6, 1-16, doi:papers2://publication/doi/10.1038/msb.2010.90 (2010); Bendall, S. C. & Nolan, G. P. Single-Cell Mass Cytometry of Differential Immune and Drug Responses Across a Human Hematopoietic Continuum. *Science (New York, N.Y.)* 332, 677-678, doi:10.1126/science.1206351 (2011))). Nevertheless, the majority of these studies have focused—by necessity—on well-characterized markers with available reagents and known roles, hindering unbiased discovery of the determinants of immune responses.

Emerging single cell genomics methods now open the possibility of using sequencing-based approaches to profile the behaviors of single cells in unprecedented detail (Islam, S. et al. Characterization of the single-cell transcriptional landscape by highly multiplex RNA-seq. Genome Research, doi:papers2://publication/doi/10.1101/gr.110882.110 (2011); Tang, F. et al. RNA-Seq analysis to capture the transcriptome landscape of a single cell. Nature Protocols 5, 516-535, doi:10.1038/nprot.2009.236 (2010); Tang, F. et al. mRNA-Seq whole-transcriptome analysis of a single cell. Nature Methods 6, 377-382, doi:10.1038/nmeth.1315 (2009); Ramskold, D. et al. Full-length mRNA-Seq from single-cell levels of RNA and individual circulating tumor cells. Nature Biotechnology 30, 777-782, doi:papers2://publication/doi/10.1038/nbt.2282 (2012); Hashimshony, T., Wagner, F., Sher, N. & Yanai, I. CEL-Seq: Single-Cell RNA-Seq by Multiplexed Linear Amplification. Cell Reports, doi:10.1016/j.celrep.2012.08.003). In principle, genome-wide single cell approaches could help determine, ab initio, new cell classification schemes, transitional states, unrecognized biological distinctions, molecular circuits, and the like. Fulfilling this potential requires the development of new experimental strategies for achieving the scale needed to address the high levels of noise inherent in single-cell measurements (Chalancon, G. et al. Interplay between gene expression noise and regulatory network architecture. *Trends in genetics: TIG* 28, 221-232, doi:10.1016/j.tig.2012.01.006 (2012); Newman, J. R. S. et al. in Nature Vol. 441 840-846 (2006); Munsky, B., Neuert, G. & van Oudenaarden, A. Using Gene Expression Noise to Understand Gene Regulation. Science (New York, N.Y.) 336, 183-187, doi:10.1126/science.1216379 (2012); Balázsi, G., Van Oudenaarden, A. & Collins, J. J. Cellular Decision Making and Biological Noise: From Microbes to Mammals. Cell 144, 910-925, doi:10.1016/j.cell.2011.01.030 (2011))—both technical, due to minute amounts of input material, and biological, due to bursts of RNA transcription (Taniguchi, Y. et al. Quantifying *E. coli* Proteome and Transcriptome with Single-Molecule Sensitivity in Single Cells. *Science* 329, 533-538, doi:10.1126/science.1188308 (2010); Cai, L., Dalal, C. K. & Elowitz, M. B. Frequency-modulated nuclear localization bursts coordinate gene regulation. *Nature* 455, 485-490, doi:papers2://publication/doi/10.1038/nature07292 (2008)).

Integrated microfluidic circuits present an elegant solution for surmounting this obstacle. Indeed, methodological precedent exists for performing each of the steps implicated in a single cell whole transcriptome (WTA) amplification protocol within a microfluidic device (Taniguchi, Y. et al. Quantifying *E. coli* Proteome and Transcriptome with Single-Molecule Sensitivity in Single Cells. *Science* 329, 533-538, doi:10.1126/science.1188308 (2010); Tay, S. et al. Single-cell NF-κB dynamics reveal digital activation and analogue information processing. *Nature* 466, 267-271, doi: papers2://publication/doi/10.1038/nature09145 (2010); Hong, J. W., Studer, V., Hang, G., Anderson, W. F. & Quake, S. R. A nanoliter-scale nucleic acid processor with parallel architecture. Nature Publishing Group 22, 435-439, doi: 10.1038/nbt951 (2004); Huang. B. et al. Counting Low-Copy Number Proteins in a Single Cell. Science (New York, N.Y.) 315, 81-84, doi:10.1126/science.1133992 (2007); Marcus, J., Anderson, W. & Quake, S. Microfluidic single-cell mRNA isolation and analysis. Analytical Chemistry 78, 3084-3089 (2006); Melin, J. & Quake, S. R. Microfluidic Large-Scale Integration: The Evolution of Design Rules for Biological Automation. Annual Review of Biophysics and Biomolecular Structure 36, 213-231, doi:10.1146/annurev.biophys.36.040306.132646 (2007); Amit, I. et al. Unbiased reconstruction of a mammalian transcriptional network mediating pathogen responses. Science 326, 257-263, doi:10.1126/science.1179050 (2009)), including cell capture, imaging, lysis, reverse transcription, and amplification (PCR). In this study, a commercially available microfluidic system (C1 Single Cell Auto Prep System, Fluidigm) was adapted to prepare single-cell SMART-seq mRNA transcriptome libraries. The system isolates up to 96 individual cells, applies multi-step molecular biology protocols to each isolated cell, and then outputs the reaction product to an SBS-format well on the chip carrier. The SMART-Seq (Ramskold. D. et al. Full-length mRNA-Seq from single-cell levels of RNA and individual circulating tumor cells. Nature Biotechnology 30, 777-782, doi:papers2://publication/doi/10.1038/nbt.2282 (2012)) double-stranded cDNA generated form each cell are then converted to Illumina sequencing libraries.

Single Cell RNA-Seq Profiling of Thousands of Bone Marrow Dendritic Cells:

the Fluidigm C1 Single-Cell Auto Prep System was utilized, combined with a high-throughput cDNA library construction protocol, to generate RNA-Seq ready libraries from a total 2000-3000 single Bone Marrow-Derived Dendritic cells (BMDCs) (Toriello, N. et al. Integrated microfluidic bioprocessor for single-cell gene expression analysis. *Proceedings of the National Academy of Sciences* 105, 20173 (2008); Chevrier, N. et al. Systematic Discovery of TLR Signaling Components Delineates Viral-Sensing Circuits. Cell 147, 853-867, doi:10.1016/j.cell.2011.10.022 (2011); Garber, M. et al. A High-Throughput Chromatin Immunoprecipitation Approach Reveals Principles of Dynamic Gene Regulation in Mammals. Molecular Cell 47, 810-822, doi:10.1016/j.molcel.2012.07.030 (2012)). BMDCs represent a good model system for studying single cell responses since they are primary, well-characterized at the population level, post-mitotic, and can be synchronized through the addition of a strong pathogenic stimulus (oriello, N. et al. Integrated microfluidic bioprocessor for single-cell gene expression analysis. *Proceedings of the National Academy of Sciences* 105, 20173 (2008)). The previous Examples examining response variability between 18 'homogenous' stimulated, single BMDCs did not allow for the examination of the evolution of noise and its molecular determinants. Moreover, the focus on one stimulus prevented the profiling and contrasting of circuit activation and heterogeneity across different stimuli.

The studies described herein were designed to address these questions. First, genome-wide mRNA expression responses were profiled at five time points (0, 1, 2, 4, & 6 hr) after activating BMDC Toll-Like Receptor (TLR) signaling with three distinct pathogenic stimuli (Chevrier, N. et al. Systematic Discovery of TLR Signaling Components Delineates Viral-Sensing Circuits. *Cell* 147, 853-867, doi: 10.1016/j.cell.2011.10.022 (2011))—lipopolysaccharide (LPS; a component of gram-negative bacteria and TLR4 agonist), Polyinosinic:polycytidylic acid (Poly(I:C), PIC; viral-like double stranded RNA and TLR3 agonist), and PAM3CSK (PAM; a synthetic mimic of bacterial lipopeptides and TLR2 agonist). For each condition, a single C1 IFC, capturing up to 96 cells (average 85±10%) was run, and libraries were also generated from 10,000 cells (population control). In all, 311, 212, and 146 cells responding to LPS, PIC, and PAM, respectively, as well as ~4000 additional cells (described below) were profiled.

Each of these samples were sequenced to an average depth of 10 million read pairs, and expression estimates (transcripts per million; TPM) were calculated for all UCSC-annotated genes using (Li, B. & Dewey, C. N. RSEM: accurate transcript quantification from RNA-Seq data with or without a reference genome. *BMC Bioinformatics* 12, 323-323 (2011)). The obtained libraries were of consistently high quality, comparable to published SMART data (Ramskold, D. et al. Full-length mRNA-Seq from single-cell levels of RNA and individual circulating tumor cells. *Nature Biotechnology* 30, 777-782, doi:papers2://publication/doi/10.1038/nbt.2282 (2012); Shalek, A. K. et al. Nanowire-mediated delivery enables functional interrogation of primary immune cells: application to the analysis of chronic lymphocytic leukemia. Nano Lett. 12(12):6498-504, doi: 10.1021/n13042917 (2012)). Median transcriptomic mapping rates were ~50-60%, while median genomic mapping rates were ~70-80%. A significant fraction of reads (~10%) failed to map due to contaminating adaptor sequence which cannot be trimmed, suggesting that the cDNA libraries are of even higher quality than appears from the transcriptomic mapping rates. Meanwhile, 3' bias levels were higher than had been observed previously, but were very similar to those previously published from Nextera data (available on the Illumina website).

Figure 24A:
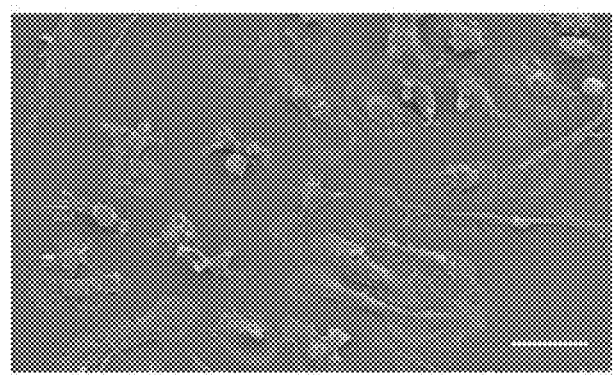
FIGS. 24A-24E are a series of graphs and illustrations depicting microfluidic enabled single-cell RNA-Seq of bone marrow derived dendritic cells (BMDCs) stimulated with pathogen components.

Expression-wise, the single cell measurements agreed closely when aggregated and compared with data from a cell population generated using a similar protocol. The correlations between in silico single-cell average RNA-Seq data and population measurements were high (R=~0.9, FIG. 24a). This represents an improvement over correlations observed for comparisons between two different library construction methods for replicates of the same bulk-population sample. (Levin, J. Z. et al. Comprehensive comparative analysis of strand-specific RNA sequencing methods. Nature Methods 7, 709-715 (2010)). This degree of correlation was robust across the expression spectrum. The correlations tended to plateau once around 30 cells had been included in other in silico single-cell average.

Figure 24B:
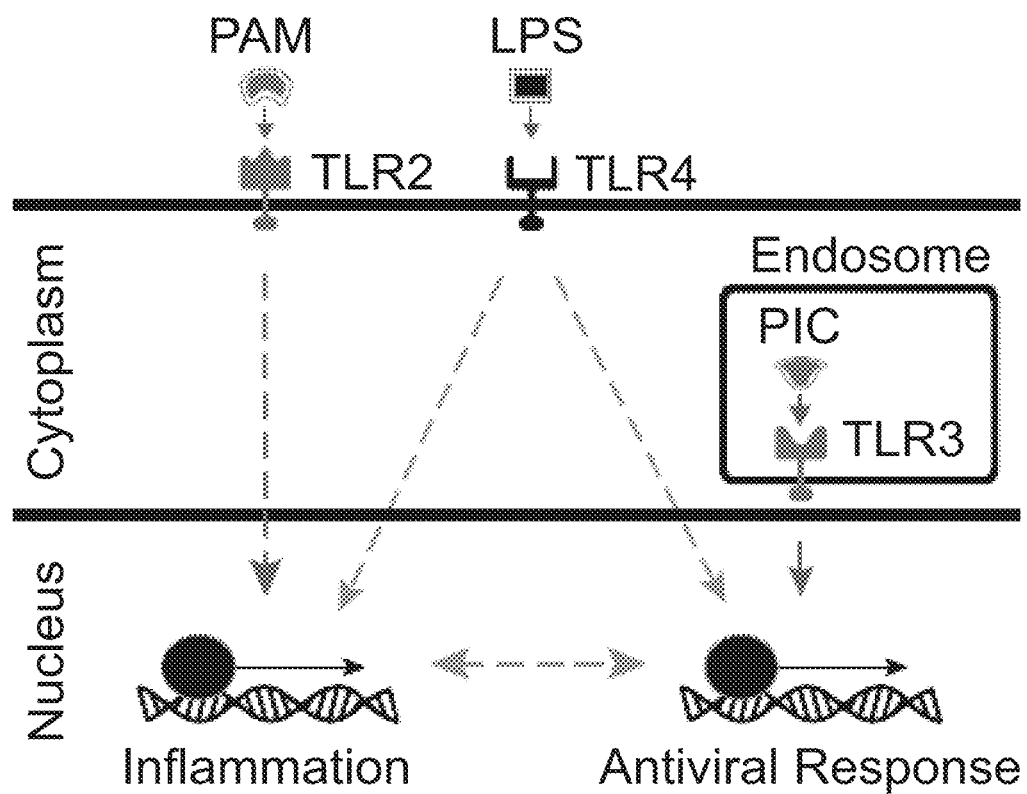
Figure 24C:
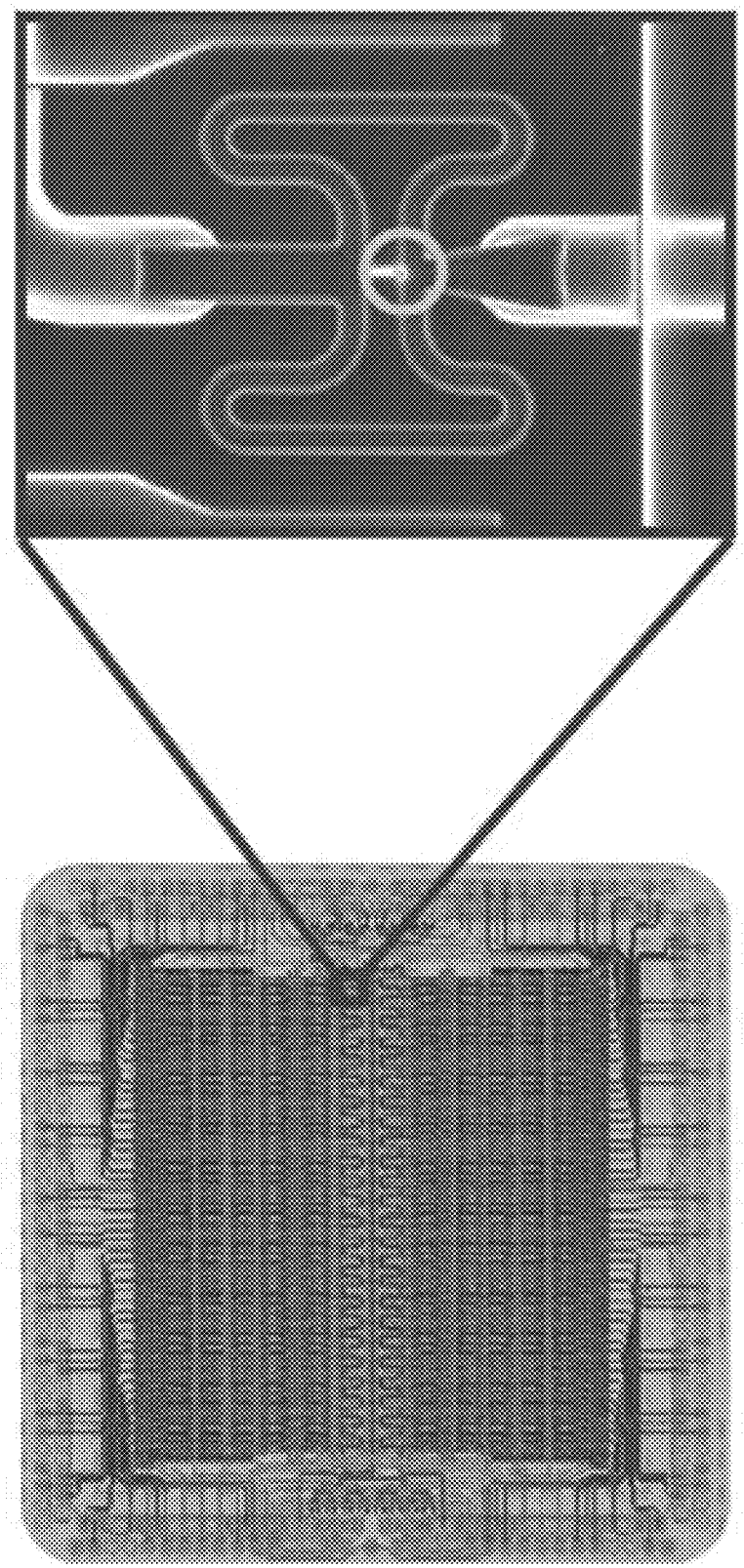

Genes were clustered based on their differential temporal responses to these three stimuli (FIG. 24b) within the population level samples. Population based measurements agreed closely with, and refined (described below), previously run microarray-based experiments (Chevrier, N. et al. Systematic Discovery of TLR Signaling Components Delineates Viral-Sensing Circuits. *Cell* 147, 853-867, doi: 10.1016/j.cell.2011.10.022 (2011)). In particular, the analysis recapitulated several previously-discovered clusters that were highly enriched for targets of NF-kB (inflammatory program. Clusters VI, VII), as well distinct clusters highly enriched for interferon responsive genes (Clusters I,II) (FIG. 24b). Broadly, while antiviral genes were typically "late-induced" at both the population and single cell levels, most inflammatory response genes were sharply peaked early (at 1-2 hrs). Still, there was a set of late-induced inflammatory genes (Cluster VI) that peaked late.

Example 7

Variation Between Cells During Immune Response

Refinement of Cell Circuits from Single Cell Data:

From this broad definition of population-level pathways, higher resolution structure was investigated by sub-clustering genes based on their expression values in single cells. (black lines, FIG. 24b). In concert with the cluster analyses, an unbiased principal components analysis (PCA) was also performed on all ~800 single cells in the timecourse dataset.

It was discovered that the high-resolution data allowed genes to be assigned to a refined set of circuits that could not be distinguished at the population level. For example, while all antiviral genes exhibited population-level induction at later timepoints after exposure to LPS and PIC, a cluster of 102 genes (Cluster ID) was observed that were distinguished not only based on their overall induction levels, but also from coherent expression within subsets of single cells (Supp. Figure). While genes in this module exhibit dramatic enrichment for antiviral and interferon response genes, genes in clusters 1A-1C do not exhibit similar functional patterns. Genes in cluster ID are also strongly distinguished by their contribution to the first principal component (PC1) in the PCA analysis. Thus, cluster ID was termed to represent the "core" antiviral response of BMDCs. Notably, the separation between core and non-core antiviral genes is not readily apparent from population level measurements and was not observed in either previous RNA-Seq (Amit, I. et al. Unbiased reconstruction of a mammalian transcriptional network mediating pathogen responses. Science 326, 257-263, doi:10.1126/science.1179050 (2009) or microarray (Chevrier, N. et al. Systematic Discovery of TLR Signaling Components Delineates Viral-Sensing Circuits. Cell 147, 853-867, doi:10.1016/j.cell.2011.10.022 (2011)) experiments.

Similarly, it was observed that the inflammatory program, broadly denoted by high projection scores of the second principal component (PC2), could be separated into multiple distinct circuits. Many canonical inflammatory markers (i.e., TNF, IL1A, CXCL2), exhibit "sharp peaked" responses to LPS (Takeuchi, O. & Akira, S. Pattern Recognition Receptors and Inflammation. *Cell* 140, 805-820, doi:10.1016/j.cell.2010.01.022 (2010), cluster 3c)—these genes are sharply induced early and are downregulated at later timepoints in the response. Other clusters shared between LPS and PAM (clusters 3b,d), in contrast, exhibit increased levels of induction throughout the timecourse. While these two clusters appear highly similar from population level measurements, cluster 3b genes are marked by strong projection scores for the third principal component (PC3) and are highly enriched for markers of dendritic cell maturation, in particular cell surface markers, receptors and transporters (CD83, CD86, CCR7) and cytokines (CCL17 and CCL22) which are essential for proper communication with and activation of T cells. These genes are highly and induced in the response to LPS, but only in a distinct subset of cells.

The refined single cell circuits allow for the identification of novel molecular regulators which may play key roles in the immune response. For example, while the "maturation" cluster (denoted by high projection scores for PC3) contains many well known markers of BMDC maturation, the remainder of the genes in the signature compromise a rich list of transcription factors, G protein coupled receptors, lincRNAs, and transmembrane proteins whose strong single-cell correlations with known maturity markers implicates their role in activating the adaptive immune system. Many of these genes are do not have characterized roles in BMDC maturation, or even in the regulation of immune response.

Others, such as the transcription factor IRF8 and the transmembrane protein TMEM39A, have been significantly associated with autoimmune disease via unknown molecular mechanisms. Similarly, the refinement of a "core" antiviral module highlights the potential role of previously uncharacterized regulators, including nuclear-dot associated proteins (ex. Sp100 and Sp140), chromatin regulators (ex. Phf11), putative transcriptional regulators (ex. Znfx1) and ubiquitin ligases (ex. Dtx31).

Figure 24D:
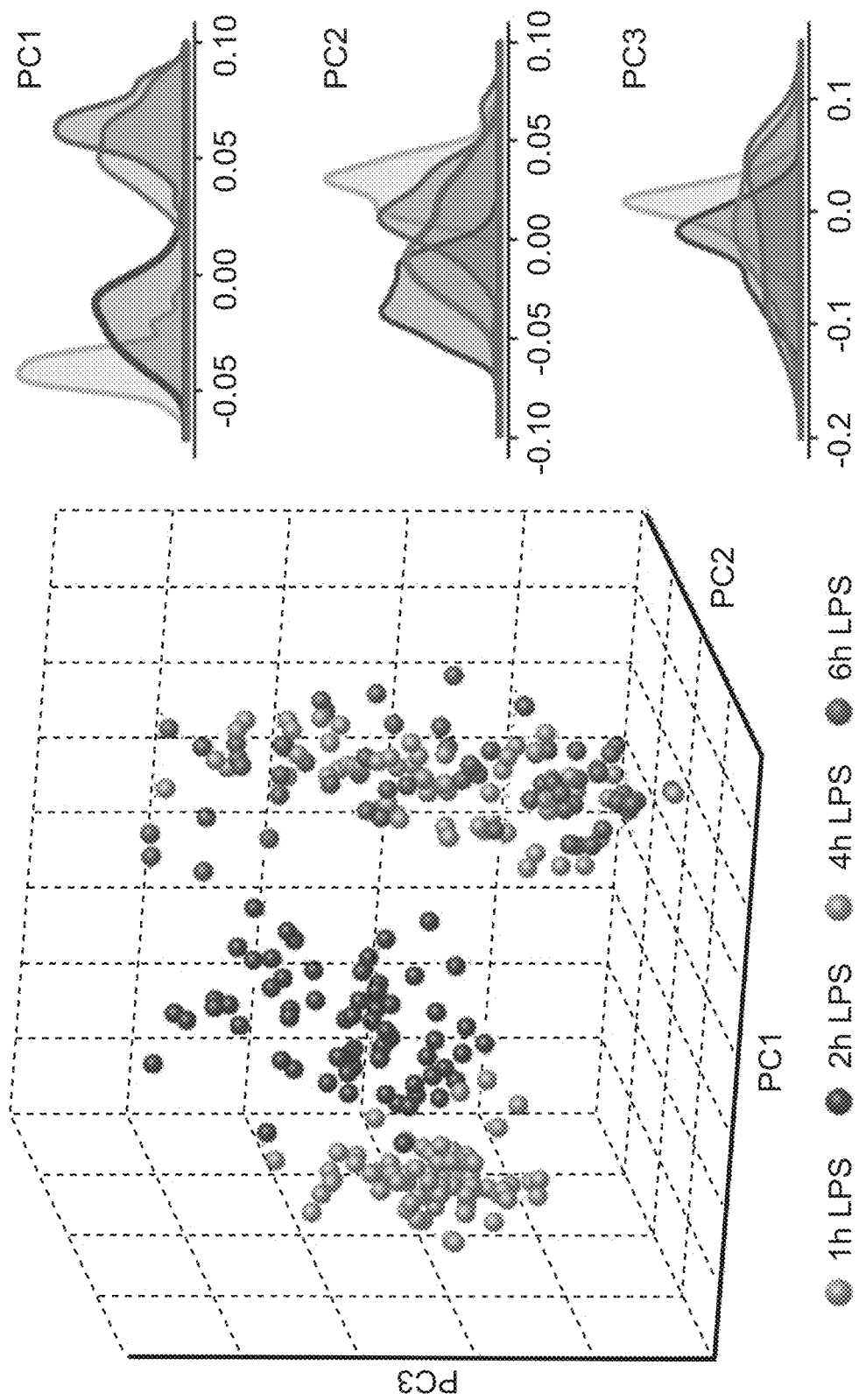
Figure 24E:
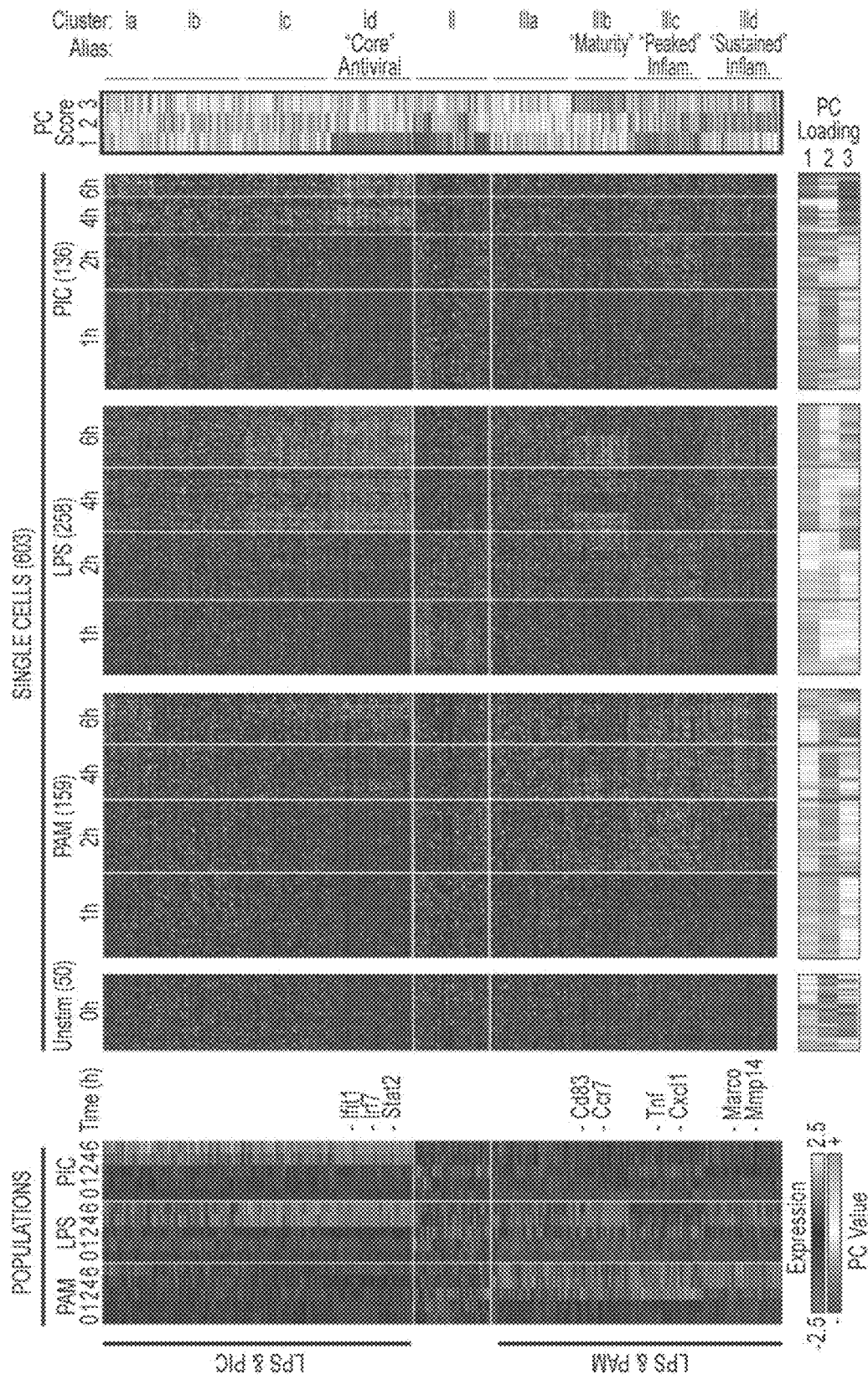
Figure 25A:
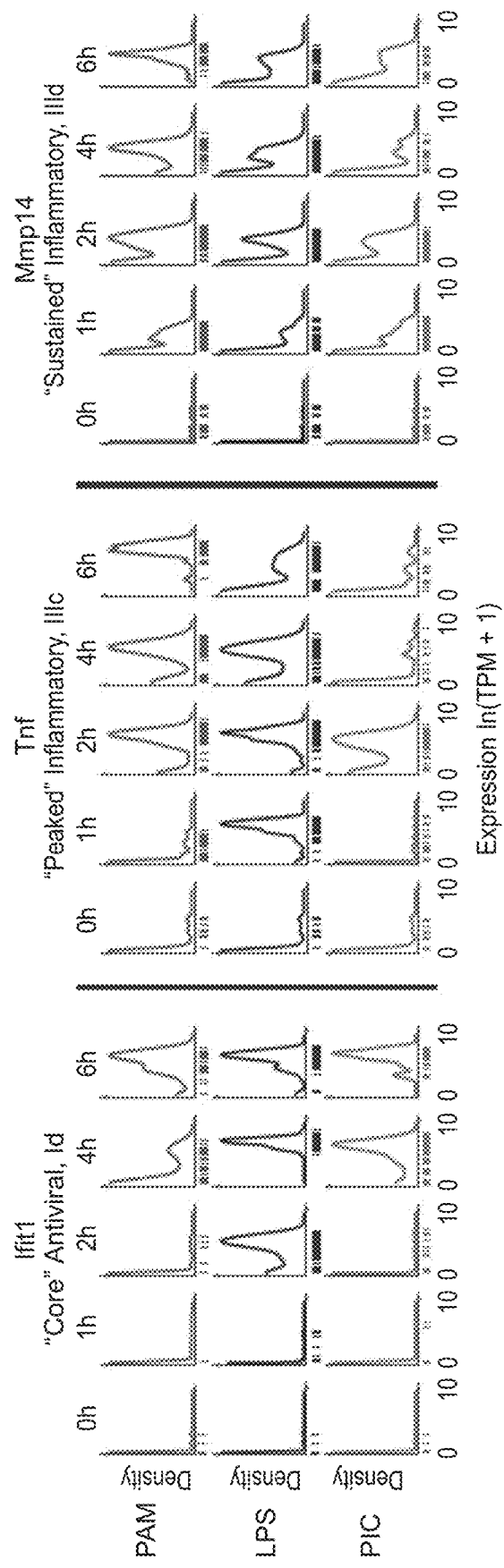
Figure 25C:
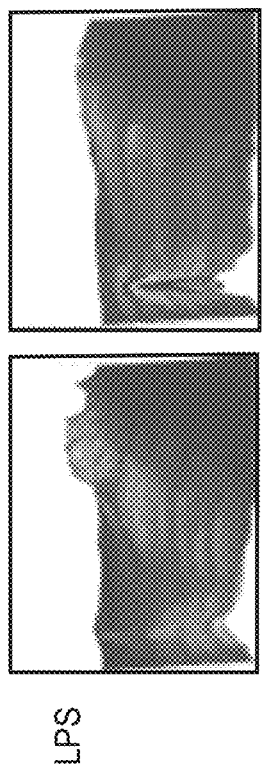
Figure 25C:
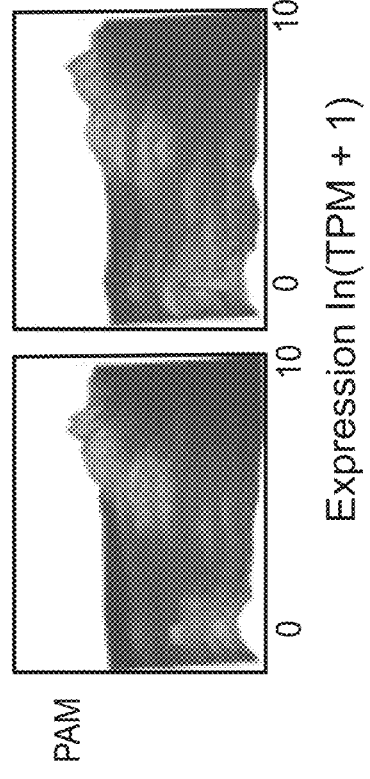
Figure 25B:
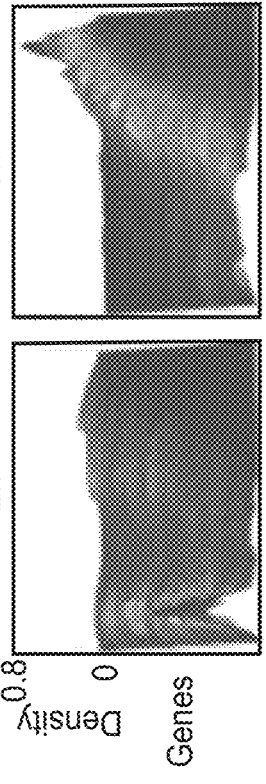
Figure 25B:
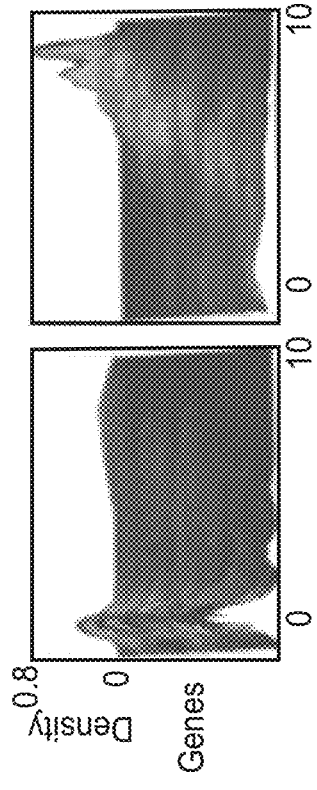

Temporal and Developmental Heterogeneity are Defined by a Continuous Spectrum:

The principal components analysis indicates that, rather than separating into multiple distinct subgroupings, the dendritic cells represent individual points on a continuous landscape of cellular variation. For example, while the first principal component broadly separates single cells based on their stimulation time point, there is significant spread between PC1 loadings for cells within any given dataset (FIG. 24d).

This is particularly true early in the response (1 and 2 hr), which is clearly separated from later timepoints as the cells begin to synchronize their core antiviral response four hours post-stimulation. In contrast to antiviral response, however, it is seen that the diversity in maturity state between single cells steadily increases during the duration of the LPS time course. While the identified circuit is only induced in a subset cells, the highly variable levels of induction result in a continuous range of intermediate states (FIG. 24f). These studies were unable to identify clearly defined, discrete subpopulations after performing separate PCA analyses on each of the three stimulation timecourses, or even on each individual timepoint, highlighting the continuous nature of single cell noise observed in the system. This is likely a reflection of the experimental system having been chosen upfront as a homogenous, post-mitotic, and synchronized population of immune cells.

Parameterization of Single Cell Data:

In the previous analysis of 18 individual BMDC transcriptomes, extensive bimodality was observed in individual gene expression levels between single cells, observing that most transcripts were not detected in every cell either by RNA-Seq or RNA-FISH. The scale of the current experiment, however, provides sufficient scale to begin to model and parameterize single cell data from a single condition.

Thus, the studies here attempted to fit a series of nested statistical models to each single cell distribution, initially focusing the efforts on the LPS response genes. While a small percentage (~5%) of transcripts were well described by a unimodal log-normal distribution (parameterized by the mean, mu, and the standard deviation, sigma), the remainder benefited statistically (likelihood ratio test, P<0.01) from the introduction of a third parameter (alpha) which defined the percentage of cells expressing the transcript at non-negligible levels (ln(TPM)>1). This explicit parameterization of single cell data as a bimodal distribution allows us to break single cell heterogeneity into two components: one level of variability is represented by the percentage of cells expressing a transcript (parameterized by alpha, as referred to herein, this is digital noise), a second layer reflects the spread in RNA levels amongst expressing cells (parameterized by sigma, which is referred to herein as analogue noise).

The vast majority (~80-90%, goodness of fit test, SM) of single cell distributions were well described by this three parameter, explicitly bimodal, distribution, implying that the new parameterization could be broadly applied to analyze changes in single cell noise systematically. Interestingly, the majority (70-80%) of transcripts that did not fit the three-parameter distribution at one LPS timepoint were well described by a mixture model of normal distributions and also failed the goodness-of-fit test at another timepoint, suggesting the existence of multiple regulated "bursting states" for these genes.

Quantitative Chromatin Levels Agree with Single Cell Noise Parameters:

While strong correlations between mRNA levels and chromatin states at have been well described (see e.g., Ram, O. et al. Combinatorial Patterning of Chromatin Regulators Uncovered by Genome-wide Location Analysis in Human Cells. *Cell* 147, 1628-1639 (2011); Garber, M. et al. A High-Throughput Chromatin Immunoprecipitation Approach Reveals Principles of Dynamic Gene Regulation in Mammals. *Molecular Cell* 47, 810-822, doi:10.1016/j.molcel.2012.07.030 (2012) the single cell data here allow for the reanalysis of this relationship at a new level. Population maps of histone marks, often assayed with ChIP-seq, exhibit a wide quantitative range. Since chromatin marks are either present or absent from a DNA molecule, it was reasoned that quantitative chromatin measurements of active marks at a promoter should correlate with the digital noise levels of a gene, i.e. the percentage of cells expressing the transcript, rather than the overall population expression level. Indeed, a strong relationship was observed between the alpha parameter of the single cell distributions for a gene and the population level of K27 present at the gene's promoter, even after controlling for population expression level. In stark contrast, no relationship was observed between the population level mRNA expression and quantitative chromatin levels after controlling for the percentage of cells expressing the transcript. These relationships were robust for the active chromatin mark K27ac as well as RNA PolII levels, but not for the H3K4me3, in line with previous observations that K27ac is more tightly correlated with active transcription.

Distinct Heterogeneity Profiles of Immune Response Circuits:

The parameterization of single cell distributions were applied to analyze changes in the single cell heterogeneity of immune response circuits across experimental conditions. This study started by examining the structure of the core antiviral program, which is typically classified as "late-induced" from population studies (Amit, I. et al. Unbiased reconstruction of a mammalian transcriptional network mediating pathogen responses. *Science* 326, 257-263, doi: 10.1126/science.1179050 (2009)) and identifying substantial bimodality during a snapshot of the response in previous work (Chevrier, N. et al. Systematic Discovery of TLR Signaling Components Delineates Viral-Sensing Circuits. Cell 147, 853-867, doi:10.1016/j.cell.2011.10.022 (2011)). The most significant single cell patterns in the antiviral response occurred between the two hour and four hour timepoints, as key antiviral genes shifted their expression patterns from bimodal to unimodal across single cells. This shift in digital noise, however, is accompanied by a significant reduction in analogue noise-again with the most dramatic shifts in all parameters occurring between two and four hours (median sigma shift=0.6 to 0.9, pvalue=$3.5 \times 10^{-5}$). Thus, single cells tightly synchronize their antiviral response during the observed timecourse, exhibited by robust and tightly regulated expression of core antiviral genes at later timepoints.

Genes participating in the inflammatory program tend to display starkly opposite temporal heterogeneity profiles compared to their antiviral counterparts. In particular, genes exhibiting sharp peaked responses (cluster IIIc)—including canonical anti-inflammatory cytokines such as IIIa and TNF-alpha were sharply induced at early timepoints, but are downregulated later in the response. The exact cause of this temporal dephasing is unknown, although cross-inhibitory feedback loops and RNA degradation factors may be responsible for creating a peaked response. Remarkably, it was observed that the dynamics of these bulk expression estimates are due almost entirely to changes in digital noise. While the percentage of cells expressing these transcripts exhibited significant change between all temporal transitions, parameters representing the distribution of expressing cells were statistically unchanged throughout the response-including at the unstimulated timepoint.

A distinct cluster of inflammatory genes (cluster IIId) are continually induced over the timecourse, exhibiting patterns of digital noise that are similar to the core antiviral cluster—again with the most significant shift occurring between two and four hours. In contrast to antiviral synchronization, however, no change was observed in the analogue noise of this circuit. Thus while, late-induced antiviral and inflammatory genes show similar temporal profiles at the population level in LPS, the two responses exhibit different heterogeneity profiles at the 4 h timepoint, with the former resembling a tightly regulated circuit while the latter exhibits a noisier induction. Taken together, these analyses highlight the vastly different temporal heterogeneity patterns of functionally distinct LPS response modules, and exemplify the ability of single cell RNA-seq to distinguish both tightly regulated and noisy circuits.

Changes in Single Cell Noise Across Stimuli:

It has been previously noted that while PIC and PAM are specific antagonists of the antiviral and inflammatory pathways respectively, LPS is capable of activating both defense programs in BMDC populations (Takeuchi, O. & Akira, S. Pattern Recognition Receptors and Inflammation. *Cell* 140, 805-820, doi:10.1016/j.cell.2010.01.022 (2010).). Given the non-specific nature of TLR4 signaling, it was hypothesized that immune response circuits may behave differently in response to a more directed stimulus.

For example, it was hypothesized that exposure to PIC may reduce single cell heterogeneity in the antiviral cluster. It was observed, however, that antiviral temporal heterogeneity patterns were slightly delayed in the PIC timecourse in comparison to LPS. In particular, the core genes transitioned from bimodal to unimodal expression between the four and six hour timepoints, and the delay in antiviral synchronization indicated that PIC in fact acted as a weaker stimulus. These observations are in line with previous reports.

The temporal variability patterns of inflammatory circuits, however, differed greatly after exposure to PAM. As in the LPS response, sharp peaked response genes exhibited a sharp induction in the percentage of expressing cells at early timepoints. These genes, however, tend to "plateau" instead of "peak" at the two hour timepoint, and failed to desynchronize at later timepoints (no statistically significant change in either digital or analogue noise). Likewise, it was found that inflammatory circuits began to synchronize (significant reduction in analogue noise between T=2 hr and 4 h, p-value=0.0014), their response at later timepoints, similar to the antiviral core circuit during the LPS response. The changing temporal noise patterns of these circuits after exposure to distinct stimuli strongly argues that single cell heterogeneity is not purely a consequence of unconstrained transcriptional stochaticity, but is instead a controlled phenomenon that is regulated during immune response. The next studies thus further investigated the role of both intracellular and intercellular determinants in driving single cell variability.

Example 8

Environmental Determinants of Temporal Noise

While variable levels of internal components can drive differences in response phenotype (Taniguchi, Y. et al. Quantifying *E. coli* Proteome and Transcriptome with Single-Molecule Sensitivity in Single Cells. Science 329, 533-538, doi:10.1126/science.1188308 (2010); Tay, S. et al. Single-cell NF-κB dynamics reveal digital activation and analogue information processing. Nature 466, 267-271, doi: papers2://publication/doi/10.1038/nature09145 (2010); Raj, A. & Van Oudenaarden, A. Single-Molecule Approaches to Stochastic Gene Expression. Annual Review of Biophysics 38, 255-270, doi:10.1146/annurev.biophys.37.032807.125928 (2009); Cohen, A. A. et al. Dynamic Proteomics of Individual Cancer Cells in Response to a Drug. Science 322, 1511-1516, doi:10.1126/science.11160165 (2008); Altschuler, S. J. & Wu, L. F. Cellular Heterogeneity: Do Differences Make a Difference? Cell 141, 559-563, doi:10.1016/j.cell.2010.04.033 (2010); Warren, L., Bryder, D., Weissman, I. L. & Quake, S. R. Transcription factor profiling in individual hematopoietic progenitors by digital RT-PCR. Proceedings of the National Academy of Sciences of the United States of America 103, 17807-17812, doi:10.1073/pnas.0608512103 (2006); Paszek, P. et al. Population robustness arising from cellular heterogeneity. Proceedings of the National Academy of Sciences of the United States of America 107, 11644-11649, doi:10.1073/pnas.0913798107 (2010); Slack, M. D., Martinez, E. D., Wu, L. F. & Altschuler, S. J. Characterizing heterogeneous cellular responses to perturbations. Proceedings of the National Academy of Sciences 105, 19306-19311, doi: 10.1073/pnas.0807038105 (2008); Niepel, M., Spencer, S. L. & Sorger, P. K. Non-genetic cell-to-cell variability and the consequences for pharmacology. Curr. Opin. Chem. Biol. 13, 556-561, doi:10.1016/j.cbpa.2009.09.015 (2009); Sharma, S. V. et al. A chromatin-mediated reversible drug-tolerant state in cancer cell subpopulations. Cell 141, 69-80, doi:10.1016/j.cell.2010.02.027 (2010); Gascoigne, K. E. & Taylor, S. S. Cancer cells display profound intra- and interline variation following prolonged exposure to antimitotic drugs. Cancer cell 14, 111-122, doi:10.1016/j.ccr.2008.07.002 (2008)), local differences in the cellular microenvironment can afford an external, confounding source of heterogeneity (Fan, R. et al. Integrated barcode chips for rapid, multiplexed analysis of proteins in microliter quantities of blood. Nature Biotechnology 26, 1373-1378, doi:10.1038/nbt.1507 (2008); Gómez-Sjöberg, R., Leyrat, A., Pirone, D., Chen, C. & Quake, S. Versatile, fully automated, microfluidic cell culture system. Analytical Chemistry 79, 8557-8563 (2007); Huang, S. Non-genetic heterogeneity of cells in development: more than just noise. Development 136, 3853-3862, doi:papers2://publication/doi/10.1242/dev.035139 (2009); Kalisky, T., Blainey, P. & Quake, S. R. Genomic Analysis at the Single-Cell Level. Annual review of genetics 45, 431-445, doi:papers2://publication/doi/10.1146/annurev-genet-102209-163607 (2011); Lecault, V. et al. High-throughput analysis of single hematopoietic stem cell proliferation in microfluidic cell culture arrays. Nature Methods 8, 581-586, doi:papers2://publication/doi/10.1038/nmeth.1614 (2011); Loewer, A. & Lahav, G. We are all individuals: causes and consequences of non-genetic heterogeneity in mammalian cells. Current opinion in genetics & amp; development 21, 753-758, doi:10.1016/j.gde.2011.09.010 (2011); Millet, L. J., Stewart, M. E., Sweedler, J. V., Nuzzo, R. G. & Gillette, M. U. Microfluidic devices for culturing primary mammalian neurons at low densities. Lab on a Chip 7, 987, doi:10.1039/b705266a (2007); Raser, J. M. Control of Stochasticity in Eukaryotic Gene Expression. Science (New York, N.Y.) 304, 1811-1814, doi:10.1126/science.1098641 (2004)). The response of each BMDC is dominated by the expression of mRNAs for cytokines and chemokines, that can, in turn, activate additional intracellular signaling pathways. Thus, heterogeneous intercellular signaling, coupled with slow diffusion, could easily give rise to a rich local diversity in environmental conditions, forcing each cell to compute its response under different constraints.

Uniform Interferon Stimulus Removes Bimodality from Antiviral Response:

It was previously hypothesized (Shalek, A. K. et al. Nanowire-mediated delivery enables functional interrogation of primary immune cells: application to the analysis of chronic lymphocytic leukemia. Nano Lett. 12(12):6498-504, doi: 10.1021/n13042917 (2012)) that variability in a secondary wave of interferon (IFN) signaling was responsible for the widespread bimodality that was observed in the antiviral response at the 4 h timepoint. To test this further, BMDCs were stimulated directly with IFN-β so as to provide all of the cells with equal access to this antiviral feedback. At 2 hr after stimulation (equivalent to a 4 h LPS stimulus since IFN-β peaks under LPS at 2 hr (Amit, I. et al. Unbiased reconstruction of a mammalian transcriptional network mediating pathogen responses. *Science* 326, 257-263, doi:10.1126/science.1179050 (2009))), a dramatic shift in the digital noise of the antiviral cluster was observed, with key genes shifting from a bimodal expression distribution in LPS to a unimodal one under IFN-β. This finding suggests that early heterogeneity in the expression of antiviral genes might not arise from intracellular timing differences (Nachman et al., Dissecting timing variability in yeast meiosis, Cell 131, 544-556 (2007)) but rather from differences in IFN-β exposure. This, coupled with the early rise in Ifnb1 mRNA expression seen from 0 to 2 h under LPS stimulation in a select set of cells, suggests that a subset of cells may, in fact, be responsible for generating a primary wave of interferon signaling, which eventually synchronizes the antiviral response as the IFN-β enshrouds the entire population. In such a case, it would be expected the cells that produced IFN-β and their nearest neighbors to exhibit early antiviral induction due to autocrine and paracrine signaling.

A Rare Population of Cells Precociously Expresses Late-Induced Antiviral Genes at Early Timepoints:

In support of this hypothesis, three cells that exhibited precocious expression of antiviral response genes after only 1 hr of LPS stimulation were intriguingly discovered. These cells could be clearly distinguished by robust expression the general antiviral signature, including Ifit1, as well as by their projection across the second principle component. To verify the existence of this population, RNA-FISH was performed, co-staining cells for expression of Ifit1 and Ifnb1. Thus, this population exists, but it is a rare population.

Ablation of Paracrine Signaling Dramatically Alters Cellular Heterogeneity:

While highly suggestive, the discovery of the "early responder" subpopulation does not definitively show that intracellular signaling is required for antiviral synchronization in the population. Validating this hypothesis requires methods for isolating cells and culturing them individually. In the absence of paracrine signaling, the former hypothesis would suggest a shift in the digital antiviral noise.

To accomplish this, unstimulated BMDCs were loaded and isolated onto the C1 IFC, and proceeded to stimulate each cell with LPS individually inside the sealed microfluidic chamber. To closely mirror the standard stimulation protocols, the C1 system was programmed to deliver LPS-laced media via one of the IFC's washing ports and then incubated the cells at 37° C. for four hours prior to normal imaging, lysis, and cDNA synthesis and amplification. Importantly, the cell density for this on-chip stimulation (1 cell per 4.5 nL) tightly matched the normal, in tube, stimulations (1 cell per 5 nL), enabling direct comparison of this experiment with the existing LPS data. As originally hypothesized, the absence of paracrine signaling strongly desynchronized the antiviral response. A dramatic increase in digital noise was observed as antiviral gene distributions shifted from unimodal (bulk LPS stimulation) to bimodal (on-chip stimulation). Notably, a subset of cells—likely analogous to the identified early responders, did exhibit robust activation of the core antiviral response. Similarly, the ablation of paracrine signaling severely restricted the maturation process for all BMDCs, ablating expression of maturation markers in all cells. This is likely due to the abrogation of TNF-mediated signaling, which is known to drive maturation in BMDCs. Still, not all induced genes behaved different in the absence of paracrine signaling: many late-induced inflammatory genes were unaffected, demonstrating that isolated cells were capable of undergoing a natural response to LPS in a microfluidic chamber.

To test this, paracrine signaling was ablated by isolated and then stimulated individual BMDCs for 4 hr inside of the C1 IFC. To match the normal activating conditions, the C1 system was programmed to deliver LPS-laced media via one of the IFC's washing ports and then incubated the cells at 37° C. for the duration of the stimulation, before imaging and lysing as normal. Importantly, the cell density for the on chip stimulation (1 cell per 4.5 nL) tightly matched the normal, in tube, stimulations (1 cell per 5 nL), enabling direct comparison of the two. As originally hypothesized, the absence of paracrine signaling strongly desynchronized the antiviral response. A dramatic increase in digital noise was observed as limited coherent induction of key antiviral markers in a small subset of cells shifted the antiviral gene distributions from unimodal to bimodal. Importantly, not all induced genes behaved different in the absence of paracrine signaling: many late-induced inflammatory genes were unaffected, demonstrating that isolated cells were capable of undergoing a natural response to LPS in a microfluidic chamber.

While the presence of paracrine signaling is necessary for antiviral synchronization, intracellular communication has the opposite effect on other immune response circuits. Surprisingly, ablation of paracrine signaling dramatically reduced both digital and analogue noise after four hours of LPS stimulation. Canonical inflammatory markers such as TNF, I11a, and INHBA all shifted from bimodal to unimodal distributions upon paracrine ablation—resembling their uniform expression at the two-hour timepoint. Thus, the results strongly point to paracrine signaling as an upstream determinant of this desynchronization, and highlight the extensive—and, at times, opposing—roles that intercellular communication performs in driving heterogeneity in both the antiviral and inflammatory pathways.

Interferon Feedback Increases Inflammatory Heterogeneity:

Since the on-chip isolation experiment bluntly abrogates all paracrine signaling, it cannot discern the individual, or combination of, paracrine signals which are responsible for the results observed above. To more specifically address the roles of individual signaling pathways, this study turned to profiling knockout mice deficient for specific receptor molecules. To better understand the upstream source of inflammatory noise, this study began by profiling BMDCs from mice deficient for TNF receptor. Consistent with previous findings and hypotheses, TNFR−/− BMDCs exhibited no induction of maturation markers. However, many sharply peaked response genes exhibited highly similar distributions in both the wild type and TNFR−/− BMDCs at the four-hour timepoint. Similar results were seen when profiling BMDCs deficient for IL1 receptor; BMDCs failed to mature, but coherent changes were not observed amongst sharp peaked response genes.

BMDCs from interferon receptor knock-out (Ifnar1−/−) mice were next profiled. As expected, and in accordance with previous findings (Shalek, A. K. et al. Nanowire-mediated delivery enables functional interrogation of primary immune cells: application to the analysis of chronic lymphocytic leukemia. Nano Lett. 12(12):6498-504, doi: 10.1021/nl3042917 (2012)), inhibiting interferon signaling fully blocked expression of antiviral genes. The ablation of the antiviral pathway was essentially complete, with no cells exhibiting any antiviral response, implying that even the "early responders" may require autocrine signaling of IfnB in order to activate their antiviral response. However, once again inflammatory "sharp peaked" genes displayed strikingly reduced levels of both digital and analogue variability in these knockout cells. Ifnar1−/− clustered closely with cells from the on-chip stimulation, and shifts in noise compared to LPS were significantly correlated between both experiments. Given the known role of interferon signaling in inducing the antiviral pathway, these finding cohesively point to extensive antiviral cross-inhibition as a primary upstream mechanism of inflammatory-response de-synchronization.

Example 9

Removal of "Cluster-Disrupted" Cells

In the Examples above, it was identified that BMDCs fell into two distinct subpopulations, corresponding to distinct maturity states. BMDC maturation is a developmental process in which BMDCs switch from antigen-capturing to antigen-presenting cells in order to prime the adaptive immune system (see e.g., Jiang, A. et al. Disruption of E-Cadherin-Mediated Adhesion Induces a Functionally Distinct Pathway of Dendritic Cell Maturation. Immunity 27, 610-624, doi:10.1016/j.immuni.2007.08.015 (2007)). Maturation can occur either in response to pathogen-derived ligands, such as LPS, or as a result of disrupting clusters of BMDCs in culture (Ibid.), both of which lead to up-regulation of specific cell-surface markers. Pathogen-dependent maturation occurs over a prolonged time after pathogen exposure and cells fall along a developmental continuum in the dataset (FIGS. 24d,e).

However, pathogen-independent maturation, also referred to as 'cluster disruption', is a known artifact of the culturing process, occurs prior to stimulation, and represents a distinct cellular state. Thus, to measure changes in gene expression variation from a 'homogenous' population appropriately, the studies provided herein sought to remove all cluster-disrupted cells from all further analyses.

In the previous Examples that performed PCA on 18 cells, it was found that the first principal component (PC1) discriminated these two cellular populations. Many genes with high PC1 loadings were known markers of BMDC maturation (Jiang Immunity 2007), such as the cell-surface receptors Ccr7, Cd83, and Cd86. These genes are up-regulated in both the pathogen-dependent and pathogen-independent maturation pathways, and thus are all induced at a population-level in the LPS time course (Amit, I. et al. Unbiased reconstruction of a mammalian transcriptional network mediating pathogen responses. Science 326, 257-263, doi: 10.1126/science.1179050 (2009); Shalek, Nature 2013). Among the PC1 genes, Lyz1 had the strongest loading, and was the best discriminator of cluster-disrupted cells. It was (ln(TPM+1)>9) in the 15 maturing (non-cluster disrupted) cells, but was completely absent (TPM=0) in the three cluster-disrupted cells. Furthermore, Lyz1 was not differentially regulated in two cells undergoing pathogen-dependent maturation, and this did not appreciably change in its single-cell or population-averaged levels throughout the LPS time course. Similarly, a complementary marker (Serpinb6b) was identified, and this marker was found to be highly expressed only in cluster-disrupted cells, but absent from all others, yet did not appreciably change its overall expression during the LPS time course. Thus, these markers are unlikely to be differentially regulated in cells undergoing pathogen-dependent maturation, and it was reasoned that the expression patterns of these marker transcripts provided a method for identifying cluster disrupted cells. To independently confirm the two markers, further qRTPCR analysis was performed on cells pre-sorted for CD83 (maturation marker) expression before stimulation and then stimulated the two sorted sub-populations (CD83+, CD83−) with LPS for 4 h. The level of the two mRNAs in the two subpopulations was measured both before and after stimulation. These studies successfully validated that these markers cleanly distinguish between the two subpopulations over the pathogen response.

Primers Used:

| Gene | Primer | Sequence |
|---|---|---|
| Lyz1_1 | Lyz1_1_F: | GAGCATGGGTGGCATGG (SEQ ID NO: 279) |
|  | Lyz1_1_R: | CAGAATGGGCTGCAGTAGAA (SEQ ID NO: 280) |

-continued

| Gene | Primer | Sequence |
|---|---|---|
| Lyz1_2 | Lyz1_2_F: | GACATCACTGCAGCCATACAA (SEQ ID NO: 281) |
| | Lyz1_2_R: | CCATGCCACCCATGCTC (SEQ ID NO: 282) |
| SerpinB6b_1 | SerpinB6b_1_F: | AGTTGCTATCTTCGGGTTCAG (SEQ ID NO: 283) |
| | SerpinB6b_1_R: | ACCACATCCTTGGTGACATT (SEQ ID NO: 284) |
| SerpinB6b_2 | SerpinB6b_2_F: | CAAACACTCCACTGGTCCTT (SEQ ID NO: 285) |
| | SerpinB6b_2_R: | AGGTTTCACCACATCCTTGG (SEQ ID NO: 286) |
| Gapdh | Gapdh_L: | GGCAAATTCAACGGCACAGT (SEQ ID NO: 287) |
| | Gapdh_R: | AGATGGTGATGGGCTTCCC (SEQ ID NO: 288) |

Accordingly, to stringently remove all potentially cluster-disrupted cells, all libraries where ln(TPM+1)<6 for Lyz1 or ln(TPM+1)>4 for Serpinb6b were excluded from further analyses. This was done for each experiment without exception.

To make sure that cluster disruption was not linked to early activation of the "core" antiviral module, it was confirmed that there was no correlation between the expression of cluster disruption markers and the activation of the "core" antiviral module for both the 1 h LPS stimulation and the 4 h LPS "on-chip" stimulation experiments.

The invention is further described by the following numbered paragraphs:

1. A method of modulating one or more dendritic cell responses, the method comprising contacting a dendritic cell or a population of dendritic cells with a modulating agent in an amount sufficient to modify the one or more dendritic cell responses as compared to one or more responses of the dendritic cell or population of dendritic cells in the absence of the modulating agent.

2. The method of paragraph 1, wherein the modulating agent is an agent that modulates the expression, activity and/or function of one or more target genes or one or more products of one or more target genes that regulate one or more genes selected from those listed in Tables 1-5A.

3. The method of paragraph 2, wherein a desired gene or combination of target genes is selected and identified as a positive regulator of one or more dendritic cell responses or a negative regulator of one or more dendritic cell responses.

4. The method of paragraph 3, wherein the modulating agent is in an amount sufficient to modulate one or more dendritic cell response(s) selected from the group consisting of modulating one or more genes that regulate dendritic cell maturation; modulating one or more genes that regulate an immune response of a dendritic cell; modulating one or more genes that regulate an antiviral immune response of a dendritic cell; and modulating one or more genes that regulate an inflammatory immune response of a dendritic cell.

5. The method according to any one of paragraphs 1 to 4, wherein the modulating agent is an antibody, a soluble polypeptide, a polypeptide agent, a peptide agent, a nucleic acid agent, a nucleic acid ligand, or a small molecule agent.

6. The method of paragraph 5, wherein the agent is an antibody.

7. The method of paragraph 6, wherein the antibody is a monoclonal antibody.

8. The method of paragraph 6, wherein the antibody is a chimeric, humanized or fully human monoclonal antibody.

9. The method according to any one of paragraphs 1 to 8, wherein the modulating agent is one or more agents selected from a kinase, a transmembrane receptor, a chemical drug, a biologic drug, an agent that modulates a kinase, an agent that modulates a transmembrane receptor, an agent that modulates a chemical drug, and an agent that modulates a biologic drug.

10. A method of identifying a signature gene, a gene signature or other genetic element associated with a dendritic cell response comprising:
    a) contacting a dendritic cell with an inhibitor of the dendritic cell response or an agent that enhances the dendritic cell response; and
    b) identifying a signature gene, a gene signature or other genetic element whose expression is modulated by step (a).

11. The method of paragraph 10, further comprising
    c) perturbing expression of the signature gene, gene signature or genetic element identified in step (b) in a dendritic cell that has been contacted with an inhibitor of the dendritic cell response or an agent that enhances the dendritic cell response; and
    d) identifying a target gene whose expression is modulated by step (c).

12. The method of paragraph 10 or paragraph 11, wherein the inhibitor of the dendritic cell response is an agent that inhibits the expression, activity and/or function of a target gene or one or more products of one or more target genes that regulates one or more genes selected from those listed in Tables 1-5A.

13. The method of paragraph 10 or paragraph 11, wherein the agent that enhances the dendritic cell response is an agent that enhances the expression, activity and/or function of a target gene or one or more products of one or more target genes that regulates one or more genes selected from those listed in Tables 1-5A.

14. The method of paragraph 12 or paragraph 13, wherein the agent is an antibody, a soluble polypeptide, a polypeptide antagonist, a peptide antagonist, a nucleic acid antagonist, a nucleic acid ligand, or a small molecule antagonist.

15. A method of diagnosing an immune response in a subject, comprising detecting a level of expression, activity and/or function of one or more signature genes or one or more products of one or more signature genes selected from those listed in Tables 1, 1A, 2, 2A, 3, 3A, 4, 4A, 5 and 5A and comparing the detected level to a control of level of signature gene or gene product expression, activity and/or function, wherein a difference between the detected level and the control level indicates that the presence of an immune response in the subject.

16. The method of paragraph 15, wherein the immune response is an autoimmune response.

17. The method of paragraph 15, wherein the immune response is an inflammatory response.

18. A method of monitoring an immune response in a subject, comprising detecting a first level of expression, activity and/or function of one or more signature genes or one or more products of one or more signature genes selected from those listed in Tables 1, 1A, 2, 2A, 3, 3A, 4, 4A, 5 and 5A at a first time point, detecting a second level of expression, activity and/or function of the one or more signature genes or one or more products of one or more signature genes selected from those listed in Tables 1, 1A, 2, 2A, 3, 3A, 4, 4A, 5 and 5A at a second time point, and comparing the first detected level of expression, activity and/or function with the second detected level of expression, activity and/or function, wherein a change in the first and second detected levels indicates a change in the immune response in the subject.

19. The method of paragraph 18, wherein the immune response is an autoimmune response.

20. The method of paragraph 18, wherein the immune response is an inflammatory response.

21. A method of diagnosing an aberrant dendritic cell response in a subject, comprising detecting a level of expression, activity and/or function of one or more signature genes or one or more products of one or more signature genes selected from those listed in Tables 1, 1A, 2, 2A, 3, 3A, 4, 4A, 5 and 5A and comparing the detected level to a control of level of signature gene or gene product expression, activity and/or function, wherein a difference between the detected level and the control level indicates that the presence of an aberrant dendritic cell response in the subject.

22. The method of paragraph 21, wherein the aberrant dendritic cell response is an autoimmune response.

23. The method of paragraph 21, wherein the immune response is an inflammatory response.

24. A method of monitoring an aberrant dendritic cell response in a subject, comprising detecting a first level of expression, activity and/or function of one or more signature genes or one or more products of one or more signature genes selected from those listed in Tables 1, 1A, 2, 2A, 3, 3A, 4, 4A, 5 and 5A at a first time point, detecting a second level of expression, activity and/or function of the one or more signature genes or one or more products of one or more signature genes selected from those listed in Tables 1, 1A, 2, 2A, 3, 3A, 4, 4A, 5 and 5A at a second time point, and comparing the first detected level of expression, activity and/or function with the second detected level of expression, activity and/or function, wherein a change in the first and second detected levels indicates a change in the dendritic cell response in the subject.

25. The method of paragraph 24, wherein the aberrant dendritic cell response is an autoimmune response.

26. The method of paragraph 24, wherein the aberrant dendritic cell response is an inflammatory response.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of detecting single dendritic cells expressing a maturation gene signature in a subject, comprising:
  detecting increased expression of TMEM39A, or TMEM39A and one or more signature genes or one or more products of one or more signature genes selected from the group consisting of AKNA, APOL7C, APPL1, ARL5C, BATF, BC035044, BCL2L1, BIRC3, BLNK, CCL22, CCR7, CD72, CD80, CD83, CD86, CDKN1A, CHAC2, CRLF3, CSF1, DENND5A, EBI3, EIF2C3, ETS2, ETV3, EXOC3L4, FAM129A, FAM177A1, GPR85, H2-Q7, HSD17B11, IL12B, IL23A, IL4I1, IRF8, ITGA4, KTELC1, LACC1, MKIAA0769, MMP25, NFKBIB, NUDT17, OSGIN2, PALM2, PDZK1IP1, PGAP2, PLAT, PPP1CB, PVR, PVRL2, RAB8B, REL, RHOB, RND3, SAMSN1, SEMA6D, SERPINB9, SRGN, ST3GAL1, STAT3, STAT5A, SWAP70, TBC1D1, TIMP1, TNIP3 and VCAM1 in single dendritic cells of a population of dendritic cells obtained from the subject using single-cell RNA-seq, RNA-fluorescence in situ hybridization (FISH), single-cell quantitative reverse-transcription polymerase chain reaction, fluorescence-activated cell-sorting (FACS), Immunofluorescence (IF), or a combination thereof, wherein the expression is compared to the average expression of the single cells of the population of dendritic cells.

2. The method of claim 1, wherein TMEM39A and one or more signature genes or one or more products of one or more signature genes selected from the group consisting of IRF8, SERPINB9, CCR7, CD83, CD86, and CCL22 are detected.

3. The method of claim 1, wherein TMEM39A and IRF8 are detected.

4. The method of claim 1, wherein TMEM39A and SERPINB9 are detected.

5. The method of claim 1, wherein the subject is suffering from or is at risk for an autoimmune response.

6. A method for identifying an agent capable of modulating a maturation gene signature in a population of dendritic cells comprising:
   a) applying a candidate agent to the population of dendritic cells; and
   b) detecting single dendritic cells expressing a maturation gene signature according to claim 1, thereby identifying the agent.

* * * * *

UNITED STATES PATENT AND TRADEMARK OFFICE
CERTIFICATE OF CORRECTION

PATENT NO. : 10,870,885 B2  
APPLICATION NO. : 14/846219  
DATED : December 22, 2020  
INVENTOR(S) : Aviv Regev et al.

Page 1 of 5

It is certified that error appears in the above-identified patent and that said Letters Patent is hereby corrected as shown below:

In the Specification

In Column 8, Line 28, delete "Cxc11" and insert -- Cxcl1 --.

In Column 10, Line 5, delete "10.000" and insert -- 10,000 --.

In Column 10, Line 21, delete "(Cc13, Cc14," and insert -- (Ccl3, Ccl4, --.

In Column 10, Line 22, delete "Ccr12)," and insert -- Ccrl2), --.

In Column 10, Line 22, delete "(Cxc12)," and insert -- (Cxcl2), --.

In Column 10, Line 31, delete "(Hashimshony." and insert -- (Hashimshony, --.

In Column 10, Line 52, delete "barcodes (SEQ ID NOs: 289-369)," and insert -- barcodes, --.

In Column 11, Line 32, delete "I11b," and insert -- Il1b --.

In Column 11, Line 38, delete "Cxc110" and insert -- Cxcl10 --.

In Column 11, Line 40, delete "Cc122" and insert -- Ccl22 --.

In Column 11, Line 43, delete "Cxc11" and insert -- Cxcl1 --.

In Column 12, Line 9, delete "Cxc110" and insert -- Cxcl10 --.

In Column 12, Line 35, delete "Stat1" and insert -- Stat1, --.

In Column 13, Line 10, delete "Cxc11" and insert -- Cxcl1 --.

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,870,885 B2

In Column 13, Line 10, delete "Cxc110" and insert -- Cxcl10 --.

In Column 13, Line 12, delete "Cxc110" and insert -- Cxcl10 --.

In Column 13, Line 12, delete "Cxc11," and insert -- Cxcl1, --.

In Column 13, Line 22, delete "TLR2." and insert -- TLR2, --.

In Column 14, Line 18, delete "a" and insert -- α --.

In Column 14, Line 19, delete "26f." and insert -- 26f, --.

In Column 14, Line 20, delete "26c," and insert -- 26e, --.

In Column 14, Line 22, delete "(α:" and insert -- (α; --.

In Column 15, Line 4, delete "bar" and insert -- bar: --.

In Column 15, Line 63, delete "specifically." and insert -- specifically, --.

In Columns 22-23 (Table 6), Line 12, delete "RBS2" and insert -- RBMS2 --.

In Columns 22-23 (Table 6), Line 13, delete "GRAMDIB" and insert -- GRAMD1B --.

In Columns 22-23 (Table 6), Line 18, delete "FILIPIL" and insert -- FILIP1L --.

In Columns 22-23 (Table 6), Line 28, delete "TMC03" and insert -- TMCO3 --.

In Columns 23-24 (Table 6-continued), Line 7, delete "ZFP80" and insert -- ZFP800 --.

In Columns 23-24 (Table 6-continued), Line 9, delete "PALM3" and insert -- PALM2 --.

In Columns 23-24 (Table 6-continued), Line 13, delete "BIRDC3" and insert -- BIRC3 --.

In Columns 23-24 (Table 6-continued), Line 15, delete "CD38" and insert -- CD83 --.

In Columns 25-26 (Table 7-continued), Line 47, delete "SPATA" and insert -- SPATA13 --.

In Columns 37-38 (Table 11-continued), Line 11, delete "INFAIP2" and insert -- TNFAIP2 --.

In Column 39, Line 30, delete "Cohen." and insert -- Cohen, --.

In Column 40, Line 17, delete "Cohen." and insert -- Cohen, --.

In Column 40, Line 50, delete "(Islam." and insert -- (Islam, --.

CERTIFICATE OF CORRECTION (continued)
U.S. Pat. No. 10,870,885 B2

In Column 41, Line 47, delete "Apostolou." and insert -- Apostolou, --.

In Column 41, Line 48, delete "Thanos." and insert -- Thanos, --.

In Column 42, Line 45, delete "(Gather," and insert -- (Garber, --.

In Column 43, Line 32, delete "Margolin." and insert -- Margolin, --.

In Column 46, Line 59, delete "(>20 k" and insert -- (>20k --.

In Column 50, Line 64, delete "A." and insert -- A, --.

In Column 52, Line 18, delete "acid." and insert -- acid, --.

In Column 52, Line 58, delete "murabutide." and insert -- murabutide, --.

In Column 53, Line 64, delete "MARK2." and insert -- MARK2, --.

In Column 54, Line 54, delete "1," and insert -- I, --.

In Column 55, Line 18, delete "vorinostat." and insert -- vorinostat, --.

In Column 55, Line 28-29, delete "deoxyspergualin." and insert -- deoxyspergualin, --.

In Column 56, Line 43, delete "lipoarabinomannan." and insert -- lipoarabinomannan, --.

In Column 56, Line 51, delete "LY294002." and insert -- LY294002, --.

In Column 56, Line 51, delete "1," and insert -- I, --.

In Column 57, Line 34, delete "doxycycline." and insert -- doxycycline, --.

In Column 57, Line 54, delete "methylprednisolone." and insert -- methylprednisolone, --.

In Column 58, Line 19, delete "Blaug." and insert -- Blaug, --.

In Column 60, Line 38, delete "Easton." and insert -- Easton, --.

In Column 60, Line 41, delete "Sciences." and insert -- Sciences, --.

In Column 61, Line 42, delete "(Clontech." and insert -- (Clontech, --.

In Column 62, Line 56, delete "–1" and insert -- –I --.

In Column 63, Line 64, delete "1.000,000" and insert -- 1,000,000 --.

In Column 65, Line 2, delete "FIG." and insert -- FIGS. --.

In Columns 73-74 (Table S6-continued), Line 28, delete "gatgacttccgagctgtg" and insert -- gatgctcttccgagctgtg --.

In Columns 75-76 (Table S6-continued), Line 20, delete "act gtaacctgctgcccaag" and insert -- actgtaacctgctgcccaag --.

In Column 78, Line 47, delete "I127–/– (I127r" and insert -- Il27–/– (Il27r --.

In Column 79, Line 19, delete "C," and insert -- C1 --.

In Column 80, Line 2, delete "C." and insert -- C., --.

In Column 80, Line 19, delete "C." and insert -- C., --.

In Column 80, Line 28, delete "C." and insert -- C., --.

In Column 81, Line 55, delete "Dewey." and insert -- Dewey, --.

In Column 83, Line 26, delete "Quake." and insert -- Quake, --.

In Column 83, Line 52, delete "(Levin." and insert -- (Levin, --.

In Column 84, Line 49, delete "top." and insert -- top, --.

In Column 84, Line 52, delete "p=1.5×10)." and insert -- p=1.5×10-6). --.

In Column 84, Line 57, delete "(Ram." and insert -- (Ram, --.

In Column 85, Line 2, delete "Cxcl1, Cxcl10," and insert -- Cxcl1, Cxcl10, --.

In Column 85, Line 18, delete "(Cc13, Cc14, Ccr12)," and insert -- (Ccl3, Ccl4, Ccrl2), --.

In Column 85, Line 19, delete "(Cxc12)," and insert -- (Cxcl2), --.

In Column 85, Line 46, delete "Wagner." and insert -- Wagner, --.

In Column 85, Line 53, delete "(Newman." and insert -- (Newman, --.

In Column 87, Line 37, delete "(Banchcreau," and insert -- (Banchereau, --.

In Column 87, Line 53, delete "(Garber." and insert -- (Garber, --.

In Column 87, Line 62, delete "Il1a, Il1b, and Cxcl10)" and insert -- Il1a, Il1b, and Cxcl10) --.

CERTIFICATE OF CORRECTION (continued)
U.S. Pat. No. 10,870,885 B2

In Column 87, Line 66, delete "Cc122," and insert -- Ccl22, --.

In Column 88, Line 27, delete "(Dalerba." and insert -- (Dalerba, --.

In Column 88, Line 37, delete "Cxc110" and insert -- Cxcl10 --.

In Column 88, Line 38, delete "Cc122" and insert -- Ccl22 --.

In Column 89, Line 25, delete "FIG." and insert -- FIGS. --.

In Column 89, Line 27, delete "(FIG." and insert -- (FIGS. --.

In Column 89, Line 42, delete "(Cxc110," and insert -- (Cxcl10, --.

In Column 90, Line 57, delete "Elowitz." and insert -- Elowitz, --.

In Column 91, Line 44, delete "Altschuler." and insert -- Altschuler, --.

In Column 92, Line 31, delete "Spencer." and insert -- Spencer, --.

In Column 92, Line 49, delete "Rainey." and insert -- Rainey, --.

In Column 92, Line 59, delete "Hematopoictic" and insert -- Hematopoietic --.

In Column 92, Line 61, delete "Hashimoto." and insert -- Hashimoto, --.

In Column 93, Line 5, delete "(Cohen." and insert -- (Cohen, --.

In Column 94, Line 24, delete "Huang." and insert -- Huang, --.

In Column 94, Line 45, delete "(Ramskold." and insert -- (Ramskold, --.

In Column 96, Line 13, delete "program." and insert -- program, --.

In Column 96, Line 14, delete "I,II)" and insert -- I, II) --.

In Column 99, Line 24, delete "IIIa" and insert -- II1a --.

In Column 103, Line 11, delete "I11a," and insert -- II1a, --.